US009265458B2

(12) United States Patent
Stack

(10) Patent No.: US 9,265,458 B2
(45) Date of Patent: Feb. 23, 2016

(54) APPLICATION OF SMOOTH PURSUIT COGNITIVE TESTING PARADIGMS TO CLINICAL DRUG DEVELOPMENT

(71) Applicant: Sync-Think, Inc., Boston, MA (US)

(72) Inventor: Matthew E. Stack, Boston, MA (US)

(73) Assignee: SYNC-THINK, INC., Boston, MA (US)

( * ) Notice: Subject to any disclaimer, the term of this patent is extended or adjusted under 35 U.S.C. 154(b) by 306 days.

(21) Appl. No.: 13/694,461

(22) Filed: Dec. 4, 2012

(65) Prior Publication Data

US 2014/0154650 A1  Jun. 5, 2014

(51) Int. Cl.
| G09B 19/00 | (2006.01) |
| A61B 5/16 | (2006.01) |
| A61B 5/00 | (2006.01) |
| G06F 3/01 | (2006.01) |
| A61B 3/113 | (2006.01) |

(52) U.S. Cl.
CPC ............... *A61B 5/162* (2013.01); *A61B 5/4076* (2013.01); *A61B 5/4848* (2013.01); *A61B 3/113* (2013.01); *G06F 3/013* (2013.01)

(58) Field of Classification Search
CPC ............. G09B 19/00; G09B 7/00; A61B 5/16
USPC .................................................. 434/236, 238
See application file for complete search history.

(56) References Cited

U.S. PATENT DOCUMENTS

| 2,700,832 A | 2/1955 | Slovinski |
| 3,144,720 A | 8/1964 | Kehl |
| 3,302,757 A | 2/1967 | Eagleson, Jr. et al. |
| 3,315,671 A | 4/1967 | Creelman |
| 3,334,423 A | 8/1967 | Hintze |
| 3,357,116 A | 12/1967 | Bazacos |
| 3,381,395 A | 5/1968 | Bergland |
| 3,390,469 A | 7/1968 | Rader |
| 3,419,972 A | 1/1969 | Kitzinger |
| 3,429,572 A | 2/1969 | Mars |
| 3,460,273 A | 8/1969 | Boyd |
| 3,496,652 A | 2/1970 | Wolfner et al. |
| 3,533,683 A | 10/1970 | Stark et al. |

(Continued)

FOREIGN PATENT DOCUMENTS

EP  1726260 A2  11/2006

OTHER PUBLICATIONS

Alexander GE, Crutcher MD. (1990). Functional architecture of basal ganglia circuits: neural substrates of parallrel,processing. TINS, 13(7):266-271.

(Continued)

*Primary Examiner* — Kesha Frisby
(74) *Attorney, Agent, or Firm* — Morgan, Lewis & Bockius LLP

(57) ABSTRACT

The invention describes the process of applying smooth pursuit eye movement tests toward the detection of the efficacy and, or, toxicity of neuro-pharmaceutical compounds throughout the clinical drug development process. Several different paradigms in smooth pursuit tracking tests and several analysis methods and metrics may be used. Application of smooth pursuit tracking tests allows for a quantifiable measurement of a subject's cognitive behavior and function. This process provides a cost effective and objective test of efficacy of neuro-pharmaceutical drugs and increase the validity of the clinical drug development process.

21 Claims, 10 Drawing Sheets

(56) References Cited

U.S. PATENT DOCUMENTS

| | | | |
|---|---|---|---|
| 3,534,273 A | 10/1970 | Thomas | |
| 3,554,597 A | 1/1971 | Gurbst | |
| 3,585,356 A | 6/1971 | Hall | |
| 3,593,433 A | 7/1971 | Dillon et al. | |
| 3,597,860 A | 8/1971 | Capecelatro | |
| 3,606,314 A | 9/1971 | Popp | |
| 3,618,231 A | 11/1971 | Nason | |
| 3,649,024 A | 3/1972 | Katzman | |
| 3,656,746 A | 4/1972 | Breslow | |
| 3,666,858 A | 5/1972 | Hughes et al. | |
| 3,670,428 A | 6/1972 | Hall | |
| 3,685,169 A | 8/1972 | Blau et al. | |
| 3,690,020 A | 9/1972 | McBratnie | |
| 3,695,736 A | 10/1972 | Brown | |
| 3,696,760 A | 10/1972 | Riley | |
| 3,712,716 A | 1/1973 | Cornsweet et al. | |
| 3,713,654 A | 1/1973 | Goldfarb | |
| 3,724,932 A | 4/1973 | Cornsweet et al. | |
| 3,725,133 A | 4/1973 | Pollack et al. | |
| 3,737,217 A | 6/1973 | Haines et al. | |
| 3,751,849 A | 8/1973 | Goldfarb et al. | |
| 3,774,908 A | 11/1973 | Greenberg | |
| 3,775,864 A | 12/1973 | Bisinger et al. | |
| 3,777,416 A | 12/1973 | Milligan et al. | |
| 3,780,449 A | 12/1973 | Stephenson | |
| 3,789,517 A | 2/1974 | Romstad | |
| 3,789,522 A | 2/1974 | Moore | |
| 3,804,417 A | 4/1974 | Dawson | |
| 3,804,496 A | 4/1974 | Crane et al. | |
| 3,809,879 A | 5/1974 | Gonzalez | |
| 3,827,177 A | 8/1974 | Wengel | |
| 3,934,226 A | 1/1976 | Stone et al. | |
| 3,935,651 A | 2/1976 | Mankoff et al. | |
| 3,940,485 A * | 2/1976 | Levinson et al. | 514/255.04 |
| 3,953,027 A | 4/1976 | Katzman et al. | |
| 3,958,344 A | 5/1976 | Lesiak | |
| 3,959,580 A | 5/1976 | Chocol et al. | |
| 3,968,686 A | 7/1976 | O'Neal | |
| RE28,921 E | 8/1976 | Haines et al. | |
| 3,982,759 A | 9/1976 | Grant | |
| 3,992,087 A | 11/1976 | Flom et al. | |
| 4,003,642 A | 1/1977 | Vogeley | |
| 4,007,273 A | 2/1977 | Levinson et al. | |
| 4,028,725 A | 6/1977 | Lewis | |
| 4,053,994 A | 10/1977 | Gess | |
| 4,057,051 A | 11/1977 | Kerouac | |
| 4,057,244 A | 11/1977 | Gaspar | |
| 4,089,967 A | 5/1978 | Bocher | |
| 4,120,975 A | 10/1978 | Orr et al. | |
| 4,122,841 A | 10/1978 | Rock et al. | |
| 4,141,985 A | 2/1979 | Strande | |
| 4,145,122 A | 3/1979 | Rinard et al. | |
| 4,163,343 A | 8/1979 | Schoenfield | |
| 4,176,473 A | 12/1979 | Rae | |
| 4,176,492 A | 12/1979 | Sims et al. | |
| 4,179,825 A | 12/1979 | Iwao | |
| 4,209,531 A | 6/1980 | Berry | |
| 4,211,032 A | 7/1980 | Robinett | |
| 4,213,616 A | 7/1980 | Dickey | |
| 4,227,337 A | 10/1980 | Murray et al. | |
| 4,249,333 A | 2/1981 | Chase et al. | |
| 4,251,872 A | 2/1981 | Bone | |
| 4,252,822 A | 2/1981 | Berry | |
| 4,267,646 A | 5/1981 | Hagwell | |
| 4,279,258 A | 7/1981 | John | |
| 4,287,410 A | 9/1981 | Crane et al. | |
| 4,299,790 A | 11/1981 | Greenberg | |
| 4,300,818 A | 11/1981 | Schachar | |
| 4,302,900 A | 12/1981 | Rayner | |
| 4,303,394 A | 12/1981 | Berke et al. | |
| 4,315,937 A | 2/1982 | Maclay et al. | |
| 4,331,424 A | 5/1982 | Crane | |
| 4,332,566 A | 6/1982 | Mazeski et al. | |
| 4,334,382 A | 6/1982 | Chase et al. | |
| 4,340,372 A | 7/1982 | Brassine | |
| 4,346,897 A | 8/1982 | Sisak | |
| 4,354,843 A | 10/1982 | Feldman | |
| 4,373,787 A | 2/1983 | Crane et al. | |
| 4,376,309 A | 3/1983 | Fenderson et al. | |
| 4,382,946 A | 5/1983 | Sjoerdsma | |
| 4,397,635 A | 8/1983 | Samuels | |
| 4,407,299 A | 10/1983 | Culver | |
| 4,420,228 A | 12/1983 | Humphrey | |
| 4,421,486 A | 12/1983 | Baldwin et al. | |
| 4,428,582 A | 1/1984 | Smith | |
| 4,433,504 A | 2/1984 | Terui | |
| 4,439,157 A | 3/1984 | Breglia et al. | |
| 4,443,075 A | 4/1984 | Crane | |
| 4,449,321 A | 5/1984 | Reiling | |
| 4,463,430 A | 7/1984 | Volk, Jr. et al. | |
| 4,474,186 A | 10/1984 | Ledley et al. | |
| 4,479,784 A | 10/1984 | Mallinson et al. | |
| 4,483,860 A | 11/1984 | Tuttle | |
| 4,499,502 A | 2/1985 | Dakin et al. | |
| 4,508,347 A | 4/1985 | Shettler | |
| 4,513,317 A | 4/1985 | Ruoff, Jr. | |
| 4,523,348 A | 6/1985 | Petrie | |
| 4,528,989 A | 7/1985 | Weinblatt | |
| 4,536,065 A | 8/1985 | Sheingorn | |
| 4,560,113 A | 12/1985 | Szalanski | |
| 4,561,658 A | 12/1985 | Peterson | |
| 4,563,306 A | 1/1986 | Sugano et al. | |
| 4,568,159 A | 2/1986 | Baldwin | |
| 4,572,513 A | 2/1986 | Evans | |
| 4,573,654 A | 3/1986 | Nottingham | |
| 4,575,510 A | 3/1986 | Sjoerdsma | |
| 4,576,184 A | 3/1986 | Westerman | |
| 4,593,406 A | 6/1986 | Stone | |
| 4,606,576 A | 8/1986 | Jones | |
| 4,606,618 A | 8/1986 | Geller | |
| 4,608,027 A | 8/1986 | Klamer et al. | |
| 4,618,938 A | 10/1986 | Sandland et al. | |
| 4,636,173 A | 1/1987 | Mossman | |
| 4,644,172 A | 2/1987 | Sandland et al. | |
| 4,644,423 A | 2/1987 | Buntsis et al. | |
| 4,645,210 A | 2/1987 | Patsy | |
| 4,648,052 A | 3/1987 | Friedman et al. | |
| 4,661,072 A | 4/1987 | White | |
| 4,661,847 A | 4/1987 | Weinblatt | |
| 4,665,056 A | 5/1987 | Sugano et al. | |
| 4,670,459 A | 6/1987 | Sjoerdsma | |
| 4,671,514 A | 6/1987 | Wilson-Diehl | |
| 4,690,149 A | 9/1987 | Ko | |
| 4,693,697 A | 9/1987 | Pagano | |
| 4,700,952 A | 10/1987 | Patsy | |
| 4,702,575 A | 10/1987 | Breglia | |
| 4,710,979 A | 12/1987 | Bull et al. | |
| 4,711,878 A | 12/1987 | Sugano et al. | |
| 4,718,567 A | 1/1988 | La Vange | |
| 4,720,189 A | 1/1988 | Heynen et al. | |
| 4,741,717 A | 5/1988 | Wolf | |
| 4,768,088 A | 8/1988 | Ando | |
| 4,776,475 A | 10/1988 | La Vange | |
| 4,789,235 A | 12/1988 | Borah et al. | |
| 4,798,214 A | 1/1989 | Haas | |
| 4,798,553 A | 1/1989 | Gentles et al. | |
| 4,799,680 A | 1/1989 | Weimar | |
| 4,800,209 A | 1/1989 | Sjoerdsma | |
| 4,800,893 A | 1/1989 | Ross et al. | |
| 4,801,200 A | 1/1989 | Hussey | |
| 4,805,121 A | 2/1989 | Scott et al. | |
| 4,807,986 A | 2/1989 | Wasserman | |
| 4,810,833 A | 3/1989 | Meyers | |
| 4,817,959 A | 4/1989 | Tinsley | |
| 4,833,469 A | 5/1989 | David | |
| 4,838,681 A | 6/1989 | Pavlidis | |
| 4,852,988 A | 8/1989 | Velez et al. | |
| 4,856,891 A | 8/1989 | Pflibsen et al. | |
| 4,862,505 A | 8/1989 | Keith et al. | |
| 4,862,513 A | 8/1989 | Bragas | |
| 4,864,333 A | 9/1989 | Barber | |
| 4,884,219 A | 11/1989 | Waldren | |
| 4,884,973 A | 12/1989 | Pak | |
| 4,889,422 A | 12/1989 | Pavlidis | |

(56) References Cited

U.S. PATENT DOCUMENTS

| | | |
|---|---|---|
| 4,897,715 A | 1/1990 | Beamon, III |
| 4,900,256 A | 2/1990 | Dara-Abrams |
| 4,909,501 A | 3/1990 | Hoffman |
| 4,921,427 A | 5/1990 | Dunn |
| 4,926,969 A | 5/1990 | Wright et al. |
| 4,932,913 A | 6/1990 | Raviv et al. |
| 4,941,590 A | 7/1990 | Pantaleo et al. |
| 4,945,103 A | 7/1990 | Cohen |
| 4,952,756 A | 8/1990 | Meyers |
| 4,961,640 A | 10/1990 | Irlen |
| 4,971,560 A | 11/1990 | Patel |
| 4,972,851 A | 11/1990 | Noble |
| 4,974,010 A | 11/1990 | Cleveland et al. |
| 4,984,179 A | 1/1991 | Waldern |
| 4,994,467 A | 2/1991 | Zimmerman |
| 5,003,997 A | 4/1991 | Stewart et al. |
| 5,005,161 A | 4/1991 | Boilen |
| 5,006,000 A | 4/1991 | House |
| 5,015,633 A | 5/1991 | Sudilovsky |
| 5,016,282 A | 5/1991 | Tomono et al. |
| 5,016,643 A | 5/1991 | Applegate et al. |
| 5,033,964 A | 7/1991 | Phelps |
| 5,035,500 A | 7/1991 | Rorabaugh et al. |
| 5,037,821 A | 8/1991 | Horovitz |
| 5,038,852 A | 8/1991 | Johnson et al. |
| 5,048,947 A | 9/1991 | Linde |
| 5,049,147 A | 9/1991 | Danon |
| 5,087,822 A | 2/1992 | Fairlie et al. |
| 5,088,810 A | 2/1992 | Galanter et al. |
| 5,089,472 A | 2/1992 | Vila et al. |
| 5,090,797 A | 2/1992 | Cleveland et al. |
| 5,098,889 A | 3/1992 | Costall et al. |
| 5,106,184 A | 4/1992 | Milbocker |
| 5,122,952 A | 6/1992 | Minkus |
| 5,129,009 A | 7/1992 | Lebeau |
| 5,135,468 A | 8/1992 | Meissner |
| 5,137,027 A | 8/1992 | Rosenfeld |
| 5,138,538 A | 8/1992 | Sperling |
| 5,157,261 A | 10/1992 | Grey et al. |
| 5,169,316 A | 12/1992 | Lorman et al. |
| 5,176,145 A | 1/1993 | Ryback et al. |
| 5,177,064 A | 1/1993 | Bodor |
| 5,177,511 A | 1/1993 | Feuerstein et al. |
| 5,189,026 A | 2/1993 | Costa et al. |
| 5,193,681 A | 3/1993 | Lievsay |
| 5,198,977 A | 3/1993 | Salb |
| 5,204,703 A | 4/1993 | Hutchinson et al. |
| 5,204,910 A | 4/1993 | Lebeau |
| 5,230,629 A | 7/1993 | Buschke |
| 5,231,674 A | 7/1993 | Cleveland et al. |
| 5,241,332 A | 8/1993 | Farrell |
| 5,247,344 A | 9/1993 | Doan |
| 5,262,806 A | 11/1993 | Szirth |
| 5,265,848 A | 11/1993 | Michaud et al. |
| 5,267,865 A | 12/1993 | Lee et al. |
| 5,270,748 A | 12/1993 | Katz |
| 5,273,433 A | 12/1993 | Kaminski et al. |
| 5,277,586 A | 1/1994 | Branch |
| 5,281,143 A | 1/1994 | Arad et al. |
| 5,286,228 A | 2/1994 | Lee et al. |
| 5,287,437 A | 2/1994 | Deering |
| 5,292,276 A | 3/1994 | Manalo |
| 5,293,187 A | 3/1994 | Knapp et al. |
| 5,293,532 A | 3/1994 | Marshall |
| 5,295,491 A | 3/1994 | Gevins |
| 5,302,583 A | 4/1994 | Costa et al. |
| 5,305,012 A | 4/1994 | Faris |
| 5,309,355 A | 5/1994 | Lockwood |
| 5,317,689 A | 5/1994 | Nack et al. |
| 5,319,453 A | 6/1994 | Copriviza et al. |
| 5,320,534 A | 6/1994 | Thomas |
| 5,327,918 A | 7/1994 | Stewart et al. |
| 5,329,322 A | 7/1994 | Yancey |
| 5,331,149 A | 7/1994 | Spitzer et al. |
| 5,331,969 A | 7/1994 | Silberstein |
| 5,333,272 A | 7/1994 | Capek et al. |
| 5,333,675 A | 8/1994 | Mullis et al. |
| 5,341,181 A | 8/1994 | Godard |
| 5,343,577 A | 9/1994 | Petrovich |
| 5,345,281 A | 9/1994 | Taboada et al. |
| 5,348,477 A | 9/1994 | Welch et al. |
| 5,350,304 A | 9/1994 | Fula et al. |
| 5,355,893 A | 10/1994 | Mick et al. |
| 5,356,287 A | 10/1994 | McIntyre |
| 5,358,448 A | 10/1994 | Stephens |
| 5,360,010 A | 11/1994 | Applegate et al. |
| 5,360,424 A | 11/1994 | Klopotek |
| 5,360,971 A | 11/1994 | Kaufman et al. |
| 5,363,154 A | 11/1994 | Galanter et al. |
| 5,370,399 A | 12/1994 | Liverance |
| 5,377,100 A | 12/1994 | Pope et al. |
| 5,388,689 A | 2/1995 | Kroop et al. |
| 5,394,202 A | 2/1995 | Deering |
| 5,408,346 A | 4/1995 | Trissel et al. |
| 5,410,376 A | 4/1995 | Cornsweet et al. |
| 5,413,488 A | 5/1995 | Gibson et al. |
| 5,413,996 A | 5/1995 | Bodor |
| 5,414,951 A | 5/1995 | Martin |
| 5,421,732 A | 6/1995 | Taylor |
| 5,422,653 A | 6/1995 | Maguire, Jr. |
| 5,422,689 A | 6/1995 | Knapp et al. |
| 5,422,690 A | 6/1995 | Rothberg et al. |
| 5,428,657 A | 6/1995 | Papanicolopoulos et al. |
| 5,430,505 A | 7/1995 | Katz |
| 5,433,549 A | 7/1995 | McGaffigan |
| 5,434,170 A | 7/1995 | Andrulis, Jr. |
| 5,435,728 A | 7/1995 | Fula et al. |
| 5,437,553 A | 8/1995 | Collins et al. |
| 5,441,415 A | 8/1995 | Lee et al. |
| 5,446,834 A | 8/1995 | Deering |
| 5,447,166 A | 9/1995 | Gevins |
| 5,453,428 A | 9/1995 | Kaminski |
| 5,456,606 A | 10/1995 | McIntyre |
| 5,459,536 A | 10/1995 | Shalon et al. |
| 5,467,104 A | 11/1995 | Furness, III et al. |
| 5,473,744 A | 12/1995 | Allen et al. |
| 5,474,548 A | 12/1995 | Knopp et al. |
| 5,481,257 A | 1/1996 | Brubaker et al. |
| 5,481,622 A | 1/1996 | Gerhardt et al. |
| 5,491,492 A | 2/1996 | Knapp et al. |
| 5,495,576 A | 2/1996 | Ritchey |
| 5,498,188 A | 3/1996 | Deahr |
| 5,500,671 A | 3/1996 | Andersson et al. |
| 5,502,481 A | 3/1996 | Dentinger et al. |
| 5,513,649 A | 5/1996 | Gevins et al. |
| 5,514,415 A | 5/1996 | Gupta |
| 5,517,021 A | 5/1996 | Kaufman et al. |
| 5,525,061 A | 6/1996 | Lord |
| 5,526,812 A | 6/1996 | Dumoulin et al. |
| 5,529,498 A | 6/1996 | Cassily et al. |
| 5,545,044 A | 8/1996 | Collins et al. |
| 5,549,632 A | 8/1996 | Lai |
| 5,550,602 A | 8/1996 | Braeuning |
| 5,551,878 A | 9/1996 | Ellenbogen |
| 5,557,459 A | 9/1996 | Samson |
| 5,568,209 A | 10/1996 | Priester et al. |
| 5,570,301 A | 10/1996 | Barrus |
| 5,570,698 A | 11/1996 | Liang et al. |
| 5,572,596 A | 11/1996 | Wildes et al. |
| 5,573,403 A | 11/1996 | Beller et al. |
| 5,576,780 A | 11/1996 | Yancey |
| 5,576,951 A | 11/1996 | Lockwood |
| 5,577,919 A | 11/1996 | Collins et al. |
| 5,583,335 A | 12/1996 | Spitzer et al. |
| 5,583,795 A | 12/1996 | Smyth |
| 5,588,139 A | 12/1996 | Lanier et al. |
| 5,595,488 A | 1/1997 | Gozlan et al. |
| 5,596,339 A | 1/1997 | Furness, III et al. |
| 5,603,502 A | 2/1997 | Nakagawa |
| 5,606,699 A | 2/1997 | De Pauw et al. |
| 5,607,186 A | 3/1997 | Schroeder et al. |
| 5,610,665 A | 3/1997 | Berman |
| 5,610,673 A | 3/1997 | Rafal et al. |
| 5,615,434 A | 4/1997 | Cracchiolo et al. |

(56) References Cited

U.S. PATENT DOCUMENTS

| | | |
|---|---|---|
| 5,618,803 A | 4/1997 | Bodor |
| 5,620,436 A | 4/1997 | Lang et al. |
| 5,626,477 A | 5/1997 | Adkison |
| 5,626,595 A | 5/1997 | Sklar et al. |
| 5,633,695 A | 5/1997 | Feke et al. |
| 5,638,176 A | 6/1997 | Hobbs et al. |
| 5,639,607 A | 6/1997 | Desnick et al. |
| 5,642,198 A | 6/1997 | Long |
| 5,644,324 A | 7/1997 | Maguire, Jr. |
| 5,645,550 A | 7/1997 | Hohla |
| 5,646,675 A | 7/1997 | Copriviza et al. |
| 5,649,061 A | 7/1997 | Smyth |
| 5,651,678 A | 7/1997 | Phillips |
| 5,656,493 A | 8/1997 | Mullis et al. |
| 5,658,590 A | 8/1997 | Heiligenstein et al. |
| 5,659,327 A | 8/1997 | Furness, III et al. |
| 5,660,548 A | 8/1997 | Ellenbogen |
| 5,662,117 A | 9/1997 | Bittman |
| 5,667,326 A | 9/1997 | McGaffigan |
| 5,671,992 A | 9/1997 | Richards |
| 5,680,159 A | 10/1997 | Lunetta |
| 5,681,170 A | 10/1997 | Rieber et al. |
| 5,684,561 A | 11/1997 | Yancey |
| 5,688,126 A | 11/1997 | Merritt |
| 5,691,324 A | 11/1997 | Sandyk |
| 5,692,906 A | 12/1997 | Corder |
| 5,694,142 A | 12/1997 | Dumoulin et al. |
| 5,696,168 A | 12/1997 | Heiligenstein et al. |
| 5,699,082 A | 12/1997 | Marks et al. |
| 5,699,089 A | 12/1997 | Murray |
| 5,703,637 A | 12/1997 | Miyazaki et al. |
| 5,704,007 A | 12/1997 | Cecys |
| 5,704,369 A | 1/1998 | Scinto et al. |
| 5,705,512 A | 1/1998 | McDonald et al. |
| 5,708,470 A | 1/1998 | Holford |
| 5,709,214 A | 1/1998 | Skinner |
| 5,717,512 A | 2/1998 | Chmielewski, Jr. et al. |
| 5,720,294 A | 2/1998 | Skinner |
| 5,724,987 A | 3/1998 | Gevins et al. |
| 5,726,916 A | 3/1998 | Smyth |
| 5,727,098 A | 3/1998 | Jacobson |
| 5,731,349 A | 3/1998 | Komissarova et al. |
| 5,731,805 A | 3/1998 | Tognazzini et al. |
| 5,734,375 A | 3/1998 | Knox et al. |
| 5,734,421 A | 3/1998 | Maguire, Jr. |
| 5,738,547 A | 4/1998 | Russo |
| 5,738,873 A | 4/1998 | Bleiweiss et al. |
| 5,740,803 A | 4/1998 | Gray et al. |
| 5,743,740 A | 4/1998 | Visser et al. |
| 5,743,744 A | 4/1998 | Cassily et al. |
| 5,748,382 A | 5/1998 | Maguire, Jr. |
| 5,751,260 A | 5/1998 | Nappi et al. |
| 5,751,836 A | 5/1998 | Wildes et al. |
| 5,753,651 A | 5/1998 | dePadova |
| 5,757,339 A | 5/1998 | Williams et al. |
| 5,760,771 A | 6/1998 | Blonder et al. |
| 5,767,941 A | 6/1998 | Ferguson |
| 5,771,778 A | 6/1998 | MacLean, IV |
| 5,774,591 A | 6/1998 | Black et al. |
| 5,775,693 A | 7/1998 | Clancy |
| 5,776,068 A | 7/1998 | Silverman et al. |
| 5,777,614 A | 7/1998 | Ando et al. |
| 5,778,825 A | 7/1998 | Krietzmen et al. |
| 5,781,939 A | 7/1998 | Bledsoe |
| 5,782,471 A | 7/1998 | Bautista et al. |
| 5,782,822 A | 7/1998 | Telfair et al. |
| 5,786,810 A | 7/1998 | Knox et al. |
| 5,788,508 A | 8/1998 | Lee et al. |
| 5,793,354 A | 8/1998 | Kaplan |
| 5,794,980 A | 8/1998 | Bigler |
| 5,796,398 A | 8/1998 | Zimmer |
| 5,797,853 A | 8/1998 | Musha et al. |
| 5,799,282 A | 8/1998 | Rakshit et al. |
| 5,800,176 A | 9/1998 | Harrison |
| 5,800,423 A | 9/1998 | Jensen |
| 5,802,220 A | 9/1998 | Black et al. |
| 5,805,167 A | 9/1998 | van Cruyningen |
| 5,817,084 A | 10/1998 | Jensen |
| 5,818,437 A | 10/1998 | Grover et al. |
| 5,818,954 A | 10/1998 | Tomono et al. |
| 5,825,458 A | 10/1998 | Cooper |
| 5,830,479 A | 11/1998 | Hall |
| 5,831,594 A | 11/1998 | Tognazzini et al. |
| 5,832,918 A | 11/1998 | Pantino |
| 5,833,189 A | 11/1998 | Rossman et al. |
| 5,837,701 A | 11/1998 | Bleiweiss et al. |
| 5,840,578 A | 11/1998 | Desnick et al. |
| 5,841,051 A | 11/1998 | Segan |
| 5,842,868 A | 12/1998 | Phillips |
| 5,844,209 A | 12/1998 | Gunther |
| 5,844,824 A | 12/1998 | Newman et al. |
| 5,849,006 A | 12/1998 | Frey et al. |
| 5,850,201 A | 12/1998 | Lasko-Harvill et al. |
| 5,859,686 A | 1/1999 | Aboutalib et al. |
| 5,860,653 A | 1/1999 | Jacobs |
| 5,861,797 A | 1/1999 | Becker |
| 5,863,043 A | 1/1999 | Bitner |
| 5,863,044 A | 1/1999 | Ince |
| 5,864,384 A | 1/1999 | McClure et al. |
| 5,865,172 A | 2/1999 | Butler et al. |
| 5,865,832 A | 2/1999 | Knopp et al. |
| 5,866,585 A | 2/1999 | Fogel |
| 5,867,308 A | 2/1999 | Pensel et al. |
| 5,867,587 A | 2/1999 | Aboutalib et al. |
| 5,869,528 A | 2/1999 | Cavazza |
| 5,870,138 A | 2/1999 | Smith et al. |
| 5,870,167 A | 2/1999 | Knopp et al. |
| 5,875,018 A | 2/1999 | Lamprecht |
| 5,880,812 A | 3/1999 | Solomon |
| 5,883,692 A | 3/1999 | Agonis et al. |
| 5,884,626 A | 3/1999 | Kuroda et al. |
| 5,886,051 A | 3/1999 | Bergeron, Jr. et al. |
| 5,886,683 A | 3/1999 | Tognazzini et al. |
| 5,886,768 A | 3/1999 | Knopp et al. |
| 5,886,822 A | 3/1999 | Spitzer |
| 5,889,033 A | 3/1999 | Kaminski |
| 5,890,152 A | 3/1999 | Rapaport et al. |
| 5,892,566 A | 4/1999 | Bullwinkel |
| 5,892,570 A | 4/1999 | Stevens |
| 5,895,220 A | 4/1999 | Beller et al. |
| 5,898,423 A | 4/1999 | Tognazzini et al. |
| 5,899,867 A | 5/1999 | Collura |
| 5,900,923 A | 5/1999 | Prendergast et al. |
| 5,901,693 A | 5/1999 | Smith |
| 5,902,116 A | 5/1999 | Rieber et al. |
| 5,905,563 A | 5/1999 | Yamamoto |
| 5,909,210 A | 6/1999 | Knox et al. |
| 5,911,581 A | 6/1999 | Reynolds et al. |
| 5,915,729 A | 6/1999 | Vap |
| 5,917,476 A | 6/1999 | Czerniecki |
| 5,926,251 A | 7/1999 | Okumura |
| 5,928,221 A | 7/1999 | Sasnett et al. |
| 5,930,755 A | 7/1999 | Cecys |
| 5,931,832 A | 8/1999 | Jensen |
| 5,932,541 A | 8/1999 | Winokur et al. |
| 5,937,852 A | 8/1999 | Butler et al. |
| 5,938,242 A | 8/1999 | Ryan |
| 5,942,954 A | 8/1999 | Galiana et al. |
| 5,943,115 A | 8/1999 | Ferguson |
| 5,944,530 A | 8/1999 | Ho et al. |
| 5,947,908 A | 9/1999 | Morris |
| 5,947,955 A | 9/1999 | Kadambi et al. |
| 5,948,047 A | 9/1999 | Jenkins et al. |
| 5,950,896 A | 9/1999 | Theodore |
| 5,951,014 A | 9/1999 | Nadel |
| 5,951,406 A | 9/1999 | Steane |
| 5,953,541 A | 9/1999 | King et al. |
| 5,954,512 A | 9/1999 | Fruge |
| 5,956,124 A | 9/1999 | Dan |
| 5,963,300 A | 10/1999 | Horwitz |
| 5,966,197 A | 10/1999 | Yee |
| 5,971,850 A | 10/1999 | Liverance |
| H1812 H | 11/1999 | Arcuri |
| 5,975,068 A | 11/1999 | Halter et al. |

(56) References Cited

U.S. PATENT DOCUMENTS

| | | |
|---|---|---|
| 5,976,037 A | 11/1999 | Watson |
| 5,980,513 A | 11/1999 | Frey et al. |
| 5,982,555 A | 11/1999 | Melville et al. |
| 5,984,916 A | 11/1999 | Lai |
| 5,991,085 A | 11/1999 | Rallison et al. |
| 5,991,726 A | 11/1999 | Immarco et al. |
| 5,999,909 A | 12/1999 | Rakshit et al. |
| 5,999,952 A | 12/1999 | Jenkins et al. |
| 6,003,991 A | 12/1999 | Viirre |
| 6,004,121 A | 12/1999 | Gupta |
| 6,005,704 A | 12/1999 | Chmielewski, Jr. et al. |
| 6,005,710 A | 12/1999 | Pensel et al. |
| 6,007,202 A | 12/1999 | Apple et al. |
| 6,007,204 A | 12/1999 | Fahrenkrug et al. |
| 6,008,781 A | 12/1999 | Furness, III et al. |
| 6,008,798 A | 12/1999 | Mato, Jr. et al. |
| 6,011,554 A | 1/2000 | King et al. |
| 6,019,476 A | 2/2000 | Kirschner |
| 6,022,109 A | 2/2000 | Dal Santo |
| 6,023,255 A | 2/2000 | Bell |
| 6,024,707 A | 2/2000 | Scinto et al. |
| 6,026,409 A | 2/2000 | Blumenthal |
| 6,027,216 A | 2/2000 | Guyton et al. |
| 6,027,494 A | 2/2000 | Frey |
| 6,028,608 A | 2/2000 | Jenkins |
| 6,028,948 A | 2/2000 | Kil et al. |
| 6,029,183 A | 2/2000 | Jenkins et al. |
| 6,030,225 A | 2/2000 | Chan |
| 6,030,376 A | 2/2000 | Arashima et al. |
| 6,032,084 A | 2/2000 | Anderson et al. |
| 6,034,205 A | 3/2000 | Dutton et al. |
| 6,034,717 A | 3/2000 | Dentinger et al. |
| 6,040,839 A | 3/2000 | Van Eldik et al. |
| 6,043,799 A | 3/2000 | Tidwell |
| 6,045,227 A | 4/2000 | Stewart et al. |
| 6,045,363 A | 4/2000 | Phillips |
| 6,046,193 A | 4/2000 | Heiligenstein |
| 6,053,739 A | 4/2000 | Stewart et al. |
| 6,053,741 A | 4/2000 | Wood |
| 6,057,373 A | 5/2000 | Fogel |
| 6,057,847 A | 5/2000 | Jenkins |
| 6,058,941 A | 5/2000 | Denebeim |
| 6,064,856 A | 5/2000 | Lee et al. |
| 6,064,961 A | 5/2000 | Hanson |
| 6,067,565 A | 5/2000 | Horvitz |
| 6,067,975 A | 5/2000 | Ginn |
| 6,067,983 A | 5/2000 | Stenzler |
| 6,069,615 A | 5/2000 | Abraham et al. |
| 6,070,098 A | 5/2000 | Moore-Ede et al. |
| 6,073,043 A | 6/2000 | Schneider |
| 6,073,628 A | 6/2000 | Butler et al. |
| 6,073,966 A | 6/2000 | Warren |
| 6,076,513 A | 6/2000 | Doherty et al. |
| 6,078,349 A | 6/2000 | Molloy |
| 6,079,829 A | 6/2000 | Bullwinkel |
| 6,082,545 A | 7/2000 | Ford et al. |
| 6,085,112 A | 7/2000 | Kleinschmidt et al. |
| 6,085,226 A | 7/2000 | Horvitz |
| 6,087,941 A | 7/2000 | Ferraz |
| 6,089,715 A | 7/2000 | Hoover et al. |
| 6,090,051 A | 7/2000 | Marshall |
| 6,091,334 A | 7/2000 | Galiana et al. |
| 6,091,378 A | 7/2000 | Richardson et al. |
| 6,094,182 A | 7/2000 | Maguire, Jr. |
| 6,094,498 A | 7/2000 | Okumura |
| 6,097,981 A | 8/2000 | Freer |
| 6,102,870 A | 8/2000 | Edwards |
| 6,105,779 A | 8/2000 | Simpson |
| 6,106,119 A | 8/2000 | Edwards |
| 6,106,300 A | 8/2000 | Kiyosaki et al. |
| 6,108,122 A | 8/2000 | Ulrich et al. |
| 6,109,609 A | 8/2000 | Ekberg |
| 6,111,582 A | 8/2000 | Jenkins |
| 6,113,538 A | 9/2000 | Bowles et al. |
| 6,120,297 A | 9/2000 | Morse, III et al. |
| 6,120,461 A | 9/2000 | Smyth |
| 6,121,261 A | 9/2000 | Glatt et al. |
| 6,121,953 A | 9/2000 | Walker |
| 6,124,838 A | 9/2000 | Lasko-Harvill et al. |
| 6,129,681 A | 10/2000 | Kuroda et al. |
| 6,132,724 A | 10/2000 | Blum |
| 6,134,339 A | 10/2000 | Luo |
| 6,139,145 A | 10/2000 | Israel |
| 6,140,979 A | 10/2000 | Gerhard et al. |
| 6,140,980 A | 10/2000 | Spitzer et al. |
| 6,142,784 A | 11/2000 | Wood |
| 6,142,785 A | 11/2000 | Williams |
| 6,147,593 A | 11/2000 | Hall et al. |
| 6,149,272 A | 11/2000 | Bergner et al. |
| 6,149,643 A | 11/2000 | Herekar et al. |
| 6,151,081 A | 11/2000 | Gold et al. |
| 6,151,167 A | 11/2000 | Melville |
| 6,152,563 A | 11/2000 | Hutchinson et al. |
| 6,154,315 A | 11/2000 | Street |
| 6,154,321 A | 11/2000 | Melville et al. |
| 6,157,533 A | 12/2000 | Sallam et al. |
| 6,157,861 A | 12/2000 | Faltys et al. |
| 6,160,667 A | 12/2000 | Smoot |
| 6,162,186 A | 12/2000 | Scinto et al. |
| 6,162,210 A | 12/2000 | Shadduck |
| 6,163,336 A | 12/2000 | Richards |
| 6,164,645 A | 12/2000 | Weiss |
| 6,164,975 A | 12/2000 | Weingarden et al. |
| 6,167,298 A | 12/2000 | Levin |
| 6,168,562 B1 | 1/2001 | Miller et al. |
| 6,175,352 B1 | 1/2001 | Kay et al. |
| 6,177,931 B1 | 1/2001 | Alexander et al. |
| 6,179,422 B1 | 1/2001 | Lai |
| 6,181,371 B1 | 1/2001 | Maguire, Jr. |
| 6,182,114 B1 | 1/2001 | Yap et al. |
| 6,182,133 B1 | 1/2001 | Horvitz |
| 6,190,375 B1 | 2/2001 | Frey |
| 6,193,373 B1 | 2/2001 | Apple et al. |
| 6,193,978 B1 | 2/2001 | Kattan |
| 6,195,640 B1 | 2/2001 | Mullaly et al. |
| 6,198,462 B1 | 3/2001 | Daily et al. |
| 6,198,483 B1 | 3/2001 | Launais |
| 6,198,485 B1 | 3/2001 | Mack et al. |
| 6,198,532 B1 | 3/2001 | Cabib et al. |
| 6,204,828 B1 | 3/2001 | Amir et al. |
| 6,206,702 B1 | 3/2001 | Hayden et al. |
| 6,210,401 B1 | 4/2001 | Lai |
| 6,210,705 B1 | 4/2001 | Mantelle et al. |
| 6,210,950 B1 | 4/2001 | Johnson et al. |
| 6,211,977 B1 | 4/2001 | Son et al. |
| 6,213,547 B1 | 4/2001 | Bowe et al. |
| 6,215,898 B1 | 4/2001 | Woodfill et al. |
| 6,216,053 B1 | 4/2001 | Cureton et al. |
| 6,222,524 B1 | 4/2001 | Salem et al. |
| 6,228,875 B1 | 5/2001 | Tsai et al. |
| 6,231,187 B1 | 5/2001 | Munoz et al. |
| 6,233,071 B1 | 5/2001 | Orr et al. |
| 6,234,534 B1 | 5/2001 | Warren |
| 6,234,965 B1 | 5/2001 | Miller et al. |
| 6,235,046 B1 | 5/2001 | Gerdt |
| 6,242,446 B1 | 6/2001 | Glatt et al. |
| 6,242,463 B1 | 6/2001 | Reitberg |
| 6,243,076 B1 | 6/2001 | Hatfield |
| 6,244,463 B1 | 6/2001 | Richards et al. |
| 6,245,590 B1 | 6/2001 | Wine et al. |
| 6,246,382 B1 | 6/2001 | Maguire, Jr. |
| 6,252,989 B1 | 6/2001 | Geisler et al. |
| 6,256,131 B1 | 7/2001 | Wine et al. |
| 6,258,032 B1 | 7/2001 | Hammesfahr |
| 6,258,043 B1 | 7/2001 | Raviv et al. |
| 6,261,220 B1 | 7/2001 | Frey et al. |
| 6,262,889 B1 | 7/2001 | Newman et al. |
| 6,267,756 B1 | 7/2001 | Feuerstein et al. |
| 6,271,914 B1 | 8/2001 | Frey et al. |
| 6,271,915 B1 | 8/2001 | Frey et al. |
| 6,276,798 B1 | 8/2001 | Gil et al. |
| 6,277,427 B1 | 8/2001 | Husz |
| 6,280,436 B1 | 8/2001 | Freeman et al. |
| 6,283,762 B1 | 9/2001 | Wiggins |

(56) References Cited

U.S. PATENT DOCUMENTS

| | | |
|---|---|---|
| 6,283,954 B1 | 9/2001 | Yee |
| 6,285,489 B1 | 9/2001 | Helsel et al. |
| 6,285,505 B1 | 9/2001 | Melville et al. |
| 6,285,993 B1 | 9/2001 | Ferrell |
| 6,286,064 B1 | 9/2001 | King et al. |
| 6,287,299 B1 | 9/2001 | Sasnett et al. |
| 6,294,775 B1 | 9/2001 | Seibel et al. |
| 6,297,803 B1 | 10/2001 | Numaoka |
| 6,299,307 B1 | 10/2001 | Oltean et al. |
| 6,299,308 B1 | 10/2001 | Voronka et al. |
| 6,300,870 B1 | 10/2001 | Nelson |
| 6,301,593 B1 | 10/2001 | Toyosato |
| 6,302,541 B1 | 10/2001 | Grossmann |
| 6,302,876 B1 | 10/2001 | Shimmick et al. |
| 6,302,877 B1 | 10/2001 | Ruiz |
| 6,302,879 B1 | 10/2001 | Frey et al. |
| 6,304,459 B1 | 10/2001 | Toyosato et al. |
| 6,305,591 B1 | 10/2001 | Jones |
| 6,307,526 B1 | 10/2001 | Mann |
| 6,307,549 B1 | 10/2001 | King et al. |
| 6,307,589 B1 | 10/2001 | Maquire, Jr. |
| 6,315,413 B1 | 11/2001 | Shimmick et al. |
| 6,315,571 B1 | 11/2001 | Lee |
| 6,317,103 B1 | 11/2001 | Furness, III et al. |
| 6,320,610 B1 | 11/2001 | Van Sant et al. |
| 6,320,976 B1 | 11/2001 | Murthy et al. |
| 6,322,216 B1 | 11/2001 | Yee et al. |
| 6,323,884 B1 | 11/2001 | Bird et al. |
| 6,324,007 B1 | 11/2001 | Melville |
| 6,324,378 B1 | 11/2001 | Schlossberg |
| 6,325,512 B1 | 12/2001 | Wei |
| 6,325,513 B1 | 12/2001 | Bergner et al. |
| 6,325,792 B1 | 12/2001 | Swinger et al. |
| 6,331,909 B1 | 12/2001 | Dunfield |
| 6,334,683 B2 | 1/2002 | Apple et al. |
| 6,337,920 B1 | 1/2002 | Muhlhoff |
| 6,338,082 B1 | 1/2002 | Schneider |
| 6,339,849 B1 | 1/2002 | Nelson et al. |
| 6,342,915 B1 | 1/2002 | Ozaki et al. |
| 6,346,887 B1 | 2/2002 | Van Orden et al. |
| 6,348,211 B1 | 2/2002 | Mantelle et al. |
| 6,351,273 B1 | 2/2002 | Lemelson et al. |
| 6,351,335 B1 | 2/2002 | Perlin |
| 6,351,388 B1 | 2/2002 | Jenkins et al. |
| 6,352,258 B1 | 3/2002 | Fitzgerald et al. |
| 6,356,437 B1 | 3/2002 | Mitchell et al. |
| 6,356,812 B1 | 3/2002 | Cragun |
| 6,358,059 B1 | 3/2002 | Li |
| 6,359,601 B1 | 3/2002 | Maguire, Jr. |
| 6,362,226 B2 | 3/2002 | Phillips, III et al. |
| 6,362,912 B1 | 3/2002 | Lewis et al. |
| 6,367,931 B2 | 4/2002 | Lai |
| 6,367,932 B1 | 4/2002 | Donaldson |
| 6,369,952 B1 | 4/2002 | Rallison et al. |
| 6,369,953 B2 | 4/2002 | Melville et al. |
| 6,373,961 B1 | 4/2002 | Richardson et al. |
| D456,908 S | 5/2002 | Cunningham et al. |
| D457,642 S | 5/2002 | Cunningham et al. |
| 6,384,406 B1 | 5/2002 | Wine et al. |
| 6,389,612 B1 | 5/2002 | Harris |
| 6,393,056 B1 | 5/2002 | Talluri et al. |
| 6,394,602 B1 | 5/2002 | Morrison et al. |
| 6,394,999 B1 | 5/2002 | Williams et al. |
| 6,400,989 B1 | 6/2002 | Eckmiller |
| 6,401,050 B1 | 6/2002 | Cooke et al. |
| 6,402,144 B1 | 6/2002 | Ekberg |
| 6,402,320 B1 | 6/2002 | Borchert |
| 6,405,159 B2 | 6/2002 | Bushey et al. |
| 6,406,472 B1 | 6/2002 | Jensen |
| 6,407,724 B2 | 6/2002 | Waldern et al. |
| 6,413,251 B1 | 7/2002 | Williams |
| 6,414,731 B2 | 7/2002 | Lasko-Harvill et al. |
| 6,415,281 B1 | 7/2002 | Anderson |
| 6,417,861 B1 | 7/2002 | Deering et al. |
| 6,419,361 B2 | 7/2002 | Cabib et al. |
| 6,419,902 B1 | 7/2002 | Wright |
| 6,420,351 B1 | 7/2002 | Tsai et al. |
| 6,421,064 B1 | 7/2002 | Lemelson et al. |
| 6,421,185 B1 | 7/2002 | Wick et al. |
| 6,424,343 B1 | 7/2002 | Deering et al. |
| 6,426,755 B1 | 7/2002 | Deering |
| 6,427,079 B1 | 7/2002 | Schneider et al. |
| 6,427,927 B1 | 8/2002 | Hall |
| 6,429,867 B1 | 8/2002 | Deering |
| 6,431,708 B2 | 8/2002 | Krebs |
| 6,432,028 B1 | 8/2002 | Ortloff |
| 6,432,413 B1 | 8/2002 | Loeb |
| 6,433,759 B1 | 8/2002 | Richardson et al. |
| 6,433,760 B1 | 8/2002 | Vaissie et al. |
| 6,433,907 B1 | 8/2002 | Lippert et al. |
| 6,433,930 B1 | 8/2002 | Son |
| 6,434,419 B1 | 8/2002 | Gevins et al. |
| 6,435,878 B1 | 8/2002 | Reynolds et al. |
| 6,437,003 B1 | 8/2002 | Roullet et al. |
| 6,437,758 B1 | 8/2002 | Nielsen et al. |
| 6,437,808 B1 | 8/2002 | Brill, III et al. |
| 6,437,819 B1 | 8/2002 | Loveland |
| 6,442,549 B1 | 8/2002 | Schneider |
| 6,443,397 B1 | 9/2002 | Morris |
| 6,445,362 B1 | 9/2002 | Tegreene |
| 6,446,862 B1 | 9/2002 | Mann |
| 6,448,980 B1 | 9/2002 | Kumar et al. |
| 6,449,892 B1 | 9/2002 | Jenkins |
| 6,451,008 B1 | 9/2002 | Frey et al. |
| 6,452,574 B1 | 9/2002 | Lasko-Harvill et al. |
| 6,454,263 B1 | 9/2002 | Bandieri |
| 6,454,411 B1 | 9/2002 | Trumbull |
| 6,455,544 B1 | 9/2002 | Friedhoff et al. |
| 6,456,262 B1 | 9/2002 | Bell |
| 6,456,438 B1 | 9/2002 | Lee et al. |
| 6,456,737 B1 | 9/2002 | Woodfill et al. |
| 6,458,157 B1 | 10/2002 | Suaning |
| 6,458,807 B1 | 10/2002 | Pratt |
| 6,459,446 B1 | 10/2002 | Harman |
| 6,463,468 B1 | 10/2002 | Buch et al. |
| 6,464,029 B2 | 10/2002 | Gu |
| 6,464,508 B1 | 10/2002 | Ryan |
| 6,466,206 B1 | 10/2002 | Deering |
| 6,466,250 B1 | 10/2002 | Hein et al. |
| 6,468,084 B1 | 10/2002 | MacMillan |
| 6,469,690 B1 | 10/2002 | Abraham et al. |
| 6,473,068 B2 | 10/2002 | Numaoka |
| 6,473,241 B1 | 10/2002 | Wick et al. |
| 6,477,267 B1 | 11/2002 | Richards |
| 6,478,792 B1 | 11/2002 | Hansel |
| 6,480,763 B1 | 11/2002 | Lappos |
| 6,487,020 B1 | 11/2002 | Favalora |
| 6,488,676 B1 | 12/2002 | Glockler et al. |
| 6,489,944 B2 | 12/2002 | Numaoka |
| 6,489,956 B1 | 12/2002 | Deering |
| 6,491,391 B1 | 12/2002 | Blum et al. |
| 6,491,394 B1 | 12/2002 | Blum et al. |
| 6,492,180 B2 | 12/2002 | Brown et al. |
| 6,496,186 B1 | 12/2002 | Deering |
| 6,496,187 B1 | 12/2002 | Deering et al. |
| 6,497,576 B1 | 12/2002 | Smith |
| 6,498,247 B2 | 12/2002 | Evans et al. |
| 6,500,171 B1 | 12/2002 | Williams et al. |
| 6,504,546 B1 | 1/2003 | Cosatto et al. |
| 6,507,353 B1 | 1/2003 | Huard et al. |
| 6,508,812 B1 | 1/2003 | Williams et al. |
| 6,511,424 B1 | 1/2003 | Moore-Ede et al. |
| 6,512,622 B2 | 1/2003 | Wine et al. |
| 6,515,278 B2 | 2/2003 | Wine et al. |
| 6,515,781 B2 | 2/2003 | Lewis et al. |
| 6,516,270 B2 | 2/2003 | Pavlak et al. |
| 6,516,300 B1 | 2/2003 | Rakshit et al. |
| 6,517,203 B1 | 2/2003 | Blum et al. |
| 6,517,206 B2 | 2/2003 | Shevlin |
| 6,517,351 B2 | 2/2003 | Spector |
| 6,520,958 B1 | 2/2003 | Shimmick et al. |
| 6,525,310 B2 | 2/2003 | Dunfield |
| 6,525,723 B1 | 2/2003 | Deering |
| 6,526,159 B1 | 2/2003 | Nickerson |

(56) References Cited

U.S. PATENT DOCUMENTS

| | | |
|---|---|---|
| 6,527,715 B2 | 3/2003 | Balkin et al. |
| 6,529,331 B2 | 3/2003 | Massof et al. |
| 6,530,884 B2 | 3/2003 | Balkin et al. |
| 6,532,482 B1 | 3/2003 | Toyosato |
| 6,535,325 B2 | 3/2003 | Helsel et al. |
| 6,541,043 B2 | 4/2003 | Lang |
| 6,542,081 B2 | 4/2003 | Torch |
| 6,545,669 B1 | 4/2003 | Kinawi et al. |
| 6,550,071 B2 | 4/2003 | Garneau |
| 6,552,899 B2 | 4/2003 | Ronzani et al. |
| 6,553,252 B2 | 4/2003 | Balkin et al. |
| 6,556,853 B1 | 4/2003 | Cabib et al. |
| 6,560,028 B2 | 5/2003 | Melville et al. |
| 6,561,648 B2 | 5/2003 | Thomas |
| 6,563,105 B2 | 5/2003 | Seibel et al. |
| 6,568,808 B2 | 5/2003 | Campin |
| 6,568,987 B1 | 5/2003 | So |
| 6,569,154 B2 | 5/2003 | Campin et al. |
| 6,570,555 B1 | 5/2003 | Prevost et al. |
| 6,570,588 B1 | 5/2003 | Ando et al. |
| 6,572,229 B2 | 6/2003 | Wei |
| 6,572,562 B2 | 6/2003 | Marshall |
| 6,574,672 B1 | 6/2003 | Mitchell et al. |
| 6,575,902 B1 | 6/2003 | Burton |
| 6,577,312 B2 | 6/2003 | Deering et al. |
| 6,577,329 B1 | 6/2003 | Flickner et al. |
| 6,578,916 B2 | 6/2003 | Longhi et al. |
| 6,578,962 B1 | 6/2003 | Amir et al. |
| 6,579,888 B2 | 6/2003 | Reitberg |
| 6,583,772 B1 | 6/2003 | Lewis et al. |
| 6,585,726 B2 | 7/2003 | Frey et al. |
| 6,586,427 B2 | 7/2003 | Hassan et al. |
| 6,590,680 B2 | 7/2003 | Orr et al. |
| 6,591,128 B1 | 7/2003 | Wu et al. |
| 6,594,687 B1 | 7/2003 | Yap et al. |
| 6,598,459 B1 | 7/2003 | Fu |
| 6,599,286 B2 | 7/2003 | Campin et al. |
| 6,601,021 B2 | 7/2003 | Card et al. |
| 6,602,172 B1 | 8/2003 | Aigner |
| 6,603,485 B2 | 8/2003 | Forman |
| 6,603,491 B2 | 8/2003 | Lemelson et al. |
| 6,603,504 B1 | 8/2003 | Son et al. |
| 6,604,049 B2 | 8/2003 | Yokota |
| 6,604,825 B2 | 8/2003 | Lai et al. |
| 6,605,081 B1 | 8/2003 | Shimmick et al. |
| 6,605,796 B2 | 8/2003 | Brandinger et al. |
| 6,606,655 B1 | 8/2003 | Yap et al. |
| 6,607,527 B1 | 8/2003 | Ruiz et al. |
| 6,609,017 B1 | 8/2003 | Shenoy et al. |
| 6,610,049 B2 | 8/2003 | Lai et al. |
| 6,613,763 B2 | 9/2003 | Comings et al. |
| 6,614,408 B1 | 9/2003 | Mann |
| 6,616,277 B1 | 9/2003 | Davenport |
| 6,618,054 B2 | 9/2003 | Deering |
| 6,619,799 B1 | 9/2003 | Blum et al. |
| 6,621,472 B2 | 9/2003 | Lasko-Harvill et al. |
| 6,623,006 B2 | 9/2003 | Weiss |
| 6,626,678 B2 | 9/2003 | Forbes et al. |
| 6,626,893 B2 | 9/2003 | Frey et al. |
| 6,626,894 B2 | 9/2003 | Frey et al. |
| 6,626,895 B2 | 9/2003 | Frey et al. |
| 6,626,896 B2 | 9/2003 | Frey et al. |
| 6,626,897 B2 | 9/2003 | Frey et al. |
| 6,626,898 B2 | 9/2003 | Frey et al. |
| RE38,284 E | 10/2003 | Allen et al. |
| 6,629,935 B1 | 10/2003 | Miller et al. |
| 6,633,820 B2 | 10/2003 | Bizar |
| 6,634,749 B1 | 10/2003 | Morrison et al. |
| 6,636,185 B1 | 10/2003 | Spitzer et al. |
| 6,637,883 B1 | 10/2003 | Tengshe et al. |
| 6,639,570 B2 | 10/2003 | Furness, III et al. |
| 6,639,605 B2 | 10/2003 | Van Dalfsen et al. |
| 6,643,721 B1 | 11/2003 | Sun |
| 6,644,976 B2 | 11/2003 | Kullok et al. |
| 6,648,820 B1 | 11/2003 | Sarel |
| 6,648,834 B2 | 11/2003 | Kajimoto et al. |
| 6,650,323 B2 | 11/2003 | Naegle et al. |
| 6,652,101 B1 | 11/2003 | Glaser |
| 6,653,102 B2 | 11/2003 | Roch et al. |
| 6,653,621 B2 | 11/2003 | Wine et al. |
| 6,654,158 B2 | 11/2003 | Helsel et al. |
| 6,659,611 B2 | 12/2003 | Amir et al. |
| 6,659,763 B2 | 12/2003 | Fisher |
| 6,660,476 B2 | 12/2003 | Comings et al. |
| 6,661,393 B2 | 12/2003 | Tegreene et al. |
| 6,663,242 B1 | 12/2003 | Davenport |
| 6,664,955 B1 | 12/2003 | Deering |
| 6,666,855 B2 | 12/2003 | Somani et al. |
| 6,666,857 B2 | 12/2003 | Smith |
| 6,667,297 B2 | 12/2003 | Tsai et al. |
| 6,667,694 B2 | 12/2003 | Ben-Ari et al. |
| 6,669,478 B2 | 12/2003 | Edwards et al. |
| 6,669,481 B2 | 12/2003 | Winter et al. |
| 6,669,684 B2 | 12/2003 | Nakamura |
| 6,670,963 B2 | 12/2003 | Osberger |
| 6,674,446 B2 | 1/2004 | Van Dalfsen et al. |
| 6,675,923 B1 | 1/2004 | Artis et al. |
| 6,678,717 B1 | 1/2004 | Schneider |
| 6,683,611 B1 | 1/2004 | Cleveland |
| 6,685,652 B1 | 2/2004 | Teicher et al. |
| 6,687,034 B2 | 2/2004 | Wine et al. |
| 6,687,389 B2 | 2/2004 | McCartney et al. |
| 6,688,744 B2 | 2/2004 | Wei et al. |
| 6,689,795 B2 | 2/2004 | Pratt |
| 6,690,351 B1 | 2/2004 | Wong |
| 6,697,506 B1 | 2/2004 | Qian et al. |
| 6,697,577 B1 | 2/2004 | Li et al. |
| 6,697,894 B1 | 2/2004 | Mitchell et al. |
| 6,699,043 B2 | 3/2004 | Ho et al. |
| 6,700,558 B1 | 3/2004 | Itoh |
| 6,702,757 B2 | 3/2004 | Fukushima et al. |
| 6,702,767 B1 | 3/2004 | Douglas et al. |
| 6,702,806 B2 | 3/2004 | Gray et al. |
| 6,702,809 B1 | 3/2004 | Knopp et al. |
| 6,705,870 B2 | 3/2004 | Penno |
| 6,706,036 B2 | 3/2004 | Lai |
| 6,710,772 B2 | 3/2004 | Van Dijk et al. |
| 6,710,927 B2 | 3/2004 | Richards |
| 6,712,468 B1 | 3/2004 | Edwards |
| 6,712,615 B2 | 3/2004 | Martin |
| 6,713,058 B2 | 3/2004 | McMichael |
| 6,714,331 B2 | 3/2004 | Lewis et al. |
| 6,717,578 B1 | 4/2004 | Deering |
| 6,717,607 B1 | 4/2004 | Lauper et al. |
| 6,717,728 B2 | 4/2004 | Putilin |
| 6,718,307 B1 | 4/2004 | Buil et al. |
| 6,721,075 B2 | 4/2004 | Orr et al. |
| 6,726,325 B2 | 4/2004 | Xie et al. |
| 6,727,866 B2 | 4/2004 | Wang et al. |
| 6,729,728 B2 | 5/2004 | Wei et al. |
| 6,731,964 B2 | 5/2004 | Shenoy et al. |
| 6,733,130 B2 | 5/2004 | Blum et al. |
| 6,733,132 B2 | 5/2004 | Shevlin |
| 6,734,850 B2 | 5/2004 | Deering |
| 6,736,508 B2 | 5/2004 | Xie et al. |
| 6,736,510 B1 | 5/2004 | Van Heugten |
| 6,740,032 B2 | 5/2004 | Balkin et al. |
| 6,741,967 B1 | 5/2004 | Wu et al. |
| 6,742,928 B2 | 6/2004 | Halpert |
| 6,743,022 B1 * | 6/2004 | Sarel .............................. 434/236 |
| 6,743,167 B2 | 6/2004 | Balkin et al. |
| 6,745,126 B1 | 6/2004 | Pavlak et al. |
| 6,748,949 B2 | 6/2004 | Smaldone |
| 6,752,498 B2 | 6/2004 | Covannon et al. |
| 6,753,847 B2 | 6/2004 | Kurtenbach et al. |
| 6,753,870 B2 | 6/2004 | Deering et al. |
| 6,755,527 B1 | 6/2004 | Goldberg |
| 6,755,817 B1 | 6/2004 | Donitzky et al. |
| 6,756,997 B1 | 6/2004 | Ward, III et al. |
| 6,757,310 B2 | 6/2004 | Lai |
| 6,757,551 B2 | 6/2004 | Newman et al. |
| 6,758,563 B2 | 7/2004 | Levola |
| 6,758,674 B2 | 7/2004 | Lee |
| 6,758,843 B2 | 7/2004 | Jensen |

(56) References Cited

U.S. PATENT DOCUMENTS

| | | |
|---|---|---|
| 6,760,746 B1 | 7/2004 | Schneider |
| 6,762,867 B2 | 7/2004 | Lippert et al. |
| 6,764,372 B1 | 7/2004 | Rae |
| 6,764,398 B2 | 7/2004 | Stone et al. |
| 6,765,498 B1 | 7/2004 | Sabatino |
| 6,768,816 B2 | 7/2004 | Hall, Jr. et al. |
| 6,778,150 B1 | 8/2004 | Maguire, Jr. |
| 6,778,970 B2 | 8/2004 | Au |
| 6,779,060 B1 | 8/2004 | Azvine et al. |
| 6,781,585 B2 | 8/2004 | Naegle et al. |
| 6,782,375 B2 | 8/2004 | Abdel-Moneim et al. |
| 6,784,942 B2 | 8/2004 | Selby et al. |
| 6,786,610 B2 | 9/2004 | Faris |
| 6,786,899 B1 | 9/2004 | Lai |
| 6,791,531 B1 | 9/2004 | Johnston et al. |
| 6,792,135 B1 | 9/2004 | Toyama |
| 6,795,221 B1 | 9/2004 | Urey |
| 6,795,486 B2 | 9/2004 | Litwin, Jr. |
| 6,795,724 B2 | 9/2004 | Hogan |
| 6,795,806 B1 | 9/2004 | Lewis et al. |
| 6,798,443 B1 | 9/2004 | Maguire, Jr. |
| 6,801,202 B2 | 10/2004 | Nelson et al. |
| 6,801,751 B1 | 10/2004 | Wood et al. |
| 6,802,837 B2 | 10/2004 | Donitzky et al. |
| 6,803,561 B2 | 10/2004 | Dunfield |
| 6,817,517 B2 | 11/2004 | Gunther |
| 6,820,897 B2 | 11/2004 | Breed et al. |
| 6,820,979 B1 | 11/2004 | Stark et al. |
| 6,823,184 B1 | 11/2004 | Nelson |
| RE38,668 E | 12/2004 | Edwards |
| 6,827,317 B1 | 12/2004 | Maki Risaliti |
| 6,827,443 B2 | 12/2004 | Fisher et al. |
| 6,832,987 B2 | 12/2004 | David et al. |
| 6,836,751 B2 | 12/2004 | Paxton et al. |
| 6,837,585 B2 | 1/2005 | Roggatz |
| 6,842,670 B2 | 1/2005 | Lin et al. |
| 6,843,564 B2 | 1/2005 | Putilin et al. |
| 6,843,787 B2 | 1/2005 | Ruiz |
| 6,847,336 B1 | 1/2005 | Lemelson et al. |
| 6,850,236 B2 | 2/2005 | Deering |
| 6,851,825 B2 | 2/2005 | Marshall |
| 6,853,436 B2 | 2/2005 | Kim |
| 6,853,854 B1 | 2/2005 | Proniewicz et al. |
| 6,853,966 B2 | 2/2005 | Bushey et al. |
| 6,853,972 B2 | 2/2005 | Friedrich et al. |
| 6,854,847 B2 | 2/2005 | Yuan et al. |
| 6,857,741 B2 | 2/2005 | Blum et al. |
| 6,859,206 B2 | 2/2005 | Cleveland |
| 6,860,601 B2 | 3/2005 | Shadduck |
| 6,863,275 B2 | 3/2005 | Chiu et al. |
| 6,863,667 B2 | 3/2005 | Webb et al. |
| 6,866,661 B2 | 3/2005 | Gray et al. |
| 6,867,753 B2 | 3/2005 | Chinthammit et al. |
| 6,871,951 B2 | 3/2005 | Blum et al. |
| 6,873,314 B1 | 3/2005 | Campbell |
| 6,873,714 B2 | 3/2005 | Witt et al. |
| 6,875,181 B2 | 4/2005 | Kajimoto et al. |
| 6,882,462 B2 | 4/2005 | Helsel et al. |
| 6,883,985 B2 | 4/2005 | Roberson |
| 6,884,238 B2 | 4/2005 | Underhill et al. |
| 6,884,980 B2 | 4/2005 | Spink |
| 6,885,882 B2 | 4/2005 | Cote et al. |
| 6,886,137 B2 | 4/2005 | Peck et al. |
| 6,889,192 B2 | 5/2005 | Friedrich et al. |
| 6,890,076 B2 | 5/2005 | Roorda |
| 6,890,077 B2 | 5/2005 | Dunn |
| 6,895,430 B1 | 5/2005 | Schneider |
| 6,896,384 B2 | 5/2005 | McWhirter et al. |
| 6,896,655 B2 | 5/2005 | Patton et al. |
| 6,897,212 B2 | 5/2005 | Comings et al. |
| 6,898,263 B2 | 5/2005 | Avinash et al. |
| 6,899,707 B2 | 5/2005 | Scholler et al. |
| 6,901,369 B2 | 5/2005 | Cureton et al. |
| 6,906,619 B2 | 6/2005 | Williams et al. |
| 6,912,492 B1 | 6/2005 | Johnson et al. |
| 6,912,509 B1 | 6/2005 | Lear |
| 6,915,991 B1 | 7/2005 | Shomer et al. |
| 6,917,368 B2 | 7/2005 | Credelle et al. |
| 6,917,715 B2 | 7/2005 | Berstis |
| 6,917,826 B2 | 7/2005 | Wei et al. |
| 6,918,670 B2 | 7/2005 | Blum et al. |
| 6,919,907 B2 | 7/2005 | Berstis |
| 6,920,358 B2 | 7/2005 | Greenberg et al. |
| 6,923,802 B2 | 8/2005 | Williams et al. |
| 6,924,476 B2 | 8/2005 | Wine et al. |
| 6,924,822 B2 | 8/2005 | Card et al. |
| 6,925,332 B2 | 8/2005 | Franck |
| 6,926,429 B2 | 8/2005 | Barlow et al. |
| 6,926,710 B2 | 8/2005 | Cox et al. |
| 6,927,674 B2 | 8/2005 | Harter, Jr. et al. |
| 6,927,694 B1 | 8/2005 | Smith et al. |
| 6,929,638 B2 | 8/2005 | Gray et al. |
| 6,933,277 B2 | 8/2005 | Brenneman et al. |
| 6,935,743 B2 | 8/2005 | Shadduck |
| 6,937,152 B2 | 8/2005 | Small |
| 6,937,272 B1 | 8/2005 | Dance |
| 6,937,745 B2 | 8/2005 | Toyama |
| 6,938,861 B1 | 9/2005 | Ballard et al. |
| 6,940,557 B2 | 9/2005 | Handjojo et al. |
| 6,940,998 B2 | 9/2005 | Garoutte |
| 6,941,342 B1 | 9/2005 | Nelson |
| 6,943,754 B2 | 9/2005 | Aughey et al. |
| 6,944,330 B2 | 9/2005 | Novak et al. |
| 6,944,658 B1 | 9/2005 | Schneider |
| 6,944,765 B1 | 9/2005 | Rose et al. |
| 6,947,790 B2 | 9/2005 | Gevins et al. |
| 6,949,089 B2 | 9/2005 | Olson et al. |
| 6,955,873 B1 | 10/2005 | Blum |
| 6,956,576 B1 | 10/2005 | Deering et al. |
| 6,958,905 B2 | 10/2005 | Hong et al. |
| 6,959,055 B2 | 10/2005 | Litwin, Jr. et al. |
| 6,959,102 B2 | 10/2005 | Peck |
| 6,961,007 B2 | 11/2005 | Ben-Ari et al. |
| 6,964,023 B2 | 11/2005 | Maes et al. |
| 6,964,572 B2 | 11/2005 | Cesa |
| 6,964,638 B2 | 11/2005 | Theodoracopulos et al. |
| 6,964,659 B2 | 11/2005 | Gross et al. |
| 6,966,649 B2 | 11/2005 | Shadduck |
| 6,967,103 B2 | 11/2005 | Schwartz et al. |
| 6,967,674 B1 | 11/2005 | Lausch |
| 6,972,733 B2 | 12/2005 | Maguire, Jr. |
| 6,973,505 B1 | 12/2005 | Schneider |
| 6,974,326 B2 | 12/2005 | Marple-Horvat |
| 6,974,821 B2 | 12/2005 | Tsai et al. |
| 6,978,179 B1 | 12/2005 | Flagg et al. |
| 6,979,698 B1 | 12/2005 | Sandberg et al. |
| 6,982,269 B2 | 1/2006 | Glasky et al. |
| 6,983,063 B1 | 1/2006 | Novak et al. |
| 6,984,129 B2 | 1/2006 | Jordan |
| 6,985,158 B2 | 1/2006 | Miller et al. |
| 6,985,290 B2 | 1/2006 | Putilin et al. |
| 6,989,843 B2 | 1/2006 | Naegle et al. |
| 6,989,845 B1 | 1/2006 | Okamoto et al. |
| 6,990,628 B1 | 1/2006 | Palmer et al. |
| 6,993,574 B2 | 1/2006 | Hall |
| 6,993,594 B2 | 1/2006 | Schneider |
| 6,996,295 B2 | 2/2006 | Tyan et al. |
| 6,997,187 B2 | 2/2006 | Wood et al. |
| 6,999,071 B2 | 2/2006 | Balogh |
| 6,999,549 B2 | 2/2006 | Sabol et al. |
| 7,000,613 B2 | 2/2006 | Wood et al. |
| 7,000,722 B2 | 2/2006 | Artis et al. |
| 7,001,020 B2 | 2/2006 | Yancey et al. |
| 7,001,376 B2 | 2/2006 | Somani et al. |
| 7,001,377 B1 | 2/2006 | Li |
| 7,002,716 B2 | 2/2006 | Wine et al. |
| 7,003,175 B2 | 2/2006 | Paladini |
| 7,006,128 B2 | 2/2006 | Xie et al. |
| 7,010,169 B2 | 3/2006 | Kortum et al. |
| 7,010,568 B1 | 3/2006 | Schneider et al. |
| 7,013,258 B1 | 3/2006 | Su et al. |
| 7,013,279 B1 | 3/2006 | Nelson |
| 7,015,910 B2 | 3/2006 | Card et al. |
| 7,016,816 B2 | 3/2006 | Mott |

(56) References Cited

U.S. PATENT DOCUMENTS

| | | |
|---|---|---|
| 7,018,376 B2 | 3/2006 | Webb et al. |
| 7,019,750 B2 | 3/2006 | Sakaguchi |
| 7,020,316 B2 | 3/2006 | Wei et al. |
| 7,022,117 B1 | 4/2006 | Hohla et al. |
| 7,022,119 B2 | 4/2006 | Hohla |
| 7,023,402 B2 | 4/2006 | Lewis et al. |
| 7,023,594 B2 | 4/2006 | Blum et al. |
| 7,027,655 B2 | 4/2006 | Keeney et al. |
| 7,029,121 B2 | 4/2006 | Edwards |
| 7,030,863 B2 | 4/2006 | Longe et al. |
| 7,031,228 B2 | 4/2006 | Born et al. |
| 7,035,896 B1 | 4/2006 | Schneider |
| 7,036,080 B1 | 4/2006 | James et al. |
| 7,037,171 B2 | 5/2006 | Clark et al. |
| 7,043,056 B2 | 5/2006 | Edwards et al. |
| 7,044,944 B2 | 5/2006 | Campin et al. |
| 7,046,825 B2 | 5/2006 | Toyama |
| 7,046,826 B2 | 5/2006 | Toyama |
| 7,046,924 B2 | 5/2006 | Miller et al. |
| 7,048,690 B2 | 5/2006 | Coleman et al. |
| 7,049,947 B2 | 5/2006 | Nath et al. |
| 7,050,624 B2 | 5/2006 | Dialameh et al. |
| 7,053,925 B2 | 5/2006 | Payne et al. |
| 7,057,618 B2 | 6/2006 | Russ et al. |
| 7,063,535 B2 | 6/2006 | Stamm et al. |
| 7,065,381 B2 | 6/2006 | Jenkins et al. |
| 7,068,813 B2 | 6/2006 | Lin |
| 7,069,518 B2 | 6/2006 | Card et al. |
| 7,071,594 B1 | 7/2006 | Yan et al. |
| 7,071,831 B2 | 7/2006 | Johns |
| 7,071,931 B2 | 7/2006 | Tegreene et al. |
| 7,072,435 B2 | 7/2006 | Metz et al. |
| 7,075,553 B2 | 7/2006 | Miller et al. |
| 7,075,687 B2 | 7/2006 | Lippert et al. |
| 7,077,405 B2 | 7/2006 | Akpom |
| 7,077,519 B2 | 7/2006 | Blum et al. |
| 7,077,521 B2 | 7/2006 | Thomas |
| 7,077,838 B2 | 7/2006 | Wong |
| 7,079,900 B2 | 7/2006 | Greenburg et al. |
| 7,082,572 B2 | 7/2006 | Pea et al. |
| 7,082,947 B2 | 8/2006 | Smaldone |
| 7,086,187 B2 | 8/2006 | Bandak |
| 7,086,735 B1 | 8/2006 | Provitola |
| 7,090,669 B2 | 8/2006 | Van Saarloos |
| 7,095,229 B2 | 8/2006 | Lorenz |
| 7,095,444 B1 | 8/2006 | Lincoln et al. |
| 7,095,522 B2 | 8/2006 | Lauper et al. |
| 7,098,871 B1 | 8/2006 | Tegreene et al. |
| 7,101,041 B2 | 9/2006 | Lindacher et al. |
| 7,103,908 B2 | 9/2006 | Tomsen |
| 7,105,110 B2 | 9/2006 | Platt et al. |
| 7,105,540 B2 | 9/2006 | Friedhoff et al. |
| 7,106,322 B2 | 9/2006 | Deering |
| 7,106,366 B2 | 9/2006 | Parker et al. |
| 7,106,852 B1 | 9/2006 | Nelson et al. |
| 7,107,231 B1 | 9/2006 | Hall et al. |
| 7,108,688 B2 | 9/2006 | Jensen |
| 7,109,949 B2 | 9/2006 | Sekiya et al. |
| 7,111,255 B2 | 9/2006 | Zlotnick |
| 7,111,939 B2 | 9/2006 | Cok et al. |
| 7,113,170 B2 | 9/2006 | Lauper et al. |
| 7,113,818 B2 | 9/2006 | Podoleanu et al. |
| 7,113,918 B1 | 9/2006 | Ahmad et al. |
| 7,114,720 B2 | 10/2006 | Whitehurst |
| 7,115,071 B1 | 10/2006 | Sunbeck |
| 7,115,099 B2 | 10/2006 | Miller et al. |
| 7,116,688 B2 | 10/2006 | Sauter et al. |
| 7,116,789 B2 | 10/2006 | Layton et al. |
| 7,118,216 B2 | 10/2006 | Roorda |
| 7,119,186 B2 | 10/2006 | Tsuji |
| 7,119,760 B2 | 10/2006 | Edge et al. |
| 7,120,236 B1 | 10/2006 | Schneider |
| 7,120,318 B2 | 10/2006 | Tyan et al. |
| 7,120,880 B1 | 10/2006 | Dryer et al. |
| 7,123,751 B1 | 10/2006 | Fujieda |
| 7,127,093 B2 | 10/2006 | Bansal et al. |
| 7,128,577 B2 | 10/2006 | Renaud |
| 7,129,981 B2 | 10/2006 | Berstis |
| 7,130,447 B2 | 10/2006 | Aughey et al. |
| 7,134,687 B2 | 11/2006 | Breed et al. |
| 7,135,970 B2 | 11/2006 | Kowal et al. |
| 7,136,073 B2 | 11/2006 | Newman |
| 7,136,725 B1 | 11/2006 | Paciorek et al. |
| 7,136,932 B1 | 11/2006 | Schneider |
| 7,139,006 B2 | 11/2006 | Wittenburg et al. |
| 7,139,554 B2 | 11/2006 | Litwin, Jr. |
| 7,139,979 B2 | 11/2006 | Schultz et al. |
| 7,139,982 B2 | 11/2006 | Card et al. |
| 7,142,209 B2 | 11/2006 | Uyttendaele et al. |
| 7,143,089 B2 | 11/2006 | Petras et al. |
| 7,143,442 B2 | 11/2006 | Scarfe et al. |
| 7,146,983 B1 | 12/2006 | Hohla et al. |
| 7,147,246 B2 | 12/2006 | Breed et al. |
| 7,147,284 B2 | 12/2006 | Mills et al. |
| 7,154,510 B2 | 12/2006 | Simon et al. |
| 7,155,393 B2 | 12/2006 | Stewart et al. |
| 7,157,679 B2 | 1/2007 | Wine et al. |
| 7,161,557 B2 | 1/2007 | Thornton |
| 7,163,009 B2 | 1/2007 | Brown et al. |
| 7,164,117 B2 | 1/2007 | Breed et al. |
| 7,166,047 B2 | 1/2007 | May et al. |
| 7,166,725 B2 | 1/2007 | Fang et al. |
| 7,169,110 B2 | 1/2007 | Lee et al. |
| 7,180,663 B2 | 2/2007 | Collender et al. |
| 7,182,351 B2 | 2/2007 | Williams |
| 7,188,138 B1 | 3/2007 | Schneider |
| 7,188,948 B2 | 3/2007 | Blum et al. |
| 7,189,701 B1 | 3/2007 | Khavinson et al. |
| 7,190,329 B2 | 3/2007 | Lewis et al. |
| 7,190,518 B1 | 3/2007 | Kleinberger et al. |
| 7,190,836 B2 | 3/2007 | Krishnan et al. |
| 7,190,843 B2 | 3/2007 | Wei et al. |
| 7,191,403 B2 | 3/2007 | Crain et al. |
| 7,191,781 B2 | 3/2007 | Wood |
| 7,194,552 B1 | 3/2007 | Schneider |
| 7,195,355 B2 | 3/2007 | Nashner |
| 7,196,638 B2 | 3/2007 | Sabatino |
| 7,197,165 B2 | 3/2007 | Ryan |
| RE39,539 E | 4/2007 | Torch |
| 7,199,767 B2 | 4/2007 | Spero |
| 7,200,269 B2 | 4/2007 | Paragios et al. |
| 7,203,349 B2 | 4/2007 | Zhang et al. |
| 7,204,815 B2 | 4/2007 | Connor |
| 7,206,022 B2 | 4/2007 | Miller et al. |
| 7,206,435 B2 | 4/2007 | Fujimura et al. |
| 7,209,271 B2 | 4/2007 | Lewis et al. |
| 7,209,574 B2 | 4/2007 | Tafuku et al. |
| 7,209,773 B2 | 4/2007 | Iuliano |
| 7,212,854 B2 | 5/2007 | Kovak et al. |
| 7,215,337 B2 | 5/2007 | Heer et al. |
| 7,220,255 B2 | 5/2007 | Lai |
| 7,221,366 B2 | 5/2007 | Uyttendaele et al. |
| 7,224,526 B2 | 5/2007 | Putilin et al. |
| 7,225,013 B2 | 5/2007 | Geva et al. |
| 7,227,886 B2 | 6/2007 | Margetts et al. |
| 7,228,283 B1 | 6/2007 | Hornstein |
| 7,233,329 B2 | 6/2007 | Moreau-Gobard |
| 7,233,330 B2 | 6/2007 | Moreau-Gobard et al. |
| 7,233,684 B2 | 6/2007 | Fedorovskaya et al. |
| 7,234,173 B2 | 6/2007 | McCalla |
| 7,234,465 B2 | 6/2007 | Wood |
| 7,234,809 B2 | 6/2007 | Blum et al. |
| 7,237,898 B1 | 7/2007 | Hohla et al. |
| 7,238,177 B2 | 7/2007 | Somani et al. |
| 7,239,293 B2 | 7/2007 | Perlin et al. |
| 7,239,976 B2 | 7/2007 | Coleman et al. |
| 7,240,291 B2 | 7/2007 | Card et al. |
| 7,243,945 B2 | 7/2007 | Breed et al. |
| 7,244,769 B2 | 7/2007 | Epstein et al. |
| 7,245,273 B2 | 7/2007 | Eberl et al. |
| 7,246,904 B2 | 7/2007 | Knaan et al. |
| 7,248,269 B2 | 7/2007 | Card et al. |
| 7,248,271 B2 | 7/2007 | Credelle et al. |
| 7,251,373 B2 | 7/2007 | Kortum et al. |

(56) References Cited

U.S. PATENT DOCUMENTS

| | | |
|---|---|---|
| 7,253,738 B2 | 8/2007 | Hammoud et al. |
| 7,253,739 B2 | 8/2007 | Hammoud et al. |
| 7,254,439 B2 | 8/2007 | Misczynski et al. |
| 7,256,780 B2 | 8/2007 | Williams et al. |
| 7,257,189 B2 | 8/2007 | Modica et al. |
| 7,257,446 B2 | 8/2007 | Greenberg et al. |
| 7,259,785 B2 | 8/2007 | Stavely et al. |
| 7,260,025 B2 | 8/2007 | Farinella et al. |
| 7,262,765 B2 | 8/2007 | Brown et al. |
| 7,264,351 B2 | 9/2007 | Shadduck |
| 7,266,413 B2 | 9/2007 | Greenberg et al. |
| 7,267,437 B2 | 9/2007 | Watkins |
| 7,272,243 B2 | 9/2007 | Toyama |
| 7,272,306 B2 | 9/2007 | Zhang et al. |
| 7,272,559 B1 | 9/2007 | Hayre |
| 7,272,563 B2 | 9/2007 | Nelson |
| 7,278,064 B1 | 10/2007 | Chan |
| 7,278,739 B2 | 10/2007 | Shadduck |
| 7,281,104 B1 | 10/2007 | Tsypliaev et al. |
| 7,284,201 B2 | 10/2007 | Cohen-Solal |
| 7,284,862 B1 | 10/2007 | Lai et al. |
| 7,286,115 B2 | 10/2007 | Longe et al. |
| 7,286,143 B2 | 10/2007 | Kang et al. |
| 7,286,649 B1 | 10/2007 | Nelson et al. |
| 7,287,857 B2 | 10/2007 | Glaser |
| 7,292,151 B2 | 11/2007 | Ferguson et al. |
| 7,292,257 B2 | 11/2007 | Kang et al. |
| 7,294,107 B2 | 11/2007 | Simon et al. |
| 7,298,414 B2 | 11/2007 | Stavely et al. |
| 7,302,103 B2 | 11/2007 | Keeney et al. |
| 7,302,475 B2 | 11/2007 | Gold et al. |
| 7,306,337 B2 | 12/2007 | Ji et al. |
| 7,307,609 B2 | 12/2007 | Chang |
| 7,308,412 B2 | 12/2007 | Rakshit et al. |
| 7,309,125 B2 | 12/2007 | Pugach et al. |
| 7,309,128 B2 | 12/2007 | Cappo et al. |
| 7,310,174 B2 | 12/2007 | Wine et al. |
| 7,313,526 B2 | 12/2007 | Roth et al. |
| 7,313,621 B2 | 12/2007 | Gudorf et al. |
| RE40,014 E | 1/2008 | Edwards |
| 7,315,598 B2 | 1/2008 | Lee et al. |
| 7,317,445 B2 | 1/2008 | Hekstra et al. |
| 7,319,780 B2 | 1/2008 | Fedorovskaya et al. |
| 7,320,685 B2 | 1/2008 | Feige et al. |
| 7,322,696 B2 | 1/2008 | Ben-Zeev et al. |
| 7,324,069 B2 | 1/2008 | Weber et al. |
| 7,328,450 B2 | 2/2008 | Macrae et al. |
| 7,330,784 B2 | 2/2008 | Johnson et al. |
| 7,331,671 B2 | 2/2008 | Hammoud |
| 7,331,929 B2 | 2/2008 | Morita et al. |
| 7,335,190 B2 | 2/2008 | Underhill et al. |
| 7,337,686 B2 | 3/2008 | Sagi-Dolev |
| 7,338,455 B2 | 3/2008 | White et al. |
| 7,340,399 B2 | 3/2008 | Friedrich et al. |
| 7,342,721 B2 | 3/2008 | Lukyanitsa |
| 7,344,248 B2 | 3/2008 | Zorn et al. |
| 7,344,251 B2 | 3/2008 | Marshall |
| 7,345,664 B2 | 3/2008 | Chang |
| 7,346,109 B2 | 3/2008 | Nair et al. |
| 7,346,195 B2 | 3/2008 | Lauper et al. |
| 7,347,551 B2 | 3/2008 | Fergason et al. |
| 7,347,552 B2 | 3/2008 | Reis |
| 7,347,818 B2 | 3/2008 | Simon |
| 7,352,340 B2 | 4/2008 | Utt et al. |
| 7,353,267 B1 | 4/2008 | Cunningham et al. |
| 7,353,355 B1 | 4/2008 | Tormasov et al. |
| 7,359,527 B2 | 4/2008 | Breed et al. |
| 7,362,946 B2 | 4/2008 | Kowald |
| 7,364,575 B2 | 4/2008 | Van Saarloos |
| 7,364,614 B2 | 4/2008 | Kwan et al. |
| 7,365,707 B2 | 4/2008 | Schobben et al. |
| 7,365,738 B2 | 4/2008 | Molander et al. |
| 7,365,856 B2 | 4/2008 | Everett et al. |
| 7,367,673 B2 | 5/2008 | McGrath et al. |
| 7,369,687 B2 | 5/2008 | Kawato et al. |
| 7,371,230 B2 | 5/2008 | Webb et al. |
| 7,376,459 B2 | 5/2008 | Rosenfeld |
| 7,376,938 B1 | 5/2008 | Van der Hoeven |
| 7,377,643 B1 | 5/2008 | Chock et al. |
| 7,380,938 B2 | 6/2008 | Chmielewski, Jr. et al. |
| 7,383,189 B2 | 6/2008 | Halonen et al. |
| 7,384,399 B2 | 6/2008 | Ghajar |
| 7,384,908 B1 | 6/2008 | Brenneman et al. |
| 7,386,372 B2 | 6/2008 | Breed et al. |
| 7,386,453 B2 | 6/2008 | Polanyi et al. |
| 7,386,516 B2 | 6/2008 | Turgeon |
| 7,386,808 B2 | 6/2008 | Skistimas et al. |
| 7,390,089 B2 | 6/2008 | Loesel et al. |
| 7,390,091 B2 | 6/2008 | Clemons et al. |
| 7,391,887 B2 | 6/2008 | Durnell |
| 7,394,921 B2 | 7/2008 | Sun et al. |
| 7,396,126 B2 | 7/2008 | Blum et al. |
| 7,396,129 B2 | 7/2008 | Endrikhovski et al. |
| 7,396,654 B2 | 7/2008 | Hayes et al. |
| 7,397,886 B2 | 7/2008 | Avinash et al. |
| 7,397,961 B2 | 7/2008 | Keeney et al. |
| 7,401,077 B2 | 7/2008 | Bobrow et al. |
| 7,401,807 B2 | 7/2008 | Breed et al. |
| 7,401,920 B1 | 7/2008 | Kranz et al. |
| 7,401,921 B2 | 7/2008 | Baker et al. |
| 7,403,815 B2 | 7/2008 | Katz et al. |
| 7,403,936 B2 | 7/2008 | Giang et al. |
| 7,406,207 B2 | 7/2008 | Kortum et al. |
| 7,406,212 B2 | 7/2008 | Mohamed et al. |
| 7,406,658 B2 | 7/2008 | Brassell et al. |
| 7,407,029 B2 | 8/2008 | Breed et al. |
| 7,407,285 B2 | 8/2008 | Lai et al. |
| 7,407,425 B2 | 8/2008 | Jeske |
| 7,409,040 B2 | 8/2008 | Cyrulnik |
| 7,415,126 B2 | 8/2008 | Breed et al. |
| 7,418,116 B2 | 8/2008 | Fedorovskaya et al. |
| 7,420,618 B2 | 9/2008 | Swartz |
| 7,421,449 B2 | 9/2008 | Williams et al. |
| 7,421,647 B2 | 9/2008 | Reiner |
| 7,424,545 B2 | 9/2008 | Ducheneaut et al. |
| 7,427,135 B2 | 9/2008 | Chen et al. |
| 7,427,136 B2 | 9/2008 | Zelinsky |
| 7,427,590 B2 | 9/2008 | Brenneman et al. |
| 7,428,001 B2 | 9/2008 | Schowengerdt et al. |
| 7,428,093 B2 | 9/2008 | Tegreene et al. |
| 7,429,108 B2 | 9/2008 | Rosenberg |
| 7,432,060 B2 | 10/2008 | Lee |
| 7,432,800 B2 | 10/2008 | Harter, Jr. et al. |
| 7,432,940 B2 | 10/2008 | Brook et al. |
| 7,437,335 B2 | 10/2008 | Baum |
| 7,438,414 B2 | 10/2008 | Rosenberg |
| 7,438,418 B2 | 10/2008 | Marshall |
| 7,439,940 B1 | 10/2008 | Maguire, Jr. |
| 7,440,531 B2 | 10/2008 | Dreps et al. |
| 7,444,286 B2 | 10/2008 | Roth et al. |
| 7,444,770 B2 | 11/2008 | Wellington, Jr. |
| 7,446,800 B2 | 11/2008 | Holmes |
| 7,448,380 B2 | 11/2008 | Bright |
| 7,448,751 B2 | 11/2008 | Kiderman et al. |
| 7,449,598 B2 | 11/2008 | Malkar et al. |
| 7,452,077 B2 | 11/2008 | Meyer et al. |
| 7,455,405 B2 | 11/2008 | Victor et al. |
| 7,456,027 B2 | 11/2008 | Wang et al. |
| 7,456,834 B2 | 11/2008 | Cleveland |
| 7,456,949 B2 | 11/2008 | Somani et al. |
| 7,457,438 B2 | 11/2008 | Nair |
| 7,459,684 B2 | 12/2008 | Wu et al. |
| 7,460,160 B2 | 12/2008 | Hershey et al. |
| 7,460,903 B2 | 12/2008 | Pineda et al. |
| 7,460,940 B2 | 12/2008 | Larsson et al. |
| 7,462,595 B2 | 12/2008 | Prange, Jr. et al. |
| 7,467,089 B2 | 12/2008 | Roth et al. |
| 7,467,159 B2 | 12/2008 | Schaepe et al. |
| 7,467,869 B2 | 12/2008 | Kahlen |
| 7,472,703 B2 | 1/2009 | Hernandez et al. |
| 7,472,707 B2 | 1/2009 | Wood et al. |
| 7,473,888 B2 | 1/2009 | Wine et al. |
| 7,474,308 B2 | 1/2009 | Deering |
| 7,474,407 B2 | 1/2009 | Gutin |

(56) References Cited

U.S. PATENT DOCUMENTS

| | | |
|---|---|---|
| 7,474,720 B2 | 1/2009 | Yuuki et al. |
| 7,475,282 B2 | 1/2009 | Tormasov et al. |
| 7,475,984 B2 | 1/2009 | Blum et al. |
| 7,475,985 B2 | 1/2009 | Blum et al. |
| 7,476,103 B1 | 1/2009 | Norman |
| 7,476,140 B1 | 1/2009 | Hendrickson |
| 7,476,142 B2 | 1/2009 | Mastrosimone-Gese |
| 7,477,758 B2 | 1/2009 | Piirainen et al. |
| 7,477,800 B2 | 1/2009 | Avidan et al. |
| 7,480,334 B2 | 1/2009 | Nair |
| 7,480,396 B2 | 1/2009 | Teiwes et al. |
| 7,480,412 B2 | 1/2009 | Liang et al. |
| 7,481,535 B2 | 1/2009 | Yancey et al. |
| 7,486,295 B2 | 2/2009 | Russ et al. |
| 7,486,302 B2 | 2/2009 | Shoemaker |
| 7,487,978 B2 | 2/2009 | Tutmaz et al. |
| 7,488,072 B2 | 2/2009 | Perlin et al. |
| 7,488,294 B2 | 2/2009 | Torch |
| 7,488,576 B2 | 2/2009 | Kelsoe, Jr. et al. |
| 7,488,747 B2 | 2/2009 | Fang et al. |
| 7,489,331 B2 | 2/2009 | Perlin |
| 7,489,825 B2 | 2/2009 | Sirohey et al. |
| 7,490,941 B2 | 2/2009 | Mintz et al. |
| 7,492,268 B2 | 2/2009 | Ferguson et al. |
| 7,492,375 B2 | 2/2009 | Toyama et al. |
| 7,492,513 B2 | 2/2009 | Fridman et al. |
| 7,492,821 B2 | 2/2009 | Berman et al. |
| 7,492,938 B2 | 2/2009 | Brinson, Jr. et al. |
| 7,493,572 B2 | 2/2009 | Card et al. |
| 7,496,174 B2 | 2/2009 | Gertner et al. |
| 7,499,494 B2 | 3/2009 | Nair et al. |
| 7,499,570 B2 | 3/2009 | Zoghlami et al. |
| 7,499,594 B2 | 3/2009 | Kortum et al. |
| 7,501,995 B2 | 3/2009 | Morita et al. |
| 7,503,653 B2 | 3/2009 | Endrikhovski et al. |
| 7,505,557 B2 | 3/2009 | Modica et al. |
| 7,505,911 B2 | 3/2009 | Roth et al. |
| 7,510,398 B1 | 3/2009 | Thornton |
| 7,511,833 B2 | 3/2009 | Breed |
| 7,512,450 B2 | 3/2009 | Ahmed |
| 7,515,054 B2 | 4/2009 | Torch |
| 7,516,213 B2 | 4/2009 | Cunningham et al. |
| 7,516,896 B2 | 4/2009 | Helsel et al. |
| 7,517,083 B2 | 4/2009 | Blum et al. |
| 7,517,085 B2 | 4/2009 | Teiwes et al. |
| 7,519,007 B2 | 4/2009 | Klein et al. |
| 7,519,138 B2 | 4/2009 | Lee et al. |
| 7,519,503 B2 | 4/2009 | Midttun et al. |
| 7,520,445 B2 | 4/2009 | Feinleib et al. |
| 7,520,614 B2 | 4/2009 | Joos et al. |
| 7,522,344 B1 | 4/2009 | Curatu et al. |
| 7,523,166 B2 | 4/2009 | Strub |
| 7,523,803 B2 | 4/2009 | Breed |
| 7,524,059 B2 | 4/2009 | Blum et al. |
| 7,526,431 B2 | 4/2009 | Roth et al. |
| 7,526,465 B1 | 4/2009 | Forsythe et al. |
| 7,528,881 B2 | 5/2009 | Ahiska |
| 7,529,772 B2 | 5/2009 | Singh |
| 7,531,670 B2 | 5/2009 | Glasky et al. |
| 7,532,197 B2 | 5/2009 | Clement et al. |
| 7,532,230 B2 | 5/2009 | Culbertson et al. |
| 7,535,607 B2 | 5/2009 | Schwerdtner et al. |
| 7,535,991 B2 | 5/2009 | Gertner |
| 7,536,324 B2 | 5/2009 | Perkowski |
| 7,537,293 B2 | 5/2009 | Lin et al. |
| 7,538,746 B2 | 5/2009 | Uhlhorn et al. |
| 7,542,210 B2 | 6/2009 | Chirieleison, Sr. |
| 7,542,595 B2 | 6/2009 | Moreau-Gobard |
| 7,545,405 B2 | 6/2009 | Provitola |
| 7,546,143 B2 | 6/2009 | Nelson et al. |
| 7,548,833 B2 | 6/2009 | Ahmed |
| 7,549,743 B2 | 6/2009 | Huxlin et al. |
| 7,553,021 B2 | 6/2009 | Fergason et al. |
| 7,555,732 B2 | 6/2009 | Van der Hoeven |
| 7,556,377 B2 | 7/2009 | Beymer |
| 7,561,143 B1 | 7/2009 | Milekic |
| 7,563,099 B1 | 7/2009 | Iftikhar |
| 7,563,808 B2 | 7/2009 | Pratt |
| 7,563,972 B2 | 7/2009 | Kubitz et al. |
| 7,564,368 B2 | 7/2009 | Segall |
| 7,564,946 B2 | 7/2009 | Gertner |
| 7,565,203 B2 | 7/2009 | Greenberg et al. |
| 7,565,402 B2 | 7/2009 | Schneider |
| 7,565,625 B2 | 7/2009 | Mullins, II et al. |
| 7,565,759 B1 | 7/2009 | Brennan |
| 7,567,702 B2 | 7/2009 | Woodfill et al. |
| 7,570,785 B2 | 8/2009 | Breed |
| 7,572,580 B2 | 8/2009 | Leonard et al. |
| 7,573,439 B2 | 8/2009 | Lau et al. |
| 7,574,876 B2 | 8/2009 | Goldschmidt |
| 7,575,248 B2 | 8/2009 | Breed |
| 7,576,757 B2 | 8/2009 | Kariathungal et al. |
| 7,577,481 B2 | 8/2009 | Firlik et al. |
| 7,577,569 B2 | 8/2009 | Roth et al. |
| 7,577,631 B2 | 8/2009 | Feldhake |
| 7,578,593 B2 | 8/2009 | Hammoud et al. |
| 7,579,370 B2 | 8/2009 | Heffernan et al. |
| 7,580,365 B2 | 8/2009 | Klein |
| 7,581,435 B2 | 9/2009 | Pelletier |
| 7,583,252 B2 | 9/2009 | Kurtenbach et al. |
| 7,583,253 B2 | 9/2009 | Jeng et al. |
| 7,583,287 B2 | 9/2009 | Cohen et al. |
| 7,583,291 B2 | 9/2009 | Holmes |
| 7,591,558 B2 | 9/2009 | Wezowski et al. |
| 7,593,547 B2 | 9/2009 | Mittal et al. |
| 7,593,995 B1 | 9/2009 | He et al. |
| 7,596,242 B2 | 9/2009 | Breed et al. |
| 7,596,505 B2 | 9/2009 | Keil et al. |
| 7,596,759 B2 | 9/2009 | Verna |
| 7,600,872 B2 | 10/2009 | Esser et al. |
| 7,600,873 B2 | 10/2009 | Grundig |
| 7,602,941 B2 | 10/2009 | Xie et al. |
| 7,602,994 B2 | 10/2009 | Tellenbach et al. |
| 7,603,533 B1 | 10/2009 | Tsypliaev et al. |
| 7,606,215 B2 | 10/2009 | Poniatowski |
| 7,606,779 B2 | 10/2009 | Brinson, Jr. et al. |
| 7,607,776 B1 | 10/2009 | Lewis et al. |
| 7,607,777 B2 | 10/2009 | Zelinsky |
| 7,612,794 B2 | 11/2009 | He et al. |
| 7,612,795 B2 | 11/2009 | Provitola |
| 7,613,630 B2 | 11/2009 | Wolinsky et al. |
| 7,615,572 B2 | 11/2009 | Fang et al. |
| 7,616,125 B2 | 11/2009 | Johns |
| 7,617,000 B2 | 11/2009 | Franck |
| 7,617,094 B2 | 11/2009 | Aoki et al. |
| 7,618,144 B2 | 11/2009 | Hutchin |
| 7,619,005 B2 | 11/2009 | Epstein et al. |
| 7,620,147 B2 | 11/2009 | Gertner et al. |
| 7,620,216 B2 | 11/2009 | Hammoud |
| 7,620,501 B2 | 11/2009 | Tek et al. |
| 7,620,521 B2 | 11/2009 | Breed et al. |
| 7,624,023 B2 | 11/2009 | Clay et al. |
| 7,626,151 B2 | 12/2009 | Sander |
| 7,626,569 B2 | 12/2009 | Lanier |
| 7,626,571 B2 | 12/2009 | Conti et al. |
| 7,626,644 B2 | 12/2009 | Shestak et al. |
| 7,627,078 B2 | 12/2009 | Hsieh et al. |
| 7,627,370 B2 | 12/2009 | Marks |
| 7,630,524 B2 | 12/2009 | Lauper et al. |
| 7,634,108 B2 | 12/2009 | Cohen et al. |
| 7,634,133 B2 | 12/2009 | Jerebko et al. |
| 7,634,403 B2 | 12/2009 | Roth et al. |
| 7,640,062 B2 | 12/2009 | Shalev |
| 7,640,513 B2 | 12/2009 | Card et al. |
| RE41,071 E | 1/2010 | Anderson |
| 7,641,341 B2 | 1/2010 | Weinblatt |
| 7,641,342 B2 | 1/2010 | Eberl et al. |
| 7,643,035 B2 | 1/2010 | Toyama et al. |
| 7,643,653 B2 | 1/2010 | Garoutte |
| 7,644,048 B2 | 1/2010 | Vane et al. |
| 7,644,058 B2 | 1/2010 | Haimov |
| 7,647,098 B2 | 1/2010 | Prichep |
| 7,647,827 B2 | 1/2010 | Pelecanos et al. |
| 7,650,034 B2 | 1/2010 | Hammoud |

(56) References Cited

U.S. PATENT DOCUMENTS

| | | |
|---|---|---|
| 7,650,212 B2 | 1/2010 | Breed et al. |
| 7,651,220 B1 | 1/2010 | Pattikonda |
| 7,652,761 B2 | 1/2010 | Somani et al. |
| 7,653,213 B2 | 1/2010 | Longhurst et al. |
| 7,655,415 B2 | 2/2010 | Lee |
| 7,655,895 B2 | 2/2010 | Breed |
| 7,657,062 B2 | 2/2010 | Pilu |
| 7,657,603 B1 | 2/2010 | He et al. |
| 7,659,920 B2 | 2/2010 | Cohen et al. |
| 7,660,437 B2 | 2/2010 | Breed |
| 7,663,502 B2 | 2/2010 | Breed |
| 7,664,530 B2 | 2/2010 | Skelton |
| 7,664,747 B2 | 2/2010 | Petras et al. |
| 7,665,842 B2 | 2/2010 | Ho et al. |
| 7,665,845 B2 | 2/2010 | Kiderman et al. |
| 7,666,908 B2 | 2/2010 | Pomytkin et al. |
| 7,668,599 B2 | 2/2010 | Greenberg et al. |
| 7,670,769 B2 | 3/2010 | Lee |
| 7,671,887 B2 | 3/2010 | Pescatore et al. |
| 7,672,482 B2 | 3/2010 | Bolin et al. |
| 7,673,064 B2 | 3/2010 | Ducheneaut et al. |
| 7,673,254 B2 | 3/2010 | Corbett et al. |
| 7,676,062 B2 | 3/2010 | Breed et al. |
| 7,676,063 B2 | 3/2010 | Cohen et al. |
| 7,676,754 B2 | 3/2010 | Basson et al. |
| 7,676,970 B2 | 3/2010 | Charbonneau |
| 7,677,967 B2 | 3/2010 | Jessop et al. |
| 7,679,622 B2 | 3/2010 | Lee et al. |
| 7,680,244 B2 | 3/2010 | Gertner et al. |
| 7,680,245 B2 | 3/2010 | Gertner |
| 7,680,335 B2 | 3/2010 | Okada et al. |
| 7,680,453 B2 | 3/2010 | McDonnell |
| 7,682,023 B2 | 3/2010 | Van Saarloos |
| 7,682,024 B2 | 3/2010 | Plant et al. |
| 7,682,025 B2 | 3/2010 | Sur et al. |
| 7,686,450 B2 | 3/2010 | Heiberger |
| 7,686,451 B2 | 3/2010 | Cleveland |
| 7,689,008 B2 | 3/2010 | Hammoud et al. |
| 7,689,434 B2 | 3/2010 | Cureton et al. |
| 7,691,582 B2 | 4/2010 | Markovitz et al. |
| 7,693,256 B2 | 4/2010 | Brahme et al. |
| 7,693,258 B2 | 4/2010 | Gertner |
| 7,693,259 B2 | 4/2010 | Gertner |
| 7,693,260 B2 | 4/2010 | Gertner et al. |
| 7,693,343 B2 | 4/2010 | Klompenhouwer et al. |
| 7,695,136 B2 | 4/2010 | Dai |
| 7,697,032 B2 | 4/2010 | Kim et al. |
| 7,697,663 B2 | 4/2010 | Gertner |
| 7,697,979 B2 | 4/2010 | Martinerie et al. |
| 7,698,141 B2 | 4/2010 | Aoki et al. |
| 7,698,161 B2 | 4/2010 | Keil et al. |
| 7,699,837 B2 | 4/2010 | Cox et al. |
| 7,703,919 B2 | 4/2010 | Thompson et al. |
| 7,703,921 B2 | 4/2010 | Dick et al. |
| 7,704,978 B2 | 4/2010 | Tsai et al. |
| 7,705,816 B2 | 4/2010 | Chen et al. |
| 7,705,877 B2 | 4/2010 | Jackson |
| 7,708,407 B2 | 5/2010 | Yang et al. |
| 7,708,676 B2 | 5/2010 | Sunbeck |
| 7,708,700 B2 | 5/2010 | Ghajar |
| 7,710,654 B2 | 5/2010 | Ashkenazi et al. |
| 7,711,160 B2 | 5/2010 | O'Donnell et al. |
| 7,711,598 B2 | 5/2010 | Perkowski |
| 7,712,777 B2 | 5/2010 | Breed |
| 7,712,899 B2 | 5/2010 | Tanassi et al. |
| 7,714,859 B2 | 5/2010 | Shoemaker et al. |
| 7,715,646 B2 | 5/2010 | Johnson |
| 7,716,058 B2 | 5/2010 | Roth et al. |
| 7,716,194 B2 | 5/2010 | Williams et al. |
| 7,719,520 B2 | 5/2010 | Singh et al. |
| 7,720,779 B1 | 5/2010 | Perry et al. |
| 7,721,138 B1 | 5/2010 | Lyadvinsky et al. |
| 7,724,278 B2 | 5/2010 | Maguire, Jr. |
| 7,725,191 B2 | 5/2010 | Greenberg et al. |
| RE41,374 E | 6/2010 | Wine et al. |
| RE41,375 E | 6/2010 | Wine et al. |
| RE41,376 E | 6/2010 | Torch |
| 7,727,116 B2 | 6/2010 | Kaplan et al. |
| 7,729,739 B2 | 6/2010 | Acar et al. |
| 7,731,358 B2 | 6/2010 | Blum et al. |
| 7,731,360 B2 | 6/2010 | MacDougall et al. |
| 7,734,061 B2 | 6/2010 | Breed et al. |
| 7,734,075 B2 | 6/2010 | Sun et al. |
| 7,736,000 B2 | 6/2010 | Enriquez et al. |
| 7,738,678 B2 | 6/2010 | Breed et al. |
| 7,738,684 B2 | 6/2010 | Kariathungal et al. |
| 7,738,972 B2 | 6/2010 | Pouchak |
| 7,742,621 B2 | 6/2010 | Hammoud et al. |
| 7,742,623 B1 | 6/2010 | Moon et al. |
| 7,743,051 B1 | 6/2010 | Kashyap et al. |
| 7,744,214 B2 | 6/2010 | Blum et al. |
| 7,745,486 B2 | 6/2010 | Lines |
| 7,745,487 B2 | 6/2010 | Lines |
| 7,746,235 B2 | 6/2010 | Hammoud et al. |
| 7,746,321 B2 | 6/2010 | Banning |
| 7,747,040 B2 | 6/2010 | Toyama |
| 7,747,050 B2 | 6/2010 | Lau et al. |
| 7,747,068 B1 | 6/2010 | Smyth et al. |
| 7,747,107 B2 | 6/2010 | Avidan et al. |
| 7,748,069 B2 | 7/2010 | Dawley |
| 7,748,072 B2 | 7/2010 | Rycroft |
| 7,749,767 B2 | 7/2010 | Lebret et al. |
| 7,750,024 B2 | 7/2010 | Ishiuchi |
| 7,750,891 B2 | 7/2010 | Stephanick et al. |
| 7,751,878 B1 | 7/2010 | Merkle et al. |
| 7,753,523 B2 | 7/2010 | Kiderman et al. |
| 7,755,627 B2 | 7/2010 | Anderson et al. |
| 7,755,769 B2 | 7/2010 | Everett et al. |
| 7,756,274 B2 | 7/2010 | Layton et al. |
| 7,756,294 B2 | 7/2010 | Toyama |
| 7,760,182 B2 | 7/2010 | Ahmad et al. |
| 7,760,910 B2 | 7/2010 | Johnson et al. |
| 7,762,582 B2 | 7/2010 | Breed |
| 7,762,665 B2 | 7/2010 | Vertegaal et al. |
| 7,763,588 B2 | 7/2010 | van Praag et al. |
| 7,764,247 B2 | 7/2010 | Blanco et al. |
| 7,764,288 B2 | 7/2010 | Anderson et al. |
| 7,765,178 B1 | 7/2010 | Roizen et al. |
| 7,766,383 B2 | 8/2010 | Breed et al. |
| 7,768,380 B2 | 8/2010 | Breed et al. |
| 7,769,439 B2 | 8/2010 | Vesely et al. |
| 7,769,513 B2 | 8/2010 | Breed et al. |
| 7,770,920 B2 | 8/2010 | Breed et al. |
| 7,773,101 B2 | 8/2010 | Shoemaker |
| 7,773,111 B2 | 8/2010 | Cleveland et al. |
| 7,774,716 B2 | 8/2010 | Crain et al. |
| 7,775,661 B2 | 8/2010 | Zuccolotto et al. |
| 7,776,088 B2 | 8/2010 | Shadduck |
| 7,776,551 B2 | 8/2010 | Shohat et al. |
| 7,777,877 B2 | 8/2010 | Walker et al. |
| 7,777,971 B2 | 8/2010 | Moller et al. |
| 7,778,818 B2 | 8/2010 | Longe et al. |
| 7,779,221 B1 | 8/2010 | Tsypliaev et al. |
| 7,779,956 B2 | 8/2010 | Breed et al. |
| 7,780,981 B2 | 8/2010 | DiPierro et al. |
| 7,782,344 B2 | 8/2010 | Whittaker |
| 7,783,120 B2 | 8/2010 | Kortum et al. |
| 7,785,262 B2 | 8/2010 | Melker et al. |
| 7,787,683 B2 | 8/2010 | Khamene et al. |
| 7,787,688 B1 | 8/2010 | Kass |
| 7,788,008 B2 | 8/2010 | Breed |
| 7,788,075 B2 | 8/2010 | DeYoe et al. |
| 7,788,279 B2 | 8/2010 | Mohajer et al. |
| 7,788,592 B2 | 8/2010 | Williams et al. |
| 7,790,921 B2 | 9/2010 | Malkar et al. |
| 7,791,491 B2 | 9/2010 | Johns |
| 7,792,249 B2 | 9/2010 | Gertner et al. |
| 7,796,134 B2 | 9/2010 | Vesely et al. |
| 7,796,835 B2 | 9/2010 | Matsumoto |
| 7,798,643 B2 | 9/2010 | Waldorf et al. |
| 7,801,271 B2 | 9/2010 | Gertner et al. |
| 7,801,686 B2 | 9/2010 | Hyde et al. |
| 7,801,741 B2 | 9/2010 | Fracek, Jr. et al. |
| 7,804,502 B2 | 9/2010 | Azuma |

(56) References Cited

U.S. PATENT DOCUMENTS

| | | |
|---|---|---|
| 7,804,507 B2 | 9/2010 | Yang et al. |
| 7,805,009 B2 | 9/2010 | Everett et al. |
| 7,805,320 B2 | 9/2010 | Deitsch et al. |
| 7,808,484 B1 | 10/2010 | Bareli |
| 7,809,160 B2 | 10/2010 | Vertegaal et al. |
| 7,809,442 B2 | 10/2010 | Bolea et al. |
| 7,809,574 B2 | 10/2010 | Roth et al. |
| 7,810,926 B2 | 10/2010 | Connell, II |
| 7,810,928 B2 | 10/2010 | Kandel et al. |
| 7,813,954 B1 | 10/2010 | Price et al. |
| 7,813,976 B2 | 10/2010 | Sick et al. |
| 7,814,517 B2 | 10/2010 | Ducheneaut et al. |
| 7,814,518 B2 | 10/2010 | Ducheneaut et al. |
| 7,815,311 B2 | 10/2010 | Johns et al. |
| 7,815,507 B2 | 10/2010 | Parrott et al. |
| 7,818,770 B2 | 10/2010 | Ducheneaut et al. |
| 7,818,771 B2 | 10/2010 | Ducheneaut et al. |
| 7,819,003 B2 | 10/2010 | Breed et al. |
| 7,819,525 B2 | 10/2010 | Connell, II |
| 7,819,818 B2 | 10/2010 | Ghajar |
| 7,821,503 B2 | 10/2010 | Stephanick et al. |
| 7,822,158 B2 | 10/2010 | Ishii et al. |
| 7,822,175 B2 | 10/2010 | Gertner |
| 7,822,607 B2 | 10/2010 | Aoki et al. |
| 7,823,058 B2 | 10/2010 | Pea et al. |
| 7,824,860 B2 | 11/2010 | Tsuji |
| 7,825,948 B2 | 11/2010 | Van Geest et al. |
| 7,826,647 B2 | 11/2010 | Capolunghi et al. |
| 7,827,183 B2 | 11/2010 | Fraser et al. |
| 7,827,203 B2 | 11/2010 | Keil et al. |
| 7,831,358 B2 | 11/2010 | Breed et al. |
| 7,831,444 B2 | 11/2010 | Brown et al. |
| 7,831,472 B2 | 11/2010 | Yufik |
| 7,831,834 B2 | 11/2010 | Hickman et al. |
| 7,832,866 B2 | 11/2010 | Chao |
| 7,835,498 B2 | 11/2010 | Bonfiglio et al. |
| 7,835,798 B2 | 11/2010 | Greenberg et al. |
| 7,835,834 B2 | 11/2010 | Smith et al. |
| 7,839,292 B2 | 11/2010 | Wang et al. |
| 7,839,378 B2 | 11/2010 | Krijn et al. |
| 7,839,380 B2 | 11/2010 | Chen et al. |
| 7,839,407 B2 | 11/2010 | Anderson et al. |
| 7,839,430 B2 | 11/2010 | Hentschke |
| 7,840,274 B2 | 11/2010 | Greenberg et al. |
| 7,841,719 B2 | 11/2010 | Podoleanu |
| 7,841,950 B2 | 11/2010 | Davidson et al. |
| 7,844,088 B2 | 11/2010 | Brinson, Jr. et al. |
| 7,846,152 B2 | 12/2010 | Chernyak et al. |
| 7,849,115 B2 | 12/2010 | Reiner |
| 7,850,306 B2 | 12/2010 | Uusitalo et al. |
| 7,850,552 B2 | 12/2010 | Marty et al. |
| 7,852,338 B1 | 12/2010 | Baraff |
| 7,854,669 B2 | 12/2010 | Marty et al. |
| 7,857,452 B2 | 12/2010 | Martinez-Conde et al. |
| 7,862,171 B2 | 1/2011 | Varnas et al. |
| 7,863,247 B1 | 1/2011 | Brenneman et al. |
| 7,864,180 B1 | 1/2011 | Baraff et al. |
| 7,864,181 B1 | 1/2011 | Baraff |
| 7,865,420 B1 | 1/2011 | Daman et al. |
| 7,865,495 B1 | 1/2011 | Roizen et al. |
| 7,866,818 B2 | 1/2011 | Schroeder et al. |
| 7,868,889 B2 | 1/2011 | Azuma |
| 7,868,900 B2 | 1/2011 | Sirohey et al. |
| 7,869,848 B2 | 1/2011 | Proniewicz et al. |
| 7,870,589 B2 | 1/2011 | Ducheneaut et al. |
| 7,871,270 B2 | 1/2011 | Seeliger et al. |
| 7,872,635 B2 | 1/2011 | Mitchell |
| 7,872,649 B1 | 1/2011 | Arvo |
| 7,873,771 B2 | 1/2011 | Krueger et al. |
| 7,873,983 B2 | 1/2011 | Ducheneaut et al. |
| 7,877,703 B1 | 1/2011 | Fleming |
| RE42,168 E | 2/2011 | Jenkins et al. |
| 7,878,652 B2 | 2/2011 | Chen et al. |
| 7,878,654 B2 | 2/2011 | Mattioli et al. |
| 7,878,910 B2 | 2/2011 | Wells |
| 7,881,493 B1 | 2/2011 | Edwards et al. |
| 7,882,530 B2 | 2/2011 | Ducheneaut et al. |
| 7,883,008 B1 | 2/2011 | Miller et al. |
| 7,884,124 B2 | 2/2011 | Heffernan et al. |
| 7,884,826 B1 | 2/2011 | Baraff |
| 7,885,454 B1 | 2/2011 | Kass |
| 7,885,818 B2 | 2/2011 | Vignoli |
| 7,887,089 B2 | 2/2011 | Breed et al. |
| 7,889,197 B2 | 2/2011 | Kraver |
| 7,890,500 B2 | 2/2011 | Bobrow et al. |
| 7,890,871 B2 | 2/2011 | Etkin |
| 7,892,735 B2 | 2/2011 | Brennan et al. |
| 7,893,098 B2 | 2/2011 | Fang et al. |
| 7,894,682 B2 | 2/2011 | Kortum et al. |
| 7,894,911 B2 | 2/2011 | Greenberg et al. |
| 7,897,361 B2 | 3/2011 | Westbrook et al. |
| 7,898,519 B2 | 3/2011 | Feng |
| 7,899,226 B2 | 3/2011 | Pescatore et al. |
| 7,899,512 B2 | 3/2011 | Labadie et al. |
| 7,899,560 B2 | 3/2011 | Eck |
| 7,899,871 B1 | 3/2011 | Kumar et al. |
| 7,900,736 B2 | 3/2011 | Breed |
| 7,901,075 B2 | 3/2011 | Rooney et al. |
| 7,901,948 B2 | 3/2011 | Hairault et al. |
| 7,902,252 B2 | 3/2011 | Heffernan et al. |
| 7,903,064 B2 | 3/2011 | Shiomi |
| 7,903,783 B2 | 3/2011 | Modica et al. |
| 7,903,870 B1 | 3/2011 | Budagavi |
| 7,904,114 B2 | 3/2011 | Skelton |
| 7,904,331 B2 | 3/2011 | Keil et al. |
| 7,904,333 B1 | 3/2011 | Perkowski |
| 7,908,166 B2 | 3/2011 | Keil et al. |
| 7,908,569 B2 | 3/2011 | Ala-Rantala |
| 7,911,469 B1 | 3/2011 | Baraff |
| 7,912,178 B2 | 3/2011 | Gertner |
| 7,912,179 B2 | 3/2011 | Gertner et al. |
| 7,912,701 B1 | 3/2011 | Gray et al. |
| 7,912,898 B2 | 3/2011 | Gold et al. |
| 7,913,184 B1 | 3/2011 | Zhang et al. |
| 7,914,148 B2 | 3/2011 | Fisher et al. |
| 7,914,442 B1 | 3/2011 | Gazdzinski |
| 7,916,099 B2 | 3/2011 | Steer et al. |
| 7,918,808 B2 | 4/2011 | Simmons |
| 7,920,132 B2 | 4/2011 | Longe et al. |
| 7,920,725 B2 | 4/2011 | Li |
| 7,921,810 B2 | 4/2011 | Lumbroso et al. |
| 7,922,330 B2 | 4/2011 | Van Saarloos |
| 7,922,670 B2 | 4/2011 | Jones et al. |
| 7,923,801 B2 | 4/2011 | Tian et al. |
| 7,925,077 B2 | 4/2011 | Woodfill et al. |
| 7,925,354 B2 | 4/2011 | Greenberg et al. |
| 7,925,355 B2 | 4/2011 | Quick |
| 7,925,887 B2 | 4/2011 | Burton |
| 7,926,490 B2 | 4/2011 | Dai et al. |
| 7,926,828 B2 | 4/2011 | Merchant |
| 7,926,944 B2 | 4/2011 | Thompson et al. |
| 7,928,115 B2 | 4/2011 | Forbes et al. |
| 7,928,927 B1 | 4/2011 | Krenz et al. |
| 7,929,737 B2 | 4/2011 | Sirohey et al. |
| 7,930,199 B1 | 4/2011 | Hill |
| 7,933,226 B2 | 4/2011 | Woodruff et al. |
| H2253 H | 5/2011 | Petrovic et al. |
| D638,943 S | 5/2011 | Daniel |
| 7,935,365 B2 | 5/2011 | Dror et al. |
| 7,936,257 B2 | 5/2011 | Stahel et al. |
| 7,937,612 B1 | 5/2011 | Lyadvinsky et al. |
| 7,938,540 B2 | 5/2011 | Brentnall, III et al. |
| 7,938,785 B2 | 5/2011 | Aguilar et al. |
| 7,940,240 B2 | 5/2011 | Takeuchi et al. |
| 7,940,962 B2 | 5/2011 | Hammoud |
| 7,941,318 B2 | 5/2011 | Lu |
| 7,941,441 B2 | 5/2011 | Svanteson et al. |
| 7,941,495 B2 | 5/2011 | Maghsoodnia et al. |
| 7,942,828 B2 | 5/2011 | Teicher et al. |
| 7,946,238 B2 | 5/2011 | Colsher et al. |
| 7,946,480 B2 | 5/2011 | Miller et al. |
| 7,948,493 B2 | 5/2011 | Klefenz et al. |
| 7,949,317 B2 | 5/2011 | Krueger et al. |
| 7,949,616 B2 | 5/2011 | Levy et al. |

(56) References Cited

U.S. PATENT DOCUMENTS

| | | |
|---|---|---|
| 7,950,802 B2 | 5/2011 | Schwerdtner et al. |
| 7,952,483 B2 | 5/2011 | Ferguson et al. |
| 7,952,582 B1 | 5/2011 | Arvo |
| 7,953,203 B2 | 5/2011 | Gertner et al. |
| 7,953,723 B1 | 5/2011 | Dutton et al. |
| 7,953,948 B1 | 5/2011 | Dyatlov et al. |
| RE42,471 E | 6/2011 | Torch |
| 7,954,703 B2 | 6/2011 | Miller et al. |
| 7,954,875 B2 | 6/2011 | Bohner et al. |
| 7,957,810 B2 | 6/2011 | Greenberg et al. |
| 7,959,578 B2 | 6/2011 | Lonky |
| 7,961,845 B2 | 6/2011 | Gertner et al. |
| 7,962,397 B2 | 6/2011 | Hemingway et al. |
| 7,963,652 B2 | 6/2011 | Vertegaal et al. |
| 7,963,835 B2 | 6/2011 | Jessop et al. |
| 7,967,436 B2 | 6/2011 | Dai |
| 7,967,439 B2 | 6/2011 | Shelhamer et al. |
| 7,968,112 B2 | 6/2011 | Ben Dror et al. |
| 7,968,343 B2 | 6/2011 | Poullain et al. |
| 7,969,433 B2 | 6/2011 | Anderson et al. |
| 7,971,168 B1 | 6/2011 | Swanson et al. |
| 7,972,140 B2 | 7/2011 | Renaud |
| 7,972,266 B2 | 7/2011 | Gobeyn et al. |
| 7,972,633 B2 | 7/2011 | Smith |
| 7,973,079 B2 | 7/2011 | Mata et al. |
| 7,973,789 B2 | 7/2011 | Cook |
| 7,973,805 B1 | 7/2011 | Baraff et al. |
| 7,974,787 B2 | 7/2011 | Hyde et al. |
| 7,975,227 B2 | 7/2011 | Covannon et al. |
| 7,976,060 B2 | 7/2011 | Breed |
| 7,978,203 B1 | 7/2011 | Bogart et al. |
| 7,978,211 B2 | 7/2011 | Chen et al. |
| 7,978,407 B1 | 7/2011 | Connor |
| 7,978,818 B2 | 7/2011 | Gertner et al. |
| 7,978,819 B2 | 7/2011 | Gertner et al. |
| 7,980,693 B2 | 7/2011 | Reichow et al. |
| 7,981,210 B2 | 7/2011 | Kwan et al. |
| 7,982,765 B2 | 7/2011 | Lewis et al. |
| 7,983,473 B2 | 7/2011 | Tigges |
| 7,983,817 B2 | 7/2011 | Breed |
| 7,983,920 B2 | 7/2011 | Sinclair, II |
| 7,984,097 B2 | 7/2011 | Fernandez |
| 7,985,194 B2 | 7/2011 | Hoffman et al. |
| 7,985,558 B2 | 7/2011 | Lee |
| 7,986,300 B2 | 7/2011 | Masselle et al. |
| 7,986,816 B1 | 7/2011 | Hoanca et al. |
| 7,986,990 B2 | 7/2011 | Dinwiddie |
| 7,986,991 B2 | 7/2011 | Prichep |
| RE42,665 E | 8/2011 | Schneider |
| 7,988,190 B2 | 8/2011 | Breed |
| 7,988,287 B1 | 8/2011 | Butler et al. |
| 7,988,288 B2 | 8/2011 | Donaldson |
| 7,989,210 B2 | 8/2011 | Lee |
| 7,991,099 B2 | 8/2011 | Xia et al. |
| 7,991,618 B2 | 8/2011 | Boeckmann et al. |
| 7,991,770 B2 | 8/2011 | Covell et al. |
| 7,995,031 B2 | 8/2011 | Manal |
| 7,995,059 B1 | 8/2011 | Arvo |
| 7,995,060 B2 | 8/2011 | Murrah et al. |
| 7,995,078 B2 | 8/2011 | Baar |
| 7,995,090 B2 | 8/2011 | Liu et al. |
| 7,995,818 B2 | 8/2011 | Mahesh et al. |
| 7,997,727 B2 | 8/2011 | Ho et al. |
| 7,997,730 B2 | 8/2011 | Cleveland |
| 7,997,733 B2 | 8/2011 | Blum et al. |
| 7,998,135 B2 | 8/2011 | Donitzky |
| 7,999,760 B2 | 8/2011 | Giegold et al. |
| 7,999,844 B2 | 8/2011 | Richards |
| 7,999,852 B2 | 8/2011 | Deroo et al. |
| 8,000,008 B2 | 8/2011 | Sander |
| 8,002,408 B2 | 8/2011 | Reichow et al. |
| 8,004,057 B2 | 8/2011 | Tian et al. |
| 8,005,288 B2 | 8/2011 | Chen et al. |
| 8,006,216 B1 | 8/2011 | Chen et al. |
| 8,007,846 B2 | 8/2011 | Thompson et al. |
| 8,008,563 B1 | 8/2011 | Hastings |
| 8,010,175 B2 | 8/2011 | O'Donnell et al. |
| 8,011,042 B1 | 9/2011 | Rose et al. |
| 8,013,412 B2 | 9/2011 | Tian |
| 8,013,837 B1 | 9/2011 | Schroeder |
| 8,016,421 B2 | 9/2011 | Eberl et al. |
| 8,017,578 B2 | 9/2011 | Brenneman et al. |
| 8,018,796 B2 | 9/2011 | Farinella et al. |
| 8,019,124 B2 | 9/2011 | Nair |
| 8,019,155 B2 | 9/2011 | Hibino et al. |
| 8,019,317 B2 | 9/2011 | Litwin |
| 8,019,428 B2 | 9/2011 | Greenberg et al. |
| 8,019,712 B2 | 9/2011 | Rigdon et al. |
| 8,019,744 B1 | 9/2011 | Roizen et al. |
| 8,019,749 B2 | 9/2011 | Leban |
| 8,048,002 B2 | 11/2011 | Ghajar |
| 2001/0000636 A1 | 5/2001 | Weiss |
| 2001/0003040 A1 | 6/2001 | Spector |
| 2001/0005186 A1 | 6/2001 | Van Dalfsen et al. |
| 2001/0006426 A1 | 7/2001 | Son et al. |
| 2001/0009409 A1 | 7/2001 | Lasko-Harvill et al. |
| 2001/0010003 A1 | 7/2001 | Lai |
| 2001/0011211 A1 | 8/2001 | Bushey et al. |
| 2001/0011388 A1 | 8/2001 | Nelson et al. |
| 2001/0014868 A1 | 8/2001 | Herz et al. |
| 2001/0016733 A1 | 8/2001 | Frey et al. |
| 2001/0016734 A1 | 8/2001 | Frey et al. |
| 2001/0016735 A1 | 8/2001 | Frey et al. |
| 2001/0016737 A1 | 8/2001 | Frey et al. |
| 2001/0019390 A1 | 9/2001 | Itoh et al. |
| 2001/0021846 A1 | 9/2001 | Frey et al. |
| 2001/0022648 A1 | 9/2001 | Lai |
| 2001/0024266 A1 | 9/2001 | Apple et al. |
| 2001/0025172 A1 | 9/2001 | Frey et al. |
| 2001/0028309 A1 | 10/2001 | Torch |
| 2001/0028352 A1 | 10/2001 | Naegle et al. |
| 2001/0029439 A1 | 10/2001 | Crain et al. |
| 2001/0029478 A1 | 10/2001 | Laster et al. |
| 2001/0031082 A1 | 10/2001 | Numaoka |
| 2001/0031958 A1 | 10/2001 | Frey et al. |
| 2001/0033287 A1 | 10/2001 | Naegle et al. |
| 2001/0033330 A1 | 10/2001 | Garoutte |
| 2001/0033364 A1 | 10/2001 | Cabib et al. |
| 2001/0033410 A1 | 10/2001 | Helsel et al. |
| 2001/0033844 A1 | 10/2001 | Wilson et al. |
| 2001/0033872 A1 | 10/2001 | Corson et al. |
| 2001/0034077 A1 | 10/2001 | Wine et al. |
| 2001/0035938 A1 | 11/2001 | Lai et al. |
| 2001/0036623 A1 | 11/2001 | Johnson |
| 2001/0036840 A1 | 11/2001 | Jenkins et al. |
| 2001/0038386 A1 | 11/2001 | Numaoka |
| 2001/0039000 A1 | 11/2001 | Parsons |
| 2001/0041688 A1 | 11/2001 | Waeber et al. |
| 2001/0041884 A1 | 11/2001 | Frey et al. |
| 2001/0041885 A1 | 11/2001 | Hohla |
| 2001/0043163 A1 | 11/2001 | Waldern et al. |
| 2001/0043208 A1 | 11/2001 | Furness et al. |
| 2001/0043402 A1 | 11/2001 | Melville et al. |
| 2001/0044408 A1 | 11/2001 | Reitberg |
| 2001/0044446 A1 | 11/2001 | Phillips, III et al. |
| 2001/0047290 A1 | 11/2001 | Petras et al. |
| 2001/0048503 A1 | 12/2001 | Krebs |
| 2001/0051489 A1 | 12/2001 | Gu |
| 2001/0055025 A1 | 12/2001 | Deering et al. |
| 2001/0055152 A1 | 12/2001 | Richards |
| 2002/0003543 A1 | 1/2002 | Deering |
| 2002/0005790 A1 | 1/2002 | Georgalis |
| 2002/0005862 A1 | 1/2002 | Deering |
| 2002/0006763 A1 | 1/2002 | Forbes et al. |
| 2002/0007176 A1 | 1/2002 | Campin et al. |
| 2002/0007177 A1 | 1/2002 | Campin et al. |
| 2002/0007178 A1 | 1/2002 | Donitzky |
| 2002/0007798 A1 | 1/2002 | Pavlak et al. |
| 2002/0008091 A1 | 1/2002 | Brandinger et al. |
| 2002/0008706 A1 | 1/2002 | Van Dalfsen et al. |
| 2002/0010496 A1 | 1/2002 | Greenberg et al. |
| 2002/0010745 A1 | 1/2002 | Schneider |
| 2002/0012012 A1 | 1/2002 | Crain et al. |
| 2002/0013307 A1 | 1/2002 | Lapuerta et al. |

(56) References Cited

U.S. PATENT DOCUMENTS

| | | |
|---|---|---|
| 2002/0013573 A1 | 1/2002 | Telfair et al. |
| 2002/0013575 A1 | 1/2002 | Lai et al. |
| 2002/0013576 A1 | 1/2002 | Gray et al. |
| 2002/0013577 A1 | 1/2002 | Frey et al. |
| 2002/0013950 A1 | 1/2002 | Tomsen |
| 2002/0014579 A1 | 2/2002 | Dunfield |
| 2002/0015007 A1 | 2/2002 | Perlin et al. |
| 2002/0015041 A1 | 2/2002 | Naegle et al. |
| 2002/0015044 A1 | 2/2002 | Edge et al. |
| 2002/0015064 A1 | 2/2002 | Robotham et al. |
| 2002/0016965 A1 | 2/2002 | Tomsen |
| 2002/0019055 A1 | 2/2002 | Brown et al. |
| 2002/0020810 A1 | 2/2002 | Wine et al. |
| 2002/0022499 A1 | 2/2002 | Newman et al. |
| 2002/0024708 A1 | 2/2002 | Lewis et al. |
| 2002/0026180 A1 | 2/2002 | Nakamura |
| 2002/0028006 A1 | 3/2002 | Novak et al. |
| 2002/0028008 A1 | 3/2002 | Fan et al. |
| 2002/0030789 A1 | 3/2002 | Campin |
| 2002/0031253 A1 | 3/2002 | Dialameh et al. |
| 2002/0032581 A1 | 3/2002 | Reitberg |
| 2002/0035145 A1 | 3/2002 | Tsai et al. |
| 2002/0036648 A1 | 3/2002 | Putilin |
| 2002/0038134 A1 | 3/2002 | Greenberg et al. |
| 2002/0038310 A1 | 3/2002 | Reitberg |
| 2002/0039073 A1 | 4/2002 | Ben-Ari et al. |
| 2002/0040038 A1 | 4/2002 | Pratt |
| 2002/0040338 A1 | 4/2002 | Sick et al. |
| 2002/0040377 A1 | 4/2002 | Newman et al. |
| 2002/0040484 A1 | 4/2002 | Roch et al. |
| 2002/0044152 A1 | 4/2002 | Abbott, III et al. |
| 2002/0045201 A1 | 4/2002 | Roch et al. |
| 2002/0045988 A1 | 4/2002 | Yokota |
| 2002/0047297 A1 | 4/2002 | Longhi et al. |
| 2002/0048612 A1 | 4/2002 | Evans et al. |
| 2002/0048769 A1 | 4/2002 | Roch et al. |
| 2002/0049230 A1 | 4/2002 | Hassan et al. |
| 2002/0050956 A1 | 5/2002 | Gerhard et al. |
| 2002/0051116 A1 | 5/2002 | Van Saarloos et al. |
| 2002/0054876 A1 | 5/2002 | Roch et al. |
| 2002/0055735 A1 | 5/2002 | Ruiz |
| 2002/0056009 A1 | 5/2002 | Affif et al. |
| 2002/0058239 A1 | 5/2002 | Wang |
| 2002/0058881 A1 | 5/2002 | Raviv et al. |
| 2002/0059653 A1 | 5/2002 | Roch et al. |
| 2002/0063780 A1 | 5/2002 | Harman et al. |
| 2002/0063850 A1 | 5/2002 | Barry et al. |
| 2002/0065612 A1 | 5/2002 | Bizar |
| 2002/0066780 A1 | 6/2002 | Balolia |
| 2002/0069086 A1 | 6/2002 | Fracek, Jr. et al. |
| 2002/0069424 A1 | 6/2002 | Roch et al. |
| 2002/0070284 A1 | 6/2002 | Hall |
| 2002/0072859 A1 | 6/2002 | Kajimoto et al. |
| 2002/0073424 A1 | 6/2002 | Ward, III et al. |
| 2002/0075384 A1 | 6/2002 | Harman |
| 2002/0076398 A1 | 6/2002 | Tully et al. |
| 2002/0076684 A1 | 6/2002 | Blevins et al. |
| 2002/0080147 A1 | 6/2002 | Edge et al. |
| 2002/0082590 A1 | 6/2002 | Potgieter |
| 2002/0082629 A1 | 6/2002 | Cox et al. |
| 2002/0083101 A1 | 6/2002 | Card et al. |
| 2002/0083623 A1 | 7/2002 | Joseph |
| 2002/0085007 A1 | 7/2002 | Nelson et al. |
| 2002/0085656 A1 | 7/2002 | Lee et al. |
| 2002/0085843 A1 | 7/2002 | Mann |
| 2002/0086272 A1 | 7/2002 | Ho et al. |
| 2002/0087388 A1 | 7/2002 | Keil et al. |
| 2002/0091421 A1 | 7/2002 | Greenberg et al. |
| 2002/0091422 A1 | 7/2002 | Greenberg et al. |
| 2002/0091764 A1 | 7/2002 | Yale |
| 2002/0094511 A1 | 7/2002 | Li |
| 2002/0095142 A1 | 7/2002 | Ming |
| 2002/0097498 A1 | 7/2002 | Melville et al. |
| 2002/0099305 A1 | 7/2002 | Fukushima et al. |
| 2002/0099363 A1 | 7/2002 | Woodward et al. |
| 2002/0101612 A1 | 8/2002 | Lauper et al. |
| 2002/0102291 A1 | 8/2002 | Mantelle et al. |
| 2002/0102909 A1 | 8/2002 | Derraugh et al. |
| 2002/0103481 A1 | 8/2002 | Webb et al. |
| 2002/0103482 A1 | 8/2002 | Scholler et al. |
| 2002/0103625 A1 | 8/2002 | Card et al. |
| 2002/0105482 A1 | 8/2002 | Lemelson et al. |
| 2002/0106057 A1 | 8/2002 | Halpert |
| 2002/0106676 A1 | 8/2002 | Roch et al. |
| 2002/0106773 A1 | 8/2002 | Roch et al. |
| 2002/0107697 A1 | 8/2002 | Jensen |
| 2002/0107972 A1 | 8/2002 | Keane |
| 2002/0109071 A1 | 8/2002 | Spink |
| 2002/0109701 A1 | 8/2002 | Deering |
| 2002/0111301 A1 | 8/2002 | Brenneman et al. |
| 2002/0111384 A1 | 8/2002 | Boudrie et al. |
| 2002/0113782 A1 | 8/2002 | Verberne et al. |
| 2002/0113802 A1 | 8/2002 | Card et al. |
| 2002/0113823 A1 | 8/2002 | Card et al. |
| 2002/0114799 A1 | 8/2002 | Roch et al. |
| 2002/0115081 A1 | 8/2002 | Lee et al. |
| 2002/0115119 A1 | 8/2002 | Roch et al. |
| 2002/0115606 A1 | 8/2002 | Roch et al. |
| 2002/0115607 A1 | 8/2002 | Roch et al. |
| 2002/0116200 A1 | 8/2002 | Cureton et al. |
| 2002/0118230 A1 | 8/2002 | Card et al. |
| 2002/0118284 A1 | 8/2002 | Newman et al. |
| 2002/0118339 A1 | 8/2002 | Lowe |
| 2002/0119155 A1 | 8/2002 | Roch et al. |
| 2002/0119927 A1 | 8/2002 | Roch et al. |
| 2002/0120947 A1 | 8/2002 | Roch et al. |
| 2002/0122024 A1 | 9/2002 | Roggatz |
| 2002/0124026 A1 | 9/2002 | Weber |
| 2002/0124271 A1 | 9/2002 | Herrmann et al. |
| 2002/0124273 A1 | 9/2002 | Roch et al. |
| 2002/0126090 A1 | 9/2002 | Kirkpatrick et al. |
| 2002/0126331 A1 | 9/2002 | Orr et al. |
| 2002/0126891 A1 | 9/2002 | Osberger |
| 2002/0128634 A1 | 9/2002 | Donitzky et al. |
| 2002/0132793 A1 | 9/2002 | Epstein et al. |
| 2002/0133378 A1 | 9/2002 | Mault et al. |
| 2002/0133394 A1 | 9/2002 | Bushey et al. |
| 2002/0134929 A1 | 9/2002 | Wine et al. |
| 2002/0135618 A1 | 9/2002 | Maes et al. |
| 2002/0135738 A1 | 9/2002 | Cok et al. |
| 2002/0138455 A1 | 9/2002 | Abdel-Moneim et al. |
| 2002/0139920 A1 | 10/2002 | Seibel et al. |
| 2002/0140215 A1 | 10/2002 | Breed et al. |
| 2002/0140899 A1 | 10/2002 | Blum et al. |
| 2002/0141614 A1 | 10/2002 | Lin |
| 2002/0141650 A1 | 10/2002 | Keeney et al. |
| 2002/0144276 A1 | 10/2002 | Radford et al. |
| 2002/0149611 A1 | 10/2002 | May |
| 2002/0150262 A1 | 10/2002 | Carter |
| 2002/0152180 A1 | 10/2002 | Turgeon |
| 2002/0154141 A1 | 10/2002 | Forman |
| 2002/0154272 A1 | 10/2002 | Shevlin |
| 2002/0156078 A1 | 10/2002 | Comings et al. |
| 2002/0156866 A1 | 10/2002 | Schneider |
| 2002/0163484 A1 | 11/2002 | Furness et al. |
| 2002/0164054 A1 | 11/2002 | McCartney et al. |
| 2002/0164061 A1 | 11/2002 | Paik et al. |
| 2002/0164655 A1 | 11/2002 | Roch et al. |
| 2002/0167794 A1 | 11/2002 | Ronzani et al. |
| 2002/0169440 A1 | 11/2002 | Jensen |
| 2002/0169665 A1 | 11/2002 | Hughes et al. |
| 2002/0171759 A1 | 11/2002 | Handjojo et al. |
| 2002/0174214 A1 | 11/2002 | Carl et al. |
| 2002/0174230 A1 | 11/2002 | Gudorf et al. |
| 2002/0176604 A1 | 11/2002 | Shekhar et al. |
| 2002/0178215 A1 | 11/2002 | Laksono et al. |
| 2002/0180660 A1 | 12/2002 | Wang et al. |
| 2002/0180756 A1 | 12/2002 | Lee et al. |
| 2002/0180799 A1 | 12/2002 | Peck et al. |
| 2002/0180868 A1 | 12/2002 | Lippert et al. |
| 2002/0181115 A1 | 12/2002 | Massof et al. |
| 2002/0181733 A1 | 12/2002 | Peck |
| 2002/0182573 A1 | 12/2002 | Watson |
| 2002/0186177 A1 | 12/2002 | Hong et al. |

(56) References Cited

U.S. PATENT DOCUMENTS

| | | |
|---|---|---|
| 2002/0186220 A1 | 12/2002 | Sakaguchi |
| 2002/0186348 A1 | 12/2002 | Covannon et al. |
| 2002/0187474 A1 | 12/2002 | Comings et al. |
| 2002/0188202 A1 | 12/2002 | Hammesfahr |
| 2002/0188872 A1 | 12/2002 | Willeby |
| 2002/0191153 A1 | 12/2002 | Wei et al. |
| 2002/0192159 A1 | 12/2002 | Reitberg |
| 2002/0193429 A1 | 12/2002 | Tsai et al. |
| 2002/0193845 A1 | 12/2002 | Greenberg et al. |
| 2002/0194081 A1 | 12/2002 | Perkowski |
| 2002/0194308 A1 | 12/2002 | Hall |
| 2002/0195107 A1 | 12/2002 | Smaldone |
| 2002/0196226 A1 | 12/2002 | Tegreene et al. |
| 2002/0196290 A1 | 12/2002 | Zlotnick |
| 2002/0197930 A1 | 12/2002 | Derraugh et al. |
| 2002/0198515 A1 | 12/2002 | Somani et al. |
| 2002/0198791 A1 | 12/2002 | Perkowski |
| 2003/0001846 A1 | 1/2003 | Davis et al. |
| 2003/0007121 A1 | 1/2003 | Wei et al. |
| 2003/0007128 A1 | 1/2003 | Wei |
| 2003/0007681 A1 | 1/2003 | Baker |
| 2003/0008919 A1 | 1/2003 | Roullet et al. |
| 2003/0009392 A1 | 1/2003 | Perkowski |
| 2003/0011618 A1 | 1/2003 | Deering |
| 2003/0011743 A1 | 1/2003 | Povlotsky |
| 2003/0014371 A1 | 1/2003 | Turgeon |
| 2003/0019005 A1 | 1/2003 | Burnett |
| 2003/0020709 A1 | 1/2003 | Naegle et al. |
| 2003/0020755 A1 | 1/2003 | Lemelson et al. |
| 2003/0020842 A1 | 1/2003 | Lasko-Harvill et al. |
| 2003/0020874 A1 | 1/2003 | Smith et al. |
| 2003/0022892 A1 | 1/2003 | Glasky et al. |
| 2003/0023592 A1 | 1/2003 | Modica et al. |
| 2003/0025877 A1 | 2/2003 | Yancey et al. |
| 2003/0028115 A1 | 2/2003 | Thomas |
| 2003/0031334 A1 | 2/2003 | Layton et al. |
| 2003/0032866 A1 | 2/2003 | Winter et al. |
| 2003/0035001 A1 | 2/2003 | Van Geest et al. |
| 2003/0035803 A1 | 2/2003 | McMichael |
| 2003/0036907 A1 | 2/2003 | Stewart et al. |
| 2003/0038423 A1 | 2/2003 | Turner et al. |
| 2003/0038754 A1 | 2/2003 | Goldstein et al. |
| 2003/0040532 A1 | 2/2003 | Pratt |
| 2003/0040914 A1 | 2/2003 | Friedrich et al. |
| 2003/0040921 A1 | 2/2003 | Hughes et al. |
| 2003/0044472 A1 | 3/2003 | Lang |
| 2003/0045894 A1 | 3/2003 | Holladay |
| 2003/0046254 A1 | 3/2003 | Ryu et al. |
| 2003/0046401 A1 | 3/2003 | Abbott et al. |
| 2003/0050569 A1 | 3/2003 | Shenoy et al. |
| 2003/0050785 A1 | 3/2003 | Friedrich et al. |
| 2003/0052900 A1 | 3/2003 | Card et al. |
| 2003/0052903 A1 | 3/2003 | Weast |
| 2003/0052911 A1 | 3/2003 | Cohen-solal |
| 2003/0053026 A1 | 3/2003 | Roorda |
| 2003/0054326 A1 | 3/2003 | Aaron-Barrada |
| 2003/0055040 A1 | 3/2003 | Friedhoff et al. |
| 2003/0055328 A1 | 3/2003 | Paladini |
| 2003/0056279 A1 | 3/2003 | Garneau |
| 2003/0057859 A1 | 3/2003 | Van Dijk et al. |
| 2003/0058190 A1 | 3/2003 | Lewis et al. |
| 2003/0058253 A1 | 3/2003 | Edge et al. |
| 2003/0058406 A1 | 3/2003 | Blum et al. |
| 2003/0060878 A1 | 3/2003 | Shadduck |
| 2003/0064785 A1 | 4/2003 | Stone et al. |
| 2003/0065768 A1 | 4/2003 | Malik |
| 2003/0067476 A1 | 4/2003 | Miller et al. |
| 2003/0068605 A1 | 4/2003 | Kullok et al. |
| 2003/0069566 A1 | 4/2003 | Williams et al. |
| 2003/0071917 A1 | 4/2003 | Selby et al. |
| 2003/0073984 A1 | 4/2003 | Maeda |
| 2003/0076300 A1 | 4/2003 | Lauper et al. |
| 2003/0078513 A1 | 4/2003 | Marshall |
| 2003/0078753 A1 | 4/2003 | Campin et al. |
| 2003/0080182 A1 | 5/2003 | Gunther |
| 2003/0086062 A1 | 5/2003 | Shevlin |
| 2003/0086136 A1 | 5/2003 | Orr et al. |
| 2003/0090437 A1 | 5/2003 | Adams |
| 2003/0090626 A1 | 5/2003 | Lai et al. |
| 2003/0091215 A1 | 5/2003 | Lauper et al. |
| 2003/0091229 A1 | 5/2003 | Edge et al. |
| 2003/0093275 A1 | 5/2003 | Polanyi et al. |
| 2003/0093792 A1 | 5/2003 | Labeeb et al. |
| 2003/0095081 A1 | 5/2003 | Furness, III et al. |
| 2003/0097636 A1 | 5/2003 | Cleveland |
| 2003/0098954 A1 | 5/2003 | Amir et al. |
| 2003/0099920 A1 | 5/2003 | Edwards et al. |
| 2003/0099978 A1 | 5/2003 | Tsuji |
| 2003/0101124 A1 | 5/2003 | Semret et al. |
| 2003/0101449 A1 | 5/2003 | Bentolila et al. |
| 2003/0101451 A1 | 5/2003 | Bentolila et al. |
| 2003/0103664 A1 | 6/2003 | Wei et al. |
| 2003/0105395 A1 | 6/2003 | Fan et al. |
| 2003/0107707 A1 | 6/2003 | Fisher et al. |
| 2003/0108836 A1 | 6/2003 | Fisher |
| 2003/0110161 A1 | 6/2003 | Schneider |
| 2003/0110215 A1 | 6/2003 | Joao |
| 2003/0114808 A1 | 6/2003 | Underhill et al. |
| 2003/0117369 A1 | 6/2003 | Spitzer et al. |
| 2003/0117689 A1 | 6/2003 | Helsel et al. |
| 2003/0118975 A1 | 6/2003 | Stamm et al. |
| 2003/0119884 A1 | 6/2003 | Epstein et al. |
| 2003/0120140 A1 | 6/2003 | Bango, Jr. |
| 2003/0122066 A1 | 7/2003 | Dunfield |
| 2003/0122733 A1 | 7/2003 | Blackham et al. |
| 2003/0122828 A1 | 7/2003 | Lukyanitsa |
| 2003/0122942 A1 | 7/2003 | Parker et al. |
| 2003/0123027 A1 | 7/2003 | Amir et al. |
| 2003/0123754 A1 | 7/2003 | Toyama |
| 2003/0129576 A1 | 7/2003 | Wood et al. |
| 2003/0130992 A1 | 7/2003 | Tyan et al. |
| 2003/0133196 A1 | 7/2003 | Wine et al. |
| 2003/0134257 A1 | 7/2003 | Morsy et al. |
| 2003/0135186 A1 | 7/2003 | Olson et al. |
| 2003/0137730 A1 | 7/2003 | Fridman et al. |
| 2003/0138080 A1 | 7/2003 | Nelson et al. |
| 2003/0139942 A1 | 7/2003 | Rakshit et al. |
| 2003/0140088 A1 | 7/2003 | Robinson et al. |
| 2003/0142041 A1 | 7/2003 | Barlow et al. |
| 2003/0142067 A1 | 7/2003 | Kurtenbach et al. |
| 2003/0142099 A1 | 7/2003 | Deering et al. |
| 2003/0143119 A1 | 7/2003 | Schwartz et al. |
| 2003/0144598 A1 | 7/2003 | Zhang et al. |
| 2003/0144650 A1 | 7/2003 | Smith |
| 2003/0144651 A1 | 7/2003 | Teiwes et al. |
| 2003/0146901 A1 | 8/2003 | Ryan |
| 2003/0146915 A1 | 8/2003 | Brook et al. |
| 2003/0147046 A1 | 8/2003 | Shadduck |
| 2003/0147554 A1 | 8/2003 | Wei et al. |
| 2003/0149356 A1 | 8/2003 | Wei et al. |
| 2003/0149480 A1 | 8/2003 | Shadduck |
| 2003/0149549 A1 | 8/2003 | Paxton et al. |
| 2003/0152277 A1 | 8/2003 | Hall, Jr. et al. |
| 2003/0153841 A1 | 8/2003 | Kilborn |
| 2003/0153846 A1 | 8/2003 | Marple-Horvat |
| 2003/0153904 A1 | 8/2003 | Patel |
| 2003/0154291 A1 | 8/2003 | Ocheltree et al. |
| 2003/0156077 A1 | 8/2003 | Balogh |
| 2003/0156257 A1 | 8/2003 | Levola |
| 2003/0156260 A1 | 8/2003 | Putilin et al. |
| 2003/0156383 A1 | 8/2003 | Jenkins et al. |
| 2003/0156742 A1 | 8/2003 | Witt et al. |
| 2003/0157201 A1 | 8/2003 | Pandita et al. |
| 2003/0158543 A1 | 8/2003 | Van Saarloos |
| 2003/0160942 A1 | 8/2003 | Xie et al. |
| 2003/0160943 A1 | 8/2003 | Xie et al. |
| 2003/0161020 A1 | 8/2003 | Wine et al. |
| 2003/0161672 A1 | 8/2003 | Roberson |
| 2003/0162152 A1 | 8/2003 | Lee |
| 2003/0162161 A1 | 8/2003 | Horchler |
| 2003/0162825 A1 | 8/2003 | Heefner et al. |
| 2003/0163536 A1 | 8/2003 | Pettine, Jr. |
| 2003/0169213 A1 | 9/2003 | Spero |
| 2003/0169907 A1 | 9/2003 | Edwards et al. |

(56) References Cited

U.S. PATENT DOCUMENTS

| | | |
|---|---|---|
| 2003/0170690 A1 | 9/2003 | Shatz et al. |
| 2003/0174883 A1 | 9/2003 | Krishnan |
| 2003/0176855 A1 | 9/2003 | Gross et al. |
| 2003/0178031 A1 | 9/2003 | Du Pen et al. |
| 2003/0179427 A1 | 9/2003 | Lewis et al. |
| 2003/0184065 A1 | 10/2003 | Breed et al. |
| 2003/0184996 A1 | 10/2003 | Marshall |
| 2003/0186317 A1 | 10/2003 | Roch et al. |
| 2003/0191627 A1 | 10/2003 | Au |
| 2003/0194141 A1 | 10/2003 | Kortum et al. |
| 2003/0194142 A1 | 10/2003 | Kortum et al. |
| 2003/0194453 A1 | 10/2003 | Coleman et al. |
| 2003/0198393 A1 | 10/2003 | Berstis |
| 2003/0199769 A1 | 10/2003 | Podoleanu et al. |
| 2003/0201895 A1 | 10/2003 | Harter et al. |
| 2003/0208109 A1 | 11/2003 | David et al. |
| 2003/0208397 A1 | 11/2003 | VanDusen |
| 2003/0208409 A1 | 11/2003 | Mault |
| 2003/0208756 A1 | 11/2003 | Macrae et al. |
| 2003/0209893 A1 | 11/2003 | Breed et al. |
| 2003/0212579 A1 | 11/2003 | Brown et al. |
| 2003/0212811 A1 | 11/2003 | Thornton |
| 2003/0223039 A1 | 12/2003 | Thomas |
| 2003/0225031 A1 | 12/2003 | Quay |
| 2003/0225321 A1 | 12/2003 | Cote et al. |
| 2003/0225342 A1 | 12/2003 | Hong et al. |
| 2003/0225398 A1 | 12/2003 | Zepkin et al. |
| 2003/0225400 A1 | 12/2003 | Hohla |
| 2003/0225591 A1 | 12/2003 | Clay et al. |
| 2003/0227483 A1 | 12/2003 | Schultz et al. |
| 2003/0228058 A1 | 12/2003 | Xie et al. |
| 2003/0231293 A1 | 12/2003 | Blum et al. |
| 2003/0232319 A1 | 12/2003 | Grisham et al. |
| 2003/0232829 A1 | 12/2003 | Hassan et al. |
| 2003/0232890 A1 | 12/2003 | Epstein et al. |
| 2003/0234909 A1 | 12/2003 | Collender et al. |
| 2003/0235337 A1 | 12/2003 | Paragios et al. |
| 2003/0235571 A1 | 12/2003 | Gojon-Romanillos |
| 2003/0236086 A1 | 12/2003 | Litwin, Jr. |
| 2004/0002500 A1 | 1/2004 | Kramer et al. |
| 2004/0003409 A1 | 1/2004 | Berstis |
| 2004/0004376 A1 | 1/2004 | Cabebe |
| 2004/0005083 A1 | 1/2004 | Fujimura et al. |
| 2004/0008157 A1 | 1/2004 | Brubaker et al. |
| 2004/0010803 A1 | 1/2004 | Berstis |
| 2004/0012762 A1 | 1/2004 | Faris |
| 2004/0016287 A1 | 1/2004 | Fu |
| 2004/0017845 A1 | 1/2004 | Margetts et al. |
| 2004/0017865 A1 | 1/2004 | Litwin, Jr. et al. |
| 2004/0020983 A1 | 2/2004 | Feige et al. |
| 2004/0021768 A1 | 2/2004 | Payne et al. |
| 2004/0024287 A1 | 2/2004 | Patton et al. |
| 2004/0027501 A1 | 2/2004 | Blum et al. |
| 2004/0028359 A1 | 2/2004 | Tirloni et al. |
| 2004/0029088 A1 | 2/2004 | Forbes et al. |
| 2004/0030741 A1 | 2/2004 | Wolton et al. |
| 2004/0042347 A1 | 3/2004 | Born et al. |
| 2004/0043373 A1 | 3/2004 | Kaiserman |
| 2004/0045204 A1 | 3/2004 | Miano et al. |
| 2004/0047013 A1 | 3/2004 | Cai et al. |
| 2004/0048286 A1 | 3/2004 | Lee |
| 2004/0051846 A1 | 3/2004 | Blum et al. |
| 2004/0052409 A1 | 3/2004 | Bansal et al. |
| 2004/0053257 A1 | 3/2004 | Kelsoe, Jr. et al. |
| 2004/0054359 A1 | 3/2004 | Ruiz et al. |
| 2004/0054507 A1 | 3/2004 | Mott |
| 2004/0056421 A1 | 3/2004 | Chiu et al. |
| 2004/0056900 A1 | 3/2004 | Blume |
| 2004/0056986 A1 | 3/2004 | Blum et al. |
| 2004/0057001 A1 | 3/2004 | Kim |
| 2004/0057013 A1 | 3/2004 | Cappo et al. |
| 2004/0057498 A1 | 3/2004 | Litwin, Jr. |
| 2004/0058304 A1 | 3/2004 | Morsy et al. |
| 2004/0058308 A1 | 3/2004 | Neal |
| 2004/0059249 A1 | 3/2004 | Kajimoto et al. |
| 2004/0061041 A1 | 4/2004 | Ben-Ari et al. |
| 2004/0061831 A1 | 4/2004 | Aughey et al. |
| 2004/0066455 A1 | 4/2004 | Holmes |
| 2004/0070567 A1 | 4/2004 | Longe et al. |
| 2004/0072133 A1 | 4/2004 | Kullok et al. |
| 2004/0073931 A1 | 4/2004 | Trussell et al. |
| 2004/0075624 A1 | 4/2004 | Tegreene et al. |
| 2004/0075744 A1 | 4/2004 | Newman |
| 2004/0078031 A1 | 4/2004 | Somani et al. |
| 2004/0080467 A1 | 4/2004 | Chinthammit et al. |
| 2004/0081945 A1 | 4/2004 | Reeves et al. |
| 2004/0085261 A1 | 5/2004 | Lewis et al. |
| 2004/0085292 A1 | 5/2004 | Spitzer et al. |
| 2004/0085617 A1 | 5/2004 | Helsel et al. |
| 2004/0092530 A1 | 5/2004 | Tsai et al. |
| 2004/0095359 A1 | 5/2004 | Simon et al. |
| 2004/0097577 A1 | 5/2004 | Kruisinga |
| 2004/0100088 A1 | 5/2004 | Tellenbach et al. |
| 2004/0100466 A1 | 5/2004 | Deering |
| 2004/0100567 A1 | 5/2004 | Miller et al. |
| 2004/0100620 A1 | 5/2004 | Glaser |
| 2004/0100704 A1 | 5/2004 | Shadduck |
| 2004/0101086 A1 | 5/2004 | Sabol et al. |
| 2004/0101104 A1 | 5/2004 | Avinash et al. |
| 2004/0101178 A1 | 5/2004 | Fedorovskaya et al. |
| 2004/0101212 A1 | 5/2004 | Fedorovskaya et al. |
| 2004/0102713 A1 | 5/2004 | Dunn |
| 2004/0103021 A1 | 5/2004 | Scarfe et al. |
| 2004/0103111 A1 | 5/2004 | Miller et al. |
| 2004/0105010 A1 | 6/2004 | Osen |
| 2004/0105264 A1 | 6/2004 | Spero |
| 2004/0106929 A1 | 6/2004 | Masket |
| 2004/0108971 A1 | 6/2004 | Waldern et al. |
| 2004/0111083 A1 | 6/2004 | Gross et al. |
| 2004/0111366 A1 | 6/2004 | Schneider |
| 2004/0111411 A1 | 6/2004 | Koch |
| 2004/0114632 A1 | 6/2004 | Yuuki et al. |
| 2004/0115603 A1 | 6/2004 | Reynolds |
| 2004/0116502 A1 | 6/2004 | Comings et al. |
| 2004/0119004 A1 | 6/2004 | Wine et al. |
| 2004/0121419 A1 | 6/2004 | Markovitz et al. |
| 2004/0122051 A1 | 6/2004 | Pratt |
| 2004/0124971 A1 | 7/2004 | MacTavish et al. |
| 2004/0125121 A1 | 7/2004 | Pea et al. |
| 2004/0125133 A1 | 7/2004 | Pea et al. |
| 2004/0125148 A1 | 7/2004 | Pea et al. |
| 2004/0129478 A1 | 7/2004 | Breed et al. |
| 2004/0135968 A1 | 7/2004 | Morgan et al. |
| 2004/0137414 A1 | 7/2004 | Ho et al. |
| 2004/0140699 A1 | 7/2004 | Akpom |
| 2004/0143244 A1 | 7/2004 | Gray et al. |
| 2004/0143245 A1 | 7/2004 | Gray et al. |
| 2004/0148243 A1 | 7/2004 | Rosenblatt |
| 2004/0150657 A1 | 8/2004 | Wittenburg et al. |
| 2004/0152062 A1 | 8/2004 | Adams |
| 2004/0152946 A1 | 8/2004 | Franck |
| 2004/0156020 A1 | 8/2004 | Edwards |
| 2004/0156554 A1 | 8/2004 | McIntyre |
| 2004/0158883 A1 | 8/2004 | Crawford et al. |
| 2004/0160576 A1 | 8/2004 | Lai et al. |
| 2004/0160995 A1 | 8/2004 | Sauter et al. |
| 2004/0161134 A1 | 8/2004 | Kawato et al. |
| 2004/0165099 A1 | 8/2004 | Stavely et al. |
| 2004/0167380 A1 | 8/2004 | Simon |
| 2004/0167585 A1 | 8/2004 | Kovak et al. |
| 2004/0168117 A1 | 8/2004 | Renaud |
| 2004/0172252 A1 | 9/2004 | Aoki et al. |
| 2004/0172255 A1 | 9/2004 | Aoki et al. |
| 2004/0174375 A1 | 9/2004 | Credelle et al. |
| 2004/0174496 A1 | 9/2004 | Ji et al. |
| 2004/0174498 A1 | 9/2004 | Zorn et al. |
| 2004/0175020 A1 | 9/2004 | Bradski et al. |
| 2004/0178890 A1 | 9/2004 | Williams et al. |
| 2004/0179254 A1 | 9/2004 | Lewis et al. |
| 2004/0179716 A1 | 9/2004 | Tafuku et al. |
| 2004/0181168 A1 | 9/2004 | Plant et al. |
| 2004/0182397 A1 | 9/2004 | Wood |
| 2004/0183749 A1 | 9/2004 | Vertegaal |
| 2004/0184145 A1 | 9/2004 | Fridman et al. |

(56) References Cited

U.S. PATENT DOCUMENTS

| | | |
|---|---|---|
| 2004/0184158 A1 | 9/2004 | Shadduck |
| 2004/0185468 A1 | 9/2004 | Leonard et al. |
| 2004/0189939 A1 | 9/2004 | Dick et al. |
| 2004/0193068 A1* | 9/2004 | Burton et al. ............ 600/544 |
| 2004/0196214 A1 | 10/2004 | Maguire, Jr. |
| 2004/0196359 A1 | 10/2004 | Blackham |
| 2004/0196399 A1 | 10/2004 | Stavely |
| 2004/0196433 A1 | 10/2004 | Durnell |
| 2004/0196518 A1 | 10/2004 | Wine et al. |
| 2004/0196830 A1 | 10/2004 | Poniatowski |
| 2004/0197750 A1 | 10/2004 | Donaher et al. |
| 2004/0199150 A1 | 10/2004 | Lai |
| 2004/0200748 A1 | 10/2004 | Klassen et al. |
| 2004/0203317 A1 | 10/2004 | Small |
| 2004/0203556 A1 | 10/2004 | Litwin |
| 2004/0205065 A1 | 10/2004 | Petras et al. |
| 2004/0205505 A1 | 10/2004 | Vans et al. |
| 2004/0205579 A1 | 10/2004 | Brassell et al. |
| 2004/0205651 A1 | 10/2004 | Dutta et al. |
| 2004/0207599 A1 | 10/2004 | Kurtenbach et al. |
| 2004/0207632 A1 | 10/2004 | Miller et al. |
| 2004/0207635 A1 | 10/2004 | Miller et al. |
| 2004/0210139 A1 | 10/2004 | Coleman et al. |
| 2004/0210159 A1 | 10/2004 | Kibar |
| 2004/0210479 A1 | 10/2004 | Perkowski et al. |
| 2004/0212149 A1 | 10/2004 | Farmer |
| 2004/0212695 A1 | 10/2004 | Stavely et al. |
| 2004/0212712 A1 | 10/2004 | Stavely et al. |
| 2004/0213829 A1 | 10/2004 | Coleman et al. |
| 2004/0215095 A1 | 10/2004 | Lee et al. |
| 2004/0215464 A1 | 10/2004 | Nelson |
| 2004/0216049 A1 | 10/2004 | Lewis et al. |
| 2004/0219496 A1 | 11/2004 | Stevinson |
| 2004/0219499 A1 | 11/2004 | Cesa |
| 2004/0219502 A1 | 11/2004 | Bechard et al. |
| 2004/0220493 A1 | 11/2004 | Teicher et al. |
| 2004/0220704 A1 | 11/2004 | Lin et al. |
| 2004/0223202 A1 | 11/2004 | Lippert et al. |
| 2004/0223218 A1 | 11/2004 | Putilin et al. |
| 2004/0225284 A1 | 11/2004 | Webb et al. |
| 2004/0225555 A1 | 11/2004 | Persidis et al. |
| 2004/0227699 A1 | 11/2004 | Mitchell |
| 2004/0227769 A9 | 11/2004 | Edge et al. |
| 2004/0227992 A1 | 11/2004 | Putilin et al. |
| 2004/0229198 A1 | 11/2004 | Boyd et al. |
| 2004/0229948 A1 | 11/2004 | Summar et al. |
| 2004/0230549 A1* | 11/2004 | Freer et al. ............ 706/61 |
| 2004/0231206 A1 | 11/2004 | Liebman et al. |
| 2004/0233061 A1 | 11/2004 | Johns |
| 2004/0233157 A1 | 11/2004 | Sekiya et al. |
| 2004/0233200 A1 | 11/2004 | Karren |
| 2004/0233277 A1 | 11/2004 | Miller et al. |
| 2004/0235795 A1 | 11/2004 | Jager et al. |
| 2004/0240709 A1 | 12/2004 | Shoemaker |
| 2004/0243681 A1 | 12/2004 | Strub |
| 2004/0247183 A1 | 12/2004 | Molander |
| 2004/0252277 A1 | 12/2004 | Chmielewski, Jr. et al. |
| 2004/0254441 A1 | 12/2004 | Schrunder |
| 2004/0257529 A1 | 12/2004 | Thomas |
| 2004/0260156 A1 | 12/2004 | David et al. |
| 2004/0264012 A1 | 12/2004 | McWhirter et al. |
| 2004/0265312 A1 | 12/2004 | McMichael |
| 2004/0267320 A1 | 12/2004 | Taylor et al. |
| 2005/0001013 A1 | 1/2005 | Xie et al. |
| 2005/0004046 A1 | 1/2005 | Praag et al. |
| 2005/0004446 A1 | 1/2005 | Cowan et al. |
| 2005/0004838 A1 | 1/2005 | Perkowski et al. |
| 2005/0005245 A1 | 1/2005 | Card et al. |
| 2005/0005246 A1 | 1/2005 | Card et al. |
| 2005/0007479 A1 | 1/2005 | Ahiska |
| 2005/0007552 A1 | 1/2005 | Fergason et al. |
| 2005/0008208 A1 | 1/2005 | Cowan et al. |
| 2005/0010443 A1 | 1/2005 | Zammitt |
| 2005/0010475 A1 | 1/2005 | Perkowski et al. |
| 2005/0010949 A1 | 1/2005 | Ward et al. |
| 2005/0012897 A1 | 1/2005 | Watkins |
| 2005/0013002 A1 | 1/2005 | Faris |
| 2005/0015309 A1 | 1/2005 | Fracek, Jr. et al. |
| 2005/0015376 A1 | 1/2005 | Fraser et al. |
| 2005/0015744 A1 | 1/2005 | Bushey et al. |
| 2005/0017488 A1 | 1/2005 | Breed et al. |
| 2005/0017877 A1 | 1/2005 | Sabatino |
| 2005/0017924 A1 | 1/2005 | Utt et al. |
| 2005/0018911 A1 | 1/2005 | Deever |
| 2005/0019734 A1 | 1/2005 | Peled |
| 2005/0020910 A1 | 1/2005 | Quadling et al. |
| 2005/0024586 A1 | 2/2005 | Teiwes et al. |
| 2005/0027538 A1 | 2/2005 | Halonen et al. |
| 2005/0028221 A1 | 2/2005 | Liu et al. |
| 2005/0028821 A1 | 2/2005 | Wood et al. |
| 2005/0030305 A1 | 2/2005 | Brown et al. |
| 2005/0033122 A1 | 2/2005 | Balkin et al. |
| 2005/0033143 A1 | 2/2005 | O'Donnell et al. |
| 2005/0033632 A1 | 2/2005 | Wu et al. |
| 2005/0038653 A1 | 2/2005 | Roth et al. |
| 2005/0038657 A1 | 2/2005 | Roth et al. |
| 2005/0039121 A1 | 2/2005 | Cleveland |
| 2005/0041100 A1 | 2/2005 | Maguire, Jr. |
| 2005/0043947 A1 | 2/2005 | Roth et al. |
| 2005/0043949 A1 | 2/2005 | Roth et al. |
| 2005/0043954 A1 | 2/2005 | Roth et al. |
| 2005/0045182 A1 | 3/2005 | Wood et al. |
| 2005/0046584 A1 | 3/2005 | Breed |
| 2005/0046953 A1 | 3/2005 | Repetto et al. |
| 2005/0047629 A1 | 3/2005 | Farrell et al. |
| 2005/0049880 A1 | 3/2005 | Roth et al. |
| 2005/0051177 A1 | 3/2005 | Wood et al. |
| 2005/0052406 A1 | 3/2005 | Stephanick et al. |
| 2005/0053274 A1 | 3/2005 | Mayer et al. |
| 2005/0054837 A1 | 3/2005 | Brenneman et al. |
| 2005/0055069 A1 | 3/2005 | Franck |
| 2005/0058328 A1 | 3/2005 | Moreau-Gobard |
| 2005/0059743 A1 | 3/2005 | Epstein et al. |
| 2005/0060362 A1 | 3/2005 | Wolinsky et al. |
| 2005/0060365 A1 | 3/2005 | Robinson et al. |
| 2005/0068185 A1 | 3/2005 | Nath et al. |
| 2005/0068343 A1 | 3/2005 | Pan et al. |
| 2005/0071214 A1 | 3/2005 | Kover et al. |
| 2005/0073136 A1 | 4/2005 | Larsson et al. |
| 2005/0074277 A1 | 4/2005 | Brown et al. |
| 2005/0079636 A1 | 4/2005 | White et al. |
| 2005/0080592 A1 | 4/2005 | Buscema et al. |
| 2005/0080878 A1 | 4/2005 | Cunningham et al. |
| 2005/0083516 A1 | 4/2005 | Baker |
| 2005/0085343 A1 | 4/2005 | Burrows et al. |
| 2005/0086610 A1 | 4/2005 | Mackinlay et al. |
| 2005/0088981 A1 | 4/2005 | Woodruff et al. |
| 2005/0091742 A1 | 5/2005 | Bennett |
| 2005/0093861 A1 | 5/2005 | Moreau-Gobard |
| 2005/0094262 A1 | 5/2005 | Spediacci et al. |
| 2005/0095055 A1 | 5/2005 | Kwan et al. |
| 2005/0096317 A1 | 5/2005 | Glasky et al. |
| 2005/0096521 A1 | 5/2005 | Andersen et al. |
| 2005/0096640 A1 | 5/2005 | Dai et al. |
| 2005/0097570 A1 | 5/2005 | Bomers |
| 2005/0099416 A1 | 5/2005 | Moreau-Gobard et al. |
| 2005/0099600 A1 | 5/2005 | Frey et al. |
| 2005/0099601 A1 | 5/2005 | MacDougall et al. |
| 2005/0100195 A1 | 5/2005 | Li |
| 2005/0101877 A1 | 5/2005 | Miller et al. |
| 2005/0102008 A1 | 5/2005 | Wong |
| 2005/0102171 A1 | 5/2005 | Ashley et al. |
| 2005/0104900 A1 | 5/2005 | Toyama et al. |
| 2005/0105768 A1 | 5/2005 | Yang et al. |
| 2005/0106536 A1 | 5/2005 | Liebermann |
| 2005/0108092 A1 | 5/2005 | Campbell et al. |
| 2005/0108642 A1 | 5/2005 | Sinclair II |
| 2005/0110950 A1 | 5/2005 | Thorpe et al. |
| 2005/0110951 A1 | 5/2005 | Yancey et al. |
| 2005/0116929 A1 | 6/2005 | Molander et al. |
| 2005/0116961 A9 | 6/2005 | Edge et al. |
| 2005/0119059 A1 | 6/2005 | Marshall |
| 2005/0119638 A1 | 6/2005 | Jensen |
| 2005/0119642 A1 | 6/2005 | Grecu et al. |

(56) References Cited

U.S. PATENT DOCUMENTS

| | | |
|---|---|---|
| 2005/0121037 A1 | 6/2005 | Wood |
| 2005/0124851 A1 | 6/2005 | Patton et al. |
| 2005/0124983 A1 | 6/2005 | Frey et al. |
| 2005/0130136 A1 | 6/2005 | Lee |
| 2005/0130937 A1 | 6/2005 | Ben Dror et al. |
| 2005/0131607 A1 | 6/2005 | Breed |
| 2005/0132290 A1 | 6/2005 | Buchner et al. |
| 2005/0133039 A1 | 6/2005 | Wood |
| 2005/0133040 A1 | 6/2005 | Wood |
| 2005/0134589 A1 | 6/2005 | Heer et al. |
| 2005/0134600 A1 | 6/2005 | Credelle et al. |
| 2005/0134735 A1 | 6/2005 | Swartz |
| 2005/0134799 A1 | 6/2005 | Thompson et al. |
| 2005/0135482 A1 | 6/2005 | Nair et al. |
| 2005/0135483 A1 | 6/2005 | Nair |
| 2005/0135485 A1 | 6/2005 | Nair et al. |
| 2005/0137543 A1 | 6/2005 | Underhill et al. |
| 2005/0137586 A1 | 6/2005 | Gray et al. |
| 2005/0138564 A1 | 6/2005 | Fogg |
| 2005/0139678 A1 | 6/2005 | Helsel et al. |
| 2005/0140924 A1 | 6/2005 | Blum et al. |
| 2005/0141765 A1 | 6/2005 | Liang et al. |
| 2005/0142524 A1 | 6/2005 | Simon et al. |
| 2005/0143434 A1 | 6/2005 | Fang et al. |
| 2005/0143443 A1 | 6/2005 | Fang et al. |
| 2005/0143630 A1 | 6/2005 | Darby et al. |
| 2005/0146787 A1 | 7/2005 | Lukyanitsa |
| 2005/0148894 A1 | 7/2005 | Misczynski et al. |
| 2005/0149183 A1 | 7/2005 | Shadduck |
| 2005/0149286 A1 | 7/2005 | Acar et al. |
| 2005/0150496 A1 | 7/2005 | Smaldone |
| 2005/0153268 A1 | 7/2005 | Junkin et al. |
| 2005/0156594 A1 | 7/2005 | Lorenz |
| 2005/0157359 A1 | 7/2005 | Bjelkhagen et al. |
| 2005/0159790 A1 | 7/2005 | Shalev |
| 2005/0159948 A1 | 7/2005 | Roth et al. |
| 2005/0159950 A1 | 7/2005 | Roth et al. |
| 2005/0159957 A1 | 7/2005 | Roth et al. |
| 2005/0162511 A1 | 7/2005 | Jackson |
| 2005/0163278 A1 | 7/2005 | Metz et al. |
| 2005/0165009 A1 | 7/2005 | Ishiuchi |
| 2005/0165327 A1 | 7/2005 | Thibault et al. |
| 2005/0165849 A1 | 7/2005 | Moradi et al. |
| 2005/0167439 A1 | 8/2005 | Chandler et al. |
| 2005/0168402 A1 | 8/2005 | Culbertson et al. |
| 2005/0168492 A1 | 8/2005 | Hekstra et al. |
| 2005/0168687 A1 | 8/2005 | Blum et al. |
| 2005/0168809 A1 | 8/2005 | Moller et al. |
| 2005/0169527 A1 | 8/2005 | Longe et al. |
| 2005/0171416 A1 | 8/2005 | Proniewicz et al. |
| 2005/0171514 A1 | 8/2005 | Van Saarloos |
| 2005/0173172 A1 | 8/2005 | Artis et al. |
| 2005/0175218 A1 | 8/2005 | Vertegaal et al. |
| 2005/0177065 A1 | 8/2005 | Ghajar |
| 2005/0177375 A1 | 8/2005 | Friedrich et al. |
| 2005/0180264 A1 | 8/2005 | Farinella et al. |
| 2005/0180541 A1 | 8/2005 | Avinash et al. |
| 2005/0180604 A1 | 8/2005 | Toyama |
| 2005/0180605 A1 | 8/2005 | Toyama |
| 2005/0184954 A1 | 8/2005 | Adams et al. |
| 2005/0185051 A1 | 8/2005 | Perlin |
| 2005/0185281 A1 | 8/2005 | Perlin et al. |
| 2005/0185841 A1 | 8/2005 | Tyan et al. |
| 2005/0185945 A1 | 8/2005 | Zhang et al. |
| 2005/0186006 A1 | 8/2005 | Roberson |
| 2005/0186881 A1 | 8/2005 | Gatto |
| 2005/0187436 A1 | 8/2005 | Doniger et al. |
| 2005/0190180 A1 | 9/2005 | Jin et al. |
| 2005/0192202 A1 | 9/2005 | Felton et al. |
| 2005/0192563 A1 | 9/2005 | Platt et al. |
| 2005/0193954 A1 | 9/2005 | Cureton et al. |
| 2005/0195165 A1 | 9/2005 | Mitchell |
| 2005/0195190 A1 | 9/2005 | Williams et al. |
| 2005/0195278 A1 | 9/2005 | Nair |
| 2005/0196018 A1 | 9/2005 | Toyama |
| 2005/0196041 A1 | 9/2005 | Jerebko et al. |
| 2005/0196045 A1 | 9/2005 | Zoghlami et al. |
| 2005/0196735 A1 | 9/2005 | Buschke |
| 2005/0197556 A1 | 9/2005 | Stoler |
| 2005/0197655 A1 | 9/2005 | Telfair et al. |
| 2005/0198316 A1 | 9/2005 | Gold et al. |
| 2005/0200609 A1 | 9/2005 | Van der Hoeven |
| 2005/0200806 A1 | 9/2005 | Knaan et al. |
| 2005/0201601 A1 | 9/2005 | Sun et al. |
| 2005/0206583 A1 | 9/2005 | Lemelson et al. |
| 2005/0206844 A1 | 9/2005 | Blum et al. |
| 2005/0207486 A1 | 9/2005 | Lee et al. |
| 2005/0213027 A1 | 9/2005 | Blum et al. |
| 2005/0213792 A1 | 9/2005 | Hammoud |
| 2005/0215986 A1 | 9/2005 | Chernyak et al. |
| 2005/0216243 A1 | 9/2005 | Graham et al. |
| 2005/0219458 A1 | 10/2005 | Lindacher et al. |
| 2005/0219460 A1 | 10/2005 | Blum et al. |
| 2005/0222524 A1 | 10/2005 | Fielding et al. |
| 2005/0223340 A1 | 10/2005 | Repka |
| 2005/0223341 A1 | 10/2005 | Repka |
| 2005/0223342 A1 | 10/2005 | Repka et al. |
| 2005/0225723 A1 | 10/2005 | Pilu |
| 2005/0227578 A1 | 10/2005 | Clark et al. |
| 2005/0227929 A1 | 10/2005 | Masferrer |
| 2005/0228256 A1 | 10/2005 | Labadie et al. |
| 2005/0231683 A1 | 10/2005 | Ben-Zeev et al. |
| 2005/0233755 A1 | 10/2005 | Jacovi et al. |
| 2005/0233772 A1 | 10/2005 | McDonnell |
| 2005/0233976 A1 | 10/2005 | Pearlman |
| 2005/0235031 A1 | 10/2005 | Schneider et al. |
| 2005/0235999 A1 | 10/2005 | Wood et al. |
| 2005/0236000 A1 | 10/2005 | Wood |
| 2005/0237390 A1 | 10/2005 | Mittal et al. |
| 2005/0237485 A1 | 10/2005 | Blum et al. |
| 2005/0239036 A1 | 10/2005 | McGar et al. |
| 2005/0239584 A1 | 10/2005 | Willyerd |
| 2005/0240099 A1 | 10/2005 | Sun et al. |
| 2005/0240253 A1 | 10/2005 | Tyler et al. |
| 2005/0240432 A1 | 10/2005 | Jensen |
| 2005/0243054 A1 | 11/2005 | Beymer et al. |
| 2005/0244510 A1 | 11/2005 | Smith |
| 2005/0245444 A1 | 11/2005 | Echelard et al. |
| 2005/0246318 A1 | 11/2005 | Giang et al. |
| 2005/0246734 A1 | 11/2005 | Kover et al. |
| 2005/0247635 A1 | 11/2005 | Vo et al. |
| 2005/0247745 A1 | 11/2005 | Spor et al. |
| 2005/0248136 A1 | 11/2005 | Breed et al. |
| 2005/0248503 A1 | 11/2005 | Schobben et al. |
| 2005/0249399 A1 | 11/2005 | Tek et al. |
| 2005/0249827 A1 | 11/2005 | Gardiner et al. |
| 2005/0250812 A1 | 11/2005 | Pratt |
| 2005/0250851 A1 | 11/2005 | Tsai et al. |
| 2005/0251115 A1 | 11/2005 | Cox et al. |
| 2005/0251456 A1 | 11/2005 | Perkowski |
| 2005/0251746 A1 | 11/2005 | Basson et al. |
| 2005/0251755 A1 | 11/2005 | Mullins et al. |
| 2005/0252515 A1 | 11/2005 | Wood |
| 2005/0253845 A1 | 11/2005 | Russ et al. |
| 2005/0253846 A1 | 11/2005 | Russ et al. |
| 2005/0254009 A1 | 11/2005 | Baker et al. |
| 2005/0256399 A1 | 11/2005 | Sirohey et al. |
| 2005/0257137 A1 | 11/2005 | Weber et al. |
| 2005/0259848 A1 | 11/2005 | Garoutte |
| 2005/0260547 A1 | 11/2005 | Moody |
| 2005/0260654 A1 | 11/2005 | Wang et al. |
| 2005/0260697 A1 | 11/2005 | Wang et al. |
| 2005/0261557 A1 | 11/2005 | Baker |
| 2005/0262447 A1 | 11/2005 | Shoemaker |
| 2005/0264558 A1 | 12/2005 | Vesely et al. |
| 2005/0264559 A1 | 12/2005 | Vesely et al. |
| 2005/0264857 A1 | 12/2005 | Vesely et al. |
| 2005/0264858 A1 | 12/2005 | Vesely et al. |
| 2005/0264894 A1 | 12/2005 | Shoemaker et al. |
| 2005/0265317 A1 | 12/2005 | Reeves et al. |
| 2005/0265977 A1 | 12/2005 | Elliott et al. |
| 2005/0266767 A1 | 12/2005 | Jeske |
| 2005/0267826 A1 | 12/2005 | Levy et al. |
| 2005/0268250 A1 | 12/2005 | Skistimas et al. |

(56) References Cited

U.S. PATENT DOCUMENTS

| | | |
|---|---|---|
| 2005/0270481 A1 | 12/2005 | Blum et al. |
| 2005/0270486 A1 | 12/2005 | Teiwes et al. |
| 2005/0270494 A1 | 12/2005 | Banning |
| 2005/0271600 A1 | 12/2005 | Coleman et al. |
| 2005/0272992 A1 | 12/2005 | O'Donnell et al. |
| 2005/0273017 A1 | 12/2005 | Gordon |
| 2005/0273141 A1 | 12/2005 | Greenberg et al. |
| 2005/0273185 A1 | 12/2005 | Teiwes et al. |
| 2005/0274858 A1 | 12/2005 | Fedewa |
| 2005/0275262 A1 | 12/2005 | Mills et al. |
| 2005/0275525 A1 | 12/2005 | Ahmed |
| 2005/0275620 A1 | 12/2005 | Manal |
| 2005/0275913 A1 | 12/2005 | Vesely et al. |
| 2005/0275914 A1 | 12/2005 | Vesely et al. |
| 2005/0275915 A1 | 12/2005 | Vesely et al. |
| 2005/0277101 A1 | 12/2005 | Cadman |
| 2005/0278047 A1 | 12/2005 | Ahmed |
| 2005/0280603 A1 | 12/2005 | Aughey et al. |
| 2005/0281411 A1 | 12/2005 | Vesely et al. |
| 2005/0281440 A1 | 12/2005 | Pemer |
| 2005/0282120 A1 | 12/2005 | Whittaker |
| 2005/0282603 A1 | 12/2005 | Parrott et al. |
| 2005/0283202 A1 | 12/2005 | Gellman |
| 2005/0285861 A1 | 12/2005 | Fraser |
| 2005/0285875 A1 | 12/2005 | Kang et al. |
| 2005/0286759 A1 | 12/2005 | Zitnick, III et al. |
| 2005/0288375 A1 | 12/2005 | Hobden et al. |
| 2005/0288564 A1 | 12/2005 | Iuliano |
| 2005/0288733 A1 | 12/2005 | Greenberg et al. |
| 2005/0288734 A1 | 12/2005 | Greenberg et al. |
| 2005/0288735 A1 | 12/2005 | Greenberg et al. |
| 2005/0289582 A1 | 12/2005 | Tavares et al. |
| 2005/0289662 A1 | 12/2005 | Meier |
| 2006/0002070 A1 | 1/2006 | Jenkins et al. |
| 2006/0003989 A1 | 1/2006 | Quay et al. |
| 2006/0006988 A1 | 1/2006 | Harter, Jr. et al. |
| 2006/0007188 A1 | 1/2006 | Reiner |
| 2006/0007396 A1 | 1/2006 | Clement et al. |
| 2006/0011716 A1 | 1/2006 | Perkowski |
| 2006/0013473 A1 | 1/2006 | Woodfill et al. |
| 2006/0016109 A1 | 1/2006 | Nicolaas |
| 2006/0017887 A1 | 1/2006 | Jacobson et al. |
| 2006/0018839 A1 | 1/2006 | Ieni et al. |
| 2006/0018921 A1 | 1/2006 | Levenson et al. |
| 2006/0019227 A1 | 1/2006 | Hardwicke |
| 2006/0020299 A1 | 1/2006 | Shalev |
| 2006/0022833 A1 | 2/2006 | Ferguson et al. |
| 2006/0024391 A1 | 2/2006 | Lak |
| 2006/0026081 A1 | 2/2006 | Keil et al. |
| 2006/0027147 A1 | 2/2006 | Liabraaten et al. |
| 2006/0028400 A1 | 2/2006 | Lapstun et al. |
| 2006/0028473 A1 | 2/2006 | Uyttendaele et al. |
| 2006/0028489 A1 | 2/2006 | Uyttendaele et al. |
| 2006/0029295 A1 | 2/2006 | Wine et al. |
| 2006/0031525 A1 | 2/2006 | Reeves et al. |
| 2006/0033762 A1 | 2/2006 | Card et al. |
| 2006/0036200 A1 | 2/2006 | Connor |
| 2006/0036296 A1 | 2/2006 | Greenberg et al. |
| 2006/0040582 A1 | 2/2006 | Hopper et al. |
| 2006/0044136 A1 | 3/2006 | Kowal et al. |
| 2006/0046232 A1 | 3/2006 | Peter |
| 2006/0047226 A1 | 3/2006 | Wood |
| 2006/0048059 A1 | 3/2006 | Etkin |
| 2006/0050091 A1 | 3/2006 | Shoemaker et al. |
| 2006/0050384 A1 | 3/2006 | Agostinelli |
| 2006/0052428 A1 | 3/2006 | Chez |
| 2006/0052675 A1 | 3/2006 | Grand |
| 2006/0052690 A1 | 3/2006 | Sirohey et al. |
| 2006/0058241 A1 | 3/2006 | Geier et al. |
| 2006/0058619 A1 | 3/2006 | DeYoe et al. |
| 2006/0058853 A1 | 3/2006 | Bentwich |
| 2006/0059065 A1 | 3/2006 | Glinberg et al. |
| 2006/0059112 A1 | 3/2006 | Cheng et al. |
| 2006/0061729 A1 | 3/2006 | Shadduck |
| 2006/0062838 A1 | 3/2006 | DiPierro et al. |
| 2006/0062859 A1 | 3/2006 | Blum et al. |
| 2006/0063703 A1 | 3/2006 | Prange et al. |
| 2006/0066067 A1 | 3/2006 | Williams |
| 2006/0066738 A1 | 3/2006 | Hershey et al. |
| 2006/0069107 A1 | 3/2006 | Shiozaki et al. |
| 2006/0069635 A1 | 3/2006 | Ram et al. |
| 2006/0070426 A1 | 4/2006 | Pelletier |
| 2006/0074049 A1 | 4/2006 | Krathwohl et al. |
| 2006/0074686 A1 | 4/2006 | Vignoli |
| 2006/0074742 A1 | 4/2006 | Santandrea |
| 2006/0078184 A1 | 4/2006 | Shen et al. |
| 2006/0079355 A1 | 4/2006 | May et al. |
| 2006/0079495 A1 | 4/2006 | Blum |
| 2006/0081251 A1 | 4/2006 | Hernandez et al. |
| 2006/0081252 A1 | 4/2006 | Wood |
| 2006/0082542 A1 | 4/2006 | Morita et al. |
| 2006/0082852 A1 | 4/2006 | Wine et al. |
| 2006/0082901 A1 | 4/2006 | Shoemaker |
| 2006/0084952 A1 | 4/2006 | Pallikaris et al. |
| 2006/0087614 A1 | 4/2006 | Shadduck |
| 2006/0087617 A1 | 4/2006 | Roorda |
| 2006/0087618 A1 | 4/2006 | Smart et al. |
| 2006/0088143 A1 | 4/2006 | Tapaninen |
| 2006/0090362 A1 | 5/2006 | Wood |
| 2006/0090381 A1 | 5/2006 | Bandak |
| 2006/0090626 A1 | 5/2006 | Harrison |
| 2006/0092164 A1 | 5/2006 | Takeuchi et al. |
| 2006/0093187 A1 | 5/2006 | Mittal et al. |
| 2006/0093998 A1 | 5/2006 | Vertegaal |
| 2006/0095418 A1 | 5/2006 | Anderson |
| 2006/0095419 A1 | 5/2006 | Anderson |
| 2006/0095453 A1 | 5/2006 | Miller et al. |
| 2006/0098028 A1 | 5/2006 | Baar |
| 2006/0098087 A1 | 5/2006 | Brandt et al. |
| 2006/0098164 A1 | 5/2006 | Blum et al. |
| 2006/0098882 A1 | 5/2006 | Kortum et al. |
| 2006/0099239 A1 | 5/2006 | Coleman et al. |
| 2006/0100642 A1 | 5/2006 | Yang et al. |
| 2006/0103839 A1 | 5/2006 | Somani et al. |
| 2006/0104545 A1 | 5/2006 | Matsumoto |
| 2006/0109237 A1 | 5/2006 | Morita et al. |
| 2006/0109238 A1 | 5/2006 | Lau et al. |
| 2006/0109242 A1 | 5/2006 | Simpkins |
| 2006/0109283 A1 | 5/2006 | Shipman et al. |
| 2006/0110008 A1 | 5/2006 | Vertegaal et al. |
| 2006/0111448 A1 | 5/2006 | Epstein et al. |
| 2006/0111910 A1 | 5/2006 | Nelson |
| 2006/0111918 A1 | 5/2006 | Ducheneaut et al. |
| 2006/0112325 A1 | 5/2006 | Ducheneaut et al. |
| 2006/0112334 A1 | 5/2006 | Endrikhovski et al. |
| 2006/0112343 A1 | 5/2006 | Ducheneaut et al. |
| 2006/0112344 A1 | 5/2006 | Ducheneaut et al. |
| 2006/0114414 A1 | 6/2006 | McGrath et al. |
| 2006/0116597 A1 | 6/2006 | Vesely et al. |
| 2006/0116598 A1 | 6/2006 | Vesely et al. |
| 2006/0116600 A1 | 6/2006 | Vesely et al. |
| 2006/0116900 A1 | 6/2006 | Jensen |
| 2006/0118118 A1 | 6/2006 | Smaldone |
| 2006/0119572 A1 | 6/2006 | Lanier |
| 2006/0123978 A1 | 6/2006 | Kubitz et al. |
| 2006/0124131 A1 | 6/2006 | Chandran et al. |
| 2006/0130253 A1 | 6/2006 | Rycroft |
| 2006/0132790 A1 | 6/2006 | Gutin |
| 2006/0132915 A1 | 6/2006 | Yang et al. |
| 2006/0135460 A1 | 6/2006 | Widder et al. |
| 2006/0135879 A1 | 6/2006 | Liley |
| 2006/0136245 A1 | 6/2006 | Denissov |
| 2006/0136292 A1 | 6/2006 | Bhati et al. |
| 2006/0136385 A1 | 6/2006 | Bobrow et al. |
| 2006/0136451 A1 | 6/2006 | Denissov |
| 2006/0136839 A1 | 6/2006 | Makela |
| 2006/0139318 A1 | 6/2006 | Kariathungal et al. |
| 2006/0139319 A1 | 6/2006 | Kariathungal et al. |
| 2006/0139321 A1 | 6/2006 | Sakaguchi |
| 2006/0139570 A1 | 6/2006 | Blum et al. |
| 2006/0139711 A1 | 6/2006 | Leister et al. |
| 2006/0139750 A1 | 6/2006 | Solomon |
| 2006/0140495 A1 | 6/2006 | Keeney et al. |
| 2006/0142742 A1 | 6/2006 | Donitzky |

(56) References Cited

U.S. PATENT DOCUMENTS

| | | |
|---|---|---|
| 2006/0143501 A1 | 6/2006 | Tormasov et al. |
| 2006/0145945 A1 | 7/2006 | Lewis et al. |
| 2006/0146046 A1 | 7/2006 | Longhurst et al. |
| 2006/0146187 A1 | 7/2006 | Handjojo et al. |
| 2006/0147883 A1 | 7/2006 | Herman |
| 2006/0149602 A1 | 7/2006 | Zammit |
| 2006/0149628 A1 | 7/2006 | Chefalas et al. |
| 2006/0150207 A1 | 7/2006 | Tutmaz et al. |
| 2006/0150982 A1 | 7/2006 | Wood |
| 2006/0150989 A1 | 7/2006 | Migaly |
| 2006/0152106 A1 | 7/2006 | Yan et al. |
| 2006/0155757 A1 | 7/2006 | Williams et al. |
| 2006/0156237 A1 | 7/2006 | Williams et al. |
| 2006/0156245 A1 | 7/2006 | Williams et al. |
| 2006/0156246 A1 | 7/2006 | Williams et al. |
| 2006/0156597 A1 | 7/2006 | Charbonneau |
| 2006/0158462 A1 | 7/2006 | Toyama et al. |
| 2006/0158639 A1 | 7/2006 | Campin et al. |
| 2006/0158731 A1 | 7/2006 | Eichenlaub |
| 2006/0160060 A1 | 7/2006 | Algayed |
| 2006/0160104 A1 | 7/2006 | Johnson et al. |
| 2006/0161144 A1 | 7/2006 | Li |
| 2006/0161218 A1 | 7/2006 | Danilov |
| 2006/0162036 A1 | 7/2006 | McCalla |
| 2006/0164653 A1 | 7/2006 | Everett et al. |
| 2006/0167050 A1 | 7/2006 | Kruisinga |
| 2006/0167088 A1 | 7/2006 | Widder et al. |
| 2006/0167111 A1 | 7/2006 | Epstein et al. |
| 2006/0167112 A1 | 7/2006 | Epstein et al. |
| 2006/0167434 A1 | 7/2006 | Ashton et al. |
| 2006/0167595 A1 | 7/2006 | Breed et al. |
| 2006/0170764 A1 | 8/2006 | Hentschke |
| 2006/0171008 A1 | 8/2006 | Mintz et al. |
| 2006/0173510 A1 | 8/2006 | Besio et al. |
| 2006/0173828 A1 | 8/2006 | Rosenberg |
| 2006/0174263 A1 | 8/2006 | Ducheneaut et al. |
| 2006/0174292 A1 | 8/2006 | Ducheneaut et al. |
| 2006/0174293 A1 | 8/2006 | Ducheneaut et al. |
| 2006/0174311 A1 | 8/2006 | Ducheneaut et al. |
| 2006/0174312 A1 | 8/2006 | Ducheneaut et al. |
| 2006/0174313 A1 | 8/2006 | Ducheneaut et al. |
| 2006/0174887 A1 | 8/2006 | Chandran et al. |
| 2006/0176447 A1 | 8/2006 | Reis |
| 2006/0176951 A1 | 8/2006 | Berman et al. |
| 2006/0177851 A1 | 8/2006 | Brennan et al. |
| 2006/0179044 A1 | 8/2006 | Rosenberg |
| 2006/0181503 A1 | 8/2006 | Feng |
| 2006/0182215 A1 | 8/2006 | Dreps et al. |
| 2006/0183776 A9 | 8/2006 | Pratt |
| 2006/0184485 A1 | 8/2006 | Horvitz |
| 2006/0188139 A1 | 8/2006 | Khamene et al. |
| 2006/0189886 A1 | 8/2006 | Jones et al. |
| 2006/0192340 A1 | 8/2006 | Vaughan |
| 2006/0192918 A1 | 8/2006 | Blum |
| 2006/0192921 A1 | 8/2006 | Loesel et al. |
| 2006/0193494 A1 | 8/2006 | Toyama |
| 2006/0195078 A1 | 8/2006 | Webb et al. |
| 2006/0195428 A1 | 8/2006 | Peckover |
| 2006/0196490 A1 | 9/2006 | Davidson et al. |
| 2006/0199157 A1 | 9/2006 | Stamm et al. |
| 2006/0199468 A1 | 9/2006 | Mastrosimone-Gese |
| 2006/0200662 A1 | 9/2006 | Fulton et al. |
| 2006/0202810 A1 | 9/2006 | Nath et al. |
| 2006/0202841 A1 | 9/2006 | Johns |
| 2006/0202945 A1 | 9/2006 | Feng |
| 2006/0203088 A1 | 9/2006 | Hammoud et al. |
| 2006/0203197 A1 | 9/2006 | Marshall |
| 2006/0204041 A1 | 9/2006 | Hammoud et al. |
| 2006/0204042 A1 | 9/2006 | Hammoud et al. |
| 2006/0206713 A1 | 9/2006 | Hickman et al. |
| 2006/0208169 A1 | 9/2006 | Breed et al. |
| 2006/0209013 A1 | 9/2006 | Fengels |
| 2006/0209257 A1 | 9/2006 | Bullwinkel |
| 2006/0210122 A1 | 9/2006 | Cleveland et al. |
| 2006/0211721 A1 | 9/2006 | Roberts |
| 2006/0214874 A1 | 9/2006 | Hudson |
| 2006/0215014 A1 | 9/2006 | Cohen et al. |
| 2006/0215016 A1 | 9/2006 | Cohen et al. |
| 2006/0215017 A1 | 9/2006 | Cohen et al. |
| 2006/0215811 A1 | 9/2006 | Modica et al. |
| 2006/0215893 A1 | 9/2006 | Johnson |
| 2006/0215894 A1 | 9/2006 | Lakare |
| 2006/0216755 A1 | 9/2006 | Lee |
| 2006/0217385 A1 | 9/2006 | Edwards et al. |
| 2006/0217386 A1 | 9/2006 | Edwards et al. |
| 2006/0217688 A1 | 9/2006 | Lai |
| 2006/0217864 A1 | 9/2006 | Johnson et al. |
| 2006/0218162 A1 | 9/2006 | Keil et al. |
| 2006/0218485 A1 | 9/2006 | Blumenthal |
| 2006/0221852 A1 | 10/2006 | Klein |
| 2006/0222601 A1 | 10/2006 | Sabnis et al. |
| 2006/0224445 A1 | 10/2006 | Axe et al. |
| 2006/0224678 A1 | 10/2006 | Hall |
| 2006/0228011 A1 | 10/2006 | Everett et al. |
| 2006/0232665 A1 | 10/2006 | Schowengerdt et al. |
| 2006/0233422 A1 | 10/2006 | Toyama |
| 2006/0233915 A1 | 10/2006 | Puski et al. |
| 2006/0235331 A1 | 10/2006 | Kiderman |
| 2006/0235961 A1 | 10/2006 | Klein et al. |
| 2006/0238442 A1 | 10/2006 | Uhlhorn et al. |
| 2006/0238701 A1 | 10/2006 | Blum |
| 2006/0238877 A1 | 10/2006 | Ashkenazi et al. |
| 2006/0239670 A1 | 10/2006 | Cleveland |
| 2006/0240393 A1 | 10/2006 | Reeves et al. |
| 2006/0241077 A1 | 10/2006 | Wurtman et al. |
| 2006/0241080 A1 | 10/2006 | Dror et al. |
| 2006/0241506 A1 | 10/2006 | Melker et al. |
| 2006/0241718 A1 | 10/2006 | Tyler et al. |
| 2006/0242218 A1 | 10/2006 | Okada et al. |
| 2006/0243071 A1 | 11/2006 | Sagi-Dolev |
| 2006/0244246 A1 | 11/2006 | Breed et al. |
| 2006/0250322 A1 | 11/2006 | Hall et al. |
| 2006/0250671 A1 | 11/2006 | Schwerdtner et al. |
| 2006/0251293 A1 | 11/2006 | Piirainen et al. |
| 2006/0251325 A1 | 11/2006 | Florin et al. |
| 2006/0251541 A1 | 11/2006 | Santandrea |
| 2006/0252014 A1 | 11/2006 | Simon et al. |
| 2006/0252978 A1 | 11/2006 | Vesely et al. |
| 2006/0252979 A1 | 11/2006 | Vesely et al. |
| 2006/0253781 A1 | 11/2006 | Pea et al. |
| 2006/0256007 A1 | 11/2006 | Rosenberg |
| 2006/0256083 A1 | 11/2006 | Rosenberg |
| 2006/0256133 A1 | 11/2006 | Rosenberg |
| 2006/0258390 A1 | 11/2006 | Cui et al. |
| 2006/0258672 A1 | 11/2006 | Barbosa et al. |
| 2006/0258691 A1 | 11/2006 | Barbosa et al. |
| 2006/0259206 A1 | 11/2006 | Smith et al. |
| 2006/0261502 A1 | 11/2006 | Platt et al. |
| 2006/0264774 A1 | 11/2006 | Rosenberg |
| 2006/0264915 A1 | 11/2006 | Jensen |
| 2006/0265435 A1 | 11/2006 | Denissov |
| 2006/0265999 A1 | 11/2006 | Dupre, Jr. et al. |
| 2006/0266356 A1 | 11/2006 | Sotos et al. |
| 2006/0268101 A1 | 11/2006 | He et al. |
| 2006/0270945 A1 | 11/2006 | Ghajar |
| 2006/0271640 A1 | 11/2006 | Muldoon et al. |
| 2006/0274051 A1 | 12/2006 | Longe et al. |
| 2006/0274076 A1 | 12/2006 | Cook |
| 2006/0274085 A1 | 12/2006 | Cook |
| 2006/0274973 A1 | 12/2006 | Mohamed et al. |
| 2006/0280815 A1 | 12/2006 | Gardiner et al. |
| 2006/0281061 A1 | 12/2006 | Hightower et al. |
| 2006/0282283 A1 | 12/2006 | Monahan |
| 2006/0282317 A1 | 12/2006 | Rosenberg |
| 2006/0282387 A1 | 12/2006 | Ahmad et al. |
| 2006/0282671 A1 | 12/2006 | Burton |
| 2006/0284790 A1 | 12/2006 | Tegreene et al. |
| 2006/0284983 A1 | 12/2006 | Holmes |
| 2006/0287748 A1 | 12/2006 | Layton et al. |
| 2006/0287779 A1 | 12/2006 | Smith et al. |
| 2006/0290663 A1 | 12/2006 | Mitchell |
| 2006/0290855 A1 | 12/2006 | Itoh et al. |
| 2006/0292141 A1 | 12/2006 | Holers et al. |
| 2006/0292622 A1 | 12/2006 | Tsuji |

(56) References Cited

U.S. PATENT DOCUMENTS

| | | |
|---|---|---|
| 2006/0293613 A1 | 12/2006 | Fatehi et al. |
| 2007/0002130 A1 | 1/2007 | Hartkop |
| 2007/0002990 A1 | 1/2007 | Lee et al. |
| 2007/0004312 A1 | 1/2007 | Jeske |
| 2007/0005190 A1 | 1/2007 | Feinleib et al. |
| 2007/0005257 A1 | 1/2007 | Cheng et al. |
| 2007/0006086 A1 | 1/2007 | Kokko et al. |
| 2007/0008250 A1 | 1/2007 | Hoppenbrouwers et al. |
| 2007/0011155 A1 | 1/2007 | Sarkar |
| 2007/0011609 A1 | 1/2007 | Adjouadi et al. |
| 2007/0012321 A1 | 1/2007 | Zelinsky |
| 2007/0013652 A1 | 1/2007 | Kim et al. |
| 2007/0013657 A1 | 1/2007 | Banning |
| 2007/0013868 A1 | 1/2007 | Pugach et al. |
| 2007/0013873 A9 | 1/2007 | Jacobson et al. |
| 2007/0014431 A1 | 1/2007 | Hammoud et al. |
| 2007/0014480 A1 | 1/2007 | Sirohey et al. |
| 2007/0015128 A1 | 1/2007 | Renaud |
| 2007/0015194 A1 | 1/2007 | Shohat et al. |
| 2007/0015827 A1 | 1/2007 | Widder et al. |
| 2007/0016926 A1 | 1/2007 | Ward, III et al. |
| 2007/0018704 A1 | 1/2007 | Ishii et al. |
| 2007/0021242 A1 | 1/2007 | Krickler |
| 2007/0022385 A1 | 1/2007 | Denissov |
| 2007/0024577 A1 | 2/2007 | Nurmi |
| 2007/0024579 A1 | 2/2007 | Rosenberg |
| 2007/0025597 A1 | 2/2007 | Breed et al. |
| 2007/0026974 A1 | 2/2007 | Marty et al. |
| 2007/0026975 A1 | 2/2007 | Marty et al. |
| 2007/0027406 A1 | 2/2007 | LaPlaca et al. |
| 2007/0032352 A1 | 2/2007 | Sunbeck |
| 2007/0032737 A1 | 2/2007 | Causevic et al. |
| 2007/0032782 A1 | 2/2007 | Youssefi et al. |
| 2007/0033531 A1 | 2/2007 | Marsh |
| 2007/0033613 A1 | 2/2007 | Ward, III et al. |
| 2007/0035114 A1 | 2/2007 | Breed et al. |
| 2007/0035492 A1 | 2/2007 | Chang |
| 2007/0035493 A1 | 2/2007 | Chang |
| 2007/0036870 A1 | 2/2007 | Bryan et al. |
| 2007/0037664 A1 | 2/2007 | Kaplan et al. |
| 2007/0040691 A1 | 2/2007 | Lau et al. |
| 2007/0040799 A1 | 2/2007 | Singh et al. |
| 2007/0040892 A1 | 2/2007 | Aoki et al. |
| 2007/0040908 A1 | 2/2007 | Cleveland et al. |
| 2007/0041552 A1 | 2/2007 | Moscato |
| 2007/0049608 A1 | 3/2007 | Fink et al. |
| 2007/0049844 A1 | 3/2007 | Rosenfeld |
| 2007/0052672 A1 | 3/2007 | Ritter et al. |
| 2007/0055143 A1 | 3/2007 | Deroo et al. |
| 2007/0055222 A1 | 3/2007 | Hohla et al. |
| 2007/0055336 A1 | 3/2007 | Greenberg et al. |
| 2007/0055490 A1 | 3/2007 | Aoki et al. |
| 2007/0057460 A1 | 3/2007 | Swaab et al. |
| 2007/0057842 A1 | 3/2007 | Coleman et al. |
| 2007/0059349 A1 | 3/2007 | Mantelle et al. |
| 2007/0060347 A1 | 3/2007 | Itou |
| 2007/0060390 A1 | 3/2007 | Wells |
| 2007/0060974 A1 | 3/2007 | Lozano |
| 2007/0063134 A1 | 3/2007 | Wine et al. |
| 2007/0064018 A1 | 3/2007 | Shoemaker et al. |
| 2007/0066916 A1 | 3/2007 | Lemos |
| 2007/0078552 A1 | 4/2007 | Rosenberg |
| 2007/0081090 A1 | 4/2007 | Singh |
| 2007/0081126 A1 | 4/2007 | Blum et al. |
| 2007/0081707 A1 | 4/2007 | Sirohey et al. |
| 2007/0083819 A1 | 4/2007 | Shoemaker |
| 2007/0084095 A1 | 4/2007 | Wellington, Jr. |
| 2007/0085697 A1 | 4/2007 | Breed |
| 2007/0086624 A1 | 4/2007 | Breed et al. |
| 2007/0089591 A1 | 4/2007 | Boys |
| 2007/0091258 A1 | 4/2007 | Blum et al. |
| 2007/0091264 A1 | 4/2007 | Kahlen |
| 2007/0094085 A1 | 4/2007 | Redmond et al. |
| 2007/0096445 A1 | 5/2007 | Breed |
| 2007/0096446 A1 | 5/2007 | Breed |
| 2007/0097109 A1 | 5/2007 | Shoemaker et al. |
| 2007/0099999 A1 | 5/2007 | Epstein et al. |
| 2007/0100000 A1 | 5/2007 | Epstein et al. |
| 2007/0100217 A1 | 5/2007 | Proniewicz et al. |
| 2007/0100251 A1 | 5/2007 | Prichep |
| 2007/0100898 A1 | 5/2007 | Petras et al. |
| 2007/0103546 A1 | 5/2007 | Collender et al. |
| 2007/0104369 A1 | 5/2007 | Weatherhead |
| 2007/0105071 A1 | 5/2007 | Weatherhead |
| 2007/0106402 A1 | 5/2007 | Cai et al. |
| 2007/0106557 A1 | 5/2007 | Varghese |
| 2007/0109619 A1 | 5/2007 | Eberl et al. |
| 2007/0111172 A1 | 5/2007 | Kinard |
| 2007/0112585 A1 | 5/2007 | Breiter et al. |
| 2007/0112719 A1 | 5/2007 | Reich et al. |
| 2007/0112916 A1 | 5/2007 | Singh |
| 2007/0116327 A1 | 5/2007 | Breed et al. |
| 2007/0116338 A1 | 5/2007 | Fidrich et al. |
| 2007/0116695 A1 | 5/2007 | Fallon |
| 2007/0117071 A1 | 5/2007 | Bedell |
| 2007/0117869 A1 | 5/2007 | Epstein et al. |
| 2007/0118024 A1 | 5/2007 | Capolunghi et al. |
| 2007/0118101 A1 | 5/2007 | Mahesh et al. |
| 2007/0120347 A1 | 5/2007 | Breed et al. |
| 2007/0121065 A1 | 5/2007 | Cox et al. |
| 2007/0121066 A1 | 5/2007 | Nashner |
| 2007/0121068 A1 | 5/2007 | MacDougall et al. |
| 2007/0121201 A1 | 5/2007 | Sander |
| 2007/0122017 A1 | 5/2007 | Binnig et al. |
| 2007/0122776 A1 | 5/2007 | Stone |
| 2007/0122787 A1 | 5/2007 | Pembleton et al. |
| 2007/0122824 A1 | 5/2007 | Tucker et al. |
| 2007/0123757 A1 | 5/2007 | Chervinsky |
| 2007/0124669 A1 | 5/2007 | Makela |
| 2007/0124756 A1 | 5/2007 | Covell et al. |
| 2007/0124801 A1 | 5/2007 | Thomas et al. |
| 2007/0126928 A1 | 6/2007 | Klompnhouwer et al. |
| 2007/0127795 A1 | 6/2007 | Lau et al. |
| 2007/0129626 A1 | 6/2007 | Mahesh et al. |
| 2007/0130580 A1 | 6/2007 | Covell et al. |
| 2007/0132219 A1 | 6/2007 | Breed |
| 2007/0132220 A1 | 6/2007 | Breed et al. |
| 2007/0132841 A1 | 6/2007 | MacDougall et al. |
| 2007/0132950 A1 | 6/2007 | Victor et al. |
| 2007/0133884 A1 | 6/2007 | Hammoud |
| 2007/0134633 A1 | 6/2007 | Chan et al. |
| 2007/0135982 A1 | 6/2007 | Breed et al. |
| 2007/0135984 A1 | 6/2007 | Breed et al. |
| 2007/0136425 A1 | 6/2007 | Sabatino |
| 2007/0136657 A1 | 6/2007 | Blumenthal et al. |
| 2007/0136964 A1 | 6/2007 | Dawley |
| 2007/0138744 A1 | 6/2007 | Hall |
| 2007/0139409 A1 | 6/2007 | Anderson et al. |
| 2007/0139416 A1 | 6/2007 | Azuma |
| 2007/0139419 A1 | 6/2007 | Azuma |
| 2007/0139432 A1 | 6/2007 | Anderson et al. |
| 2007/0139433 A1 | 6/2007 | Anderson et al. |
| 2007/0141538 A1 | 6/2007 | Quinn et al. |
| 2007/0143778 A1 | 6/2007 | Covell et al. |
| 2007/0145819 A1 | 6/2007 | Lin et al. |
| 2007/0146319 A1 | 6/2007 | Masselle et al. |
| 2007/0146627 A1 | 6/2007 | Blum et al. |
| 2007/0146634 A1 | 6/2007 | LeBlanc et al. |
| 2007/0146635 A1 | 6/2007 | LeBlanc et al. |
| 2007/0146637 A1 | 6/2007 | Johnson et al. |
| 2007/0149527 A1 | 6/2007 | Hassan et al. |
| 2007/0151299 A1 | 7/2007 | Goldschmidt |
| 2007/0154063 A1 | 7/2007 | Breed |
| 2007/0156029 A1 | 7/2007 | Morris |
| 2007/0156317 A1 | 7/2007 | Breed |
| 2007/0156443 A1 | 7/2007 | Gurvey |
| 2007/0156645 A1 | 7/2007 | Mohajer et al. |
| 2007/0159470 A1 | 7/2007 | Jeng et al. |
| 2007/0159601 A1 | 7/2007 | Ho et al. |
| 2007/0161972 A1 | 7/2007 | Felberg et al. |
| 2007/0162602 A1 | 7/2007 | Anderson et al. |
| 2007/0164990 A1 | 7/2007 | Bjorklund et al. |
| 2007/0165016 A1 | 7/2007 | Lewis et al. |
| 2007/0165050 A1 | 7/2007 | Baar |

(56) References Cited

U.S. PATENT DOCUMENTS

| | | |
|---|---|---|
| 2007/0171194 A1 | 7/2007 | Conti et al. |
| 2007/0171227 A1 | 7/2007 | Anderson et al. |
| 2007/0171228 A1 | 7/2007 | Anderson et al. |
| 2007/0171363 A1 | 7/2007 | Chen et al. |
| 2007/0171369 A1 | 7/2007 | Grundig |
| 2007/0172551 A1 | 7/2007 | Thompson et al. |
| 2007/0174777 A1 | 7/2007 | Finley et al. |
| 2007/0175788 A1 | 8/2007 | Holba et al. |
| 2007/0178600 A1 | 8/2007 | Lebret et al. |
| 2007/0178950 A1 | 8/2007 | Lewis et al. |
| 2007/0179197 A1 | 8/2007 | Henderson |
| 2007/0179361 A1 | 8/2007 | Brown et al. |
| 2007/0180378 A1 | 8/2007 | McCall et al. |
| 2007/0182595 A1 | 8/2007 | Ghasabian |
| 2007/0182812 A1 | 8/2007 | Ritchey |
| 2007/0185533 A1 | 8/2007 | Gerdes |
| 2007/0186240 A1 | 8/2007 | Ward, III et al. |
| 2007/0187580 A1 | 8/2007 | Kykta et al. |
| 2007/0189582 A1 | 8/2007 | Hamza et al. |
| 2007/0189627 A1 | 8/2007 | Cohen et al. |
| 2007/0190187 A1 | 8/2007 | Kneller et al. |
| 2007/0192461 A1 | 8/2007 | Reich et al. |
| 2007/0192727 A1 | 8/2007 | Finley |
| 2007/0193811 A1 | 8/2007 | Breed et al. |
| 2007/0193908 A1 | 8/2007 | Torchia et al. |
| 2007/0194902 A1 | 8/2007 | Blanco et al. |
| 2007/0195612 A1 | 8/2007 | Brinson et al. |
| 2007/0195680 A1 | 8/2007 | Brinson et al. |
| 2007/0196793 A1 | 8/2007 | Seeliger et al. |
| 2007/0197663 A1 | 8/2007 | Epstein et al. |
| 2007/0197932 A1 | 8/2007 | Feke et al. |
| 2007/0198907 A1 | 8/2007 | Degala et al. |
| 2007/0198951 A1 | 8/2007 | Frank |
| 2007/0200927 A1 | 8/2007 | Krenik |
| 2007/0201731 A1 | 8/2007 | Fedorovskaya et al. |
| 2007/0211927 A1 | 9/2007 | Groszmann et al. |
| 2007/0213948 A1 | 9/2007 | Hornstein |
| 2007/0216862 A1 | 9/2007 | Blum et al. |
| 2007/0218979 A1 | 9/2007 | Momoda et al. |
| 2007/0219938 A1 | 9/2007 | Boersma et al. |
| 2007/0219968 A1 | 9/2007 | Frank |
| 2007/0220010 A1 | 9/2007 | Ertugrul |
| 2007/0220108 A1 | 9/2007 | Whitaker |
| 2007/0221220 A1 | 9/2007 | Bright |
| 2007/0222855 A1 | 9/2007 | Krijn et al. |
| 2007/0225692 A1 | 9/2007 | Somani et al. |
| 2007/0229396 A1 | 10/2007 | Rajasingham |
| 2007/0230764 A1 | 10/2007 | Khamene et al. |
| 2007/0233692 A1 | 10/2007 | Lisa et al. |
| 2007/0234224 A1 | 10/2007 | Leavitt et al. |
| 2007/0236507 A1 | 10/2007 | Tigges |
| 2007/0236663 A1 | 10/2007 | Waldorf et al. |
| 2007/0240078 A1 | 10/2007 | Bobrow et al. |
| 2007/0243211 A1 | 10/2007 | Jaffe |
| 2007/0248273 A1 | 10/2007 | Kortum et al. |
| 2007/0248938 A1 | 10/2007 | Ronald |
| 2007/0250119 A1 | 10/2007 | Tyler et al. |
| 2007/0250138 A1 | 10/2007 | Nofzinger |
| 2007/0251529 A1 | 11/2007 | Wood |
| 2007/0251749 A1 | 11/2007 | Breed et al. |
| 2007/0252795 A1 | 11/2007 | Shiomi |
| 2007/0253941 A1 | 11/2007 | Naidu et al. |
| 2007/0254314 A1 | 11/2007 | Geier et al. |
| 2007/0256499 A1 | 11/2007 | Pelecanos et al. |
| 2007/0257891 A1 | 11/2007 | Esenther et al. |
| 2007/0258104 A1 | 11/2007 | Chen et al. |
| 2007/0258243 A1 | 11/2007 | Segall |
| 2007/0258335 A1 | 11/2007 | Farinella et al. |
| 2007/0260280 A1 | 11/2007 | Dunn et al. |
| 2007/0262574 A1 | 11/2007 | Breed et al. |
| 2007/0262928 A1 | 11/2007 | Steer et al. |
| 2007/0262988 A1 | 11/2007 | Christensen |
| 2007/0265507 A1 | 11/2007 | de Lemos |
| 2007/0265910 A1 | 11/2007 | Varghese |
| 2007/0266359 A1 | 11/2007 | Esbensen et al. |
| 2007/0268455 A1 | 11/2007 | Roser |
| 2007/0268579 A1 | 11/2007 | Yang |
| 2007/0269900 A1 | 11/2007 | Lebret et al. |
| 2007/0270393 A1 | 11/2007 | Buckley et al. |
| 2007/0270658 A1 | 11/2007 | Mitchell |
| 2007/0271613 A1 | 11/2007 | Joyce |
| 2007/0272249 A1 | 11/2007 | Chandran et al. |
| 2007/0273611 A1 | 11/2007 | Torch |
| 2007/0273832 A1 | 11/2007 | Weinblatt |
| 2007/0275029 A1 | 11/2007 | Clement et al. |
| 2007/0279588 A1 | 12/2007 | Hammoud et al. |
| 2007/0279591 A1 | 12/2007 | Wezowski et al. |
| 2007/0280505 A1 | 12/2007 | Breed |
| 2007/0280638 A1 | 12/2007 | Aoki et al. |
| 2007/0281010 A1 | 12/2007 | Reynolds |
| 2007/0281961 A1 | 12/2007 | Reynolds |
| 2007/0282216 A1 | 12/2007 | Vesely et al. |
| 2007/0282506 A1 | 12/2007 | Breed et al. |
| 2007/0282779 A1 | 12/2007 | Haimov |
| 2007/0282912 A1 | 12/2007 | Reiner |
| 2007/0282937 A1 | 12/2007 | Brinson et al. |
| 2007/0283380 A1 | 12/2007 | Aoki et al. |
| 2007/0284821 A1 | 12/2007 | Hall |
| 2007/0286457 A1 | 12/2007 | Hammoud et al. |
| 2007/0288159 A1 | 12/2007 | Skelton |
| 2007/0288310 A1 | 12/2007 | Boos et al. |
| 2007/0291227 A1 | 12/2007 | Yang et al. |
| 2007/0291232 A1 | 12/2007 | Marshall |
| 2007/0291983 A1 | 12/2007 | Hammoud |
| 2007/0294419 A1 | 12/2007 | Ulevitch |
| 2007/0294636 A1 | 12/2007 | Sullivan |
| 2007/0299484 A1 | 12/2007 | Greenberg et al. |
| 2007/0299487 A1 | 12/2007 | Shadduck |
| 2007/0299631 A1 | 12/2007 | Macbeth et al. |
| 2008/0002262 A1 | 1/2008 | Chirieleison |
| 2008/0003199 A1 | 1/2008 | Lee |
| 2008/0003208 A1 | 1/2008 | Nivaggioli |
| 2008/0004327 A1 | 1/2008 | Heffernan et al. |
| 2008/0004328 A1 | 1/2008 | Dorsey et al. |
| 2008/0004509 A1 | 1/2008 | Sahakian et al. |
| 2008/0004660 A1 | 1/2008 | Assaf et al. |
| 2008/0004725 A1 | 1/2008 | Wacker |
| 2008/0005071 A1 | 1/2008 | Flake et al. |
| 2008/0005074 A1 | 1/2008 | Flake et al. |
| 2008/0005104 A1 | 1/2008 | Flake et al. |
| 2008/0005127 A1 | 1/2008 | Schneider |
| 2008/0005342 A1 | 1/2008 | Schneider |
| 2008/0007774 A1 | 1/2008 | Ruemmele |
| 2008/0008746 A1 | 1/2008 | Mantelle et al. |
| 2008/0009772 A1 | 1/2008 | Tyler et al. |
| 2008/0009956 A1 | 1/2008 | Pouchak |
| 2008/0010049 A1 | 1/2008 | Pouchak et al. |
| 2008/0010365 A1 | 1/2008 | Schneider |
| 2008/0012860 A1 | 1/2008 | Klefenz et al. |
| 2008/0015247 A1 | 1/2008 | Lines |
| 2008/0015660 A1 | 1/2008 | Herekar |
| 2008/0015841 A1 | 1/2008 | Longe et al. |
| 2008/0016142 A1 | 1/2008 | Schneider |
| 2008/0016233 A1 | 1/2008 | Schneider |
| 2008/0016493 A1 | 1/2008 | Pouchak et al. |
| 2008/0018571 A1 | 1/2008 | Feng |
| 2008/0020814 A1 | 1/2008 | Kernene |
| 2008/0021516 A1 | 1/2008 | Greenberg et al. |
| 2008/0021783 A1 | 1/2008 | Varghese |
| 2008/0024594 A1 | 1/2008 | Ritchey |
| 2008/0024597 A1 | 1/2008 | Yang et al. |
| 2008/0024598 A1 | 1/2008 | Perlin et al. |
| 2008/0030501 A1 | 2/2008 | Kariathungal et al. |
| 2008/0030685 A1 | 2/2008 | Fergason et al. |
| 2008/0032270 A1 | 2/2008 | Katz et al. |
| 2008/0032271 A1 | 2/2008 | Johnson |
| 2008/0032965 A1 | 2/2008 | Hirst et al. |
| 2008/0032987 A1 | 2/2008 | Lines |
| 2008/0033858 A1 | 2/2008 | Hemingway et al. |
| 2008/0033917 A1 | 2/2008 | Jones et al. |
| 2008/0034435 A1 | 2/2008 | Grabarnik et al. |
| 2008/0036185 A1 | 2/2008 | Breed |
| 2008/0036187 A1 | 2/2008 | Breed |
| 2008/0036252 A1 | 2/2008 | Breed |

(56) References Cited

U.S. PATENT DOCUMENTS

| | | |
|---|---|---|
| 2008/0036580 A1 | 2/2008 | Breed |
| 2008/0036875 A1 | 2/2008 | Jones et al. |
| 2008/0037803 A1 | 2/2008 | Breed |
| 2008/0039698 A1 | 2/2008 | Burton |
| 2008/0040205 A1 | 2/2008 | Gold et al. |
| 2008/0040668 A1 | 2/2008 | Ala-Rantala |
| 2008/0042408 A1 | 2/2008 | Breed et al. |
| 2008/0042409 A1 | 2/2008 | Breed |
| 2008/0042953 A1 | 2/2008 | De Haan et al. |
| 2008/0043013 A1 | 2/2008 | Gruttadauria et al. |
| 2008/0043094 A1 | 2/2008 | Ijzerman et al. |
| 2008/0043850 A1 | 2/2008 | Nair et al. |
| 2008/0044801 A1 | 2/2008 | Modica et al. |
| 2008/0044910 A1 | 2/2008 | Hairault et al. |
| 2008/0046200 A1 | 2/2008 | Breed et al. |
| 2008/0046931 A1 | 2/2008 | Corbett et al. |
| 2008/0047770 A1 | 2/2008 | Breed et al. |
| 2008/0047902 A1 | 2/2008 | Beswick et al. |
| 2008/0048931 A1 | 2/2008 | Ben-Ari |
| 2008/0049186 A1 | 2/2008 | MacDougall et al. |
| 2008/0049187 A1 | 2/2008 | Joos et al. |
| 2008/0050703 A1 | 2/2008 | Katz |
| 2008/0051957 A1 | 2/2008 | Breed et al. |
| 2008/0052152 A1 | 2/2008 | Yufik |
| 2008/0052646 A1 | 2/2008 | Tuncer et al. |
| 2008/0052653 A1 | 2/2008 | Tuncer et al. |
| 2008/0054019 A1 | 3/2008 | Stechschulte et al. |
| 2008/0054696 A1 | 3/2008 | McConnell et al. |
| 2008/0055194 A1 | 3/2008 | Baudino et al. |
| 2008/0055543 A1 | 3/2008 | Meyer et al. |
| 2008/0056542 A1 | 3/2008 | Hung et al. |
| 2008/0057911 A1 | 3/2008 | Lauper |
| 2008/0058395 A1 | 3/2008 | Heffernan et al. |
| 2008/0058894 A1 | 3/2008 | Dewhurst |
| 2008/0059441 A1 | 3/2008 | Gaug et al. |
| 2008/0059607 A1 | 3/2008 | Schneider |
| 2008/0059970 A1 | 3/2008 | Gonen |
| 2008/0059990 A1 | 3/2008 | Marr et al. |
| 2008/0061949 A1 | 3/2008 | Ferguson et al. |
| 2008/0062161 A1 | 3/2008 | Brown et al. |
| 2008/0062382 A1 | 3/2008 | Endrikhovski et al. |
| 2008/0062383 A1 | 3/2008 | Endrikhovski et al. |
| 2008/0065291 A1 | 3/2008 | Breed |
| 2008/0065397 A1 | 3/2008 | Huang et al. |
| 2008/0065468 A1 | 3/2008 | Berg et al. |
| 2008/0068195 A1 | 3/2008 | Ritter et al. |
| 2008/0069403 A1 | 3/2008 | Breed |
| 2008/0069463 A1 | 3/2008 | Keeney et al. |
| 2008/0070215 A1 | 3/2008 | Hunter |
| 2008/0070316 A1 | 3/2008 | Poullain et al. |
| 2008/0070995 A1 | 3/2008 | Westbrook et al. |
| 2008/0071507 A1 | 3/2008 | Hodgins et al. |
| 2008/0071688 A1 | 3/2008 | Corbett et al. |
| 2008/0072174 A1 | 3/2008 | Corbett et al. |
| 2008/0072175 A1 | 3/2008 | Corbett et al. |
| 2008/0074614 A1 | 3/2008 | Leblanc et al. |
| 2008/0077121 A1 | 3/2008 | Rathjen |
| 2008/0077194 A1 | 3/2008 | Greenberg et al. |
| 2008/0077195 A1 | 3/2008 | Greenberg et al. |
| 2008/0077196 A1 | 3/2008 | Greenberg et al. |
| 2008/0077469 A1 | 3/2008 | Philport et al. |
| 2008/0082020 A1 | 4/2008 | Collura |
| 2008/0084316 A1 | 4/2008 | Panton |
| 2008/0084387 A1 | 4/2008 | MCardle |
| 2008/0085319 A1 | 4/2008 | Dror et al. |
| 2008/0085320 A1 | 4/2008 | Dror et al. |
| 2008/0088636 A1 | 4/2008 | Ho |
| 2008/0088650 A1 | 4/2008 | Chen et al. |
| 2008/0089480 A1 | 4/2008 | Gertner et al. |
| 2008/0089481 A1 | 4/2008 | Gertner |
| 2008/0091512 A1 | 4/2008 | Marci et al. |
| 2008/0091515 A1 | 4/2008 | Thieberger et al. |
| 2008/0093838 A1 | 4/2008 | Tropper et al. |
| 2008/0095766 A1 | 4/2008 | Koenig et al. |
| 2008/0096171 A1 | 4/2008 | Movahhedi |
| 2008/0096691 A1 | 4/2008 | Kang |
| 2008/0097555 A1 | 4/2008 | Greenberg et al. |
| 2008/0101621 A1 | 5/2008 | Zimmerman |
| 2008/0101659 A1 | 5/2008 | Hammoud et al. |
| 2008/0103407 A1 | 5/2008 | Bolea et al. |
| 2008/0103488 A1 | 5/2008 | Dressler et al. |
| 2008/0103545 A1 | 5/2008 | Bolea et al. |
| 2008/0103828 A1 | 5/2008 | Squilla et al. |
| 2008/0104415 A1 | 5/2008 | Palti-Wasserman et al. |
| 2008/0106523 A1 | 5/2008 | Conrad |
| 2008/0106633 A1 | 5/2008 | Blum et al. |
| 2008/0111833 A1 | 5/2008 | Thorn et al. |
| 2008/0115206 A1 | 5/2008 | Feige et al. |
| 2008/0116632 A1 | 5/2008 | Russell |
| 2008/0118103 A1 | 5/2008 | Pescatore et al. |
| 2008/0118125 A1 | 5/2008 | Mahesh et al. |
| 2008/0118899 A1 | 5/2008 | Sahakian et al. |
| 2008/0119554 A1 | 5/2008 | Jalan et al. |
| 2008/0120141 A1 | 5/2008 | Kariathungal et al. |
| 2008/0120548 A1 | 5/2008 | Morita et al. |
| 2008/0124688 A1 | 5/2008 | Kay |
| 2008/0124690 A1 | 5/2008 | Redlich |
| 2008/0126073 A1 | 5/2008 | Longe et al. |
| 2008/0127265 A1 | 5/2008 | Ward et al. |
| 2008/0127266 A1 | 5/2008 | Ward et al. |
| 2008/0129677 A1 | 6/2008 | Li et al. |
| 2008/0129694 A1 | 6/2008 | Haven |
| 2008/0131019 A1 | 6/2008 | Ng |
| 2008/0136742 A1 | 6/2008 | Tegreene et al. |
| 2008/0136916 A1 | 6/2008 | Wolff |
| 2008/0137916 A1 | 6/2008 | Lauper et al. |
| 2008/0138717 A1 | 6/2008 | Bjelkhagen et al. |
| 2008/0139598 A1 | 6/2008 | Barbosa et al. |
| 2008/0139662 A1 | 6/2008 | Brinkmann et al. |
| 2008/0139941 A1 | 6/2008 | Njemanze |
| 2008/0140458 A1 | 6/2008 | Moore |
| 2008/0142713 A1 | 6/2008 | Breed et al. |
| 2008/0143085 A1 | 6/2008 | Breed et al. |
| 2008/0143674 A1 | 6/2008 | Molander et al. |
| 2008/0144771 A1 | 6/2008 | Gertner |
| 2008/0144944 A1 | 6/2008 | Breed |
| 2008/0145492 A1 | 6/2008 | Logsdon |
| 2008/0146577 A1 | 6/2008 | Matalon et al. |
| 2008/0146596 A1 | 6/2008 | Barbosa et al. |
| 2008/0146600 A1 | 6/2008 | Barbosa et al. |
| 2008/0147502 A1 | 6/2008 | Baker |
| 2008/0148149 A1 | 6/2008 | Singh et al. |
| 2008/0148308 A1 | 6/2008 | Hughes et al. |
| 2008/0150734 A1 | 6/2008 | Johns |
| 2008/0151249 A1 | 6/2008 | Walker et al. |
| 2008/0152057 A1 | 6/2008 | Lee et al. |
| 2008/0152733 A1 | 6/2008 | Logsdon |
| 2008/0153168 A1 | 6/2008 | Hairault et al. |
| 2008/0153591 A1 | 6/2008 | Deligiannidis |
| 2008/0153811 A1 | 6/2008 | Barbosa et al. |
| 2008/0153918 A1 | 6/2008 | Broquaire et al. |
| 2008/0157510 A1 | 7/2008 | Breed et al. |
| 2008/0157940 A1 | 7/2008 | Breed et al. |
| 2008/0160877 A1 | 7/2008 | Lipman |
| 2008/0161386 A1 | 7/2008 | French et al. |
| 2008/0162261 A1 | 7/2008 | Velazquez et al. |
| 2008/0164769 A1 | 7/2008 | Eck |
| 2008/0165084 A1 | 7/2008 | Giegold et al. |
| 2008/0165108 A1 | 7/2008 | Shen et al. |
| 2008/0165320 A1 | 7/2008 | Heiberger |
| 2008/0167343 A1 | 7/2008 | Ieni et al. |
| 2008/0167571 A1 | 7/2008 | Gevins |
| 2008/0167964 A1 | 7/2008 | Chefalas et al. |
| 2008/0168274 A1 | 7/2008 | Natanzon et al. |
| 2008/0170120 A1 | 7/2008 | Senior |
| 2008/0170203 A1 | 7/2008 | Esser et al. |
| 2008/0170204 A1 | 7/2008 | Podoleanu |
| 2008/0170788 A1 | 7/2008 | Guo |
| 2008/0171584 A1 | 7/2008 | Roberts et al. |
| 2008/0171750 A1 | 7/2008 | Barlow et al. |
| 2008/0176203 A1 | 7/2008 | Kuntz et al. |
| 2008/0177197 A1 | 7/2008 | Lee et al. |
| 2008/0180436 A1 | 7/2008 | Kraver |
| 2008/0181362 A1 | 7/2008 | Gertner |

(56) References Cited

U.S. PATENT DOCUMENTS

| | | |
|---|---|---|
| 2008/0183560 A1 | 7/2008 | Kaplan et al. |
| 2008/0183575 A1 | 7/2008 | Kaplan et al. |
| 2008/0186449 A1 | 8/2008 | Sur et al. |
| 2008/0187098 A1 | 8/2008 | Gertner et al. |
| 2008/0187099 A1 | 8/2008 | Gertner |
| 2008/0187100 A1 | 8/2008 | Gertner |
| 2008/0187101 A1 | 8/2008 | Gertner |
| 2008/0187102 A1 | 8/2008 | Gertner |
| 2008/0187201 A1 | 8/2008 | Liang et al. |
| 2008/0188510 A1 | 8/2008 | Yoshino |
| 2008/0188777 A1 | 8/2008 | Bedziouk et al. |
| 2008/0189053 A1 | 8/2008 | Breed et al. |
| 2008/0189168 A1 | 8/2008 | Kaplan et al. |
| 2008/0189173 A1 | 8/2008 | Bakar et al. |
| 2008/0189175 A1 | 8/2008 | Chan |
| 2008/0189621 A1 | 8/2008 | Reich et al. |
| 2008/0189752 A1 | 8/2008 | Moradi et al. |
| 2008/0190430 A1 | 8/2008 | Melker et al. |
| 2008/0192065 A1 | 8/2008 | Selbrede et al. |
| 2008/0192202 A1 | 8/2008 | Lewkowski |
| 2008/0192893 A1 | 8/2008 | Gertner |
| 2008/0194488 A1 | 8/2008 | Gozes et al. |
| 2008/0194803 A1 | 8/2008 | Sinclair et al. |
| 2008/0195179 A1 | 8/2008 | Quick |
| 2008/0195261 A1 | 8/2008 | Breed |
| 2008/0195460 A1 | 8/2008 | Varghese |
| 2008/0195465 A1 | 8/2008 | Redmond et al. |
| 2008/0196060 A1 | 8/2008 | Varghese |
| 2008/0196518 A1 | 8/2008 | Sagi-Dolev |
| 2008/0201706 A1 | 8/2008 | Nordtvedt et al. |
| 2008/0201728 A1 | 8/2008 | Midttun et al. |
| 2008/0204374 A1 | 8/2008 | Weitbruch et al. |
| 2008/0204658 A1 | 8/2008 | Van Saarloos |
| 2008/0205700 A1 | 8/2008 | Nir |
| 2008/0208073 A1 | 8/2008 | Causevic |
| 2008/0208177 A1 | 8/2008 | Mrochen |
| 2008/0208624 A1 | 8/2008 | Morita et al. |
| 2008/0208630 A1 | 8/2008 | Fors et al. |
| 2008/0208631 A1 | 8/2008 | Morita et al. |
| 2008/0209480 A1 | 8/2008 | Eide et al. |
| 2008/0212738 A1 | 9/2008 | Gertner et al. |
| 2008/0213401 A1 | 9/2008 | Smith |
| 2008/0213406 A1 | 9/2008 | Stock et al. |
| 2008/0214668 A1 | 9/2008 | Roullet et al. |
| 2008/0219186 A1 | 9/2008 | Bell et al. |
| 2008/0219239 A1 | 9/2008 | Bell et al. |
| 2008/0219493 A1 | 9/2008 | Tadmor |
| 2008/0219587 A1 | 9/2008 | Avidan et al. |
| 2008/0220092 A1 | 9/2008 | Dipierro et al. |
| 2008/0220399 A1 | 9/2008 | Giwa |
| 2008/0221819 A1 | 9/2008 | Everett et al. |
| 2008/0222573 A1 | 9/2008 | Abeckaser |
| 2008/0227857 A1 | 9/2008 | Wei |
| 2008/0228239 A1 | 9/2008 | Tyler et al. |
| 2008/0228577 A1 | 9/2008 | Decre et al. |
| 2008/0228786 A1 | 9/2008 | Svanteson et al. |
| 2008/0229204 A1 | 9/2008 | Johnson et al. |
| 2008/0231804 A1 | 9/2008 | Gagne et al. |
| 2008/0231805 A1 | 9/2008 | Schwerdtner |
| 2008/0234382 A1 | 9/2008 | Malkar et al. |
| 2008/0234514 A1 | 9/2008 | Malkar et al. |
| 2008/0234667 A1 | 9/2008 | Lang et al. |
| 2008/0234899 A1 | 9/2008 | Breed et al. |
| 2008/0235383 A1 | 9/2008 | Schneider |
| 2008/0236275 A1 | 10/2008 | Breed et al. |
| 2008/0238820 A1 | 10/2008 | Enami et al. |
| 2008/0240250 A1 | 10/2008 | Lin et al. |
| 2008/0240560 A1 | 10/2008 | Hibino et al. |
| 2008/0242718 A1 | 10/2008 | Jasuja |
| 2008/0242950 A1 | 10/2008 | Jung et al. |
| 2008/0243005 A1 | 10/2008 | Jung et al. |
| 2008/0244428 A1 | 10/2008 | Fain |
| 2008/0245966 A1 | 10/2008 | Wu et al. |
| 2008/0247510 A1 | 10/2008 | Gertner et al. |
| 2008/0247616 A1 | 10/2008 | Pescatore et al. |
| 2008/0247620 A1 | 10/2008 | Lewis et al. |
| 2008/0248453 A1 | 10/2008 | Cadman |
| 2008/0249588 A1 | 10/2008 | Greenberg et al. |
| 2008/0249987 A1 | 10/2008 | Ogasawara |
| 2008/0252718 A1 | 10/2008 | Provitola |
| 2008/0252849 A1 | 10/2008 | Van Saarloos |
| 2008/0253519 A1 | 10/2008 | Bonfiglio et al. |
| 2008/0254017 A1 | 10/2008 | Kane et al. |
| 2008/0254419 A1 | 10/2008 | Cohen |
| 2008/0254423 A1 | 10/2008 | Cohen |
| 2008/0254424 A1 | 10/2008 | Cohen |
| 2008/0254425 A1 | 10/2008 | Cohen |
| 2008/0254426 A1 | 10/2008 | Cohen |
| 2008/0255949 A1 | 10/2008 | Genco et al. |
| 2008/0256454 A1 | 10/2008 | Latzina et al. |
| 2008/0257047 A1 | 10/2008 | Pelecanos et al. |
| 2008/0258397 A1 | 10/2008 | Torkelson |
| 2008/0263632 A1 | 10/2008 | Keon |
| 2008/0266129 A1 | 10/2008 | Chiang |
| 2008/0266257 A1 | 10/2008 | Chiang |
| 2008/0266394 A1 | 10/2008 | Groenenboom |
| 2008/0266458 A1 | 10/2008 | Whittaker |
| 2008/0267474 A1 | 10/2008 | Chen et al. |
| 2008/0267501 A1 | 10/2008 | Keeney et al. |
| 2008/0267528 A1 | 10/2008 | Avidan et al. |
| 2008/0269731 A1 | 10/2008 | Swinger et al. |
| 2008/0273084 A1 | 11/2008 | MacDougall et al. |
| 2008/0273783 A1 | 11/2008 | Toth et al. |
| 2008/0275527 A1 | 11/2008 | Greenberg et al. |
| 2008/0275528 A1 | 11/2008 | Greenberg et al. |
| 2008/0276186 A1 | 11/2008 | Feduszczak et al. |
| 2008/0278422 A1 | 11/2008 | Xu et al. |
| 2008/0278589 A1 | 11/2008 | Thorn |
| 2008/0278682 A1 | 11/2008 | Huxlin et al. |
| 2008/0278685 A1 | 11/2008 | MacDougall et al. |
| 2008/0278781 A1 | 11/2008 | Sander |
| 2008/0282356 A1 | 11/2008 | Grabarnik et al. |
| 2008/0284729 A1 | 11/2008 | Kurtenbach et al. |
| 2008/0284980 A1 | 11/2008 | Skogo et al. |
| 2008/0285801 A1 | 11/2008 | Heinzmann et al. |
| 2008/0286323 A1 | 11/2008 | Tornoe et al. |
| 2008/0286416 A1 | 11/2008 | Euber et al. |
| 2008/0287372 A1 | 11/2008 | Henderson |
| 2008/0287821 A1 | 11/2008 | Jung et al. |
| 2008/0287928 A1 | 11/2008 | Arnoldussen et al. |
| 2008/0287929 A1 | 11/2008 | Holliday et al. |
| 2008/0288018 A1 | 11/2008 | Rezai et al. |
| 2008/0288854 A1 | 11/2008 | Brassell et al. |
| 2008/0289658 A1 | 11/2008 | Eli |
| 2008/0290281 A1 | 11/2008 | Martin et al. |
| 2008/0292146 A1 | 11/2008 | Breed et al. |
| 2008/0292151 A1 | 11/2008 | Kurtz et al. |
| 2008/0292597 A1 | 11/2008 | Steenblock |
| 2008/0293698 A1 | 11/2008 | Johnson |
| 2008/0293726 A1 | 11/2008 | Caron et al. |
| 2008/0294012 A1 | 11/2008 | Kurtz et al. |
| 2008/0294013 A1 | 11/2008 | Gobeyn et al. |
| 2008/0294016 A1 | 11/2008 | Gobeyn et al. |
| 2008/0294017 A1 | 11/2008 | Gobeyn et al. |
| 2008/0294018 A1 | 11/2008 | Kurtz et al. |
| 2008/0294224 A1 | 11/2008 | Greenberg et al. |
| 2008/0296374 A1 | 12/2008 | Gonen et al. |
| 2008/0297586 A1 | 12/2008 | Kurtz et al. |
| 2008/0297587 A1 | 12/2008 | Kurtz et al. |
| 2008/0297588 A1 | 12/2008 | Kurtz et al. |
| 2008/0297589 A1 | 12/2008 | Kurtz et al. |
| 2008/0297590 A1 | 12/2008 | Barber et al. |
| 2008/0298571 A1 | 12/2008 | Kurtz et al. |
| 2008/0300010 A1 | 12/2008 | Border et al. |
| 2008/0301100 A1 | 12/2008 | Wroblewski et al. |
| 2008/0301573 A1 | 12/2008 | Chi |
| 2008/0304012 A1 | 12/2008 | Kwon et al. |
| 2008/0304892 A1 | 12/2008 | Baker |
| 2008/0306364 A1 | 12/2008 | Petrig |
| 2008/0307310 A1 | 12/2008 | Segal et al. |
| 2008/0309616 A1 | 12/2008 | Massengill |
| 2008/0309874 A1 | 12/2008 | Zuccolotto et al. |
| 2008/0312513 A1 | 12/2008 | Simon et al. |
| 2008/0316302 A1 | 12/2008 | Vos et al. |

(56) References Cited

U.S. PATENT DOCUMENTS

| | | |
|---|---|---|
| 2008/0316425 A1 | 12/2008 | Blum et al. |
| 2008/0316427 A1 | 12/2008 | Fisher et al. |
| 2008/0319276 A1 | 12/2008 | Jung et al. |
| 2009/0002559 A1 | 1/2009 | Poon |
| 2009/0003525 A1 | 1/2009 | Gertner et al. |
| 2009/0005654 A1 | 1/2009 | Jung et al. |
| 2009/0005702 A1 | 1/2009 | Zelinsky |
| 2009/0005835 A1 | 1/2009 | Greenberg et al. |
| 2009/0005837 A1 | 1/2009 | Olmstead |
| 2009/0006448 A1 | 1/2009 | Pall et al. |
| 2009/0007168 A1 | 1/2009 | Finamore |
| 2009/0009718 A1 | 1/2009 | Legatt |
| 2009/0010555 A1 | 1/2009 | Kortum et al. |
| 2009/0011048 A1 | 1/2009 | Coleman et al. |
| 2009/0012039 A1 | 1/2009 | Kurtz |
| 2009/0012177 A1 | 1/2009 | Shafa et al. |
| 2009/0012371 A1 | 1/2009 | Brennan et al. |
| 2009/0012419 A1 | 1/2009 | McKee |
| 2009/0012821 A1 | 1/2009 | Besson et al. |
| 2009/0014363 A1 | 1/2009 | Gonen et al. |
| 2009/0015785 A1 | 1/2009 | Blum et al. |
| 2009/0018407 A1 | 1/2009 | Jung et al. |
| 2009/0018419 A1 | 1/2009 | Torch |
| 2009/0018616 A1 | 1/2009 | Quick et al. |
| 2009/0018867 A1 | 1/2009 | Reiner |
| 2009/0021522 A1 | 1/2009 | Burley et al. |
| 2009/0022274 A1 | 1/2009 | Gertner et al. |
| 2009/0023119 A1 | 1/2009 | Breidner |
| 2009/0023501 A1 | 1/2009 | Kidakarn |
| 2009/0023705 A1 | 1/2009 | Roberts et al. |
| 2009/0023755 A1 | 1/2009 | Shiozaki et al. |
| 2009/0023977 A1 | 1/2009 | Sperling et al. |
| 2009/0024049 A1 | 1/2009 | Pradeep et al. |
| 2009/0024050 A1 | 1/2009 | Jung et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0024476 A1 | 1/2009 | Baar et al. |
| 2009/0024479 A1 | 1/2009 | Gonen et al. |
| 2009/0024964 A1 | 1/2009 | Kantamneni |
| 2009/0025023 A1 | 1/2009 | Pradeep et al. |
| 2009/0025602 A1 | 1/2009 | Kwan et al. |
| 2009/0027391 A1 | 1/2009 | Burley et al. |
| 2009/0030287 A1 | 1/2009 | Pradeep et al. |
| 2009/0030303 A1 | 1/2009 | Pradeep et al. |
| 2009/0030710 A1 | 1/2009 | Levine |
| 2009/0030717 A1 | 1/2009 | Pradeep et al. |
| 2009/0030801 A1 | 1/2009 | Meggs |
| 2009/0030930 A1 | 1/2009 | Pradeep et al. |
| 2009/0033662 A1 | 2/2009 | Murrah et al. |
| 2009/0033866 A1 | 2/2009 | Blum et al. |
| 2009/0033867 A1 | 2/2009 | Dai |
| 2009/0034796 A1 | 2/2009 | Johns |
| 2009/0034801 A1 | 2/2009 | Hammoud |
| 2009/0034816 A1 | 2/2009 | Ghanem et al. |
| 2009/0036755 A1 | 2/2009 | Pradeep et al. |
| 2009/0036756 A1 | 2/2009 | Pradeep et al. |
| 2009/0037400 A1 | 2/2009 | Cragun et al. |
| 2009/0040054 A1 | 2/2009 | Wang et al. |
| 2009/0040461 A1 | 2/2009 | Efron et al. |
| 2009/0042939 A1 | 2/2009 | Ieni et al. |
| 2009/0042940 A1 | 2/2009 | Ieni et al. |
| 2009/0043661 A1 | 2/2009 | Chong et al. |
| 2009/0046250 A1 | 2/2009 | Mattioli et al. |
| 2009/0046538 A1 | 2/2009 | Breed et al. |
| 2009/0047325 A1 | 2/2009 | Elliot et al. |
| 2009/0048908 A1 | 2/2009 | Kaplan et al. |
| 2009/0051877 A1 | 2/2009 | Delahunt et al. |
| 2009/0052728 A1 | 2/2009 | Blonde et al. |
| 2009/0054079 A1 | 2/2009 | Dubinsky |
| 2009/0054123 A1 | 2/2009 | Mityagin et al. |
| 2009/0054958 A1 | 2/2009 | Nofzinger |
| 2009/0055436 A1 | 2/2009 | Ayeni |
| 2009/0058660 A1 | 3/2009 | Torch |
| 2009/0060987 A1 | 3/2009 | Kaemmerer |
| 2009/0062043 A1 | 3/2009 | Wellington, Jr. |
| 2009/0062629 A1 | 3/2009 | Pradeep et al. |
| 2009/0062660 A1 | 3/2009 | Chance |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0063521 A1 | 3/2009 | Bull et al. |
| 2009/0063744 A1 | 3/2009 | Krueger et al. |
| 2009/0063974 A1 | 3/2009 | Bull et al. |
| 2009/0063975 A1 | 3/2009 | Bull et al. |
| 2009/0064202 A1 | 3/2009 | Lee et al. |
| 2009/0066065 A1 | 3/2009 | Breed et al. |
| 2009/0066810 A1 | 3/2009 | Holmes |
| 2009/0069707 A1 | 3/2009 | Sandford |
| 2009/0070121 A1 | 3/2009 | Leonelli et al. |
| 2009/0070162 A1 | 3/2009 | Leonelli et al. |
| 2009/0073386 A1 | 3/2009 | Petito et al. |
| 2009/0074677 A1 | 3/2009 | Marx et al. |
| 2009/0074857 A1 | 3/2009 | Dror et al. |
| 2009/0076487 A1 | 3/2009 | Somani et al. |
| 2009/0076793 A1 | 3/2009 | Hoefelmeyer et al. |
| 2009/0077493 A1 | 3/2009 | Hempel et al. |
| 2009/0077501 A1 | 3/2009 | Partridge et al. |
| 2009/0079816 A1 | 3/2009 | Qvarfordt et al. |
| 2009/0079937 A1 | 3/2009 | Chen et al. |
| 2009/0079938 A1 | 3/2009 | Blum et al. |
| 2009/0082643 A1 | 3/2009 | Pradeep et al. |
| 2009/0082690 A1 | 3/2009 | Phillips et al. |
| 2009/0082692 A1 | 3/2009 | Hale et al. |
| 2009/0083071 A1 | 3/2009 | Phillips et al. |
| 2009/0083129 A1 | 3/2009 | Pradeep et al. |
| 2009/0083197 A1 | 3/2009 | Gofman et al. |
| 2009/0083417 A1 | 3/2009 | Hughes et al. |
| 2009/0086103 A1 | 4/2009 | Nair |
| 2009/0086165 A1 | 4/2009 | Beymer |
| 2009/0087029 A1 | 4/2009 | Coleman et al. |
| 2009/0087436 A1 | 4/2009 | Roch et al. |
| 2009/0087868 A1 | 4/2009 | Wang et al. |
| 2009/0088399 A1 | 4/2009 | Balya et al. |
| 2009/0088435 A1 | 4/2009 | Mata et al. |
| 2009/0089062 A1 | 4/2009 | Lu |
| 2009/0089704 A1 | 4/2009 | Makela |
| 2009/0091422 A1 | 4/2009 | Minoo et al. |
| 2009/0092284 A1 | 4/2009 | Breed et al. |
| 2009/0092314 A1 | 4/2009 | Varshney et al. |
| 2009/0094286 A1 | 4/2009 | Lee et al. |
| 2009/0094627 A1 | 4/2009 | Lee et al. |
| 2009/0094628 A1 | 4/2009 | Lee et al. |
| 2009/0094629 A1 | 4/2009 | Lee et al. |
| 2009/0094652 A1 | 4/2009 | Al Adham et al. |
| 2009/0095303 A1 | 4/2009 | Sher et al. |
| 2009/0096983 A1 | 4/2009 | Provitola |
| 2009/0096987 A1 | 4/2009 | Lai et al. |
| 2009/0097705 A1 | 4/2009 | Thorn |
| 2009/0098145 A1 | 4/2009 | Mata et al. |
| 2009/0098221 A1 | 4/2009 | Nivaggioli |
| 2009/0099248 A1 | 4/2009 | Heffernan et al. |
| 2009/0104171 A1 | 4/2009 | Pardee et al. |
| 2009/0105933 A1 | 4/2009 | Wlotzka |
| 2009/0107506 A1 | 4/2009 | Collazo et al. |
| 2009/0107507 A1 | 4/2009 | Moore |
| 2009/0108559 A1 | 4/2009 | Merchant |
| 2009/0109130 A1 | 4/2009 | Murphy et al. |
| 2009/0110245 A1 | 4/2009 | Thorn |
| 2009/0110674 A1 | 4/2009 | Loizou |
| 2009/0111082 A1 | 4/2009 | Jorgensen |
| 2009/0111817 A1 | 4/2009 | Caron et al. |
| 2009/0111818 A1 | 4/2009 | Caron et al. |
| 2009/0112538 A1 | 4/2009 | Anderson et al. |
| 2009/0112541 A1 | 4/2009 | Anderson et al. |
| 2009/0112616 A1 | 4/2009 | Jung et al. |
| 2009/0112617 A1 | 4/2009 | Jung et al. |
| 2009/0112620 A1 | 4/2009 | Jung et al. |
| 2009/0112621 A1 | 4/2009 | Jung et al. |
| 2009/0112899 A1 | 4/2009 | Johnson |
| 2009/0113037 A1 | 4/2009 | Pouchak |
| 2009/0114230 A1 | 5/2009 | Hernandez et al. |

(56) References Cited

U.S. PATENT DOCUMENTS

| | | |
|---|---|---|
| 2009/0115588 A1 | 5/2009 | Stahel et al. |
| 2009/0115965 A1 | 5/2009 | Waldorf et al. |
| 2009/0116557 A1 | 5/2009 | Nair |
| 2009/0116688 A1 | 5/2009 | Monacos et al. |
| 2009/0118588 A1 | 5/2009 | Robinson et al. |
| 2009/0118593 A1 | 5/2009 | Jung et al. |
| 2009/0118636 A1 | 5/2009 | Collura |
| 2009/0119154 A1 | 5/2009 | Jung et al. |
| 2009/0122812 A1 | 5/2009 | Steiner et al. |
| 2009/0123031 A1 | 5/2009 | Smith et al. |
| 2009/0123433 A1 | 5/2009 | Shroff |
| 2009/0125498 A1 | 5/2009 | Cao et al. |
| 2009/0125849 A1 | 5/2009 | Bouvin et al. |
| 2009/0128901 A1 | 5/2009 | Tilleman et al. |
| 2009/0130030 A1 | 5/2009 | Ribi |
| 2009/0132275 A1 | 5/2009 | Jung et al. |
| 2009/0132279 A1 | 5/2009 | Yeluri |
| 2009/0132758 A1 | 5/2009 | Jiang et al. |
| 2009/0132895 A1 | 5/2009 | Jiang et al. |
| 2009/0132961 A1 | 5/2009 | Baar |
| 2009/0135108 A1 | 5/2009 | Lindfors et al. |
| 2009/0135134 A1 | 5/2009 | Prager et al. |
| 2009/0135913 A1 | 5/2009 | Nair et al. |
| 2009/0136091 A1 | 5/2009 | Woodfill et al. |
| 2009/0136465 A1 | 5/2009 | Merenick et al. |
| 2009/0138358 A1 | 5/2009 | Gonen et al. |
| 2009/0138507 A1 | 5/2009 | Burckart et al. |
| 2009/0138906 A1 | 5/2009 | Eide et al. |
| 2009/0141044 A1 | 6/2009 | Shoemaker |
| 2009/0141980 A1 | 6/2009 | Elliott |
| 2009/0143656 A1 | 6/2009 | Manwaring et al. |
| 2009/0145369 A1 | 6/2009 | Lumbroso et al. |
| 2009/0146775 A1 | 6/2009 | Bonnaud et al. |
| 2009/0146848 A1 | 6/2009 | Ghassabian |
| 2009/0146950 A1 | 6/2009 | Maringelli |
| 2009/0147080 A1 | 6/2009 | Inada |
| 2009/0149257 A1 | 6/2009 | Ferguson et al. |
| 2009/0149726 A1 | 6/2009 | Hyde et al. |
| 2009/0149742 A1 | 6/2009 | Kato et al. |
| 2009/0149769 A1 | 6/2009 | Pettigrew |
| 2009/0149770 A1 | 6/2009 | Sing |
| 2009/0150919 A1 | 6/2009 | Lee et al. |
| 2009/0152664 A1 | 6/2009 | Klem et al. |
| 2009/0152892 A1 | 6/2009 | Bohner et al. |
| 2009/0153472 A1 | 6/2009 | Bloem et al. |
| 2009/0153565 A1 | 6/2009 | Anderson et al. |
| 2009/0153566 A1 | 6/2009 | Anderson et al. |
| 2009/0153796 A1 | 6/2009 | Rabner |
| 2009/0155748 A1 | 6/2009 | Huskey |
| 2009/0155754 A1 | 6/2009 | Shankle et al. |
| 2009/0156907 A1 | 6/2009 | Jung et al. |
| 2009/0156955 A1 | 6/2009 | Jung et al. |
| 2009/0157323 A1 | 6/2009 | Jung et al. |
| 2009/0157388 A1 | 6/2009 | Boeckmann et al. |
| 2009/0157481 A1 | 6/2009 | Jung et al. |
| 2009/0157482 A1 | 6/2009 | Jung et al. |
| 2009/0157625 A1 | 6/2009 | Jung et al. |
| 2009/0157660 A1 | 6/2009 | Jung et al. |
| 2009/0157672 A1 | 6/2009 | Vemuri |
| 2009/0157751 A1 | 6/2009 | Jung et al. |
| 2009/0157813 A1 | 6/2009 | Jung et al. |
| 2009/0157889 A1 | 6/2009 | Treuhaft |
| 2009/0158179 A1 | 6/2009 | Brooks |
| 2009/0159084 A1 | 6/2009 | Sher et al. |
| 2009/0161826 A1 | 6/2009 | Gertner et al. |
| 2009/0161827 A1 | 6/2009 | Gertner et al. |
| 2009/0162826 A1 | 6/2009 | Ayati et al. |
| 2009/0163777 A1 | 6/2009 | Jung et al. |
| 2009/0163898 A1 | 6/2009 | Gertner et al. |
| 2009/0164131 A1 | 6/2009 | Jung et al. |
| 2009/0164132 A1 | 6/2009 | Jung et al. |
| 2009/0164302 A1 | 6/2009 | Jung et al. |
| 2009/0164339 A1 | 6/2009 | Rothman |
| 2009/0164401 A1 | 6/2009 | Jung et al. |
| 2009/0164403 A1 | 6/2009 | Jung et al. |
| 2009/0164458 A1 | 6/2009 | Jung et al. |
| 2009/0164503 A1 | 6/2009 | Jung et al. |
| 2009/0164549 A1 | 6/2009 | Jung et al. |
| 2009/0164629 A1 | 6/2009 | Klein et al. |
| 2009/0164896 A1 | 6/2009 | Thorn |
| 2009/0167948 A1 | 7/2009 | Berman et al. |
| 2009/0168014 A1 | 7/2009 | Rooney et al. |
| 2009/0170916 A1 | 7/2009 | Fang et al. |
| 2009/0171164 A1 | 7/2009 | Jung et al. |
| 2009/0171240 A1 | 7/2009 | Aguilar et al. |
| 2009/0171788 A1 | 7/2009 | Tropper et al. |
| 2009/0172100 A1 | 7/2009 | Callanan et al. |
| 2009/0172540 A1 | 7/2009 | Jung et al. |
| 2009/0172587 A1 | 7/2009 | Carlisle et al. |
| 2009/0172725 A1 | 7/2009 | Heilbron et al. |
| 2009/0172731 A1 | 7/2009 | Heilbron et al. |
| 2009/0174864 A1 | 7/2009 | Hutchin |
| 2009/0175841 A1 | 7/2009 | Berry et al. |
| 2009/0175987 A1 | 7/2009 | Shecter |
| 2009/0176433 A1 | 7/2009 | Forti |
| 2009/0176434 A1 | 7/2009 | Forti |
| 2009/0176715 A1 | 7/2009 | Javitt |
| 2009/0177714 A1 | 7/2009 | Obermeyer et al. |
| 2009/0179380 A1 | 7/2009 | Hall |
| 2009/0181081 A1 | 7/2009 | Gojon-Romanillos |
| 2009/0181352 A1 | 7/2009 | Hood |
| 2009/0181992 A1 | 7/2009 | Barbosa et al. |
| 2009/0182037 A1 | 7/2009 | Sies |
| 2009/0182499 A1 | 7/2009 | Bravo |
| 2009/0183095 A1 | 7/2009 | Deitsch et al. |
| 2009/0185552 A1 | 7/2009 | Poniatowski |
| 2009/0185748 A1 | 7/2009 | Kortum et al. |
| 2009/0187842 A1 | 7/2009 | Collins et al. |
| 2009/0189830 A1 | 7/2009 | Deering et al. |
| 2009/0189974 A1 | 7/2009 | Deering |
| 2009/0190093 A1 | 7/2009 | Tanassi et al. |
| 2009/0191531 A1 | 7/2009 | Saccocci et al. |
| 2009/0192078 A1 | 7/2009 | Lee |
| 2009/0192097 A1 | 7/2009 | Agarwal |
| 2009/0192319 A1 | 7/2009 | Glasky et al. |
| 2009/0192950 A1 | 7/2009 | King et al. |
| 2009/0192962 A1 | 7/2009 | Rigdon et al. |
| 2009/0195749 A1 | 8/2009 | Blum et al. |
| 2009/0196460 A1 | 8/2009 | Jakobs et al. |
| 2009/0198111 A1 | 8/2009 | Nearman et al. |
| 2009/0198144 A1 | 8/2009 | Phillips et al. |
| 2009/0198148 A1 | 8/2009 | Lonky |
| 2009/0201309 A1 | 8/2009 | Demos |
| 2009/0201363 A1 | 8/2009 | Grossmann |
| 2009/0202175 A1 | 8/2009 | Guerzhoy et al. |
| 2009/0202964 A1 | 8/2009 | Simon |
| 2009/0203316 A1 | 8/2009 | Krueger et al. |
| 2009/0203393 A1 | 8/2009 | Krueger et al. |
| 2009/0203786 A1 | 8/2009 | Waldron et al. |
| 2009/0204015 A1 | 8/2009 | Phillips et al. |
| 2009/0204672 A1 | 8/2009 | Jetha et al. |
| 2009/0207957 A1 | 8/2009 | Fukuda et al. |
| 2009/0212605 A1 | 8/2009 | Buckner |
| 2009/0213131 A1 | 8/2009 | DeRose et al. |
| 2009/0213134 A1 | 8/2009 | Stephanick et al. |
| 2009/0213138 A1 | 8/2009 | DeRose et al. |
| 2009/0213329 A1 | 8/2009 | Kandel et al. |
| 2009/0215015 A1 | 8/2009 | Chu |
| 2009/0219292 A1 | 9/2009 | Hahn |
| 2009/0221928 A1 | 9/2009 | Einav et al. |
| 2009/0222550 A1 | 9/2009 | McAfee et al. |
| 2009/0225001 A1 | 9/2009 | Biocca et al. |
| 2009/0225380 A1 | 9/2009 | Schwerdtner et al. |
| 2009/0228408 A1 | 9/2009 | Kaushal et al. |
| 2009/0231134 A1 | 9/2009 | Modica et al. |
| 2009/0234529 A1 | 9/2009 | Sampedro Diaz et al. |
| 2009/0234666 A1 | 9/2009 | Crawford et al. |
| 2009/0235327 A1 | 9/2009 | Jakobsson et al. |
| 2009/0237492 A1 | 9/2009 | Kikinis et al. |
| 2009/0237564 A1 | 9/2009 | Kikinis et al. |
| 2009/0238334 A1 | 9/2009 | Brahme et al. |
| 2009/0238378 A1 | 9/2009 | Kikinis et al. |
| 2009/0240136 A9 | 9/2009 | Sun et al. |
| 2009/0240327 A1 | 9/2009 | Daxer |

(56) References Cited

U.S. PATENT DOCUMENTS

| | | |
|---|---|---|
| 2009/0240366 A1 | 9/2009 | Kaushal et al. |
| 2009/0240677 A1 | 9/2009 | Parekh et al. |
| 2009/0244485 A1 | 10/2009 | Walsh et al. |
| 2009/0247457 A1 | 10/2009 | Brenneman et al. |
| 2009/0251460 A1 | 10/2009 | Dunnigan |
| 2009/0252265 A1 | 10/2009 | Xia et al. |
| 2009/0252394 A1 | 10/2009 | Liang et al. |
| 2009/0253487 A1 | 10/2009 | Gagner et al. |
| 2009/0253491 A1 | 10/2009 | Gomez et al. |
| 2009/0253745 A1 | 10/2009 | Mata et al. |
| 2009/0254201 A1 | 10/2009 | Glaser-Seidnitzer et al. |
| 2009/0254572 A1 | 10/2009 | Redlich et al. |
| 2009/0254801 A1 | 10/2009 | Pressman et al. |
| 2009/0256904 A1 | 10/2009 | Krill et al. |
| 2009/0257026 A1 | 10/2009 | Varnas et al. |
| 2009/0257565 A1 | 10/2009 | Nelson et al. |
| 2009/0260557 A1 | 10/2009 | Colsher et al. |
| 2009/0261979 A1 | 10/2009 | Breed et al. |
| 2009/0264520 A1 | 10/2009 | Bhagat |
| 2009/0264800 A1 | 10/2009 | Gestetner |
| 2009/0265389 A1 | 10/2009 | Kalpaxis |
| 2009/0267758 A1 | 10/2009 | Hyde et al. |
| 2009/0270170 A1 | 10/2009 | Patton |
| 2009/0270692 A1 | 10/2009 | Hyde et al. |
| 2009/0270758 A1 | 10/2009 | Eagleman et al. |
| 2009/0271008 A1 | 10/2009 | Hyde et al. |
| 2009/0271010 A1 | 10/2009 | Hyde et al. |
| 2009/0271011 A1 | 10/2009 | Hyde et al. |
| 2009/0271120 A1 | 10/2009 | Hyde et al. |
| 2009/0271283 A1 | 10/2009 | Fosnacht et al. |
| 2009/0271288 A1 | 10/2009 | Chong et al. |
| 2009/0271347 A1 | 10/2009 | Hyde et al. |
| 2009/0272703 A1 | 11/2009 | Conway, Jr. |
| 2009/0273287 A1 | 11/2009 | Segall |
| 2009/0273562 A1 | 11/2009 | Baliga et al. |
| 2009/0273711 A1 | 11/2009 | Chapdelaine et al. |
| 2009/0275541 A1 | 11/2009 | Sullivan |
| 2009/0275929 A1 | 11/2009 | Zickler |
| 2009/0276299 A1 | 11/2009 | Gonen et al. |
| 2009/0279736 A1 | 11/2009 | LaConte et al. |
| 2009/0279752 A1 | 11/2009 | Sirohey et al. |
| 2009/0280899 A1 | 11/2009 | Cox et al. |
| 2009/0281111 A1 | 11/2009 | Kramer |
| 2009/0281112 A1 | 11/2009 | Kramer et al. |
| 2009/0281423 A1 | 11/2009 | Sirohey et al. |
| 2009/0281447 A1 | 11/2009 | Gerdes |
| 2009/0281529 A1 | 11/2009 | Carriazo |
| 2009/0284471 A1 | 11/2009 | Longe et al. |
| 2009/0285456 A1 | 11/2009 | Moon et al. |
| 2009/0286592 A1 | 11/2009 | Vann |
| 2009/0286820 A1 | 11/2009 | Barbosa et al. |
| 2009/0287064 A1 | 11/2009 | Dougherty, Jr. et al. |
| 2009/0287108 A1 | 11/2009 | Levy |
| 2009/0287247 A1 | 11/2009 | Chipperson et al. |
| 2009/0288168 A1 | 11/2009 | Maghsoodnia et al. |
| 2009/0289892 A1 | 11/2009 | Cox et al. |
| 2009/0289968 A1 | 11/2009 | Yoshida |
| 2009/0290132 A1 | 11/2009 | Shevlin |
| 2009/0290725 A1 | 11/2009 | Huang |
| 2009/0291759 A1 | 11/2009 | Cox et al. |
| 2009/0292588 A1 | 11/2009 | Duzevik et al. |
| 2009/0292657 A1 | 11/2009 | Jung et al. |
| 2009/0292702 A1 | 11/2009 | Jung et al. |
| 2009/0292713 A1 | 11/2009 | Jung et al. |
| 2009/0292724 A1 | 11/2009 | Jung et al. |
| 2009/0292733 A1 | 11/2009 | Jung et al. |
| 2009/0292998 A1 | 11/2009 | Kumar et al. |
| 2009/0295682 A1 | 12/2009 | Qvarfordt et al. |
| 2009/0295683 A1 | 12/2009 | Pugh et al. |
| 2009/0295738 A1 | 12/2009 | Chiang |
| 2009/0297000 A1 | 12/2009 | Shahaf et al. |
| 2009/0297492 A1 | 12/2009 | Satoh et al. |
| 2009/0298850 A1 | 12/2009 | Leahy et al. |
| 2009/0298864 A1 | 12/2009 | Vitolo et al. |
| 2009/0299347 A1 | 12/2009 | Vogler et al. |
| 2009/0299857 A1 | 12/2009 | Brubaker |
| 2009/0300550 A1 | 12/2009 | Ruland |
| 2009/0300551 A1 | 12/2009 | French et al. |
| 2009/0304819 A1 | 12/2009 | Gojon-Romanillos |
| 2009/0306092 A1 | 12/2009 | Olsen et al. |
| 2009/0306100 A1 | 12/2009 | Barbosa et al. |
| 2009/0306484 A1 | 12/2009 | Kurtz et al. |
| 2009/0306741 A1 | 12/2009 | Hogle et al. |
| 2009/0306948 A1 | 12/2009 | Irving et al. |
| 2009/0306959 A1 | 12/2009 | Rappoport et al. |
| 2009/0306985 A1 | 12/2009 | Roberts et al. |
| 2009/0307601 A1 | 12/2009 | Kumhyr et al. |
| 2009/0309709 A1 | 12/2009 | Bevacqua et al. |
| 2009/0309882 A1 | 12/2009 | Kanyuk et al. |
| 2009/0309887 A1 | 12/2009 | Moller et al. |
| 2009/0312086 A1 | 12/2009 | Kanellos et al. |
| 2009/0312595 A1 | 12/2009 | Leuthardt et al. |
| 2009/0312668 A1 | 12/2009 | Leuthardt et al. |
| 2009/0312808 A1 | 12/2009 | Tyler et al. |
| 2009/0312817 A1 | 12/2009 | Hogle et al. |
| 2009/0313047 A1 | 12/2009 | Smith et al. |
| 2009/0313286 A1 | 12/2009 | Mishra et al. |
| 2009/0315827 A1 | 12/2009 | Elvesjo et al. |
| 2009/0317805 A1 | 12/2009 | Wang et al. |
| 2009/0318208 A1 | 12/2009 | Liebowitz et al. |
| 2009/0318520 A1 | 12/2009 | Kovacs et al. |
| 2009/0318773 A1 | 12/2009 | Jung et al. |
| 2009/0318825 A1 | 12/2009 | Kilborn |
| 2009/0319001 A1 | 12/2009 | Schiff |
| 2009/0319354 A1 | 12/2009 | Gonen et al. |
| 2009/0319459 A1 | 12/2009 | Breazeal et al. |
| 2009/0322671 A1 | 12/2009 | Scott et al. |
| 2009/0322678 A1 | 12/2009 | Lashina et al. |
| 2009/0326604 A1 | 12/2009 | Tyler et al. |
| 2009/0327068 A1 | 12/2009 | Pradeep et al. |
| 2009/0327267 A1 | 12/2009 | Wong et al. |
| 2009/0327492 A1 | 12/2009 | Anderson et al. |
| 2009/0327888 A1 | 12/2009 | Woolf et al. |
| 2009/0328089 A1 | 12/2009 | Pradeep et al. |
| 2010/0001660 A1 | 1/2010 | Pas |
| 2010/0001926 A1 | 1/2010 | Amirparviz et al. |
| 2010/0002070 A1 | 1/2010 | Ahiska |
| 2010/0002071 A1 | 1/2010 | Ahiska |
| 2010/0002075 A1 | 1/2010 | Jung et al. |
| 2010/0002154 A1 | 1/2010 | Hua |
| 2010/0002837 A1 | 1/2010 | Gertner et al. |
| 2010/0003655 A1 | 1/2010 | Stephenson, Jr. |
| 2010/0003659 A1 | 1/2010 | Edmonds |
| 2010/0004557 A1 | 1/2010 | Zelinsky |
| 2010/0004762 A1 | 1/2010 | Leuthardt et al. |
| 2010/0004977 A1 | 1/2010 | Marci et al. |
| 2010/0005169 A1 | 1/2010 | Von Hilgers |
| 2010/0005952 A1 | 1/2010 | LaMon |
| 2010/0007601 A1 | 1/2010 | Lashina et al. |
| 2010/0008541 A1 | 1/2010 | Forlines |
| 2010/0008650 A1 | 1/2010 | Bull et al. |
| 2010/0009325 A1 | 1/2010 | Afanasiev et al. |
| 2010/0009331 A1 | 1/2010 | Yaskin et al. |
| 2010/0010097 A1 | 1/2010 | Epstein et al. |
| 2010/0010317 A1 | 1/2010 | De Lemos |
| 2010/0010336 A1 | 1/2010 | Pettegrew et al. |
| 2010/0010366 A1 | 1/2010 | Silberstein |
| 2010/0010370 A1 | 1/2010 | De Lemos et al. |
| 2010/0010394 A1 | 1/2010 | Liu et al. |
| 2010/0010648 A1 | 1/2010 | Bull et al. |
| 2010/0010825 A1 | 1/2010 | Kunz |
| 2010/0011023 A1 | 1/2010 | Nakaoka |
| 2010/0014053 A1 | 1/2010 | Brentnall, III et al. |
| 2010/0015579 A1 | 1/2010 | Schlabach |
| 2010/0015583 A1 | 1/2010 | Leuthardt et al. |
| 2010/0016397 A1 | 1/2010 | Fang et al. |
| 2010/0016753 A1 | 1/2010 | Firlik |
| 2010/0016754 A1 | 1/2010 | Whillock et al. |
| 2010/0017001 A1 | 1/2010 | Leuthardt et al. |
| 2010/0017268 A1 | 1/2010 | Keil et al. |
| 2010/0017353 A1 | 1/2010 | Brinson, Jr. et al. |
| 2010/0019922 A1 | 1/2010 | Van Loenen et al. |
| 2010/0019992 A1 | 1/2010 | Maguire, Jr. |
| 2010/0022612 A1 | 1/2010 | Dorsey et al. |

(56) References Cited

U.S. PATENT DOCUMENTS

| | | |
|---|---|---|
| 2010/0022631 A1 | 1/2010 | Berry et al. |
| 2010/0022658 A1 | 1/2010 | Epstein et al. |
| 2010/0022820 A1 | 1/2010 | Leuthardt et al. |
| 2010/0023863 A1 | 1/2010 | Cohen-Martin |
| 2010/0025441 A1 | 2/2010 | Blaney |
| 2010/0027083 A1 | 2/2010 | Kroll et al. |
| 2010/0028361 A1 | 2/2010 | Smith et al. |
| 2010/0029737 A1 | 2/2010 | Heffernan et al. |
| 2010/0029741 A1 | 2/2010 | Dorsey et al. |
| 2010/0029770 A1 | 2/2010 | Roberts et al. |
| 2010/0030101 A1 | 2/2010 | Durrant et al. |
| 2010/0030775 A1 | 2/2010 | Mohajer et al. |
| 2010/0030798 A1 | 2/2010 | Kumar et al. |
| 2010/0033333 A1 | 2/2010 | Victor et al. |
| 2010/0033782 A1 | 2/2010 | Olaya |
| 2010/0033813 A1 | 2/2010 | Rogoff |
| 2010/0036276 A1 | 2/2010 | Ochs |
| 2010/0036457 A1 | 2/2010 | Sarpeshkar et al. |
| 2010/0036738 A1 | 2/2010 | Dowd |
| 2010/0039380 A1 | 2/2010 | Lanier |
| 2010/0039617 A1 | 2/2010 | Martinez-Conde et al. |
| 2010/0039618 A1 | 2/2010 | De Lemos |
| 2010/0041621 A1 | 2/2010 | Renshaw et al. |
| 2010/0041958 A1 | 2/2010 | Leuthardt et al. |
| 2010/0042401 A1 | 2/2010 | Ascoli et al. |
| 2010/0042578 A1 | 2/2010 | Leuthardt et al. |
| 2010/0045596 A1 | 2/2010 | De Leon |
| 2010/0045773 A1 | 2/2010 | Ritchey |
| 2010/0045932 A1 | 2/2010 | Shelhamer et al. |
| 2010/0046049 A1 | 2/2010 | Kroll et al. |
| 2010/0046050 A1 | 2/2010 | Kroll et al. |
| 2010/0046842 A1 | 2/2010 | Conwell |
| 2010/0047795 A1 | 2/2010 | Leonard et al. |
| 2010/0048242 A1 | 2/2010 | Rhoads et al. |
| 2010/0049527 A1 | 2/2010 | Korthauer et al. |
| 2010/0049709 A1 | 2/2010 | Ravikumar et al. |
| 2010/0049879 A1 | 2/2010 | Leavitt et al. |
| 2010/0053069 A1 | 3/2010 | Tricoukes et al. |
| 2010/0053172 A1 | 3/2010 | DeRose et al. |
| 2010/0053186 A1 | 3/2010 | DeRose et al. |
| 2010/0053555 A1 | 3/2010 | Enriquez et al. |
| 2010/0054526 A1 | 3/2010 | Eckles |
| 2010/0056274 A1 | 3/2010 | Uusitalo et al. |
| 2010/0057059 A1 | 3/2010 | Makino |
| 2010/0057445 A1 | 3/2010 | Aoki et al. |
| 2010/0058238 A1 | 3/2010 | Ben Moshe |
| 2010/0059587 A1 | 3/2010 | Miller et al. |
| 2010/0061553 A1 | 3/2010 | Chaum |
| 2010/0063368 A1 | 3/2010 | Leuthardt et al. |
| 2010/0064042 A1 | 3/2010 | Paster |
| 2010/0064053 A1 | 3/2010 | Bull et al. |
| 2010/0064218 A1 | 3/2010 | Bull et al. |
| 2010/0064353 A1 | 3/2010 | Kan et al. |
| 2010/0066850 A1 | 3/2010 | Wilson et al. |
| 2010/0066975 A1 | 3/2010 | Rehnstrom |
| 2010/0067077 A1 | 3/2010 | Kroll et al. |
| 2010/0067656 A1 | 3/2010 | Gertner et al. |
| 2010/0067657 A1 | 3/2010 | Gertner et al. |
| 2010/0067658 A1 | 3/2010 | Gertner et al. |
| 2010/0069332 A1 | 3/2010 | Ben Dror et al. |
| 2010/0069724 A1 | 3/2010 | Leuthardt et al. |
| 2010/0069777 A1 | 3/2010 | Marks |
| 2010/0070268 A1 | 3/2010 | Sung |
| 2010/0070491 A1 | 3/2010 | Cragun et al. |
| 2010/0070501 A1 | 3/2010 | Walsh et al. |
| 2010/0070988 A1 | 3/2010 | Cohen et al. |
| 2010/0074460 A1 | 3/2010 | Marzetta |
| 2010/0074472 A1 | 3/2010 | Garoutte |
| 2010/0076249 A1 | 3/2010 | Leuthardt et al. |
| 2010/0077421 A1 | 3/2010 | Cohen et al. |
| 2010/0079449 A1 | 4/2010 | McCarthy |
| 2010/0079578 A1 | 4/2010 | Mihara et al. |
| 2010/0080447 A1 | 4/2010 | Kanazawa et al. |
| 2010/0081502 A1 | 4/2010 | Rasmussen et al. |
| 2010/0081648 A1 | 4/2010 | Gallagher et al. |
| 2010/0081691 A1 | 4/2010 | Barbosa et al. |
| 2010/0081707 A1 | 4/2010 | Ali et al. |
| 2010/0081860 A1 | 4/2010 | Leuthardt et al. |
| 2010/0081861 A1 | 4/2010 | Leuthardt et al. |
| 2010/0081889 A1 | 4/2010 | Downs, III et al. |
| 2010/0082566 A1 | 4/2010 | Wang et al. |
| 2010/0082634 A1 | 4/2010 | Leban |
| 2010/0083972 A1 | 4/2010 | Zelinsky |
| 2010/0085446 A1 | 4/2010 | Thorn |
| 2010/0085883 A1 | 4/2010 | Paster |
| 2010/0086656 A1 | 4/2010 | Logsdon |
| 2010/0087422 A1 | 4/2010 | Bird |
| 2010/0087701 A1 | 4/2010 | Berka et al. |
| 2010/0088670 A1 | 4/2010 | Paster |
| 2010/0092049 A1 | 4/2010 | Schroeder et al. |
| 2010/0092929 A1 | 4/2010 | Hallowell et al. |
| 2010/0094155 A1 | 4/2010 | Prichep |
| 2010/0094156 A1 | 4/2010 | Collura |
| 2010/0094161 A1 | 4/2010 | Kiderman et al. |
| 2010/0094162 A1 | 4/2010 | Benasich et al. |
| 2010/0094377 A1 | 4/2010 | Graupe |
| 2010/0097439 A1 | 4/2010 | Kroll et al. |
| 2010/0098225 A1 | 4/2010 | Ashton et al. |
| 2010/0098258 A1 | 4/2010 | Thorn |
| 2010/0099460 A1 | 4/2010 | Skelton |
| 2010/0099483 A1 | 4/2010 | Bleich et al. |
| 2010/0099714 A1 | 4/2010 | Yoshino et al. |
| 2010/0099721 A1 | 4/2010 | Niestroj et al. |
| 2010/0099763 A1 | 4/2010 | Choi et al. |
| 2010/0100001 A1 | 4/2010 | Aguilar et al. |
| 2010/0100036 A1 | 4/2010 | Leuthardt et al. |
| 2010/0100849 A1 | 4/2010 | Fram |
| 2010/0103089 A1 | 4/2010 | Yoshida et al. |
| 2010/0103244 A1 | 4/2010 | Brandsma et al. |
| 2010/0103246 A1 | 4/2010 | Schwerdtner et al. |
| 2010/0103375 A1 | 4/2010 | Chao |
| 2010/0103485 A1 | 4/2010 | Haussler |
| 2010/0105623 A1 | 4/2010 | Weinberger et al. |
| 2010/0106143 A1 | 4/2010 | Riedel et al. |
| 2010/0106547 A1 | 4/2010 | Adi et al. |
| 2010/0107106 A1 | 4/2010 | Corbett et al. |
| 2010/0107107 A1 | 4/2010 | Corbett et al. |
| 2010/0107184 A1 | 4/2010 | Shintani |
| 2010/0109881 A1 | 5/2010 | Eskandarian et al. |
| 2010/0110275 A1 | 5/2010 | Mathieu |
| 2010/0110368 A1 | 5/2010 | Chaum |
| 2010/0110371 A1 | 5/2010 | Ho et al. |
| 2010/0110379 A1 | 5/2010 | Zhou et al. |
| 2010/0111431 A1 | 5/2010 | Gharavi-Alkhansari et al. |
| 2010/0111498 A1 | 5/2010 | Weda et al. |
| 2010/0112541 A1 | 5/2010 | Templin |
| 2010/0114076 A1 | 5/2010 | Reinstein et al. |
| 2010/0116876 A1 | 5/2010 | Miller et al. |
| 2010/0118030 A1 | 5/2010 | Helfman et al. |
| 2010/0118032 A1 | 5/2010 | Helfman et al. |
| 2010/0118117 A1 | 5/2010 | Kroll et al. |
| 2010/0118141 A1 | 5/2010 | Bouchon-Meunier et al. |
| 2010/0118267 A1 | 5/2010 | Helfman et al. |
| 2010/0119111 A1 | 5/2010 | Helfman et al. |
| 2010/0119112 A1 | 5/2010 | Helfman et al. |
| 2010/0120003 A1 | 5/2010 | Herman |
| 2010/0120508 A1 | 5/2010 | Vann et al. |
| 2010/0120522 A1 | 5/2010 | Englman et al. |
| 2010/0120665 A1 | 5/2010 | Kaleko et al. |
| 2010/0120740 A1 | 5/2010 | Heffernan et al. |
| 2010/0121645 A1 | 5/2010 | Seitz et al. |
| 2010/0121700 A1 | 5/2010 | Wigder et al. |
| 2010/0121812 A1 | 5/2010 | Helfman et al. |
| 2010/0124962 A1 | 5/2010 | Chudek et al. |
| 2010/0124989 A1 | 5/2010 | Englman et al. |
| 2010/0125561 A1 | 5/2010 | Leuthardt et al. |
| 2010/0125799 A1 | 5/2010 | Roberts et al. |
| 2010/0128118 A1 | 5/2010 | Swindells et al. |
| 2010/0128222 A1 | 5/2010 | Donaldson |
| 2010/0130537 A1 | 5/2010 | Miyagawa |
| 2010/0130811 A1 | 5/2010 | Leuthardt et al. |
| 2010/0131356 A1 | 5/2010 | Stevens et al. |
| 2010/0134642 A1 | 6/2010 | Thorn |
| 2010/0134761 A1 | 6/2010 | Johns et al. |

(56) References Cited

U.S. PATENT DOCUMENTS

| | | |
|---|---|---|
| 2010/0138026 A1 | 6/2010 | Kaushal et al. |
| 2010/0138037 A1 | 6/2010 | Adelberg et al. |
| 2010/0138416 A1 | 6/2010 | Bellotti |
| 2010/0138749 A1 | 6/2010 | Covannon et al. |
| 2010/0141422 A1 | 6/2010 | Feinleib et al. |
| 2010/0141552 A1 | 6/2010 | Ferlitsch et al. |
| 2010/0144239 A1 | 6/2010 | Eck et al. |
| 2010/0144875 A1 | 6/2010 | Larson et al. |
| 2010/0145215 A1 | 6/2010 | Pradeep et al. |
| 2010/0145720 A1 | 6/2010 | Reiner |
| 2010/0145729 A1 | 6/2010 | Katz |
| 2010/0145944 A1 | 6/2010 | Punera et al. |
| 2010/0149073 A1 | 6/2010 | Chaum et al. |
| 2010/0149093 A1 | 6/2010 | Edwards |
| 2010/0149139 A1 | 6/2010 | Kroll et al. |
| 2010/0149182 A1 | 6/2010 | Butler et al. |
| 2010/0149311 A1 | 6/2010 | Kroll et al. |
| 2010/0149317 A1 | 6/2010 | Matthews |
| 2010/0149329 A1 | 6/2010 | Maguire, Jr. |
| 2010/0149488 A1 | 6/2010 | Lo et al. |
| 2010/0151461 A1 | 6/2010 | Brennan |
| 2010/0151471 A1 | 6/2010 | Faham et al. |
| 2010/0153370 A1 | 6/2010 | Gollapudi et al. |
| 2010/0153764 A1 | 6/2010 | Pratt et al. |
| 2010/0153831 A1 | 6/2010 | Beaton |
| 2010/0156781 A1 | 6/2010 | Fahn |
| 2010/0156926 A1 | 6/2010 | Furukawa et al. |
| 2010/0157045 A1 | 6/2010 | Maguire, Jr. |
| 2010/0157399 A1 | 6/2010 | Kroll et al. |
| 2010/0157400 A1 | 6/2010 | Dimov et al. |
| 2010/0159607 A1 | 6/2010 | Lee |
| 2010/0160245 A1 | 6/2010 | Lines |
| 2010/0163027 A1 | 7/2010 | Hyde et al. |
| 2010/0163035 A1 | 7/2010 | Hyde et al. |
| 2010/0164956 A1 | 7/2010 | Hyndman et al. |
| 2010/0165293 A1 | 7/2010 | Tanassi et al. |
| 2010/0166148 A1 | 7/2010 | Gertner et al. |
| 2010/0168525 A1 | 7/2010 | Hyde et al. |
| 2010/0168602 A1 | 7/2010 | Hyde et al. |
| 2010/0169958 A1 | 7/2010 | Werner et al. |
| 2010/0172473 A1 | 7/2010 | Gertner et al. |
| 2010/0174586 A1 | 7/2010 | Berg, Jr. et al. |
| 2010/0175721 A1 | 7/2010 | Eli |
| 2010/0175726 A1 | 7/2010 | Eli |
| 2010/0177163 A1 | 7/2010 | Yang et al. |
| 2010/0177278 A1 | 7/2010 | Reichow et al. |
| 2010/0177929 A1 | 7/2010 | Kurtz et al. |
| 2010/0178362 A1 | 7/2010 | Komorowski et al. |
| 2010/0179520 A1 | 7/2010 | Dai |
| 2010/0179857 A1 | 7/2010 | Kalaboukis et al. |
| 2010/0182232 A1 | 7/2010 | Zamoyski |
| 2010/0182243 A1 | 7/2010 | Singh et al. |
| 2010/0183205 A1 | 7/2010 | Pfleger et al. |
| 2010/0183279 A1 | 7/2010 | Pradeep et al. |
| 2010/0183577 A1 | 7/2010 | Stern et al. |
| 2010/0185113 A1 | 7/2010 | Peot et al. |
| 2010/0186031 A1 | 7/2010 | Pradeep et al. |
| 2010/0186032 A1 | 7/2010 | Pradeep et al. |
| 2010/0187404 A1 | 7/2010 | Klem et al. |
| 2010/0187408 A1 | 7/2010 | Klem et al. |
| 2010/0188637 A1 | 7/2010 | Reichow et al. |
| 2010/0188638 A1 | 7/2010 | Eberl et al. |
| 2010/0189354 A1 | 7/2010 | de Campos et al. |
| 2010/0189818 A1 | 7/2010 | Tsai |
| 2010/0190552 A1 | 7/2010 | Rasmussen et al. |
| 2010/0191598 A1 | 7/2010 | Toennis et al. |
| 2010/0191631 A1 | 7/2010 | Weidmann |
| 2010/0191727 A1 | 7/2010 | Malik |
| 2010/0191772 A1 | 7/2010 | Brown et al. |
| 2010/0191807 A1 | 7/2010 | Brown et al. |
| 2010/0195051 A1 | 8/2010 | Murray et al. |
| 2010/0195794 A1 | 8/2010 | Gertner |
| 2010/0196286 A1 | 8/2010 | Armer et al. |
| 2010/0198834 A1 | 8/2010 | Petras et al. |
| 2010/0198982 A1 | 8/2010 | Fernandez |
| 2010/0199197 A1 | 8/2010 | Faletski et al. |
| 2010/0204173 A1 | 8/2010 | Forbes |
| 2010/0205024 A1 | 8/2010 | Shachar et al. |
| 2010/0205043 A1 | 8/2010 | Edwards |
| 2010/0207877 A1 | 8/2010 | Woodard |
| 2010/0208035 A1 | 8/2010 | Pinault et al. |
| 2010/0208078 A1 | 8/2010 | Tian et al. |
| 2010/0208198 A1 | 8/2010 | Reichow et al. |
| 2010/0208200 A1 | 8/2010 | Levis et al. |
| 2010/0208205 A1 | 8/2010 | Tseng et al. |
| 2010/0208206 A1 | 8/2010 | Connell, II |
| 2010/0208207 A1 | 8/2010 | Connell, II |
| 2010/0208968 A1 | 8/2010 | Shoemaker et al. |
| 2010/0209542 A1 | 8/2010 | Boyer et al. |
| 2010/0209881 A1 | 8/2010 | Lin et al. |
| 2010/0209882 A1 | 8/2010 | Lin et al. |
| 2010/0209883 A1 | 8/2010 | Chin et al. |
| 2010/0209884 A1 | 8/2010 | Lin et al. |
| 2010/0209885 A1 | 8/2010 | Chin et al. |
| 2010/0209886 A1 | 8/2010 | Lin et al. |
| 2010/0209887 A1 | 8/2010 | Chin et al. |
| 2010/0209888 A1 | 8/2010 | Huang et al. |
| 2010/0209889 A1 | 8/2010 | Huang et al. |
| 2010/0209890 A1 | 8/2010 | Huang et al. |
| 2010/0209891 A1 | 8/2010 | Lin et al. |
| 2010/0209892 A1 | 8/2010 | Lin et al. |
| 2010/0211054 A1 | 8/2010 | Lemonis |
| 2010/0211270 A1 | 8/2010 | Chin et al. |
| 2010/0211439 A1 | 8/2010 | Marci et al. |
| 2010/0214318 A1 | 8/2010 | Pradeep et al. |
| 2010/0215098 A1 | 8/2010 | Chung |
| 2010/0215289 A1 | 8/2010 | Pradeep et al. |
| 2010/0217097 A1 | 8/2010 | Chen et al. |
| 2010/0220092 A1 | 9/2010 | Kimura |
| 2010/0220117 A1 | 9/2010 | Kimura |
| 2010/0220288 A1 | 9/2010 | Cleveland |
| 2010/0220291 A1 | 9/2010 | Horning et al. |
| 2010/0221688 A1 | 9/2010 | Reeves et al. |
| 2010/0222662 A1 | 9/2010 | Hegg et al. |
| 2010/0222774 A1 | 9/2010 | Hegg et al. |
| 2010/0222775 A1 | 9/2010 | Hegg et al. |
| 2010/0223261 A1 | 9/2010 | Sarkar |
| 2010/0223382 A1 | 9/2010 | Rayes et al. |
| 2010/0224872 A1 | 9/2010 | Kimura |
| 2010/0224880 A1 | 9/2010 | Kimura |
| 2010/0225576 A1 | 9/2010 | Morad et al. |
| 2010/0225668 A1 | 9/2010 | Tatke et al. |
| 2010/0225734 A1 | 9/2010 | Weller et al. |
| 2010/0225743 A1 | 9/2010 | Florencio et al. |
| 2010/0226535 A1 | 9/2010 | Kimchi et al. |
| 2010/0226878 A1 | 9/2010 | Zacks |
| 2010/0228344 A1 | 9/2010 | Shadduck |
| 2010/0228710 A1 | 9/2010 | Imig et al. |
| 2010/0231483 A1 | 9/2010 | Bazih et al. |
| 2010/0231504 A1 | 9/2010 | Bloem et al. |
| 2010/0231705 A1 | 9/2010 | Yahav et al. |
| 2010/0231706 A1 | 9/2010 | Maguire, Jr. |
| 2010/0231734 A1 | 9/2010 | Cai |
| 2010/0231752 A1 | 9/2010 | Lodge |
| 2010/0231855 A1 | 9/2010 | Thompson et al. |
| 2010/0232000 A1 | 9/2010 | Futterer et al. |
| 2010/0233304 A1 | 9/2010 | Pan |
| 2010/0235226 A1 | 9/2010 | Keil et al. |
| 2010/0235306 A1 | 9/2010 | Wagoner |
| 2010/0235330 A1 | 9/2010 | Reiner |
| 2010/0238161 A1 | 9/2010 | Varga et al. |
| 2010/0238204 A1 | 9/2010 | Chen et al. |
| 2010/0238270 A1 | 9/2010 | Bjelkhagen et al. |
| 2010/0238530 A1 | 9/2010 | Bjelkhagen et al. |
| 2010/0239067 A1 | 9/2010 | Gertner et al. |
| 2010/0239119 A1 | 9/2010 | Bazakos et al. |
| 2010/0240988 A1 | 9/2010 | Varga et al. |
| 2010/0241489 A1 | 9/2010 | Ivers et al. |
| 2010/0241564 A1 | 9/2010 | Miller et al. |
| 2010/0245585 A1 | 9/2010 | Fisher et al. |
| 2010/0245767 A1 | 9/2010 | Chao |
| 2010/0245838 A1 | 9/2010 | Everett et al. |
| 2010/0246361 A1 | 9/2010 | Miazzo et al. |
| 2010/0246666 A1 | 9/2010 | Miazzo et al. |

(56) References Cited

U.S. PATENT DOCUMENTS

| | | |
|---|---|---|
| 2010/0248828 A1 | 9/2010 | Kaing |
| 2010/0249538 A1 | 9/2010 | Pradeep et al. |
| 2010/0249636 A1 | 9/2010 | Pradeep et al. |
| 2010/0250111 A1 | 9/2010 | Gutierrez et al. |
| 2010/0250325 A1 | 9/2010 | Pradeep et al. |
| 2010/0250497 A1 | 9/2010 | Redlich et al. |
| 2010/0250522 A1 | 9/2010 | Chakrabarty |
| 2010/0253677 A1 | 10/2010 | Kroll et al. |
| 2010/0253817 A1 | 10/2010 | Ali et al. |
| 2010/0253909 A1 | 10/2010 | Dai |
| 2010/0254513 A1 | 10/2010 | Gertner |
| 2010/0254609 A1 | 10/2010 | Chen et al. |
| 2010/0254630 A1 | 10/2010 | Ali et al. |
| 2010/0255061 A1 | 10/2010 | de Juan, Jr. et al. |
| 2010/0256437 A1 | 10/2010 | Hegg et al. |
| 2010/0256467 A1 | 10/2010 | Hegg et al. |
| 2010/0256508 A1 | 10/2010 | Dinwiddie |
| 2010/0257478 A1 | 10/2010 | Longe et al. |
| 2010/0258132 A1 | 10/2010 | Moore |
| 2010/0260320 A1 | 10/2010 | Gertner |
| 2010/0261791 A1 | 10/2010 | Henderson |
| 2010/0262907 A1 | 10/2010 | Shoemaker et al. |
| 2010/0265281 A1 | 10/2010 | Furukawa et al. |
| 2010/0266051 A1 | 10/2010 | Ahmad et al. |
| 2010/0266213 A1 | 10/2010 | Hill et al. |
| 2010/0267445 A1 | 10/2010 | Gomez |
| 2010/0268696 A1 | 10/2010 | Nightengale et al. |
| 2010/0271299 A1 | 10/2010 | Stephanick et al. |
| 2010/0272780 A1 | 10/2010 | Ling et al. |
| 2010/0275346 A1 | 11/2010 | Delonas |
| 2010/0277416 A1 | 11/2010 | Longe |
| 2010/0277693 A1 | 11/2010 | Martinez-Conde et al. |
| 2010/0277779 A1 | 11/2010 | Futterer et al. |
| 2010/0279285 A1 | 11/2010 | Brennan et al. |
| 2010/0279423 A1 | 11/2010 | Brennan et al. |
| 2010/0280332 A1 | 11/2010 | Hyde et al. |
| 2010/0280372 A1 | 11/2010 | Poolman et al. |
| 2010/0280403 A1 | 11/2010 | Erdogmus et al. |
| 2010/0280432 A1 | 11/2010 | DiPierro et al. |
| 2010/0283630 A1 | 11/2010 | Alonso |
| 2010/0283732 A1 | 11/2010 | Banning |
| 2010/0283843 A1 | 11/2010 | Cai |
| 2010/0283969 A1 | 11/2010 | Cooperstock et al. |
| 2010/0283972 A1 | 11/2010 | Plant et al. |
| 2010/0287500 A1 | 11/2010 | Whitlow et al. |
| 2010/0289877 A1 | 11/2010 | Lanfranchi et al. |
| 2010/0290668 A1 | 11/2010 | Friedman et al. |
| 2010/0292330 A1 | 11/2010 | Pan et al. |
| 2010/0292545 A1 | 11/2010 | Berka et al. |
| 2010/0292676 A1 | 11/2010 | Larsen |
| 2010/0293453 A1 | 11/2010 | Schwarz |
| 2010/0295769 A1 | 11/2010 | Lundstrom |
| 2010/0295774 A1 | 11/2010 | Hennessey |
| 2010/0295921 A1 | 11/2010 | Guthrie et al. |
| 2010/0296148 A1 | 11/2010 | Reichelt et al. |
| 2010/0298382 A1 | 11/2010 | Seeman et al. |
| 2010/0298443 A1 | 11/2010 | Widder et al. |
| 2010/0299168 A1 | 11/2010 | Alonzo et al. |
| 2010/0299182 A1 | 11/2010 | Eivaz et al. |
| 2010/0302252 A1 | 12/2010 | Petrovic et al. |
| 2010/0302499 A1 | 12/2010 | Watanabe |
| 2010/0303294 A1 | 12/2010 | Zschau |
| 2010/0305843 A1 | 12/2010 | Yan et al. |
| 2010/0306661 A1 | 12/2010 | Crain et al. |
| 2010/0310627 A1 | 12/2010 | Elliott et al. |
| 2010/0311639 A1 | 12/2010 | Simard |
| 2010/0312596 A1 | 12/2010 | Saffari et al. |
| 2010/0312732 A1 | 12/2010 | Quinn et al. |
| 2010/0313048 A1 | 12/2010 | Shye et al. |
| 2010/0315482 A1 | 12/2010 | Rosenfeld et al. |
| 2010/0315594 A1 | 12/2010 | Johansson et al. |
| 2010/0316982 A1 | 12/2010 | Singh |
| 2010/0316985 A1 | 12/2010 | Lloyd |
| 2010/0317041 A1 | 12/2010 | Wang et al. |
| 2010/0317444 A1 | 12/2010 | Chandrasekar et al. |
| 2010/0321382 A1 | 12/2010 | Amaratunga et al. |
| 2010/0321482 A1 | 12/2010 | Cleveland |
| 2010/0322479 A1 | 12/2010 | Cleveland |
| 2010/0323581 A1 | 12/2010 | Goszewski et al. |
| 2010/0324454 A1 | 12/2010 | Kircher et al. |
| 2010/0324671 A1 | 12/2010 | Shadduck |
| 2010/0328306 A1 | 12/2010 | Chau et al. |
| 2010/0328444 A1 | 12/2010 | Blixt et al. |
| 2010/0329513 A1 | 12/2010 | Klefenz |
| 2010/0331337 A1 | 12/2010 | Lines |
| 2011/0001924 A1 | 1/2011 | Giraudet et al. |
| 2011/0003396 A1 | 1/2011 | Jeppesen et al. |
| 2011/0004481 A1 | 1/2011 | Jones |
| 2011/0006978 A1 | 1/2011 | Yuan |
| 2011/0007174 A1 | 1/2011 | Bacivarov et al. |
| 2011/0007275 A1 | 1/2011 | Yoo et al. |
| 2011/0007855 A1 | 1/2011 | Ishii et al. |
| 2011/0008306 A1 | 1/2011 | Nivaggioli |
| 2011/0009187 A1 | 1/2011 | Mastropietro |
| 2011/0010231 A1 | 1/2011 | Price et al. |
| 2011/0010266 A1 | 1/2011 | Edwards |
| 2011/0010323 A1 | 1/2011 | Wang et al. |
| 2011/0010973 A1 | 1/2011 | Monti |
| 2011/0013007 A1 | 1/2011 | Holmberg et al. |
| 2011/0013856 A1 | 1/2011 | Gilbert |
| 2011/0014294 A1 | 1/2011 | Gross et al. |
| 2011/0014975 A1 | 1/2011 | Grabiec et al. |
| 2011/0015468 A1 | 1/2011 | Aarts et al. |
| 2011/0016150 A1 | 1/2011 | Engstrom et al. |
| 2011/0018862 A1 | 1/2011 | Epps |
| 2011/0018880 A1 | 1/2011 | Whited et al. |
| 2011/0018903 A1 | 1/2011 | Lapstun et al. |
| 2011/0019150 A1 | 1/2011 | Schuhrke et al. |
| 2011/0019874 A1 | 1/2011 | Jarvenpaa et al. |
| 2011/0020423 A1 | 1/2011 | Elenko et al. |
| 2011/0021266 A1 | 1/2011 | Jaffe et al. |
| 2011/0022330 A1 | 1/2011 | Amos et al. |
| 2011/0022950 A1 | 1/2011 | Dallago |
| 2011/0025685 A1 | 2/2011 | Epps |
| 2011/0025951 A1 | 2/2011 | Jones |
| 2011/0025975 A1 | 2/2011 | Reichow et al. |
| 2011/0025976 A1 | 2/2011 | Reichow et al. |
| 2011/0026678 A1 | 2/2011 | Bonfiglio et al. |
| 2011/0027333 A1 | 2/2011 | Idelson et al. |
| 2011/0028549 A1 | 2/2011 | D'Alessio |
| 2011/0028800 A1 | 2/2011 | Reichow et al. |
| 2011/0029591 A1 | 2/2011 | Wood et al. |
| 2011/0029666 A1 | 2/2011 | Lopatecki et al. |
| 2011/0029894 A1 | 2/2011 | Eckstein |
| 2011/0031499 A1 | 2/2011 | Kimura et al. |
| 2011/0032328 A1 | 2/2011 | Raveendran et al. |
| 2011/0032329 A1 | 2/2011 | Bauza et al. |
| 2011/0032334 A1 | 2/2011 | Raveendran et al. |
| 2011/0032338 A1 | 2/2011 | Raveendran et al. |
| 2011/0032346 A1 | 2/2011 | Kleinberger |
| 2011/0032347 A1 | 2/2011 | Lacey et al. |
| 2011/0032587 A1 | 2/2011 | Bjelkhagen et al. |
| 2011/0034176 A1 | 2/2011 | Lord et al. |
| 2011/0034239 A1 | 2/2011 | Collette et al. |
| 2011/0034434 A1 | 2/2011 | Heffernan et al. |
| 2011/0034551 A1 | 2/2011 | McBurney |
| 2011/0034784 A1 | 2/2011 | David et al. |
| 2011/0034822 A1 | 2/2011 | Phillips et al. |
| 2011/0035232 A1 | 2/2011 | Forbes et al. |
| 2011/0035345 A1 | 2/2011 | Duan et al. |
| 2011/0035770 A1 | 2/2011 | Ward, III et al. |
| 2011/0035771 A1 | 2/2011 | Ward, III et al. |
| 2011/0036915 A1 | 2/2011 | Hamilton |
| 2011/0037505 A1 | 2/2011 | Kawamoto et al. |
| 2011/0037718 A1 | 2/2011 | Stephanick et al. |
| 2011/0037827 A1 | 2/2011 | Aoki et al. |
| 2011/0037946 A1 | 2/2011 | Blum et al. |
| 2011/0038456 A1 | 2/2011 | Gertner |
| 2011/0038949 A1 | 2/2011 | Oswal et al. |
| 2011/0041077 A1 | 2/2011 | Reiner |
| 2011/0043617 A1 | 2/2011 | Vertegaal et al. |
| 2011/0043644 A1 | 2/2011 | Munger et al. |
| 2011/0043683 A1 | 2/2011 | Beach et al. |
| 2011/0043755 A1 | 2/2011 | Gibson-Horn et al. |

(56) References Cited

U.S. PATENT DOCUMENTS

| | | |
|---|---|---|
| 2011/0043757 A1 | 2/2011 | Everett et al. |
| 2011/0043759 A1 | 2/2011 | Bushinsky |
| 2011/0045892 A1 | 2/2011 | Vann et al. |
| 2011/0045895 A1 | 2/2011 | Gagner et al. |
| 2011/0045898 A1 | 2/2011 | Anderson |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0046504 A1 | 2/2011 | Pradeep et al. |
| 2011/0047121 A1 | 2/2011 | Pradeep et al. |
| 2011/0050595 A1 | 3/2011 | Lundback et al. |
| 2011/0050640 A1 | 3/2011 | Lundback et al. |
| 2011/0052155 A1 | 3/2011 | Desmarais et al. |
| 2011/0053671 A1 | 3/2011 | Aoki et al. |
| 2011/0053859 A1 | 3/2011 | Deadwyler et al. |
| 2011/0053956 A1 | 3/2011 | Leahy et al. |
| 2011/0053981 A1 | 3/2011 | Ieni et al. |
| 2011/0055585 A1 | 3/2011 | Lee |
| 2011/0055703 A1 | 3/2011 | Lundback et al. |
| 2011/0055729 A1 | 3/2011 | Mason et al. |
| 2011/0057084 A1 | 3/2011 | Thompson |
| 2011/0057932 A1 | 3/2011 | Missbach et al. |
| 2011/0058020 A1 | 3/2011 | Dieckmann |
| 2011/0058240 A1 | 3/2011 | Dell'Eva et al. |
| 2011/0060423 A1 | 3/2011 | Bonfiglio et al. |
| 2011/0060653 A1 | 3/2011 | King et al. |
| 2011/0061027 A1 | 3/2011 | Brown |
| 2011/0063073 A1 | 3/2011 | Su et al. |
| 2011/0063570 A1 | 3/2011 | Zuccolotto et al. |
| 2011/0063572 A1 | 3/2011 | Legatt |
| 2011/0065495 A1 | 3/2011 | Hornik et al. |
| 2011/0065740 A1 | 3/2011 | Forbes et al. |
| 2011/0066067 A1 | 3/2011 | Zelinsky |
| 2011/0066239 A1 | 3/2011 | Smoot et al. |
| 2011/0069086 A1 | 3/2011 | Shoemaker et al. |
| 2011/0069277 A1 | 3/2011 | Blixt et al. |
| 2011/0069279 A1 | 3/2011 | Hacker et al. |
| 2011/0069366 A1 | 3/2011 | Antkowiak et al. |
| 2011/0070940 A1 | 3/2011 | Jaffe et al. |
| 2011/0071103 A1 | 3/2011 | Forbes et al. |
| 2011/0071591 A1 | 3/2011 | Bolea et al. |
| 2011/0072448 A1 | 3/2011 | Stiers et al. |
| 2011/0074789 A1 | 3/2011 | Helfman et al. |
| 2011/0075257 A1 | 3/2011 | Hua et al. |
| 2011/0077548 A1 | 3/2011 | Torch |
| 2011/0078130 A1 | 3/2011 | Roizen et al. |
| 2011/0078144 A1 | 3/2011 | Helfman et al. |
| 2011/0078194 A1 | 3/2011 | Helfman et al. |
| 2011/0078354 A1 | 3/2011 | Krueger et al. |
| 2011/0080423 A1 | 4/2011 | Kerofsky |
| 2011/0081000 A1 | 4/2011 | Gertner et al. |
| 2011/0081001 A1 | 4/2011 | Gertner et al. |
| 2011/0082204 A1 | 4/2011 | Wei |
| 2011/0085135 A1 | 4/2011 | Bertolli |
| 2011/0085139 A1 | 4/2011 | Blixt et al. |
| 2011/0085700 A1 | 4/2011 | Lee |
| 2011/0085745 A1 | 4/2011 | Kumar et al. |
| 2011/0086925 A1 | 4/2011 | Mastroeni et al. |
| 2011/0087130 A1 | 4/2011 | Cheema et al. |
| 2011/0087581 A1 | 4/2011 | Ram et al. |
| 2011/0091132 A1 | 4/2011 | Kumar et al. |
| 2011/0091847 A1 | 4/2011 | Carroll et al. |
| 2011/0092277 A1 | 4/2011 | Jaffe et al. |
| 2011/0092559 A1 | 4/2011 | Fang et al. |
| 2011/0096144 A1 | 4/2011 | Pea et al. |
| 2011/0096941 A1 | 4/2011 | Marzetta et al. |
| 2011/0097699 A1 | 4/2011 | Wen |
| 2011/0098101 A1 | 4/2011 | Gomez et al. |
| 2011/0098102 A1 | 4/2011 | Gomez et al. |
| 2011/0098107 A1 | 4/2011 | Gomez et al. |
| 2011/0098138 A1 | 4/2011 | Davidson et al. |
| 2011/0099588 A1 | 4/2011 | Ashton |
| 2011/0099602 A1 | 4/2011 | Apparao et al. |
| 2011/0102320 A1 | 5/2011 | Hauke et al. |
| 2011/0102433 A1 | 5/2011 | Kraver |
| 2011/0102462 A1 | 5/2011 | Birnbaum |
| 2011/0102553 A1 | 5/2011 | Corcoran et al. |
| 2011/0105218 A1 | 5/2011 | Anderson et al. |
| 2011/0105233 A1 | 5/2011 | Aoki |
| 2011/0105859 A1 | 5/2011 | Popovic et al. |
| 2011/0105937 A1 | 5/2011 | Pradeep et al. |
| 2011/0106621 A1 | 5/2011 | Pradeep et al. |
| 2011/0106750 A1 | 5/2011 | Pradeep et al. |
| 2011/0109526 A1 | 5/2011 | Bauza et al. |
| 2011/0109528 A1 | 5/2011 | Mun et al. |
| 2011/0109879 A1 | 5/2011 | Palti-Wasserman et al. |
| 2011/0109880 A1 | 5/2011 | Nummela |
| 2011/0109971 A1 | 5/2011 | Beach et al. |
| 2011/0110932 A1 | 5/2011 | Patel |
| 2011/0111008 A1 | 5/2011 | Tao et al. |
| 2011/0111384 A1 | 5/2011 | Dietrich et al. |
| 2011/0111822 A1 | 5/2011 | Faith |
| 2011/0111838 A1 | 5/2011 | Bauer et al. |
| 2011/0111839 A1 | 5/2011 | Lesley et al. |
| 2011/0111847 A1 | 5/2011 | Lesley et al. |
| 2011/0111850 A1 | 5/2011 | Beerhorst et al. |
| 2011/0111866 A1 | 5/2011 | Anthony et al. |
| 2011/0112427 A1 | 5/2011 | Phillips et al. |
| 2011/0112454 A1 | 5/2011 | Hoffman et al. |
| 2011/0115883 A1 | 5/2011 | Kellerman et al. |
| 2011/0115894 A1 | 5/2011 | Burnett |
| 2011/0116346 A1 | 5/2011 | Farinella et al. |
| 2011/0117215 A1 | 5/2011 | Brennan et al. |
| 2011/0117557 A1 | 5/2011 | Canter et al. |
| 2011/0117999 A1 | 5/2011 | Anderson et al. |
| 2011/0118000 A1 | 5/2011 | Jaffe et al. |
| 2011/0118001 A1 | 5/2011 | Vann |
| 2011/0118002 A1 | 5/2011 | Aoki |
| 2011/0118536 A1 | 5/2011 | Phillips et al. |
| 2011/0118597 A1 | 5/2011 | Labadie et al. |
| 2011/0119124 A1 | 5/2011 | Pradeep et al. |
| 2011/0119129 A1 | 5/2011 | Pradeep et al. |
| 2011/0122230 A1 | 5/2011 | Boisson et al. |
| 2011/0122467 A1 | 5/2011 | Futterer et al. |
| 2011/0124408 A1 | 5/2011 | Ward |
| 2011/0124739 A1 | 5/2011 | Brinkmann et al. |
| 2011/0126102 A1 | 5/2011 | Archer |
| 2011/0128223 A1 | 6/2011 | Lashina et al. |
| 2011/0128412 A1 | 6/2011 | Milnes et al. |
| 2011/0128448 A1 | 6/2011 | Bellers et al. |
| 2011/0128555 A1 | 6/2011 | Rotschild et al. |
| 2011/0131162 A1 | 6/2011 | Kaushal et al. |
| 2011/0134204 A1 | 6/2011 | Rodriguez et al. |
| 2011/0135771 A1 | 6/2011 | Dubey et al. |
| 2011/0137104 A1 | 6/2011 | Phillips et al. |
| 2011/0137156 A1 | 6/2011 | Razzaque et al. |
| 2011/0137735 A1 | 6/2011 | Jetha et al. |
| 2011/0137830 A1 | 6/2011 | Ozyurt et al. |
| 2011/0141011 A1 | 6/2011 | Lashina et al. |
| 2011/0141223 A1 | 6/2011 | Choe |
| 2011/0142355 A1 | 6/2011 | Li |
| 2011/0143341 A1 | 6/2011 | Brennan et al. |
| 2011/0143811 A1 | 6/2011 | Rodriguez |
| 2011/0145087 A1 | 6/2011 | Daman et al. |
| 2011/0149018 A1 | 6/2011 | Kroll et al. |
| 2011/0149239 A1 | 6/2011 | Neal et al. |
| 2011/0149241 A1 | 6/2011 | Dai |
| 2011/0150334 A1 | 6/2011 | Du et al. |
| 2011/0152966 A1 | 6/2011 | Bolea et al. |
| 2011/0153435 A1 | 6/2011 | Pisaris-Henderson |
| 2011/0153744 A1 | 6/2011 | Brown |
| 2011/0157168 A1 | 6/2011 | Bennett et al. |
| 2011/0157327 A1 | 6/2011 | Seshadri et al. |
| 2011/0157550 A1 | 6/2011 | Chen et al. |
| 2011/0157552 A1 | 6/2011 | Bublitz et al. |
| 2011/0160245 A1 | 6/2011 | Mantelle et al. |
| 2011/0160303 A1 | 6/2011 | Wei |
| 2011/0161011 A1 | 6/2011 | Hasson et al. |
| 2011/0161076 A1 | 6/2011 | Davis |
| 2011/0161160 A1 | 6/2011 | Carlson et al. |
| 2011/0161163 A1 | 6/2011 | Carlson et al. |
| 2011/0161409 A1 | 6/2011 | Nair et al. |
| 2011/0164188 A1 | 7/2011 | Karaoguz et al. |
| 2011/0165146 A1 | 7/2011 | Westbrook et al. |

(56) References Cited

U.S. PATENT DOCUMENTS

| | | |
|---|---|---|
| 2011/0166558 A1 | 7/2011 | Dai et al. |
| 2011/0167103 A1 | 7/2011 | Acosta et al. |
| 2011/0167936 A1 | 7/2011 | Sagi-Dolev |
| 2011/0169625 A1 | 7/2011 | James et al. |
| 2011/0169730 A1 | 7/2011 | Sugihara |
| 2011/0169832 A1 | 7/2011 | Brown et al. |
| 2011/0169994 A1 | 7/2011 | DiFrancesco et al. |
| 2011/0170008 A1 | 7/2011 | Koch |
| 2011/0170060 A1 | 7/2011 | Gordon |
| 2011/0170061 A1 | 7/2011 | Gordon |
| 2011/0170664 A1 | 7/2011 | Gertner et al. |
| 2011/0170665 A1 | 7/2011 | Gertner |
| 2011/0172556 A1 | 7/2011 | Jones et al. |
| 2011/0175752 A1 | 7/2011 | Augst |
| 2011/0175904 A1 | 7/2011 | van Baar et al. |
| 2011/0175916 A1 | 7/2011 | Noris et al. |
| 2011/0175920 A1 | 7/2011 | Ieperen |
| 2011/0175932 A1 | 7/2011 | Yu et al. |
| 2011/0176106 A1 | 7/2011 | Lewkowski |
| 2011/0176711 A1 | 7/2011 | Bocirnea |
| 2011/0177047 A1 | 7/2011 | Liu et al. |
| 2011/0177974 A1 | 7/2011 | Wang et al. |
| 2011/0178113 A1 | 7/2011 | Forbes et al. |
| 2011/0178939 A1 | 7/2011 | Hamill et al. |
| 2011/0179097 A1 | 7/2011 | Ala-Rantala |
| 2011/0179377 A1 | 7/2011 | Fleming |
| 2011/0181443 A1 | 7/2011 | Gutierrez et al. |
| 2011/0181606 A1 | 7/2011 | Sumner et al. |
| 2011/0181835 A1 | 7/2011 | Rooney et al. |
| 2011/0182472 A1 | 7/2011 | Hansen |
| 2011/0183301 A1 | 7/2011 | Turner |
| 2011/0184489 A1 | 7/2011 | Nicolelis et al. |
| 2011/0184498 A1 | 7/2011 | Donley |
| 2011/0184736 A1 | 7/2011 | Slotznick |
| 2011/0187706 A1 | 8/2011 | Vesely et al. |
| 2011/0187845 A1 | 8/2011 | Bazakos et al. |
| 2011/0187882 A1 | 8/2011 | Kim et al. |
| 2011/0187993 A1 | 8/2011 | Alonso Fernandez et al. |
| 2011/0188431 A1 | 8/2011 | Krueger et al. |
| 2011/0188744 A1 | 8/2011 | Sun |
| 2011/0189161 A1 | 8/2011 | Blum et al. |
| 2011/0191217 A1 | 8/2011 | Saiu et al. |
| 2011/0191751 A1 | 8/2011 | Munday et al. |
| 2011/0194176 A1 | 8/2011 | Behrend et al. |
| 2011/0195391 A1 | 8/2011 | Stone |
| 2011/0196221 A1 | 8/2011 | Hegg et al. |
| 2011/0196222 A1 | 8/2011 | Behrend et al. |
| 2011/0196239 A1 | 8/2011 | Behrend et al. |
| 2011/0196445 A1 | 8/2011 | Bolea et al. |
| 2011/0196712 A1 | 8/2011 | Norelli |
| 2011/0197156 A1 | 8/2011 | Strait et al. |
| 2011/0199202 A1 | 8/2011 | De Mers et al. |
| 2011/0201387 A1 | 8/2011 | Paek et al. |
| 2011/0201403 A1 | 8/2011 | Jaffe et al. |
| 2011/0201406 A1 | 8/2011 | Jaffe et al. |
| 2011/0201416 A1 | 8/2011 | Jaffe |
| 2011/0201428 A1 | 8/2011 | Ferguson et al. |
| 2011/0201907 A1 | 8/2011 | David et al. |
| 2011/0202017 A1 | 8/2011 | Reimer |
| 2011/0202106 A1 | 8/2011 | Bolea et al. |
| 2011/0202114 A1 | 8/2011 | Kessel et al. |
| 2011/0202842 A1 | 8/2011 | Weatherly et al. |
| 2011/0204880 A1 | 8/2011 | Braghiroli |
| 2011/0205148 A1 | 8/2011 | Corriveau et al. |
| 2011/0205167 A1 | 8/2011 | Massengill |
| 2011/0206283 A1 | 8/2011 | Quarfordt et al. |
| 2011/0206437 A1 | 8/2011 | Baker |
| 2011/0207099 A1 | 8/2011 | Chen et al. |
| 2011/0207134 A1 | 8/2011 | Faham et al. |
| 2011/0207525 A1 | 8/2011 | Allen et al. |
| 2011/0207530 A1 | 8/2011 | Chudek et al. |
| 2011/0207718 A1 | 8/2011 | Bird |
| 2011/0207789 A1 | 8/2011 | Fang et al. |
| 2011/0209670 A1 | 9/2011 | McElwain et al. |
| 2011/0210851 A1 | 9/2011 | Woodfill et al. |
| 2011/0212025 A1 | 9/2011 | Pomper et al. |
| 2011/0212717 A1 | 9/2011 | Rhoads et al. |
| 2011/0213211 A1 | 9/2011 | Stevens et al. |
| 2011/0213631 A1 | 9/2011 | Mislavsky |
| 2011/0213664 A1 | 9/2011 | Osterhout et al. |
| 2011/0214082 A1 | 9/2011 | Osterhout et al. |
| 2011/0215017 A1 | 9/2011 | Coulter et al. |
| 2011/0215932 A1 | 9/2011 | Daniel |
| 2011/0216070 A1 | 9/2011 | Witkin et al. |
| 2011/0216074 A1 | 9/2011 | Witkin et al. |
| 2011/0216160 A1 | 9/2011 | Martin |
| 2011/0216881 A1 | 9/2011 | Modica et al. |
| 2011/0217022 A1 | 9/2011 | Miller et al. |
| 2011/0217679 A1 | 9/2011 | Rosenblum |
| 2011/0218033 A1 | 9/2011 | Englman et al. |
| 2011/0218815 A1 | 9/2011 | Reiner |
| 2011/0219291 A1 | 9/2011 | Lisa |
| 2011/0221656 A1 | 9/2011 | Haddick et al. |
| 2011/0221657 A1 | 9/2011 | Haddick et al. |
| 2011/0221658 A1 | 9/2011 | Haddick et al. |
| 2011/0221659 A1 | 9/2011 | King, III et al. |
| 2011/0221668 A1 | 9/2011 | Haddick et al. |
| 2011/0221669 A1 | 9/2011 | Shams et al. |
| 2011/0221670 A1 | 9/2011 | King, III et al. |
| 2011/0221671 A1 | 9/2011 | King, III et al. |
| 2011/0221672 A1 | 9/2011 | Osterhout et al. |
| 2011/0221770 A1 | 9/2011 | Kruglick |
| 2011/0221793 A1 | 9/2011 | King, III et al. |
| 2011/0221896 A1 | 9/2011 | Haddick et al. |
| 2011/0221897 A1 | 9/2011 | Haddick et al. |
| 2011/0222059 A1 | 9/2011 | Behrend et al. |
| 2011/0222731 A1 | 9/2011 | Hacker |
| 2011/0222745 A1 | 9/2011 | Osterhout et al. |
| 2011/0224981 A1 | 9/2011 | Miglietta et al. |
| 2011/0225028 A1 | 9/2011 | Rutman |
| 2011/0225536 A1 | 9/2011 | Shams et al. |
| 2011/0225608 A1 | 9/2011 | Lopatecki et al. |
| 2011/0270123 A1* | 11/2011 | Reiner .......................... 600/558 |
| 2014/0093848 A1 | 4/2014 | Ashbrook |

OTHER PUBLICATIONS

Allred SR, Radonjic A, Gilchrist AL, Brainard DH. (2012). Lightness perception in high dynamic range images: local and remote luminance effects. Journal of Vision, 12(2): 7,1-16.

Andreasen NC. (1984). Scale for the Assessment of Negative Symptoms. Iowa City: University of Iowa Press.

Andreasen NC. (1984). Scale for the Assessment of Positive Symptoms. Iowa City: University of Iowa Press.

Arnold DH, Law P, Wallis TSA. (2008). Binocular switch suppression: a new method for persistently rendering the visible 'invisible'. Vision Research, 48:994-1001.

Baranski JV, Pigeau RA., (1997). Self-monitoring cognitive performance during sleep deprivation: effects of modafinil, d-amphetamine and placebo. J. Sleep Res., 6: 84-91.

Barnes GR, Marsden JF. (2002). Anticipatory control of hand and eye movements in humans during oculo-manual tracking. J Physiol, 539(Pt 1): 317-330.

Bartolomeo P, Bachoud-Levi AC, Chokron S, Degos JD. (2002). Visually- and motor-based knowledge of letters: evidence from a pure alexic patient. Neuropsychologia, 40: 1363-1371.

Bartolomeo P, Sieroff E, Decaix C, Chokron S. (2001). Modulating the attentional bias in unilateral neglect: the effects of the strategic set. Exp Brain Res, 137: 432-444.

Beech AR, Kalmus E, Tipper SP, Baudouin JY, Flak V, Humphreys GW. (2008).Children induce an enhanced audition blink in child molesters. 20(4): 397-402.

Beenen N, Buttner U, Lange HW. (1986). The diagnostic value of eye movement recordings in patients with Huntington's disease and their offspring. Electroencephalography and clinical Neurophysiology, 63: 119-129.

Blair RJ. (2003). Neurobiological basis of psychopathy. BJP, 182: 5-7.

Blaser E, Sperling G, Lu ZL. (1999). Measuring the amplification of attention. Proc. Natl. Acad. Sci. USA, 96: 11681-11586.

(56) References Cited

OTHER PUBLICATIONS

Block N. (2005). Two neural correlated of consciousness. Trends in Cognitive Sciences, 9(2): 46-52.

Block N. (2007). Consciousness, accessibility, and the mesh between psychology and neuroscience. Behavioral and Brain Sciences, 30:481-548.

Botvinick MM, Braver TS, Barch DM, Carter CS, Cohen JD. (2001). Conflict Monitoring and Cognitive Control. Psychological Review, 108(3): 624-652.

Bowers JS, Arguin M, Bub DN. (1996). Fast and specific access to orthographic knowledge in a case of letter-by-letter surface alexia. Cognitive Neuropsychology, 13(4): 525-567.

Brazdil M, Rektor I, Daniel P, Dufek M, Jurak P. (2001). Intracerebral event-related potentials to subthreshold target stimuli. Clinical Neurophysiology, 112: 650-661.

Brazdil M, Rektor I, Dufek M, Jurak P, Daniel P. Effect of subthreshold target stimuli on event-related potentials. Electroencephalography and clinical Neurophysiology, 107:64-68.

Buschman TJ, Miller EK. (2007). Top-down versus bottom-up control of attention in the prefrontal and posterior parietal cortices. Science, 315: 1860-1862.

Cabeza R, Nyberg L. (2000). Imaging cognition II: an empirical review of 275 PET and fMRI studies. Journal of Cognitive Neuroscience, 12(1): 1-47.

Cahill H, Rattner A, Nathans J. (2011). Preclinical assessment of CNS drug action using eye movements in mice. The Journal of Clinical Investigation, 121(9): 3528-3541.

Calhoun A. (2011). Combined hormonal contraceptives: is it time to reassess their role in migraine? Headache, 52: 648-660.

Campanella S, Petit G, Maurage P, Kornreich C, Verbanck P, Noel X. (2009). Chronic alcoholism: insights from neurophysiology. Neurophysiologie Clinique/Clinical Neurophysiology, 39: 191-207.

Ceballos NA, Bauer LO. (2004). Effects of antisocial personality, cocaine and opioid dependence, and gender on eye movement control. Psychological Reports, 95: 551-563.

Chan RCK, Hoosain R, Lee TMC, Fan YW, Fong D. (2003). Are there sub-types of attentional deficits in patients with persisting post-concussive symptoms? a cluster analytical study. 17(2): 131-148.

Chan RCK. (2005). Sustained attention in patients with mild traumatic brain injury. Clinical Rehabilitation, 19: 188-193.

Chittka L, Skorupski P, Raine NE. (2009). Speed-accuracy tradeoffs in animal decision making. Trends in Ecology and Evolution, 24(7): 400-407.

Christoff K, Gordon AM, Smallwood J, Smith R, Schooler JW. (2009). Experience sampling during fMRI reveals default network and executive system contributions to mind wandering. PNAS, 106(21): 8719-8724.

Cohen JD, Dunbar K, McClelland JL. (1990). On the control of automatic processes: a parallel distributed processing account of the stroop effect. Psychological Review, 97(3): 332-361.

Cohen L, Henry C, Dehaene S, Martinaud O, Lehericy S, Lemer C, Ferrieux S. (2004).The pathophysiology of letter-by-letter reading. Neuropsychologia, 42: 1768-1780.

Contreras R, Ghajar J, Bahar S, Suh M. (2011). Effect of cognitive load on eye-target synchronization during smooth pursuit eye movement. Brain Res, 1398:55-63.

Corallo G, Sackur J, Dehaene S, Sigman M. (2008). Limits on Introspection: distorted subjective time during the dual-task bottleneck. Psychol Sci., 19(11): 1110-1117.

Coste CP, Sadaghiani S, Friston KJ, Kleinschmidt A. (2011). Ongoing brain activity fluctuations directly account for intertribal and indirectly for intersubject variability in stroop task performance. Cerebral Cortex, 21: 2612-2619.

Cutrer FM, Smith JH. (2012). 15th International headache congress: basic science highlights. Headache, 52(5): 851-858.

Dadds MR, Allen JL, Oliver BR, Faulkner N, Legge K, Moul C, Woolgar M, Scott S. (2012). Love, eye contact and the developmental origins of empathy v. psychopathy. BJP, 200: 191-196.

Dadds MR, El Masry Y, Wimalaweera S, Guastella AJ. (2008). Reduced eye gaze explains "fear blindness" in childhood psychopathic traits. J Am Acad Child.Adolesc Psychiatry, 47(4): 455-463.

D'Andrea G, D'Arrigo A, Carbonare MD, Leon A. (2012). Pathogenesis of migraine: role of neuromodulators. Headache, 52: 1155-1163.

Dahlof C, Massen Van Den Brink A. (2012). Dihydroergotamine, ergotamine, methysergide and sumatriptan—basic science in relation to migraine treatment. Headache, 52(4):707-714.

Deacon D, Shelley-Tremblay J. (2000). How automatically is meaning accessed: a review of the effects of attention on semantic processing. Frontiers in Bioscience, 5: e82-94.

Debski EA. (2008). Smoking, nicotine and visual plasticity: does what you know, tell you what you can see? Brain Research Bulletin, 77: 221-226.

Deeley Q, Daly E, Surguladze S, Tunstall N, Mezey G, Beer D, Ambikapathy A, Robertson D, Giampietro V, Brammer MJ, Clarke A, Dowsett J, Fahy T, Phillips ML, Murphy DG. (2006). Facial emotion processing in criminal psychopathy: preliminary functional magnetic resonance imaging study. BJP, 189: 533-539.

Dehaene S, Changeux JP. (2005). Ongoing spontaneous activity controls access to • consciousness: a neuronal model for inattentional blindness. PLoS Biology, 3(5): e141.

Dehaene S, Changeux JP. (2011). Experimental and theoretical approaches to conscious processing. Neuron, 70:200-227.

Dehaene S, Cohen L, Sigman M, Vinckier F. (2005). The neural code for written words: a proposal. Trends in Cognitive Sciences, 9(7): 335-341.

Dehaene S, Cohen L. (2011). The unique role of the visual word form area in reading. Trends in Cognitive Sciences, 15(6): 254-262.

Dehaene S, Naccache L, Clec'H GL, Koechlin E, Mueller M, Dehaene-Lambertz G, van de Moortele PF, Le Bihan D. (1998). Imaging unconscious semantic priming Nature, 395(6702): 592-600.

Dehaene S, Naccache L, Cohen L, Bihan DL, Mangin JF, Poline JB, Riviere D. (2001). Cerebral mechanisms of word masking and unconscious repetition priming. Nature Neuroscience, 4(7): 752-758.

Dehaene S, Naccache L. (2001). Towards a cognitive neuroscience of consciousness: basic evidence and a workspace framework. Cognition, 79: 1-37.

Dehaene S, Pegado F, Braga LW, Ventura P, Filho GN, Jobert A, Dehaene-Lambertz G, Kolinsky R, Morais J, Cohen L. (2010). How learning to read changes the cortical networks for vision and language. Science, 330: 1359-1364.

Dehaene S. (2008). Conscious and unconscious processes distinct forms of evidence accumulation? Decision making, the human mind, and implications for institutions. US:MIT Press, pp. 21-49.

Desimone R, Duncan J. (1995). Neural mechanisms of selective visual attention. Annu. Rev. Neurosci., 18: 193-222.

Diaz MT, McCarthy G. (2007). Unconscious word processing engages a distributed network of brain regions. Journal of Cognitive Neuroscience, 19(11): 1768-1775.

Domino EF, Ni LS, Zhang H. (1997). Effects of tobacco smoking on human ocular smooth pursuit. Clin Pharmacol Ther., 61: 349-359.

Donker SF, Roerdink M, Greven AJ, Beek PJ. (2007). Regularity of center-of-pressure trajectories depends on the amount of attention invested in postural control. Exp. Brain Res, 181: 1-11.

Doshi A, Trivedi MM. (2012). Head and eye gaze dynamics during visual attention shifts in complex environments. Journal of Vision, 12(2): 9, 1-16.

Duff K, Mold JW, Roberts MM. (2008). Walking speed and global cognition: results from the Oaklahoma study. Aging, Neuropsychology, and Cognition, 15: 31-39.

Dux PE, Tombu MN, Harrison S, Rogers BP, Tong F, Marois R. (2009). Training improves multitasking performance by increasing the speed of information processing in human prefrontal cortex. Neuron, 63: 127-138.

Egeth HE, Yantis S. (1997). Visual attention: control, representation, and time course. Annu. Rev. Psychol., 48: 269-297.

Enns JT, Di Lollo V. (2000). What's new in visual masking? Trends in Cognitive Sciences, 4(9): 345-352.

(56) References Cited

OTHER PUBLICATIONS

Erwin RJ, Turetsky BI, Moberg P, Gur RC, Gur RE. (1998). P50 abnormalities in schizophrenia: relationship to clinical and neuropsychological indices of attention. Schizophrenia Research, 33: 157-167.
Etchells PJ, Benton CP, Ludwig CJH, Gilchrist ID. (2011). Testing a simplified method for measuring velocity integration in saccades using a manipulation of target contrast. Frontiers in Psychology, 2: 115.
Eysenck HJ. (1992). The definition and measurement of psychoticism. Person. Individ. Diff., 13(7): 757-785.
Fan Z, Singh K, Muthukumaraswamy S, Sigman M, Dehaene S, Shapiro K. (2011). The cost of serially chaining two cognitive operations. Psychological Research, 76(5): 566-578.
Farah MJ, Wong AB, Monheit MA, Morrow LA. (1989). Parietal lobe mechanisms of spatial attention: modality-specific or supramodal? Neuropsychologia, 27(4): 461-470.
Faugeras F, Rohaut B, Weiss N, Bekinschtein TA, Galanaud D, Puybasset L, Bolgert F, Sergent C, Cohen L, Dehaene S, Naccache L. (2011). Probing consciousness with event-related potentials in the vegetative state. Neurology, 77: 264-268.
Finkel AG, Yerry J, Scher A, Choi YS. (2012). Headaches in soldiers with mild traumatic brain injury: findings and phenomenologic descriptions. Headache, 52: 957-965.
Firth AY. (2006). Editorial: ocular effects of criminal drug use. Can J Ophthalmol, 41: 140-143.
Foerster RM, Carbone E, Koesling H, Schneider WX. (2012). Saccadic eye movements in the dark while performing an automatized sequential high-speed sensorimotor task. Journal of Vision, 12(2): 8, 1-15.
Foulkes AJ, Miall RC. (2000). Adaptation to visual feedback delays in a human manual tracking task. Exp Brain Res, 131:101-110.
Frank MC, Everett DL, Fedorenko E, Gibson E. (2008). Number as a cognitive technology: evidence from Piraha language and cognition. Cognition, 108: 819-824.
Furtner MR, Rauthmann JF, Sachse P. (2009). Nomen est omen: investigating the dominance of nouns in word comprehension with eye movement analyses. Adv Cog Psychol., 5: 91-104.
Gailard R, Cohen L, Adam C, Clemenceau S, hasboun D, Baulac M, Willer JC, Dehaene S, Naccache L. (2007). Subliminal words durably affect neuronal activity. NeuroReport, 18(15): 1527-1531.
Gaillard R, Del Cul A, Naccache L, Vinckier F, Cohen L, Dehaene S. (2006). Nonconscious semantic processing of emotional words modulates conscious access. PNAS, 103(19): 7524-7529.
Garb HN. (1994). Toward a second generation of statistical prediction rules in psychodiagnosis and personality assessment. Computers in Human Behavior, 10(3): 377-394.
Ginstfeldt T, Emanuelson I. (2010). An overview of attention deficits after paediatric traumatic brain injury. Brain Injury, 24(10): 1123-1134.
Glasel H, Leroy F, Dubois J, Hertz-Pannier L, Mangin JF, Dehaene-Lambertz G. (2011). A robust cerebral asymmetry in the infant brain: The rightward superior temporal sulcus. Neuroimage, 58:716-723.
Gibbon J, Malapani C, Dale CL, Gallistel CR. (1997). Toward a neurobiology of temporal cognition: advances and challenges. Current Opinion in Neurobiology, 7:170-184.
Goadsby PJ, Lipton RB, Ferrari MD. (2002). Migraine—current understanding and treatment. N Engl J Med, 346(4): 257-270.
Golomb D, Hertz J, Panzeri S, Treves A, Richmond B. (1997). How well can we estimate the information carried in neuronal responses from limited samples? Neural.Computation, 9: 649-665.
Gredeback G, von Hofsten C, Karlsson J, Aus K. (2005). The development of two-dimensional tracking: a longitudinal study of circular pursuit. Exp Brain Res, 163: 204-213.
Green REA, Turner GR, Thompson WF. (2004). Deficits in facial emotion perception in adults with recent traumatic brain injury. Neuropsychologia, 42:133-141.
Gregoriou GG, Gotts SJ, Zhou H, Desimone R. (2009). High-frequency, long-range coupling between prefrontal and visual cortex during attention. Science, 324(5931): 1207-1210.

Gu Q. (2003). Contribution of acetylcholine to visual cortex plasticity. Neurobiology of Learning and Memory, 80: 291-301.
Haynes JD. (2009). Decoding visual consciousness from human brain signals. Trends in Cognitive Sciences, 13(5): 194-202.
Henry C, Gaillard R, Voile E, Chiras J, Ferrieux S, Dehaene S, Cohen L. (2005). Brain activations during letter-by-letter reading: a follow-up study. Neuropsychologia, 43:1983-1989.
Hesselmann G, Flandin G, Dehaene S. (2011) Probing the cortical network underlying the psychological refractory period: a combined EEG-fMRI study. NeuroImage, 56: 1608-1621.
Ho-Phuoc T, Guyader N, Landragin F, Guerin-Dugue A. (2012). When viewing natural scenes, do abnormal colors impact on spatial or temporal parameters of eye movements? Journal of Vision, 12(2): 4, 1-13.
Huang L. (2010). What is the unit of visual attention? Object for selection, but boolean map for access. Journal of Experimental Psychology: General, 139(1): 162-179.
Hulsmann E, Erb M, Grodd W. (2003). From will to action: sequential cerebellar contributions to voluntary movement. NeuroImage, 20: 1485-1492.
Imai M, Li L, Okada H, Hirsh-Pasek K, Golinkoff RM, Shigematsu J. (2008). Novel noun and verb learning in Chinese-, English-, and Japanese-speaking children Child Development, 79(4): 979-1000.
Ivana K, Vuust P, Roepstorff A, Frith CD. (2010). Follow you, follow me: continuous mutual prediction and adaptation in joint tapping. The Quarterly Journal of.Experimental Psychology, 63(11): 2220-2230.
Izard V, Pica P, Spelke ES, Dehaene S. (2011). Flexible institutions of Euclidean geometry in an Amazonian indigene group. Proc Natl Acd Sci U S A, 108(24): 9782-9787.
Izawa Y, Suzuki H, Shinoda Y. (2011). Suppression of smooth pursuit eye movements induced by electrical stimulation of the monkey frontal eye field. J Neurophysiol, 106: 2675-2687.
Kamienkowski JE, Pashler H, Dehaene S, Sigman M. (2011). Effects of practice on task architecture: combined evidence from interference experiments and random-walk models of decision making. Cognition, 119:81-95.
Kanai R, Muggleton NG, Walsh V. (2008). TMS over the intraparietal sulcus induces perceptual fading. J Neurophysiol, 100: 3343-3350.
Kanai R, Walsh V, Tseng C. (2010). Subjective discriminability of invisibility: a framework for distinguishing perceptual and attentional failures of awareness. Consciousness and Cognition, 19: 1045-1057.
Kastner S, Weerd PD, Desimone R, Ungerleider LG. (1998). Mechanisms of directed attention in the human extrastriate cortex as revealed by functional MRI. Science, 282: 108-111.
Kathmann N. Hochrein A, Uwer R, Bondy B. (2003). Deficits in gain of smooth pursuit eye movements in schizophrenia and affective disorder patients and their unaffected relatives. Am J Psychiatry, 160(4): 696-702.
Kentridge RW, Heywood CA, Weiskrantz L. (2004). Spatial attention speeds discrimination without awareness in blindsight. Neuropsychologia, 42: 831-835.
Kiebel SJ, Daunizeau J, Friston KJ. (2008) A hierarchy of time-scales and the brain. PLoS Comput Biol 4(11): e1000209. doi:10.1371/journal.pcbi.1000209.
Kiefer M, Brendel D. (2006). Attentional modulation of unconscious "automatic" processes: evidence from event-related potentials in a masked priming paradigm. Journal of Cognitive Neuroscience, 18(2): 184-198.
Kiehl KA, Smith AM, Hare RD, Liddle PF. (2000). An event-related potential investigation of response inhibition in schizophrenia and psychopathy. Biol Psychiatry, 48: 210-221.
Kihara K, Ikeda T, Matsuyoshi D, Hirose N, Mima T, Fukuyama H, Osaka N. (2010). Differential contributions of the intraparietal sulcus and the inferior parietal lobe to attentional blink: evidence from transcranial magnetic stimulation. Journal of Cognitive Neuroscience, 23(1): 247-256.
Kinoshita S, Forster KI, Mozer MC. (2008). Unconscious cognition isn't that smart: modulation of masked repetition priming effect in the word naming task. Cognition, 107: 623-649.
Klein RM, Pontefract A. (1994). Does oculomotor readiness mediate cognitive control of visual attention? Revisited! In Attention and

(56) References Cited

OTHER PUBLICATIONS

Performance vol. XV: Conscious and Unconscious Processing (Umilta, C. and Moscovitch, M. eds), pp. 333-350, MIT Press.
Klein TA, Endrass T, Kathmann N, Neumann J. Yves von Cramon D, Ullsperger M. (2007). Neural correlates of error awareness. NeuroImage, 34: 1774-1781.
Koch C, Tsuchiya N. (2007). Attention and consciousness: two distinct brain processes.Trends Cogn Sci, 11(1): 16-22.
Koechlin E, Summerfield C. (2007). An information theoretical approach to prefrontal executive function. Trends Cogn Sci, 11(6): 229-235.
Koivisto M, Lahteenmaki M, Sorensen TA, Vangkilde S, Overgaard M, Revonsuo A. (2008). The earliest electrophysiological correlate of visual awareness? Brain and Cognition, 66: 91-103.
Koivisto M, Revonsuo A, Lehtonen M. (2006). Independence of visual awareness from the scope of attention: an electrophysiological study. Cerebral Cortex, 16: 415-424.
Kosson DS. (1998). Divided visual attention in psychopathic and nonpsychopathic offenders. Person. Individ. Diff., 24(3): 373-391.
Kranczioch C, Debener S, Maye A, Engel AK. (2007). Temporal dynamics of access to consciousness in the attentional blink. NeuroImage, 37: 947-955.
Kuhn G. (2001). Circadian rhythm, shift work, and emergency medicine. Annals of Emergency Medicine, 37(1): 88-98.
Lamme VAF. (2003). Why visual attention and awareness are different. Trends in Cognitive Sciences, 7(1): 12-18.
Lau HC, Passingham RE. (2007). Unconscious activation of the cognitive control system in the human prefrontal cortex. The Journal of Neuroscience, 27(21): 5805-5811.
Le Dantec CC, Melton EE, Seitz AR. (2012). A triple dissociation between learning of target, distractors, and spatial contexts. Journal of Vision, 12(2): 5, 1-12.
Lee EJ, Kwon G, Lee A, Ghajar J, Suh M. (2011). Individual differences in working memory capacity determine the effects of oculomotor task load on concurrent word recall performance. Brain Res, 1399: 59-65.
Leproult R, Van Reeth O, Bryne MM, Stuns J, Van Cauter E. (1997). Sleepiness, performance, and neuroendocrine function during sleep deprivation: effects of exposure to bright light or exercise. J Biol Rhythms, 12(3): 245-258.
Leroy F, Glasel H, Dubois J, Hertz-Pannier L, Thirion B, Mangin JF, Dehaene-Lambertz G. (2011). Early maturation of the linguistic dorsal pathway in human infants. The Journal of Neuroscience, 31(4):1500-1506.
Leuthold H, Kopp B. (1998). Mechanisms of priming by masked stimuli: inferences from event-related brain potentials. Psychological Science, 9(4): 263-269.
Lewine JD, Davis JT, Sloan JH, Kodituwakku PW, Orrison, Jr WW. (1999). Neuromagnetic assessment of pathophysiologic brain activity induced by minor head trauma. AJNR Am J Neuroradiol 20: 857-866.
Lipton RB, Baggish JS, Stewart WF, Codispoti JR, Fu M. (2000). Efficacy and safety of acetaminophen in the treatment of migraine. Arch Intern Med, 160: 3486-3492.
Lin Z, He S. (2009). Seeing the invisible: the scope and limits of unconscious processing in binocular rivalry. Prog Neurobiol., 87(4): 195-211.
Lindemann O, Abolafia JM, Bekkering H. (2008). Coding strategies in number space: memory requirements influence spatial-numerical associations. Q J Exp Psychol (Hove), 61(4): 515-524.
Lisberger SG. (2010). Visual guidance of smooth-pursuit eye movements: sensation, action, and what happens in between. Neuron, 66: 477-491.
Lo CC, Wang XJ. (2006). Cortico-basal ganglia circuit mechanism for a decision threshold in reaction time tasks. Nature Neuroscience, 9(7): 956-963.
Luck SJ, Hillyard SA. The operation of selective attention at multiple stages of processing: evidence from human and monkey electrophysiology. In: Gazzaniga MS, editor. The cognitive neurosciences. 2nd ed. Cambridge: MIT Press; 2000.
Lutz A, Lachaux JP, Martinerie J, Varela FJ. (2002). Guiding the study of brain dynamics by using first-person data: synchrony patterns correlate with ongoing conscious states during a simple visual task. PNAS, 99(3): 1586-1591.
Mack, A. & Rock, I. (1999). Inattentional blindness. Psyche, Cambridge, MA:MIT.
Madelain L, Krauzlis RJ. (2003). Effects of learning on smooth pursuit during transient disappearance of a visual target. J Neurophysiol 90:972-982.
Mangels JA, Craik HM, Levine B, Schwartz ML, Stuss DT. (2002). Effects of divided attention on episodic memory in chronic traumatic brain injury: a function of severity and strategy. Neuropsychologia 40:2369-2385.
Marion DW, Curley KC, Schwab K, Hicks RR, et al. (2011). Proceedings of the military mTBI diagnostics workshop, St. Pete Beach, Aug. 2010. Journal of Neurotrauma, 28: 517-526.
Markram H, Meier K, Lippert T, Grillner S, Frackowiak R, Dehaene S, Knoll A, Sompolinsky H, Verstreken K, DeFelipe J, Grant S, Changeux JP, Saria A. (2011). Introducing the human brain project. Procedia Computer Science.
Marois R, Ivanoff J. (2005). Capacity limits of information processing in the brain. Trends Cogn Sci, 9(6): 296-305.
Marois R, Yi DJ, Chun MM. (2004). The neural fate of consciously perceived and missed events in the attentional blink. Neuron, 41: 465-472.
Marsden G, Leach J. (2011). Effects of alcohol and caffeine on maritime navigational skills. Ergonomics, 43(1): 17-26.
Marshall S. P. (2002). The index of cognitive activity: measuring cognitive workload. In proceedings of the 2002 IEEE 7th Conference on Human Factors and Power Plants. IEEE Computer Society Press, Los Alamitos, CA, 7.5-7.9.
Marshall SP, Pleydell-Pearce CW, Dickson BT. (2002). Integrating psychophysiological measures of cognitive workload and eye movements to detect strategy shifts. In Proceedings of the 36th Annual Hawaii International Conference on System Sciences, Hawaii (pp. 130-135).
Martens S, Wyble B. (2010). The attentional blink: past, present, and future of a blind spot in perceptual awareness. Neuroscience and Biobehavioral Reviews, 34(6): 947-957.
Matthews N, Vawter M, Kelly JG. (2012). Right hemisfield deficits in judging simultaneity: a percentual learning study. Journal of Vision, 12(2): 1, 1-14.
Mazzaferri J, Navarro R. (2012). Wide two-dimensional field laser ray-tracing aberrometer. Journal of Vision, 12(2): 2, 1-14.
McAdams CJ, Maunsell JHR. (2000). Attention to both space and feature modulates neuronal responses in macaque area V4. J Neurophysiol, 83:1751-1755.
McCormick PA. (1997). Orienting attention without awareness. Journal of Experimental Psychology: Human Perception and Performance, 23(1): 168-180.
Mehta B, Schaal S. (2002). Forward models in visuomotor control. J Neurophysiol, 88: 942-953.
Merikle PM, Joordens S. (1997). Parallels between perception without attention and perception without awareness. Consciousness and Cognition, 6: 219-236.
Meyer AS, Roelofs A, Levelt WJM. (2003). Word length effects in object naming: the role of a response criterion. Journal of Memory and Language, 48: 131-147.
Morillon B, Lehongre K, Frackowiak RSJ, Ducorps A, Kleinschmidt A, Poeppel D, Giraud AL. (2010). Neurophysiological origin of human brain asymmetry for speech and language. PNAS, 107(43): 18688-18693.
Mort DJ, Malhotra P, Mannan SK, Rorden C, Pambakian A, Kennard C, Husain M. (2003). The anatomy of visual neglect. Brain, 126: 1986-1997.
Moschner C, Zangemeister WH, Demer JL. (1996). Anticipatory smooth eye movements of high velocity triggered by large target steps: normal performance and effect of cerebellar degeneration. Vision Res., 36(9): 1341-1348.
Mozer, M. C., Kinoshita, S., & Shettel, M. (2007). Sequential dependencies in human behavior offer insights into cognitive control. In W. Gray (Ed.), Integrated models of cognitive systems (pp. 180-193). Oxford: Oxford University Press.

(56) References Cited

OTHER PUBLICATIONS

Mu Q, Nahas Z, Johnson KA, Yamanaka K, Mishory A, Koola J, Hill S, Homer MD, Bohning DE, George MS. (2005). Decreased cortical response to verbal working memory following sleep deprivation. Sleep, 28(1): 55-67.
Muller-Gass A, Macdonald M, Schroger E, Sculthorpe L, Campbell K. (2007). Evidence for the auditory P3a reflecting an automatic process: elicitation during highly-focused continuous visual attention. Brain Research, 1170: 71-78.
Naccache L, Blandin E, Dehaene S. (2002). Unconscious masked priming depends on temporal attention. Psychological Science, 13(5): 416-424.
Naccache L, Dehaene S, Cohen L, Habert MO, Guichart-Gomez E, Galanaud D, Willer JC. (2005). Effortless control: executive attention and conscious feeling of mental effort are dossociable. Neuropsychologia, 43:1318-1328.
Naccache L, Dehaene S. (2001). Unconscious semantic priming extends to novel unseen stimuli. Cognition, 80: 215-229.
Niedeggen M, Wichmann P, Stoerig P. (2001). Change blindness and time to consciousness. European Journal of Neuroscience, 14:1719-1726.
Nieder A, Dehaene S. (2009). Representation of number in the brain. Annu. Rev. Neurosci., 32: 185-208.
Nieder A. (2009). Prefrontal cortex and the evolution of symbolic reference. Current.Opinion in Neurobiology, 19: 99-108.
Nieuwenhuis S, Ridderinkhof KR, Blom J, Band GPH, Kok A. (2001). Error-related brain potentials are differentially related to awareness of response errors: evidence from an antisaccade task. Psychophysiology, 38:752-760.
Noy L, Dekel E, Alon U. (2011). The mirror game as a paradigm for studying the dynamics of two people improvising motion together. PNAS, 108(52): 20947-20952.
Obrenović J, Nešic V, Nešic M. (1996). The reaction time in relation to the modality of stimulation. Facta Universitatis—series. Physical Education, 1:85-90.
Pallier C, Devauchelle AD, Dehaene S. (2011). Cortical representation of the constituent structure of sentences. PNAS, 108(6): 2522-2527.
Pariyadath V, Eagleman D. (2007). The effect of predictability on subjective duration PLoS ONE, 2(11): e1264. Doi:10.1371/journal.pone.0001264.
Pawlak-Osinska K, Kazmierczak H, Kazmierczak W. (2005). Saccadic and smooth-pursuit eye movement in neurootological diagnostic procedures. International Tinnitus Journal, 11(1): 52-53.
Perani D, Saccuman MC, Scifo P, Spada D, Andreolli G, Rovelli R, Baldoli C, Koelsch S. (2010). Functional specializations for music processing in the human newborn brain. PNAS, 107(10): 4758-4763.
Perbal S, Couillet J, Azouvi P, Pouthas V. (2003). Relationships between time estimation, memory, attention, and processing speed in patients with severe traumatic brain injury. Neuropsychologia, 41: 1599-1601.
Persaud N, McLeod P, Cowey A. (2007). Post-decision wagering objectively measures awareness. Nature Neuroscience, 10(2): 257-261.
Poldrack RA, Sabb FW, Foerde K, Tom SM, Asarnow RF, Bookheimer SY, Knowlton BJ. (2005). The neural correlates of motor skill automaticity. The Journal of Neuroscience, 25(22): 5356-5364.
Posner MI, Dehaene S. (1994). Attentional networks. Trends in Neurosciences, 17(2):75-79.
Rafal RD, Calabresi PA, Brennan CW, Sciolto TK. (1989). Saccade preparation inhibits reorienting to recently attended locations. Journal of Experimental Psychology: Human Perception and Performance, 15(4): 673-685.
Raffa RB. (2010). Is a picture worth a thousand (forgotten) words?: neuroimaging evidence for the cognitive deficits in 'chemo-fog'/'chemo-brain'. Journal of Clinical Pharmacy and Therapeutics, 35: 1-9.
Raffa RB, Duong PV, Finney J, Garber DA, Lam LM, Mathew SS, Patel NN, Plaskett KC, Shah M, Jen Weng HF. (2006). Is 'chemo-fog'/'chemo-brain' caused by cancer chemotherapy? Journal of Clinical Pharmacy and Therapeutics, 31: 129-138.
Raine A. (1989). Evoked potentials and psychopathy. International Journal of Psychophysiology, 8: 1-16.
Raine A. (1989). Evoked potential models of psychopathy: a critical evaluation. International Journal of Psychophysiology, 8: 29-34.
Raine A, Venables PH. (1989). Evoked potential augmenting-reducing in psychopaths and criminals with impaired smooth-pursuit eye movements. Psychiatry Research, 31: 85-98.
Rascol O, Clanet M, Montastruc JL, Simonetta M, Soulier-Esteve MJ, Doyon B, Rascol A. (1989). Abnormal ocular movements in Parkinson's disease. Evidence for involvement of dopaminergic systems. Brain, 112: 1193-1214.
Ratcliff R, Rouder JN. (1998). Modeling response times for two-choice decisions. Psychological Science, 9(5): 347-355.
Rauthmann JF, Seubert CT, Sachse P, Furtner MR. (2012). Eyes as windows to the soul: gazing behavior is related to personality. Journal of Research in Personality, 46: 147-156.
Raymond JE, Shapiro KL, Arnell KM. (1992). Temporary suppression of visual processing in an rsvp task: an attentional blink? Journal of Experimental Psychology: Human Perception and Performance, 18(3): 849-860.
Rayner K, White SJ, Johnson RL, Liversedge SP. (2005). Raeding wrods with jumbled lettres: there is a cost. Psychol Sci., 17(3): 192-193.
Reddi BAJ, Asress KN, Carpenter RHS. (2003). Accuracy, information, and response time in a saccadic decision task. J Neurophysiol, 90:3538-3546.
Reddi BAJ, Carpenter RHS. (2000). The influence of urgency on decision time. Nature Neuroscience, 3(8): 827-830.
Reilly JL, Lencer R, Bishop JR, Keedy S, Sweeney JA. (2008). Pharmacological treatment effects on eye movement control. Brain and Cognition, 68:415-435.
Repp BH. (2006). Rate limits of sensorimotor synchronization. Advances in Cognitive Psychology, 2(2-3): 163-181.
Reuter F, Del Cul A, Malikova I, Naccache L, Confort-Gouny S, Cohen L, Cherif AA, Cozzone PJ, Pelletier J, Ranjeva JP, Dehaene S, Audoin B. (2009). White matter damage impairs access to consciousness in multiple sclerosis. NeuroImage, 44: 590-599.
Robertson IH, Ridgeway V, Greenfield E, Parr A. (1997). Motor recovery after stroke depends on intact sustained attention: a 2-year follow-up study. Neuropsychology, 11(2): 290-295.
Rochester L, Hetherington V, Jones D, Nieuwboer A, Williems A, Kwakkel G, Van Wegen E. (2004). Attending to the task: interference effects of functional tasks on walking in Parkinson's disease and the roles of cognition, depression, fatigue, and balance. Arch Phys Med Rehabil., 85: 1578-1584.
Roerdink M, Hlavackova P, Vuillerme N. (2011). Center-of-pressure regularity as a marker for attentional investment in postural control: a comparison between sitting and standing postures. Human Movement Science, 30:203-212.
Rolls ET, Tovee MJ, Panzeri S. (1999). The neurophysiology of backward visual masking: information analysis. Journal of Cognitive Neuroscience, 11(3): 300-311.
Rosekind MR, Boyd JN, Gregory KB, et al. (2002). Alertness management in 24/7 settings: Lessons from aviation. Occup Med, 17:247-259.
Rowe JB, Frackowiak RSJ. (1999). The impact of brain imaging technology on our understanding of motor function and dysfunction. Current Opinion in Neurobiology, 9: 728-734.
Rushworth MFS, Krams M, Passingham RE. (2001). The attentional role of the left parietal cortex: the distinct lateralization and localization of motor attention in the human brain. Journal of Cognitive Neuroscience, 13(5): 698-710.
Sato H, Motoyoshi I, Sato T. (2012). Polarity selectivity of spatial interactions in perceived contrast. Journal of Vision, 12(2): 3, 1-10.
Saykin AJ, Gur RC, Gur RE, Mozley PD, Mozley LH, Resnick SM, Kester B, Stafiniak P. (1991). Neuropsychological function in schizophrenia: selective impairment in memory and learning. Arch Gen Psychiatry, 48: 618-624.

(56) References Cited

OTHER PUBLICATIONS

Saykin AJ, Shtasel DL, Gur RE, Kester DB, Mozley LH, Stafiniak P, Gur RC. (2011). Neuropsychological deficits in neuroleptic naive patients with first-episode schizophrenia. Arch Gen Psychiatry, 51: 124-131.
Schouten JF, Bekker JAM. (1967). Reaction time and accuracy. Acta Psychologica, 27: 143-153.
Schubert T. (2008). The central attentional limitation and executive control. Frontiers in Bioscience, 13: 3569-3580.
Schumacher EH, Seymour TL, Glass JM, Fencsik DE, Lauber EJ, Kieras DE, Meyer DE. (2001). Virtually perfect time sharing in dual-task performance: uncorking the central cognitive bottleneck. Psychological Science, 12(2): 101-108.
Sergent C, Baillet S, Dehaene S. (2005). Timing of the brain events underlying access to consciousness during the attentional blink. Nature Neuroscience, 8(10): 1391-1400.
Sergent C, Dehaene S. (2004). Is consciousness a gradual phenomenon? Evidence for an all-or-none bifurcation during the attentional blink. Psychol Sci., 15(11): 720-728.
Shepherd M, Findlay JM, Hockey RJ. (1986). The relationship between eye movements and spatial attention. The Quarterly Journal of Experimental Psychology, 38A: 475-491.
Shilling V, Jenkins V, Trapala IS. (2006). The (mis)classification of chemo-fog-methodological inconsistencies in the investigation of cognitive impairment after chemotherapy. Breast Cancer Research and Treatment, 95: 125-129.
Shtyrov Y. (2010). Automaticity and attentional control in spoken language processing. The Mental Lexicon, 5(2): 255-276.
Sigman M, Dehaene S. (2005). Parsing a cognitive task: a characterization of the mind's bottleneck. PLoS Biology, 3(2): e37.
Sigman M, Dehaene S. (2008). Brain mechanisms of serial and parallel processing during dual-task performance. The Journal of Neuroscience, 28(30): 7585-7598.
Silberstein SD, Lipton RB, Dodick DW, Freitag FG, Ramadan N, Mathew N, Brandes JL, Bigal M, Saper J, Ascher S, Jordan DM, Greenberg SJ, Hulihan J. (2007). Efficacy and safety of topiramate for the treatment of chronic migraine: a randomized, double-blind, placebo-controlled trial. Headache, 47: 170-180.
Simon JR, Berbaum K. (1990). Effect of conflicting cues on information processing: the 'stroop effect' vs. The 'simon effect'. Acta Psychologica, 73:159-170.
Sisti HM, Geurts M, Clerckx R, Gooijers J, Coxon JP, Heitger MH, Caeyenberghs K, Beets IAM, Serbruyns L, Swinnen SP. (2011). Testing multiple coordination constraints with a novel bimanual visuomotor task. PLoS ONE, 6(8): e23619. Doi: 10.1371/journal.pone.0023619.
Smith A, Taylor E, Lidzba K, Rubia K. (2003). A right hemispheric frontocerebellar network for time discrimination of several hundreds of milliseconds. Neuroimage, 20:344-350.
Song JH, Nakayama K. (2007). Automatic adjustment of visuomotor readiness. Journal of Vision, 7(5): 1-9.
Strasburger H, Rentschler I, Juttner M. (2011). Peripheral vision and pattern recognition: a review. Journal of Vision, 11(5): 13, 1-82.
Suh M, Basu S, Kolster R, Sarkar R, McCandliss B, Ghajar J. (2006). Increased oculomotor deficits during target blanking as an indicator of mild traumatic brain injury. Neuroscience Letters, 410: 203-207.
Suh M, Kolster R, Sarkar R, McCandliss B, Ghajar J. (2006). Deficits in predictive smooth pursuit after mild traumatic brain injury. Neuroscience Letters, 401:108-113.
Tang Y, Zhang W, Chen K, Feng S, Ji Y, Shen J, Reiman EM, Liu Y. (2006). Arithmetic processing in the brain shaped by cultures. PNAS, 103(28):10775-10780.
Terao M, Watanabe J, Yagi A, Nishida S. (2010). Smooth pursuit eye movements improve temporal resolution for color perception. PLoS One, 5(6):311214. Doi: 10.1371/journal.pone.0011214.
Terrace HS, Son LK. (2009). Comparative metacognition. Current Opinion in Neurobiology, 19:67-74.
Theeler BJ, Flynn FG, Erickson JC, (2012). Chronic daily headache in U.S. soldiers after concussion. Headache, 52: 732-738.
Thorpe S, Fize D, Marlot C. (1996). Speed of processing in the human visual system. Nature, 381: 520-522.

Tijerina L, Gleckler M, Stoltzfus D, Johnstone S, Goodman MJ, Wierwille WW. (1999). A preliminary assessment of algorithms for drowsy and inattentive driver detection on the road. Virginia: NHTSA.
Tombu M, Jolicoeur P. (2004). Virtually no evidence for virtually perfect time-sharing. Journal of Experimental Psychology: Human Perception and Performance, 30(5): 795-810.
Tovee MJ. (1994). How fast is the speed of thought? Current Biology, 4(12): 1125-1127.
Trimmer PC, Houston AI, Marshall JAR, Bogacz R, Paul ES, Mendl MT, McNamara JM. (2008). Mammalian choices: combining fast-but-inaccurate and slow-but-accurate decision-making systems. Proc. Biol Sci., 275(1649): 2353-2361.
Tsai Y, Viirre E, Strychacz C, Chase B, Jung TP. (2007). Task performance and eye activity: predicting behavior relating to cognitive workload. Aviat Space Environ Med, 78(5 Suppl): B176-185.
Tsuchiya N, Koch C. (2005). Continuous flash suppression reduces negative afterimages. Nature Neuroscience, 8(8): 1096-1101.
Vallesi A, Binns MA, Shallice T. (2008). An effect of spatial-temporal association of response codes: understanding the cognitive representations of time. Cognition, 107:501-527.
Van Assche M, Gos P, Giersch A. (2012). Does flexibility in perceptual organization compete with automatic grouping? Journal of Vision, 12(2):6, 1-17.
Van den Bussche E, Segers G, Reynvoet B. (2008). Conscious and unconscious proportion effects in masked priming. Consciousness and Cognition, 17:1345-1358.
Vogel EK, Luck SJ, Shapiro KL. (1998). Electrophysiological evidence for postperceptual locus of suppression during the attentional blink. Journal of Experimental Psychology: Human Perception and Performance, 24(6): 1656-1674.
Weissman DH, Warner LM, Woldorff MG. (2004). The neural mechanisms for minimizing cross-modal distraction. The Journal of Neuroscience, 24(48): 10941-10949.
Whyte J, Polansky M, Cavallucci C, Fleming M, Lhulier J, Coslett HB. (1996). Inattentive behavior after traumatic brain injury. Journal of International Neuropsychological Society, 2: 274-281.
Wickelgren WA. (1977). Speed-accuracy tradeoff and information processing dynamics. Acta Psychologica, 41: 67-85.
Wilimzig C, Tsuchiya N, Fahle M, Einhauser W, Koch C. (2008). Spatial attention increases performance but not subjective confidence in a discrimination task. Journal of Vision, 8(5): 7, 1-10.
Wilke M, Logothetis NK. (2003). Generalized flash suppression of salient visual targets. Neuron, 39: 1043-1052.
Wong KFE. (2002). The relationship between attentional blink and psychological refractory period. Journal of Experimental Psychology: Human Perception and.Performance, 28(1): 54-71.
Woodman GF, Luck SJ. (2003). Dissociations among attention, perception, and awareness during object-substitution masking. Psychological Science, 13(6): 605-611.
Wyart V, Tallon-Baudry C. (2009). How ongoing fluctuations in human visual cortex predict perceptual awareness: baseline shift versus decision bias. The Journal of Neuroscience, 29(27): 8715-8725.
Yoncheva YN, Blau VC, Maurer U, McCandliss BD. (2010). Attentional focus during learning impacts N170 ERP responses to an artificial script. Developmental Neuropsychology, 35(4): 423-445.
Youse KM, Coelho CA. (2009). Treating underlying attention deficits as a means for improving conversational discourse in individuals with closed head injury: a preliminary study. NeuroRehabilitation, 24: 355-364.
Ball, The role of higher-order motor areas in voluntary movement as revealed by high-resolution EEG and fMRI, Feb. 16, 1999, 13 pgs.
EPO OA, 06813639.9,May 31, 2011, 11 pgs.
ISR, PCT/US2006/032773, Jan. 22, 2007, 14 pgs.
Mehta, Forward models in Visuomotor control Apr. 12, 2002, 12 pgs.
Pedersen, Origin of Human Motor Readiness Field Linked to Left Middle Frontal Gyrus by MEG and PET, Jul. 7, 1997, 20 pgs.
Strauss, Intraindividual variability in cognitive performance in three groups of older adults: cross-domain links to physical status and self-perceived affect and beliefs, Sep. 5, 2000, 14 pgs.

* cited by examiner

APPLICATION OF SMOOTH PURSUIT COGNITIVE TESTING PARADIGMS TO CLINICAL DRUG DEVELOPMENT

FIELD OF THE INVENTION

This invention relates to the clinical drug development process to apply the use of neuropsychological smooth pursuit tracking tests for providing quantifiable measure of cognitive behavior and function for detecting the efficacy of neuro-pharmaceutical compounds.

BACKGROUND OF THE INVENTION

In the field of neuroscience today there are a number of cognitive testing paradigms used by physicians, clinicians and individuals to assess one's cognitive performance.

The first and the most commonly used cognitive testing paradigm, especially the one that traces its origins furthest back in time, is the survey. The survey is a multipart questionnaire that is typically administered by a physician or a clinician. The set of questions in a survey, which may comprise of qualitative or quantitative questions, ask the individual taking the survey to evaluate oneself. Once the individual is finished taking the survey, the clinician or physician then evaluates the answers to the questions. The answers are evaluated in one of two ways. The answers are either subjectively evaluated by the physician or clinician, or entered into an algorithm to be processed to generate a score. The evaluation is then used to determine whether the cognitive level of performance of an individual meets a certain threshold or not to determine cognitive impairment.

The advantages to the survey are that it is portable and fairly easy to administer. In addition, the survey cognitive testing paradigm allows the test designer a great degree of freedom and flexibility in what questions to ask and the format of the test taker to answer those questions. However, there are downsides to surveys. One downside is that surveys are unfortunately relatively qualitative. Also, surveys are often open survey forms, where multiple choice and open-ended questions alike tend to convert into subjective answers. For instance, a test that asks, "How dizzy are you? Please quantify on a scale of one to ten" is not a truly quantitative test, but rather a subjective measurement of experience of the patient filling out the survey. A similar type of measurement error occurs if the question was asked in a multiple-choice format with answer choices of yes and no. Here, the patient then must select yes if they feel something, or select no if they don't feel dizzy or don't know what they might be assessing to feel. The survey paradigm also suffers when it relates to cognitive function because it presupposes a uniformly defined normative universally appreciated and semantically similar way of describing ailments from patient to patient.

Another common type of cognitive assessment is to study the reaction time of a patient in response to a test. Reaction time is typically used with recordings, and stopwatches or clocks. In recent time, reaction time tests area administered via tests on computers or over the Internet using keyboards or mice as input methods. Such reaction tests are conducted by presenting questions on the screen that the patient reacts to by pressing the input device. The data is then collected in the form of milliseconds of response time that the patient had to think and compute. This data is then aggregated and typically processed by methods such as average and standard deviation over the course of multiple trials in order to get a midline value or range of reaction time for a certain type of test.

Reaction time tests also attempt to analyze decision making by presenting a question that the patient must respond to make very quickly by pressing one or multiple types of stimuli. An example of such a reaction time test would be the following: the test involves the display of two different icons and the patient is asked to press the space bar only if one icon appears but not when the other icon appears. The result of this is that the reaction time test also measures the quality of the reaction with the decision, and not just the reaction time in general.

Unfortunately, reaction time tests have many disadvantages. Reaction time tests, while somewhat quantitative, suffer from low "test re-test reliability" and high degree of error induced by the environmental control. There are simply too many other variables at play. Also, the process of measuring reaction time needs to be iterated many times, often in the hundreds or thousands range, in order to produce a meaningful figure. The biggest problem with these tests however is that these tests are highly reliant on the patient's willingness or will to take the test. The resulting outcome then is more oftentimes a function of patient willingness to take a test and not the patient exhibiting the symptom or the phenomena that one is looking to measure in the first place.

A more modern cognitive testing paradigm is the balance test. The balance test paradigm may ask a patient to sit or stand on a ball, such as a balance ball, in some off-center form. With the use of cameras or measuring devices such as semiconductor components being placed on the patient, the system measures how stable the patient is to determine the cognitive ability associated with the brain circuit pathway for balancing.

The downfalls of balance tests are that balance based tests are quite noisy. The noise is because of several variables being at play in the process of measuring them, and the devices used to measure the variables, such as cameras, accelerometers and other forms of driverscalpic sensing, are simply not advanced enough to produce a reliable metric. Furthermore, the measurement of balance tends to be fairly binary, i.e. stable or unstable. Moreover, connecting the instability measurements to specific types of cognitive decline is quite difficult because disorientation can be caused by effects unrelated to cognitive ability such as a headache, a blockage in the ear canal and dizziness.

Neuroimaging technologies have also been used to assess cognitive performance. Neuroimaging technologies are generally broken into two different categories of testing. The first category of neuroimaging technologies includes those that analyze images, such as fMRI and CT scans. The second category of neuroimaging technologies includes those that analyze waveforms, which typically are EEG or MEG technologies.

The neuroimaging technologies that use imaging rely on an imaging system, which captures some form of metabolic or electric activity inside the brain. This activity is typically mapped in a topological way to the three-dimensional coordinates of the brain. There is typically a one to one mapping between the section of the brain with activity and the physical location of the brain. Typically slices, map or pictures of the brain are taken at various locations inside the brain, but the mechanism underlying those imaging technologies is capturing the metabolic rate of the neurons as they are activated by the brain in order to process signals. Metabolism typically takes the form of a consumption of glucose or sugars or some form of chemical in the brain that generates some kind of activity, such as a waveform of heat or electrical activity. This is a coarse grain way of assessing what part of the brain in general is consuming energy at any given time.

The second type of imaging relies on the analysis of the movement of liquid or fluid or the emission of electrical or magnetic signals in the brain. The waveform based cognitive neuroimaging technologies rely on surface based analysis, based on sensors that are placed on the skull on the outside of the head which read electrical or magnetic activity. As the sensors are positioned on the outside surface of the head, the depth in which they can measure activity in the brain is limited. Thus the sensors generally have a more difficult time measuring waveforms or activities inside the brain closer to the brain stem. However, as a very high level measure, the sensors can also generate an assessment of where the user's brain is active at any given time.

Neuroimaging technologies suffer a variety of problems, although to date they have been perhaps the most promising and eye opening about the relationship between the physical location of impairment with behavioral impairment or change. One of the problems is the problem of not knowing what variables to compare during the testing process. For example, it is unclear if the images should be compared from one patient to another patient, a patient to a population statistical average, or a patient to their baseline taken at some previous time. However, whether it is from patient to patient, from patient to a population statistical average, or from patient to himself or herself, there are too many variables to consider and cannot make anything more than generalizations about the conclusions of the patient's cognitive performance. Furthermore, both neuroimaging and their related signal analysis in the cognitive assessment paradigms suffer from the challenge of having noisy data. The high level of noise usually drowns out the signal that one would wish to analyze. On top of the noise from the devices and the surrounding environment, the background of mental activity is often difficult to filter out of the actual signal associated with the one being tested for and prevents doing any kind of meaningful analysis.

Another paradigm of promising cognitive assessment is by biomarkers, diagnostic tests or bioassays. This form of cognitive assessment generally relies on the breakdown of particles inside the brain via some kind of emission of particles from the cell from the neuron into the blood stream. As damaged cells emit byproducts of neuron structures into the blood stream, measuring the presence or availability of those breakdown byproducts can be used to determine if any cognitive damage has occurred in the brain and the severity of the damage. The challenge of these tests in general is that they tend to be invasive or require bodily fluid sampling. In addition, it is very difficult to correlate the results of the test with the precise location of the damage with just fluid sampling alone, such as blood or urine sampling. Therefore, at best this paradigm serves as a high level indicator of brain damage, but not the location of the damage.

The most promising of these neuro-diagnostic tests and cognitive evaluation test platforms is perhaps eye tracking. Eye tracking is used to look at the movements of the eyes in a response to a series of tests or stimuli that the patient must either follow or void or count or tally with their eyes. By measuring the fluidity, momentum and precision of the movement of the eyes as they track objects that are likewise moving or reacting on the screen, a more precise level of various cognitive functions can be determined. The distinction here is that the cognitive function is evaluated as opposed to the physical structure of the brain. This is promising because as one is measuring the physical structure of the brain, the measurement has very little correlation to the actual cognitive function.

Across all of these cognitive testing paradigms, there is a general set of problems such as the long length of time to administer the test, the time taken by the test taker and the test itself from start to finish, and the requirement of trained personnel and experts. Also, the cost of running these tests is very high, not to mention the cost for the administrator to not just run the test, but to be educated about the test.

It is important to note that various cognitive testing paradigms have been employed in the past in an attempt to be used in the process of drug development. However, these paradigms have suffered a number of drawbacks over the subject matter.

Cognitive Diseases and Disorders

As research continues into understanding cognitive function and cognitive functional deterioration with age, disease, or impairment to the physical brain, much has been discovered about the different types of neurological diseases and disorders that patients develop. At a very high level the diseases can be categorized into two broad categories. The first category includes those that have an impairment of attention, which are sometimes called neurological diseases because attention is thought to be a cognitive function. The second category of impairment includes those that can be referred to as a brain injury, such as those caused by a concussion or a traumatic brain injury. This is when physical neuron structures in the brain are sheared, distorted, pulled, stretched or broken structurally. Typically the sources of structural breakage are rapid impact movement, twisting, torqueing, or anything that might break tissues inside the brain.

Regardless of the category of cognitive disorder or diseases of the brain, the same can be said about all deteriorations of the brain, which is that at the current time it is difficult to classify and quantify the nature of the brain impairments. This is because the assessment metrics and measurements are relatively primitive and rudimentary in design, and are focused primarily on assessing the patient's self-diagnosis of state and cognitive functions. Thus, the use of surveys as described previously has been the dominant paradigm of interrogating a patient in assessing the severity of decline and function. Typically this relies on two core functions of the patient. One is the ability of the patient to self-describe the ailment. The other is the patient's ability to properly assign meaningful vocabulary to the ailment.

The following is a brief description of several common forms of cognitive impairment and cognitive decline today:

Beginning with Alzheimer's disease, this appears to be linked closely with the deterioration of short-term memory as well as in some cases medium to long-term memory. It is often accompanied with deterioration in attention span, and the ability for one to engage in the meta-process of focus.

Parkinson's disease is another disease studied commonly for its impairment in motor function, and the apparent introduction of the Parkinson's disease tremor, which appears as a series of motions and movements that do not appear to be in complete control of the conscious brain of the subject or patient.

Schizophrenia is accompanied by deterioration in the ability to maintain attention and focus over long durations of time as well as feelings of paranoia and delusion, as well as a disassociation between the body and the sense of mind and the self in the brain.

Epilepsy is a thought to be a form of a deterioration of the ability of the hemispheres to synchronize electrical pulses and signals and is sometimes accompanied with memory impairments and attention impairments.

Attention deficit disorder (ADD) is thought to be accompanied by a attention impairment in the absence of an obvious currently understood physical change in the brain or the structure of the brain as is readily seen in Alzheimer's disease, Parkinson's disease, schizophrenia and epilepsy patients, as well as attention deficit disorder (ADD) or attentional deficit hyperactivity disorder (ADHD) represent deteriorations or enhancements of the function of attention in a patient.

Insomnia is an inability to control the function of sleep or an inability to maintain a ready state of sleepiness.

Dementia is a broader term which is used to categorize a number of cognitive impairments, and so is not necessarily focused on a single specific or classified specific or class of impairments, but rather have been associated with a general set or cluster or category; among those is typically an impairment of attention.

Although traumatic brain injury is a description of cognitive structural damage in the brain it is most often associated with an inability to focus, especially the eyes, reduction in attention span and the accelerated development of symptoms exhibited in some of the preceding ailments. There does not appear to be a general set of symptoms of Traumatic Brain Injury or TBI, but rather if the brain is affected in a negative way, for instance, if that section of the brain exhibits damage, the function of that section of the brain then exhibits damage.

In a similarly ambiguous definition, post-traumatic stress disorder (PTSD) typically describes the relationship of cognitive decline with a specific event. In this case, specifically a traumatic event that has the potential to change the behavior of the patient in some way is measured. It is not thought that physical structural damage would occur when this PTSD is induced, but rather that parts of the brain are shut down because of the trauma or stress presented to the brain.

Drug Development Market

The field of drug development is categorized at a very high level with a framework that encompasses two very different philosophies of determining the efficacy of a substance and its expected impact on the human body.

On the one end, there is the pharmaceutical process, which is sometimes referred to as the large molecule drug development end of the drug marketplace where the effects of particles and substances are sought and are expected to have an effect on a biological system, specifically a human or a very close approximation with a human model. The process is characterized by mining a set of compounds or chemicals in order to discover whether they have an effect on a certain system in the human body. This is typically a time intensive and relatively primitive in approach. It is similar to the effect of lining up a series of candidates based on some hypothesis that it might be effective to test them and then assessing whether that outcome is positive, negative, neutral, etc.

At the other end of the spectrum is a type of drug development referred to as small particle drug development, which is also commonly called the biotechnology process. This development process is focused on developing a specific candidate molecule that will change or modify biochemical signaling or processing, such as inhibiting or increasing the production of specific protein compounds in the body as a result of a very close bottom up targeting of a very specific chemical pathway in the human body. This development process is characterized by a set of analytical techniques that rest heavily on computational modeling.

Both of these systems have existed for some time and have exhibited varying forms of success. They have tended to favor different types of biological systems, one performing better in some cases, whereas the other will excel at different types of diseases or ailments or biological systems. Thus these two approaches have coexisted in the drug development marketplace for some time.

Independent of how the drug is developed, there are common questions asked in the process of developing a drug. For instance, one question is whether the drug is toxic. Another question is to what degree or magnitude the drug works. Those two questions tend to be the dominant questions that drive the strategy of developing drugs. Other questions include what dosage or frequency of administration are ideal, and what interactions a drug might have when combined with other chemicals, foods, and conditions of the body.

The question of toxicity is typically measured on the basis of human response or animal model response. This process takes the form of administering a certain type of chemical or compound to a human or an animal model and seeing at what dosage the negative side effects begin to occur.

This process is far from scientific and typically results on qualitative measures of surveys; how do you feel, behavioral assessments including sluggishness, motion, swelling or very physical attributes like joint pain, swelling, and water retention, which are viewed as negative side effects. Some amount of the medication less than the onset of negative side effects is then targeted as the effective dose. However, the determination of the effective dose is also bounded by the incurrence of positive effects of the drug on the system that it wishes to target.

The question of measuring efficacy is a slightly more complex one and requires typically longer periods of time for observation to assess whether the drugs are having the desired performance or not. The measurement of efficacy is complex and difficult because the attributes of cognitive function and behavior exist in a space that is not easily quantifiable with current readily available metrics. Currently the quantification of behavioral or cognitive functional enhancements must be made slowly over an extended period of time and is predominantly driven by qualitative metrics.

In the drug development process, drug candidates that are expected to have positive effects in treating a negative ailment or disease are typically staged in a series of three phases: preclinical stage, post clinical stage and premarket stage. The objective of staging the clinical drug development process in this manner is to mitigate risk or reduce expense by staging progressively increasing amounts of money for funding to assess the viability and performance of a specific drug candidate.

In the first phase of early preclinical stages, animal models are used to triage whether the drug candidate would be expected to have an effect in humans.

In the second phase of the drug development process, or the post clinical stage, the toxicity of the drug candidate is assessed.

In the third phase of the drug development process, or the premarket stage, a small candidate group of patients with ailments is given the drug candidate in order to determine if the cognitive situation or the ailment improves. If in the event that it does, a second trial is run with even more patients, and if that continues to improve the number of patients increases until a sufficient amount of data has been made to make a case between the relevant government agencies to make the case that the drug should be made available for sale on the market.

The clinical pipeline process for developing drugs that affect the cognitive function and behavior is currently insufficient and mismanaged. This can be attributed to two main problems.

One problem is the current lack of availability of readily deployable technologies for the measurement of cognitive function in order to quantify whether a cognitive impairment or improvement occurs. Due to the lack of quantitative technology, the traditional tools of the analytical researchers, namely statistical and analysis and behavioral quantification, are lacking and not available. The implication of this is that there is a tremendous risk that drugs that might have had a statistically significant effect in improving or detecting the process of impairment of cognitive functional decline may be cutoff to early. The inverse of this problem is that the process of applying luck or encouraging positive chance through the drug development process results in unnecessarily lengthened pipeline processes and higher research and development costs. Thus, if a technology were available to that detect and assess cognitive function in a quantified way, it could be applied to lower the research and development costs.

The other problem is that the drug development process has low accuracy. When a benefit is detected but cannot be quantified, it is difficult to benchmark or relate that benefit to a similar benefit exhibited by another patient without being able to apply a standard normalized consistent testing process to both of those patients. Even a baseline versus change paradigm would benefit if the cognitive function of a patient were quantified, rather than it being qualitatively evaluated. Similarly, the "test-retest reliability" and the error interval of a quantitative paradigm would be easier to determine than that of a qualitative paradigm. With such a quantitative paradigm, a high "test-retest reliability" and low error interval would better instill trust and a degree of confidence in the results.

It has been reported that eye tracking and fixation has been utilized in evaluating pharmaceuticals, but only as far as measuring its effect on the eyes to fixate on an immovable dot or icon. In this paper, "Preclinical assessment of CNS drug action using eye movements in mice," by Hugh Cahill, Amir Rattner and Jeremy Nathans, Journal of Clinical Investigation, Vol. 121, No. 9, September 2011, mice were caused to stare at a dot and the jitter in their gaze direction was quantified after compound injection.

However, fixation is not a smooth pursuit technology and is less accurate in establishing a drug reaction baseline.

SUMMARY OF THE INVENTION

It has been found that smooth pursuit tracking, whether eye tracking or mechanical tracking, can be used in drug screening to accurately evaluate toxicity and efficacy. This is because smooth pursuit eye tracking involves the autonomic system and is thought to be a reflex process in the central nervous system. On the other hand, the Cahill fixation involves a conscious thought process to not move one's eye, which invariably causes a hand off between a portion of the brain involved in thought process and a portion of the brain involved in autonomic cognitive system. Another difference between fixation and smooth pursuit is that smooth pursuit involves more complex pathways throughout the brain than fixation.

Thus, what is provided is an early drug screening system that uses smooth pursuit tracking to determine the efficacy and toxicity of drugs. Rather than using prior drug screening procedures, a quick and accurate prediction of drug efficacy and toxicity can be obtained by smooth pursuit tracking techniques. Smooth pursuit tracking involves the smooth curvilinear movement of an icon, dot or target on a screen and having an individual track the position of the dot. The degree to which the individual tracks the dot determines cognitive performance, and it is a change in cognitive performance, which if measured precisely, measures the effect of the drug on the body. Such cognitive performance can be measured using eye tracking in which the motion of the eye is captured when the individual tries to track the dot. Cognitive performance can be measured by mechanical tracking in which an individual uses his finger or other body part's motion to track an on-screen moving dot. Regardless of the smooth pursuit technique for measuring cognitive ability, it is the measure of this cognitive ability that provides for rapid drug efficacy and toxicity testing.

More particularly it has been found that a new smooth pursuit eye tracker technique yields precise quantitative results that makes smooth pursuit eye tracking ideal for rapid drug testing. The statistically significant quantitative results provided by the new eye tracking technique are the result of excluding the outside environment around the head, and using algorithms which remove outlying data as well as specialized standard deviation techniques, and in one embodiment, the use of peak performance detection.

This invention thus contemplates the use of eye tracking coupled with a paradigm of smooth pursuit tracking as a platform diagnostic to be applied throughout the clinical drug development process. Rather than administering a drug and observing any untoward effects that take hours if not days to manifest, in the subject invention drug efficacy and/or toxicity can be rapidly ascertained using smooth pursuit eye tracking. Since most drugs affect cognitive processes, accurately measuring cognitive ability using smooth pursuit techniques as a drug is administered provides early assessment of toxicity and efficacy. If there is no change in cognitive ability, then no matter what the particular drug is supposed to do, if the brain is not affected, the drug cannot be efficacious.

Thus, as a first cut, the target drug must at least have an effect on cognitive ability, with the subject smooth pursuit techniques providing a basic filtering function to filter out drugs that have no chance of working.

Secondly, if there is change in brain function one can devise a series of smooth pursuit tests to test for a particular response.

More particularly in one embodiment an eye tracking diagnostic procedure is used to measure and assess cognitive change in cognitive function or behavior, negative or positive, in response to the drug compounds. The analysis can be performed by using highly accurate eye trackers of the subject invention or by using mechanical motion of the extremities to track a moving on-screen dot or icon driven to establish smooth motion. The accurate and highly quantifiable test can also be performed by a hybrid of mechanical and optical testing by mechanical manipulation of a finger or stylus to match dot movement as the eyes track the moving icon on a screen.

The smooth pursuit test used in one embodiment of the invention can be driving the on-screen icon to execute a circular smooth pursuit path, a sinusoidal smooth pursuit path or any curvilinear smooth pursuit path. The measurement can involve a number of different indices of the ability of the test subjects' eyes to track the on-screen icon including anticipatory timing in terms of how well the test subject anticipates icon movement, regularity of the person's ability to track the onscreen icon, variability of any of the previous test results, predictability of the test results as well as other methods.

For purposes of the subject invention anticipatory timing means measuring the lead or lag time of an individual's response to tracking a smooth pursuit target icon to anticipate the future position of the icon.

Variability means the distance error as the individual follows the target icon.

Regularity means the consistency of any smooth pursuit tracking measurement, with maximum consistency meaning that the errors over time are the same.

Predictability means the degree to which the test subject's past input and errors can predict the next input.

Peak performance means increasing the maximum performance that the test subject exhibits during the duration of the test.

There are thus a number of different metrics by which one can quantify and assess changes in cognitive behavior that are described in U.S. patent application Ser. No. 13/506,840 filed May 18, 2012 and Ser. No. 13/507,991 filed Aug. 10, 2012. Data analysis proceeds as described in these patent applications and will be described herein. Specifically the testing process and analytical process must exclude as much noise as possible through data cleansing methods such as normalization and noise infiltration detection. It is important that data cleansing occurs before quantifying and assessing changes in cognitive behavior via score calculation.

Smooth pursuit eye-tracking tests should be administered during clinical trials on a patient-by-patient basis and at the beginning of the trial to collect a baseline against which testing results can be compared. The test should also be administered at various times under a mix of environmental conditions, metabolic conditions, and times of day to vary conditions of fatigue. Each of these conditions have an effect on smooth pursuit testing in general, with the magnitude of effects of these conditions cancelled or at the very least quantified to increase the accuracy and precision of the analysis. The test should also be administered on a regular basis as prescribed by a statistician looking for specific outcomes and effects, especially in a method consistent with the general statistical strategy of the current clinical phase.

The cognitive testing of the smooth pursuit variety is administered, and at the conclusion of the test the scores are evaluated. If the test score is in any way inconclusive a follow up phase may be necessary in order to quantify efficacy and validity, and to establish the lack of toxicity if such is the case.

Unlike other cognitive testing paradigms that carry significant expense and that can only be used at the beginning and end of the clinical trial, the relatively low cost of the smooth pursuit eye tracking and mechanical tracking as well as the hybrid test, mean that cognitive evaluation can be used throughout the clinical process and throughout the phases of the drug development process. This in turn increases the statistical validity or significance of this data, heightening the determination of the efficacy of a drug.

In addition, another advantage of the subject invention is that the cognitive pathway accessed with this test is complex, i.e. one requiring the simultaneous coordination of a number of different sections of the brain at once to perform a relatively straightforward, and simple mechanical or visual task. In either case, the test task is mechanical because the eyes are controlled by muscles and are positioned by the brain as they move around and refocus and relocate on the other screen icons. The test can also be accompanied other forms of mechanical smooth pursuit tracking involving the hands or other extremities such as feet, core, body, legs, arms, fingers or head. By doing so, due to the coordination cost in the brain of coordinating an anticipatory action as well as the muscle movement in order to control the fine movement of a human body part that is attempting to follow a target dot moving in a smooth path, the circuit in the brain that correlates to this activity is further stressed, and involves more complex and variable regions of the brain when using mechanical tracking.

This complex test is advantageous because it involves more areas of the brain and thus is a more accurate test of any cognitive change to the brain.

The test subject's relative positioning of a point of gaze on a dot that one is attempting to follow, controlled by the test, creates a number of readily measurable and analyzable quantitative metrics of patient cognitive performance. At one end of the spectrum a very simple metric is a simple analysis of the lead/lag or steadiness of the eye tracking result. At the other end of the spectrum, metrics of variability, reliability and consistency can be applied in order to assess the degree to which the user maintains a consistent response relative to the moving target. The diversity of these metrics is advantageous because they confer a number of variables that can be analyzed by the testing paradigm. For instance, anticipatory timing involves how a person's gaze leads or lags a moving target can be measured and quantified independent of mechanical jitter.

Moreover, while anticipatory timing involved in eye tracking is useful to assess drug efficacy for a number of diseases, it has been found that mechanical smooth pursuit tracking can catch and measure effects associated with epilepsy and Alzheimer's disease independent from schizophrenia or Parkinson's disease. Likewise, mechanical smooth pursuit tracking can measure the effects of anxiety, anticipation or the stimulation effects of stimulant compounds by measuring mechanical jitteriness, eye jitteriness or involuntary extremity movement while tracking a test target or icon moved smoothly about a curvilinear path.

A simple testing paradigm such as smooth pursuit can therefore be applied across clinical processes in order to measure a number of different analytical impairments quantifiably changed from a baseline before and after the administration of a therapeutic compound. Smooth pursuit testing can also assist in the detection of cognitive performance changes in order to catch both performance enhancement, efficacy, as well as deterioration of cognitive function associated with toxicity of a compound, as it passes through the clinical drug development pipeline process.

Other advantages include the fact that smooth pursuit eye tracking or mechanical tracking can be administered in a portable environment. With mechanical smooth pursuit, the hardware requirements for the test are merely an input source, which can be a trackball, a mouse or a touch screen, and the output source is merely a screen, such as that of a laptop or tablet computer. The test can even be administered on a projector, meaning that the test provides a reliable metric of smooth pursuit, ability and testing in a relatively portable environment.

In summary, smooth pursuit cognitive testing can be used in clinical drug development to ascertain the effect of a particular drug or compound on the cognitive function of a test subject, with the smooth pursuit cognitive testing including either eye tracking, mechanical tracking or a combination of both.

BRIEF DESCRIPTION OF DRAWINGS

These and other features of the subject invention will be better understood in connection with the detailed description in conjunction with the drawings of which.

DETAILED DESCRIPTION OF DRAWINGS

Prior to describing the subject invention, one convenient and inexpensive desk top unit for performing smooth pursuit eye tracking having the requisite precision is now described.

Precision Smooth Pursuit Eye Tracking Using a Desktop Unit

Figure 1:
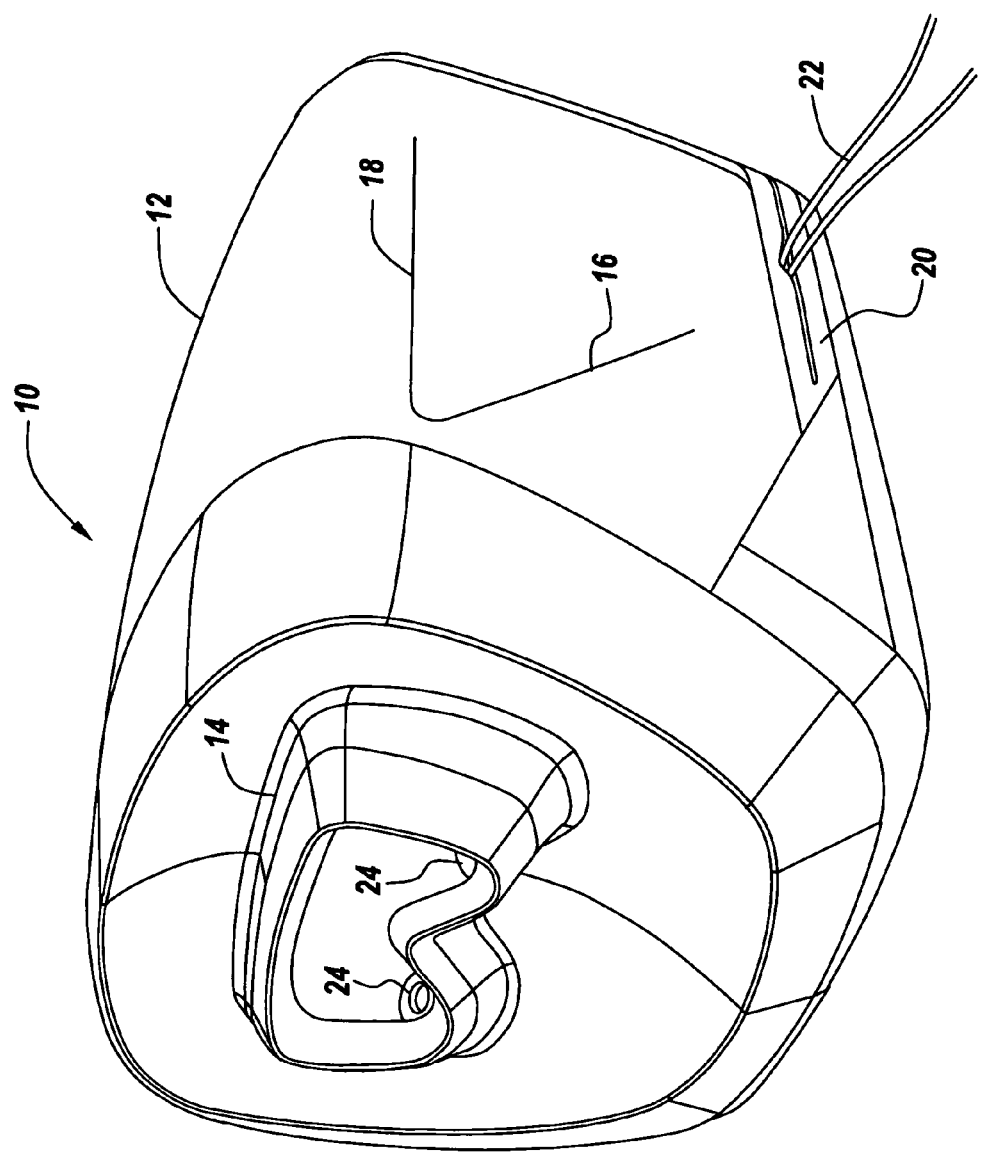
FIG. 1 is a diagrammatic illustration of an enclosure and mask for use in a desktop opto-cognitive device for cognitive assessment used for a clinical drug evaluation and development.

Referring now to FIG. 1, a desktop based opto-cognitive device 10 is provided with an enclosure 12 that has a mask 13 on its proximal face to which an individual taking a cognitive test is asked to press his or her face. It will be noted that the enclosure includes an integral angled handhold portion 16 as well as a horizontally orientated integral handhold portion 18, which is usable by the individual taking the test to press his or her face into mask 14 when the enclosure is supported on a pedestal at eye level. The enclosure also has a slit 20 to enable cabling 22 to pass from the outside of the enclosure to the inside of the enclosure to attach to an internally carried screen of a computing device, such as a laptop, personal computer or a tablet device.

As can be seen mask 14 includes cameras 24 located below the nose bridge of the mask with the camera and pointed towards the eyes of an individual taking the cognitive test to measure cognitive performance. Cognitive performance is ascertained by measuring gaze detection by detecting the position of the individual's pupils as they trail a moving dot on the screen.

Figure 2:
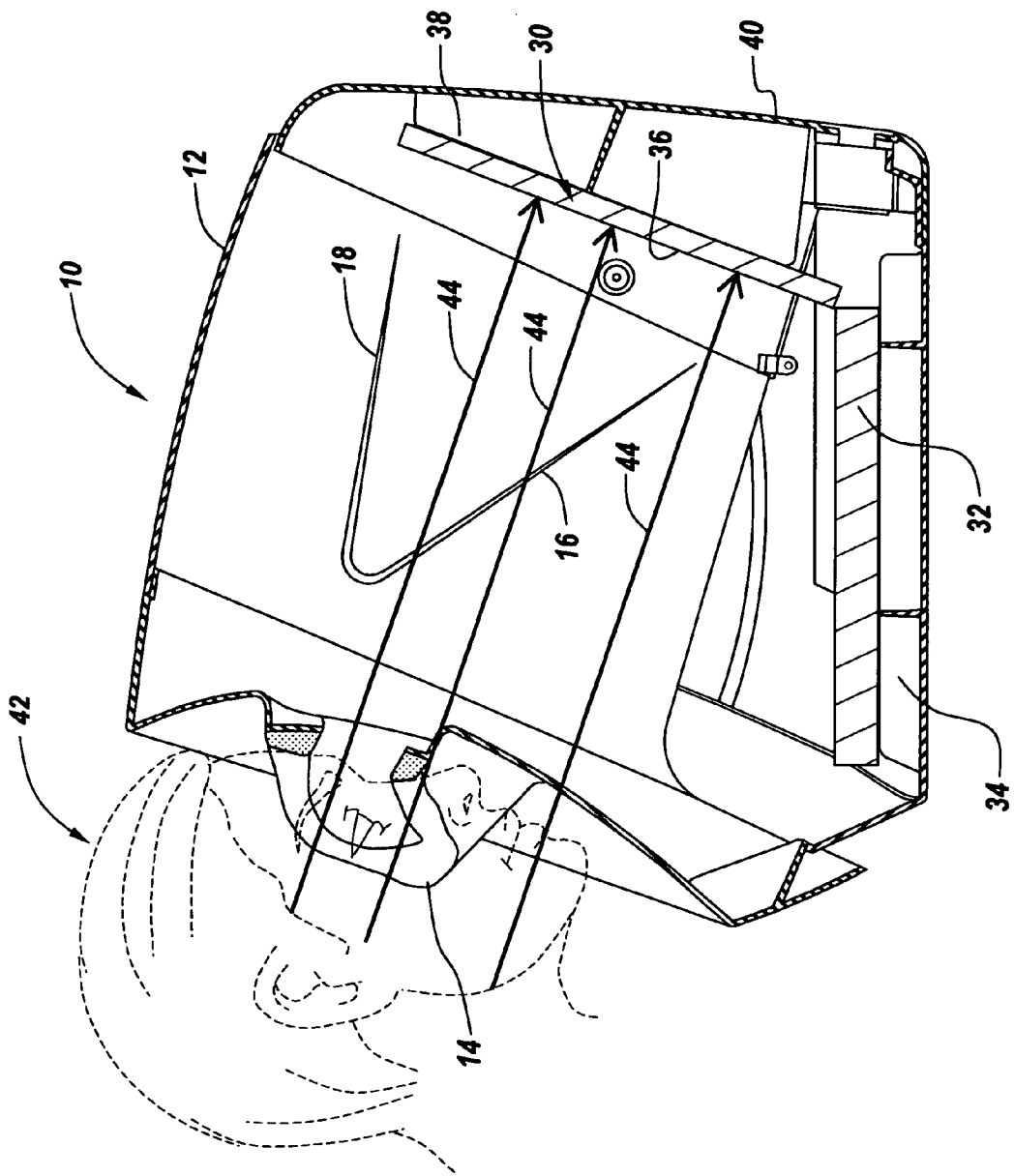
FIG. 2 is a diagrammatic illustration of the enclosure of FIG. 1, illustrating an individual having his or her face pressed to a mask which positions the eyes of the individual with respect to the screen of a laptop contained within the enclosure, thus to establish not only a fixed distance of the eyes to the screen but also that the plane of the screen is parallel to the plane across the individual's eyes such that the line of sight from the eyes to the screen is perpendicular to the plane of the screen.

Referring now to FIG. 2, enclosure 10 is provided in one embodiment with a laptop generally indicated by reference character 30 having a base 32, which rests on a support rib 34 at the base of the enclosure 12. The angled screen 36 of laptop 30 resting on a rib 38 attached to the back wall 30 of enclosure 12 to support the screen not only in its angled orientation with respect to its own base, but also, as will be discussed hereinafter to provide a plane for the screen that can be maintained perpendicular to a line from the individual's eyes to the screen, here shown in dotted outline at 42. The line of sight from the individual to the screen is indicated by arrows 44 to show that the plane of the eyes of the individual is maintained parallel to plane of the screen.

Also shown are handles 16 and 18, which in one embodiment are indents into the surface of the enclosure as illustrated in FIG. 1.

Figure 3:
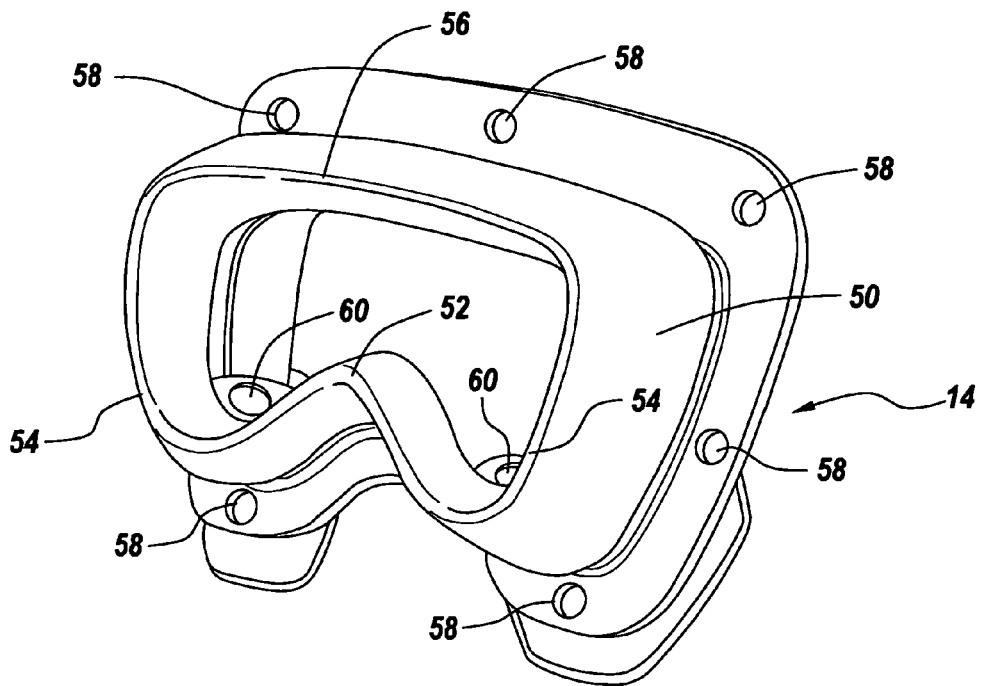
FIG. 3 is a diagrammatic illustration of a mask usable for the enclosure of FIG. 1, illustrating apertures through which cameras are adapted to protrude to measure pupil position and thus eye gaze direction.

Referring now to FIG. 3, mask 14 is shown to have an elastic rubberized mask material 50 which has a nose bridge 52 and cheeks support sides 54 as well as a forehead supporting portion 56 all of which forming a type of goggle. However, rather than being head worn, the goggles are mounted to the subject enclosure as for instance through bolt holes 58.

Also shown in this figure are apertures 60 which are adapted to house cameras pointing up towards the eyes of an individual when the individual has his head pressed to the mask, the purpose of which are to detect pupil position and thus gaze direction of the individual taking the cognitive test. Here it is to be noted that since the individual's head is immobilized with respect to the screen, a rather inexpensive single camera can be used to detect pupil position, as opposed to the rather 80 plus treated cameras used to detect gaze direction using glint detection and iris position.

Mask 14 has a number of features that make it universal and capable of fitting to any adult face, regardless of ethnicity or gender to provide a fixed distance between the eyes and the screen, and also between the eyes and the light sources used to provide the glints.

First, the mask is made from a compound foam that is non-compressible, yet comfortable. In one embodiment the foam is a polyurethane foam model PG 250 made by Spectrum Plastics Group of Westminster Colo., with the foam having a 55 shore hardness. The shape of the mask was designed by taking an average of reported face measurements across the population demographic in the 90% percentile between the ages of 8 and 20, and thus allows for a universal fit.

Secondly, the curvature of the forehead-contacting portion of mask 14 has a horizontal curvature of a radius of 79 mm at the bottom, closer to the eyes, and narrows to the top of the forehead of the mask, with a vertical curvature of a radius of 107 mm. The forehead-contacting portion of mask 14 is 165 mm wide at the bottom and 155 mm wide at the top with such measurements used to accommodate a wide variety of forehead widths and shapes.

Thirdly, the nose cutout has a nose depth of 60 mm and nose width of 90 mm, designed to accommodate even the longest and widest of noses.

Finally, the portion of the mask that engages the cheekbones was sized to give the IR LEDs enough depth in front of the eyes. Note that the cheekbone of the mask refers to a narrow horizontal cheekbone plate.

The above establishes a predetermined distance between the IR LEDs and respective eyeballs so that this distance is the same for all faces.

The mask when properly configured properly contacts the forehead and the cheekbones and creates a light tight barrier to outside light so that the mask surrounds the face with a light-tight seal. The curvature of the mask horizontally across the eye portion has a radius of 277 mm and a width of 200 mm, which assists with this light-tight seal.

As mentioned above, the design for the universal eye mask shape is concentrated on three key face areas, namely the cheekbones, the nose bridge and the forehead. These three key face areas are chosen as a pinpoint because they are the areas of the face that have the least fat deposit and variations in fat deposits on one's face is the main cause for variation from one adult face to another. The result is the facemask curvature tightly hugs the cheekbones, forehead and sides of the face to create a tight barrier, which blocks outside light from entering the enclosure of the device.

It is a feature of the desktop unit that with a computing device such as a standard laptop placed on the ribs is shown in FIG. 2, the individual's eyes are no less than 38 centimeters from the laptop screen, nor more than 42 centimeters.

Figure 4:
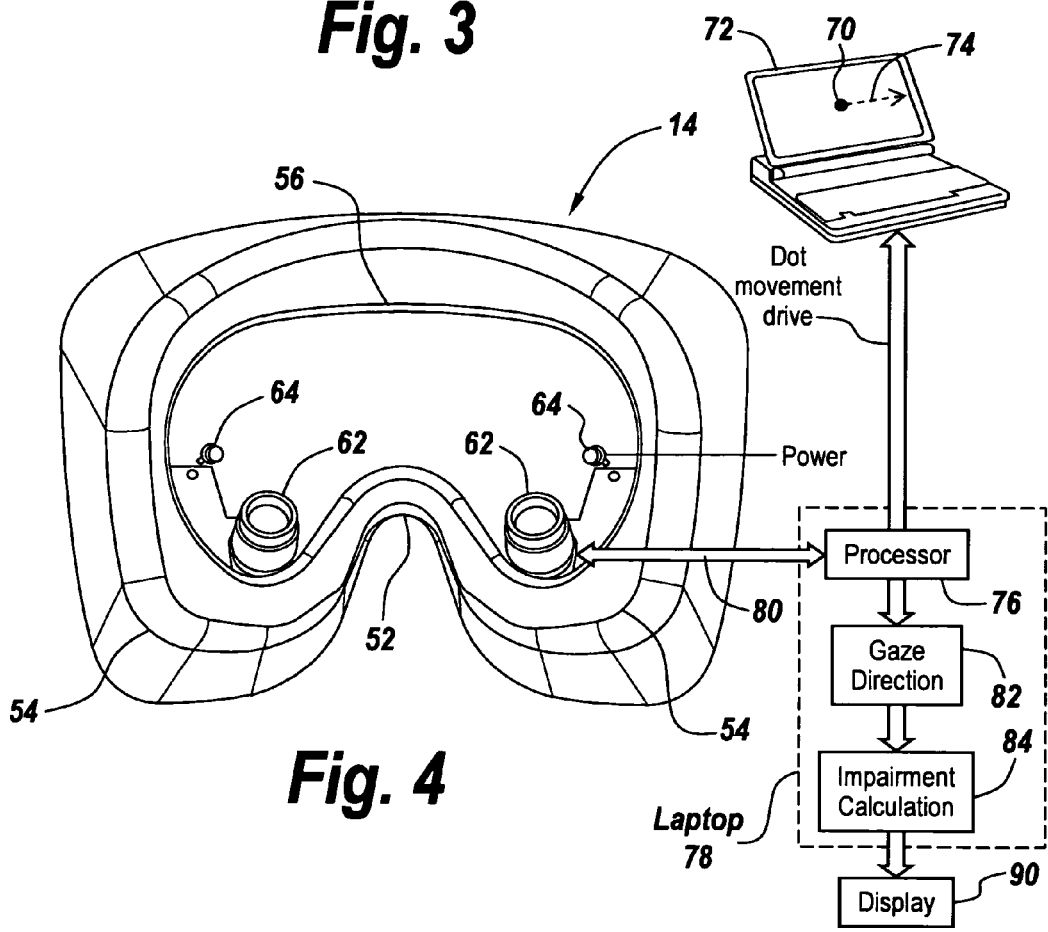
FIG. 4 is a diagrammatic illustration of the mask of FIG. 3 showing the mask-mounted cameras along with a processor, and a gaze direction and impairment calculation module for measuring cognitive function.

Referring to FIG. 4, mask 14 of FIG. 3 is shown in which like elements carry like reference characters and in which relatively inexpensive cameras 62 can be mounted into the orifices of 60 of FIG. 3 such that the cameras point upwardly towards an individual's eyes when the individual's face is pressed to the mask. Also shown are IR LEDs 64, the purpose of which is to shine a tangential light onto the eye so as to pop out the position of the pupil while at the same time illuminating the remaining part of the eye which appears white as opposed to the dark pupil.

When a moving dot 70 is placed on a computer screen 72 and is moved for instance as illustrated by dotted line 74, this movement is reflected in a change in the gaze direction of the individual taking the test. In order to obtain the gaze direction processor 76 within laptop 78 is utilized, with the output of the cameras as illustrated at 80 to detect gaze direction as illustrated at 82 in terms of the position of the pupil as detected by cameras 62. However, as illustrated at 84 cognitive abilities, or in fact cognitive impairment, may be ascertained in terms of the ability of the eye to track dot 70 as it moves. Also as illustrated in FIG. 4 the results of the cognitive impairment calculation may be displayed separately by a display 90. How gaze direction is detected in terms of pupil position measurement is as follows.

The processor and processing stage of calculation takes as an input the image of the eye and especially the dark pupil that is generated by the cameras and the infrared setup imbedded in the lower part of the face mask. The picture data is represented in pixels and the format can be anything from a raw picture to a compressed picture. The data input is specifically bounded in rectangular format such that the coordinates and position of the dark pupil appear roughly in the middle of the picture. The infrared LED illuminates the surface of the eye and also reflects into the dark pupil but not out, causing the dark pupil effect. The dark pupil effect is known in the literature and is described in the prior art as a method of eye tracking that is distinct from light pupil where the infrared LED is shown directly into the eye such that it bounces back out and illuminates itself in the form of white infrared light.

Once the pictures are generated by the cameras, these pictures are then stored to a data structure, which usually takes the form of a compressed movie or series/sequence of images. These images are stored to disk, or memory or random access memory for access by the processor and the software running on the processor.

The processor then performs a set of processing stages whereby it filters out the picture to determine where the dark pupil is in the picture. This is typically represented by a circular form of dark pixels with a hard circular ellipse edge. The ellipse edge is usually adjacent to the iris, which is either lighter colored or at least a greyer scale. In any event it is not dark or black, like the center of the pupil. Once the dark pupil pixel filter is applied, there is usually one large patch of dark pixels but also several smaller areas of dark pixels caused by for instance darkness of the eyelashes or clusters or discolorations on the surface of the eye or iris. This leads to a next stage of noise filtration where only larger sequential, continuous regions of dark pixels are identified, the largest of which is assumed to be the dark pupil.

At this point it is important to note that traditional advanced eye tracking that uses corneal reflection could be used to further define gaze direction. In this technology a byproduct of the infrared LED shown on the surface of the pupil is described in the prior art as a source of additional precision in the analysis of pupil position and location.

However, because the environment is sufficiently controlled in the desktop unit, this is not a necessary step. This is because one does not assume that the eye is moving significantly to the right or the left, and as a result one need not calculate gaze by cancelling out the effect of the head direction relative to the eye position. Instead, because the face mask fixes the head position toward the front, facing the screen, one can assume that the gaze is also in that direction and therefore one can skip the calculation of gaze utilizing corneal reflection. The circular shape of the ellipse that represents the dark pupil is then passed to a processing stage that applies an ellipse fit function onto the eye.

The state of processing for the desktop unit that calculates eye tracking parameters and variables off of two cameras and infrared lights shined onto the eye involves camera and infrared lights set up and configured on the front of the mask of the desktop eye tracking system.

After the dark pupil extreme positions are calculated, the algorithm finds the largest continuous region of ellipse parameterization and uses this as the estimated center point for the dark pupil. This dark pupil is then converted into a time stamp and dark pupil image data location, which is then passed to the next stage of the processing algorithm. The next stage of the processing algorithm takes the dark pupil data, runs the ellipse fit over it and uses the ellipse fit in order to generate the centroid of the ellipse in terms of x and y position as well as the time stamp, referred to herein as x, y and t for the names for the variables that are used in the algorithm and calculations. The pupil position is generated containing all of the x, y and t values for the frames and the centroids of the ellipses. Those are represented in a long table or vector, where each row of the table contains one triplet set of x, y and t for each eye for the left eye and the right eye. This means that there is an x, y pair for the left eye and an x, y pair for the right eye at a single time stamp shared across both. That time stamp refers to the two images, one that is the left eye and one that is the right eye.

The next stage is a data processing stage, which runs through the table of x and y positions and eliminates any points where the algorithm outputs suspicious results. For instance, if a blink occurred or if the eye tracker briefly lost track of the dark pupils of the left or the right eye or perhaps both eyes at the same time, the algorithm will cancel this out and insert nulls or no data, NA's or zeros in place of the data that previously was x and y data. In addition, simplification in calculation can be made assuming that the eyes do not move faster than a certain velocity in the frame rate the eye should not jump more than a certain amount in any given direction between consecutive frames. Thus if the eye is seen to move larger than an expected range, it is safe to say the algorithm or the inbound image contained a source of error or was corrupted, or that the user introduced some environmental error which overwhelmed the signal. In any of these events, the data is canceled out.

The resulting data post filtering is now a sequence of data points referring to x and y for the left eye and the right eye as well as a time stamp for the pairs. Thus the centroid of the dark pupil defines the gaze direction and it is this gaze direction which establishes lead and lag times as the dot moves on the screen. Note, filtration techniques of data files are described in the prior art.

The x, y, time stamp and optionally the height and width of the ellipse for each of the left and right eye data as reflected in a table is then converted and brought to the algorithmic processing stage where the eye data is assessed to determine whether it is considered valid and appropriate given the assumptions of the test taking environment. For instance, the left and the right eye should be roughly in the same position with respect to each other and that people will not be moving cross-eyed randomly.

It has been found, contrary to glint position measuring systems, that the accuracy in establishing gaze direction is significantly higher when the target, in this case the pupil, is large. It will be appreciated that the size or extent of the glint is two orders of magnitude smaller by area versus the pupil. Therefore assuming the same pixel density, the larger pupil feature centroid is computed with greater accuracy. This being the case one can achieve exceptional accuracy without glint tracking by detecting the centroid of the pupil.

More particularly, the number of pixels that define a glint can be as little as four, whereas the number of pixels which define a pupil can be orders of magnitude more. The subject system ignores the problem of the accuracy associated for instance four pixels and rather achieves a greater accuracy when considering the vast larger number of pixels associated with a pupil. Moreover, calculation of pupil position may be done in a number of different ways to reduce position error even further.

There are a number of ways in which cognitive impairment can be measured through eye tracking, most notably in the lag time or lead time of the eye as its seeks to track moving dot 70, this lag time or lead time is referred to as anticipatory timing.

Not only are the lag time and lead times indicative of cognitive ability, variations in anticipatory timing is a sensitive measurement of cognitive ability.

The net result is that one can utilize any of the number of techniques to measure cognitive ability in terms of gaze direction measurement and all such cognitive ability measurements are contemplated.

It will be noted that in a measurement system that utilizes the previously described enclosure, there is absolutely no need for calibration of the system and that one need not have a separate calculation for use by a test administrator precisely because no calibration is necessary.

Figure 5:
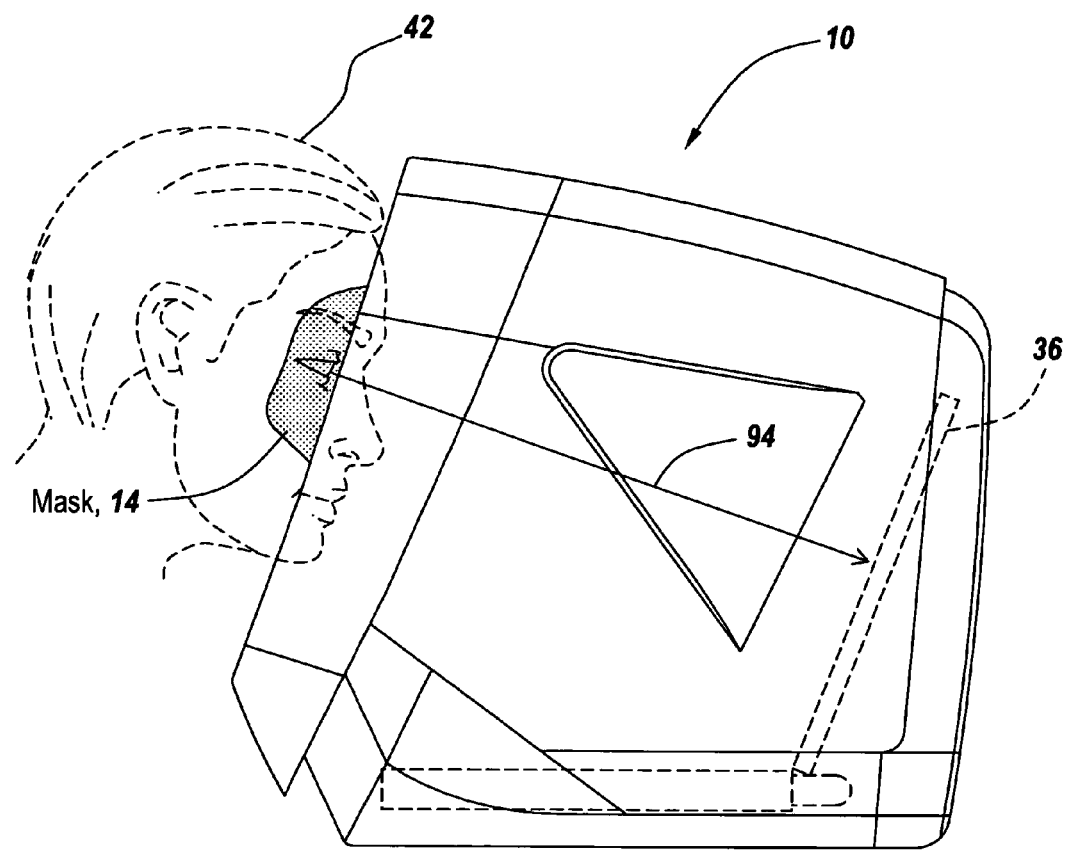
FIG. 5 is a diagrammatic illustration of the enclosure of FIG. 2 illustrating the distance between the eyes and the screen of the laptop contained within the enclosure.

Referring now to FIG. 5, it is noted that the distance of the eyes of individual 42 to screen 36 as illustrated by arrow 94 is to be no less than 38 centimeters and no more than 42 centimeters for the reasons discussed above. Thus, by pressing the individual's face to mask 14 all critical measurement parameters are established for accurate cognitive assessments.

Figure 6:
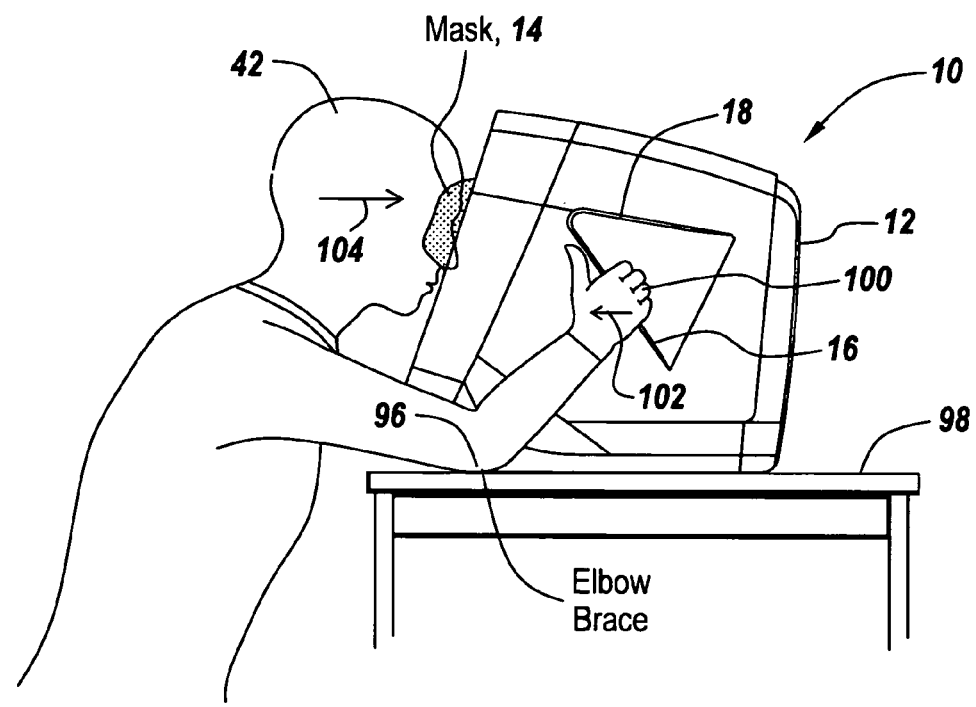
FIG. 6 is a diagrammatic illustration of the utilization of handholds to either side of the enclosure of FIG. 1 to permit the individual utilizing the machine to press his face against the mask, with the individual braced utilizing his elbows against a table on which the enclosure rests.

Referring now to FIG. 6, the ability of the individual 42 to position his face relative to mask 14 and keep it immobilized with respect to the enclosure is made easy through the utilization of handholds 16 and 18 on the exterior surface of enclosure 12. Here it can be seen that individual 42 has an elbow 96 placed on a table 98 which forms an elbow support such that when the individual's hand 100 grasping handhold 16 moves in the direction of arrow 102 the face of the individual 42 is moved in direction of arrow 104.

It will be appreciated that the accuracy of the subject system is critically due to the ability to immobilize the head of the test taking individual, both with respect to the enclosure and mask and with respect therefore to the internally carried laptop computer screen or other screen of a computing device that is provided.

By providing an easy method for the individual taking the test to clamp his face to the mask one provides for accurate cognitive ability measurement with a desktop-based opto-cognitive device and system.

It will be noted that an individual seated in front of the subject desktop enclosure may have a tendency to move his or her head during a test that swings the test.

However, by providing an ergonomically designed enclosure, mask and handhold combination, the individual if seated in front of the enclosure can brace himself or herself utilizing the elbow based method illustrated in FIG. 6.

Figure 7:
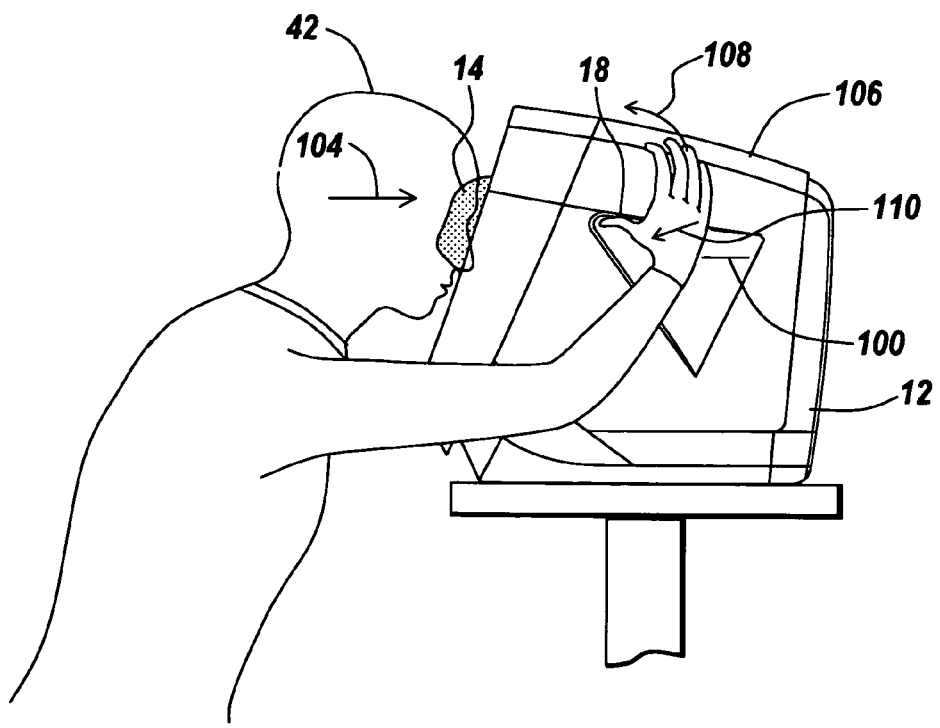
FIG. 7 is a diagrammatic illustration of the utilization of the handhold on the side of the subject enclosure in which the individual utilizing the machine can press his face to the mask with his hands gripping the handle by pushing upward inside the handhold with the thumb and grasping down the enclosure from the top with the other fingers to stabilize his face against the mask.

Referring to FIG. 7, if individual 42 is standing in front of the machine supported at eye height, the individual can nonetheless clamp his face to mask 14 utilizing handle 18 by wrapping the fingers of his hand 100 over the top portion 106 of enclosure 12 as illustrated by arrow 108. Here the individual clasps handhold 18 and moves his handhold in the direction of arrow 110 to move his head again as illustrated by arrow 104 towards mask 14. Since the individual does not have the ability to support his elbow as illustrated in FIG. 6, he can nonetheless take a test in a standing position with his face pressed to mask 14 through the gripping mechanism described in this figure.

Figure 8:
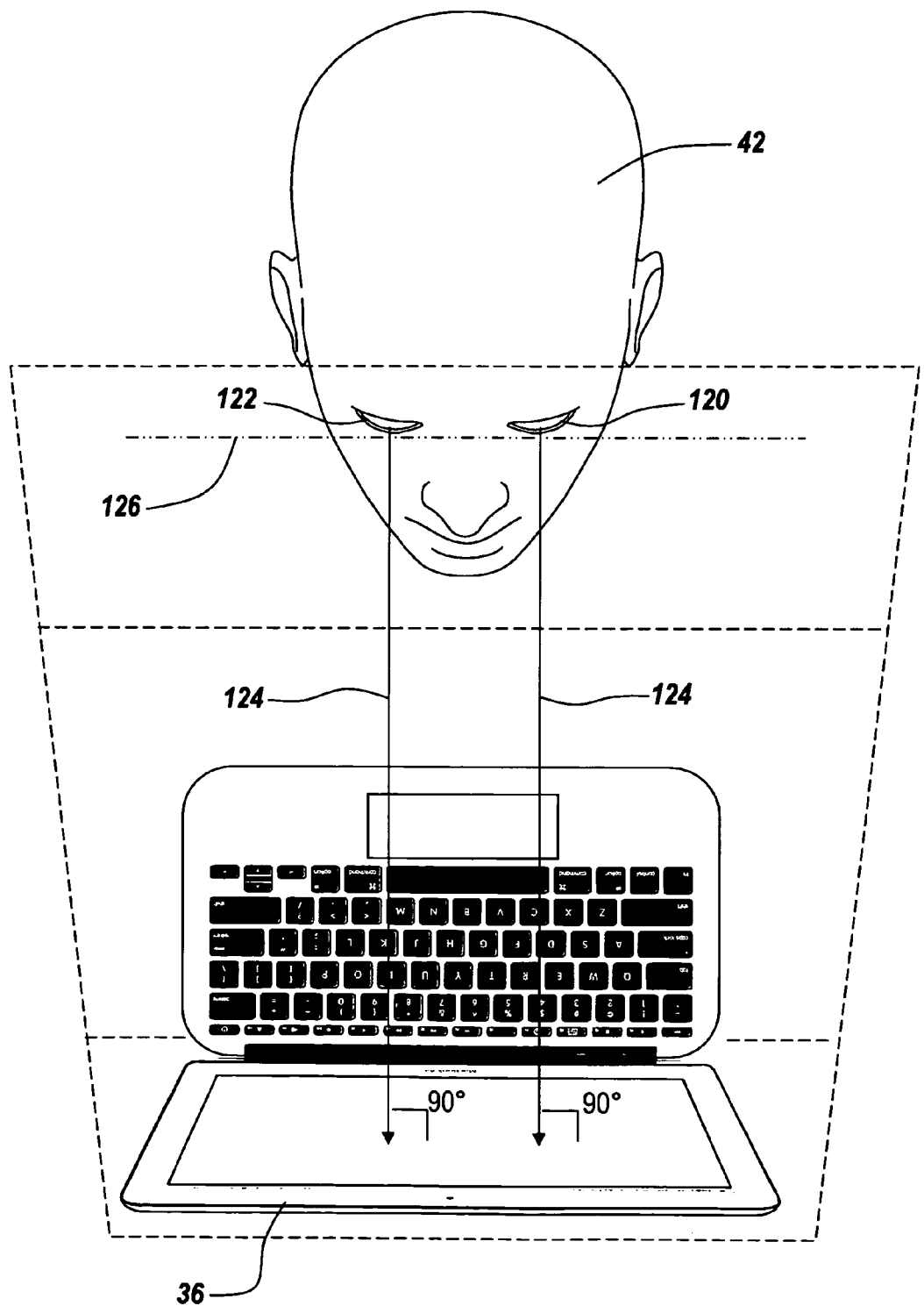
FIG. 8 is a diagrammatic illustration that the mask of FIGS. 1 through 7 maintains the line of sight from the eyes to the screen of the computing device housed inside the enclosure at 90 degrees to the plane of the screen, thereby to enable an accurate gaze direction measurement.

Referring now to FIG. 8, what is shown is that the eyes of individual 42, here shown at 120 and 122 have a line of sight direction illustrated at 124 that is orthogonal to the plane of computer screen 36 as illustrated by the 90-degree angles. It will be appreciated that when the head of individual 42 is clamped in the position illustrated in FIG. 8, the plane illustrated by dotted line 126 of eyes 120 and 122 is parallel to the plane of plane 36.

As mentioned before, the importance of such of arrangement is that no calibration is necessary to determine gaze direction due to the fixed placement of the individual's head with respect to the screen, with the sight lines normal to the screen.

Figure 9:
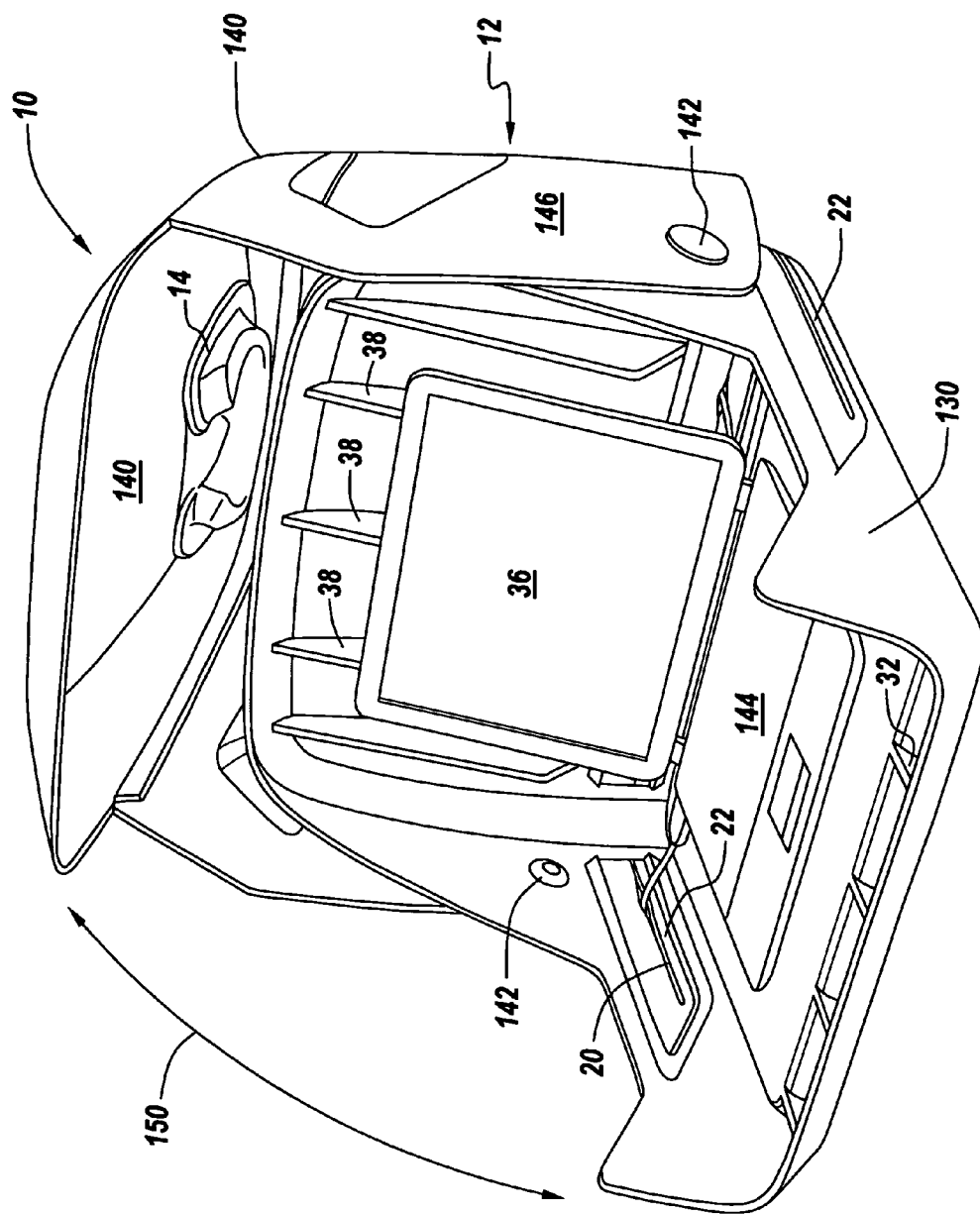
FIG. 9 is a diagrammatic illustration of the clam shell type construction of one embodiment of the enclosure of FIG. 1, illustrating a computing device supported on the base of a lower clam shell, with the screen of the computing device being supported at the appropriate couple and orientation on ribs extending from the clam shell base, with the pivot point for the clam shells being sufficiently forward so as to minimize the space required for the device.

Referring to FIG. 9, in which like elements of FIGS. 2 and 9 have like reference characters, what can be seen is that in one embodiment the enclosure is a hinged clam shell enclosure having a bottom base 130 and a top clam shell portion 140 hinged together at hinge pin 142. Here a laptop having a base portion 32 and a hinged screen portion 36 are supported by the base ribs 32 as described hereinabove. Likewise the computer screen 36 of the laptop is supported by the aforementioned ribs 38 such that not only is the angle of the screen with respect to the laptop base maintained, the plane of the screen 36 is determined by the plane of ribs 38 such that its plane is referenced to the plane of face plate 146 of top clam shell 140 that carries mask 14. Here slit structure 20 permits passage of tables 22 through the enclosure as shown.

It will be seen that with this pivoted clam shell structure, a laptop or other computing device can be easily positioned within enclosure 12, with the position of the pivot point as well as the configuration of the sidewalls 146 of the upper clam shell minimizing the amount of area that is necessary for the support of the subject device such that when the clam shell is opened as illustrated by double ended arrow 150 there is sufficient clearance for a desktop device, without having to leave a large amount of space to permit the opening of the clam shell.

Figure 10:
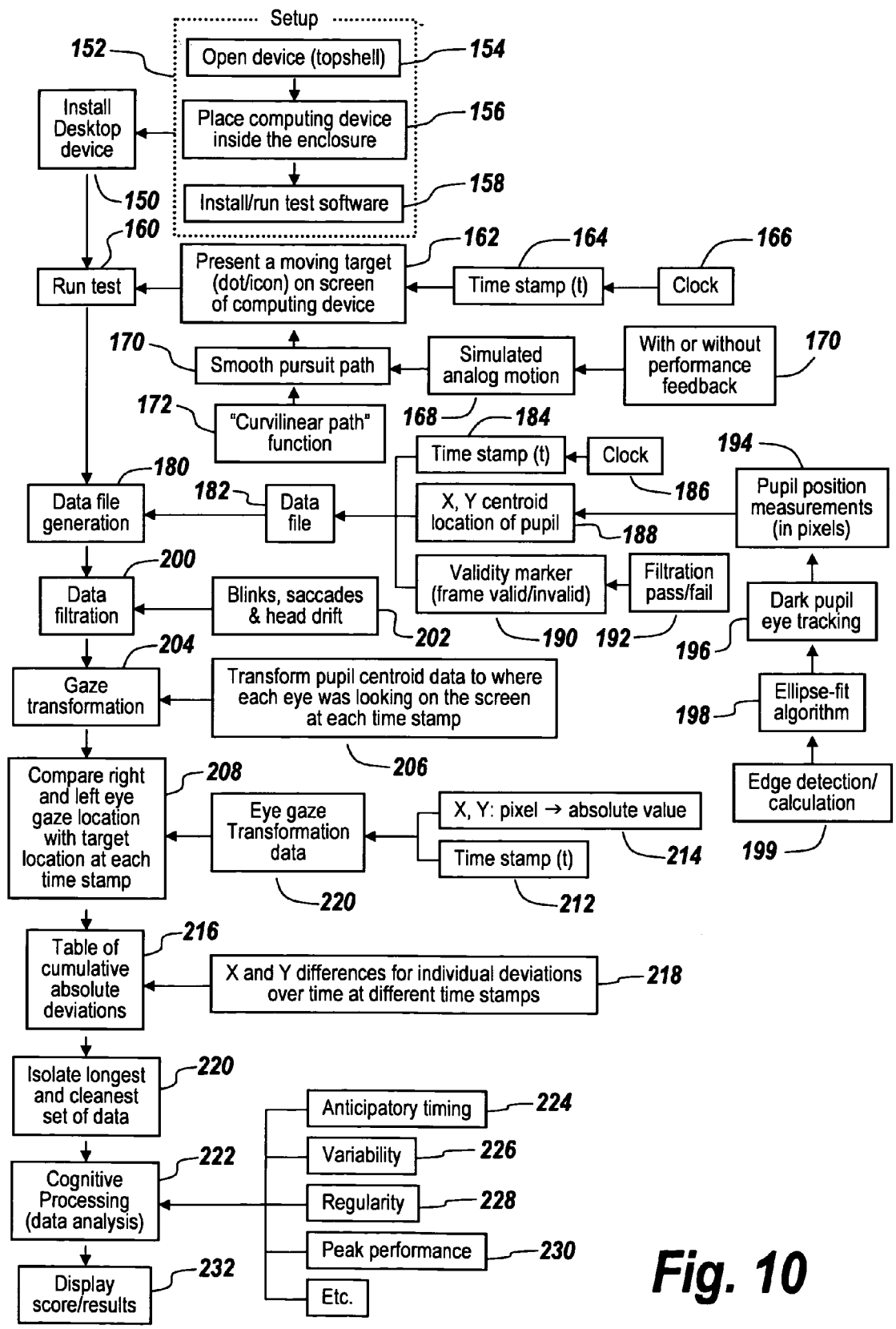
FIG. 10 is a flow chart showing one algorithm for measuring cognitive function using the desktop system.

Referring now to FIG. 10, in one embodiment for the precision measurement of cognitive awareness, as seen at 150 one initially installs a desktop device and sets it up as illustrated at 152 first by opening the top shell of the device is illustrated at 154 and by placing the computing device inside the disclosure as illustrated at 156, whereupon one installs and runs tests software as illustrated at 158. Thereafter a test is run as illustrated at 160 by presenting a moving target which is a dot or icon 162 on a screen of the computing device. This moving target is time stamped at 164 utilizing a clock 166 with simulated analog motion 168 used to generate a smooth pursuit path 170 that is utilized to drive the motion of the icon on the screen. The smooth pursuit path is in one embodiment a curvilinear path 172. Note clock 166 coupled to the simulated analog motion unit 168 as illustrated at 174 with or without a performance feedback.

When the test is run, a data file is generated at 180 from a data file 182 that is in turn time stamped at 184 utilizing a clock 186. Data file 182 stores the X,Y location of the centroid location of the pupil 188. Also stored is a validity marker 190 that a frame is valid or invalid derived from the output of pass/fail and filtration operation 192. The pupil position measurements as illustrated at 194 utilized to derive the X,Y centroid of location of the pupil. These pupil position measurements use pupil eye tracking 196 which incorporates an ellipse-fit algorithm 198 and edge detection calculations 190, thus to accurately determine gaze direction through the X,Y centroid location of the pupil. Having the generated data file 180, one utilizes a data filtration step 200 that eliminates blinks, saccades and head drift as illustrated 202.

Having filtered the data, the next step is gaze transformation 204 in which as illustrated at 206, one transforms pupil centroid data to where each eye is looking on the screen at each time stamp. Gaze direction is ascertained in the traditional manner as described above.

After having transformed the gaze to provide a gaze direction as illustrated, at 208 one compares the left eye and the right eye gaze location with target location at each time stamp. Eye gaze transformation data is available for this process at 210 having been time stamped at 212 and having been derived from an X, Y pixel location transformed into absolute values at 214.

Thereafter a table of cumulative absolute deviations is derived at 216 utilizing X and Y differences for individual deviations over time at different time stamps as illustrated at 218.

Then, the longest and cleanest set of data is isolated at 220 and cognitive processing, namely data analysis, is performed at 222. The cognitive processing includes metrics such as ascertaining anticipatory timing 224, variability 226, regularity 228 and peak performance 230, after which, depending on the metric utilized, the results are displayed at 232 either as a score or some other result representation.

The above processing provides an inordinate amount of processing to filter out outlying data, blinks, saccades, head drift and other environmental factors, such that when gaze direction is calculated all the extraneous effects of noise are eliminated from the gaze direction data. Environmental and head position noise has already been limited by the use of the subject desktop device to eliminate ambient light from getting into the system and to minimize the effect of head movement since the head is clamped to the mask on the desktop device.

What has therefore been described is a desktop system for cognitive performance which is portable and is exceptionally inexpensive and yet provides sufficient accuracy and precision to be useful in clinical drug analysis.

The Smooth Pursuit Paradigm for Clinical Drug Testing

Figure 11:
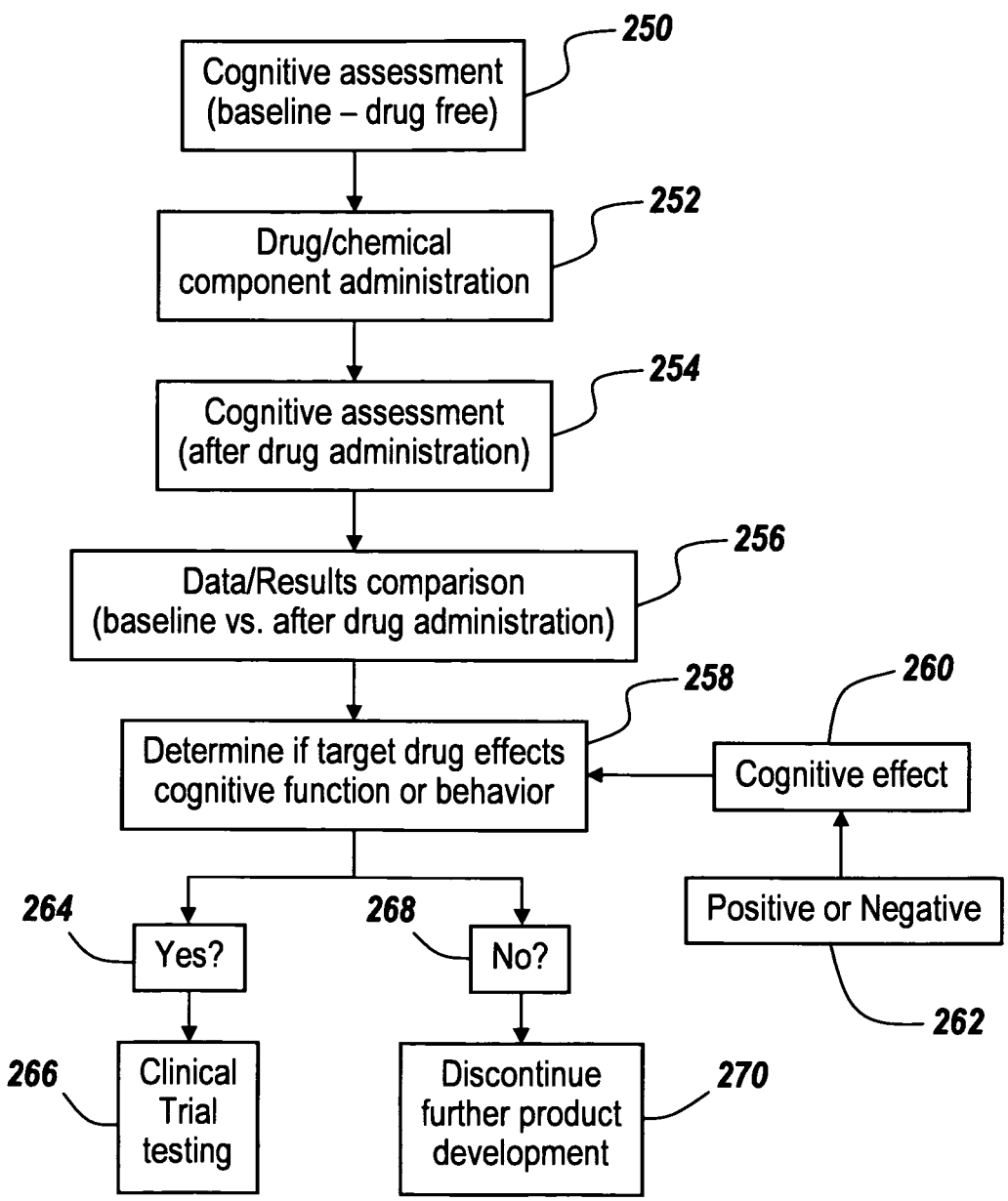
FIG. 11 is a flow chart showing the subject system for determining drug efficacy or toxicity.

What is now described in FIG. 11, is the Neuro-Pharmaceutical Product Development Process and Pipeline utilizing cognitive performance as measured using the smooth pursuit paradigm.

Here it can be seen that the cognitive assessment is based on a baseline-drug free environment as illustrated at 250. Thereafter the drug or clinical component is administered to the test subject as illustrated at 252 and cognitive assessment is made after drug administration as illustrated at 254. The results are compared between the baseline readings before and after drug administration at 256 to determine if the drug affects cognitive function or behavior as illustrated at 258.

The cognitive effect 260 is ascertained at 260 to be positive or negative as illustrated at 262. If there is a positive cognitive effect as illustrated at 264 then clinical trial testing may proceed as illustrated at 266.

On the other hand if there is no cognitive effect as illustrated at 268 then it is prudent to discontinue further product drug development as illustrated at 270.

Thus, the first test is whether or not an administered drug or compound has any effect on the cognitive processes for the test individual. The subject system permits a quick test of whether or not a drug or compound is at all useful for clinical purposes.

Figure 12:
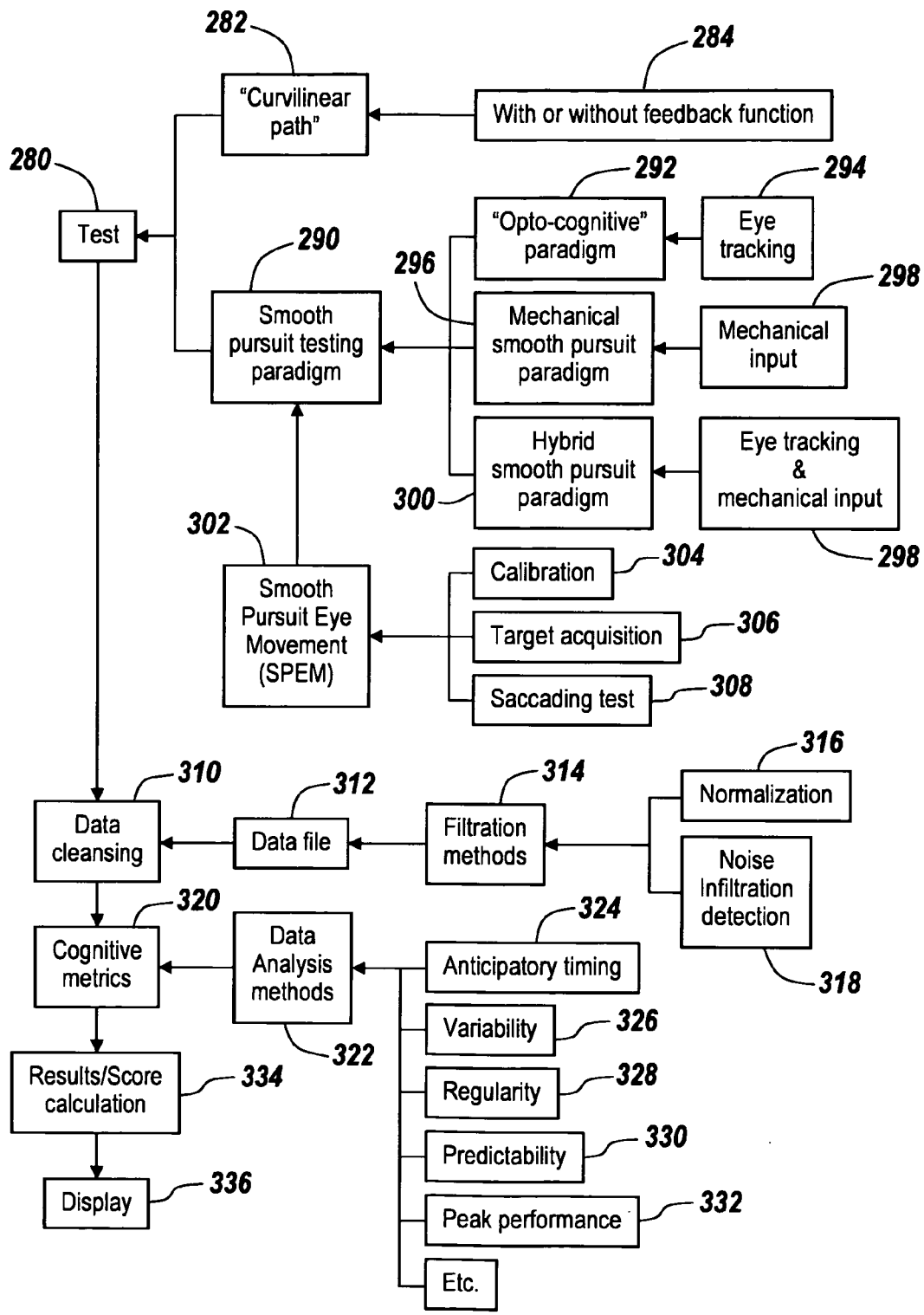
FIG. 12 is a detailed flow chart of one embodiment of the subject invention showing a precision method for determining drug efficacy or toxicity.

As to the cognitive assessment useful in the process in FIG. 11 and referring now to FIG. 12 the test is administered as illustrated at 280. The test includes presenting a test subject with an icon, target or dot travelling along a curvilinear path 282 with or without manual smooth pursuit feedback as illustrated at 284. Manual feedback in general involves an individual moving one's hand to touch a moving dot. Note, smooth pursuit eye tracking may be utilized without a manual component.

The smooth pursuit testing paradigm is illustrated at 290 in which the result of trying to follow an icon on a curvilinear path is ascertained. The smooth pursuit testing paradigm may include an opto-cognitive paradigm 292 which relates to the type of eye tracking 294 achievable of for instance by the desktop system described above.

The smooth pursuit testing paradigm may also include a mechanical smooth pursuit paradigm 296 including a mechanical input 298. This is the same type of mechanical or smooth pursuit that is envisioned when one uses one's finger to trace a path on a screen occupied by the moving icon.

Finally, as illustrated at 300 a hybrid smooth pursuit paradigm may be employed employing both eye tracking and mechanical input as illustrated at 302.

In one embodiment smooth pursuit testing 290 includes a smooth pursuit eye movement paradigm at 302 which involves for instance a calibration step 304, a target acquisition step 306 and a saccading test 308. This type of test procedure is described hereinbefore in connection with the desktop eye tracking apparatus.

As seen at 310, data cleansing is performed. This data cleansing can include cleansing a data file 312 utilizing filtration methods 314 that include both a normalization technique 316 and a noise infiltration detection technique 318.

After data cleaning, cognitive metrics are applied to the data as illustrated at 320. The cognitive metrics include data analysis methods 322 that in turn include anticipatory timing 324, variability metric 326, a regularity metric 328, a predictability metric 330 and a peak performance metric 332. The mathematical definitions of these metrics are presented below:

Anticipatory Timing:

$$f(f) = \frac{1}{N}\sum_{j=1}^{N}\left(\sum_{i=1}^{N}(|t-i|)_{ij} - \sum_{i=1}^{N}(|t-i|)_i\right)$$

The standard deviation of the sum of the absolute value of a set of target position arrays subtracted from a set of user position arrays.
N=The length of the target position (the number of elements in the array).
j=The standard deviation index for the absolute value target minus user array
i=The index for the sum of absolute value target minus user array
t=Target position arrays.
i=User position arrays.

Variability:

$$f(e) = \frac{1}{N^2}\sum_{k=1}^{N}\left(\sum_{j=1}^{N}((d_t - d_i)_j - (d_t \bar{-} d_i))_k - \sum_{j=1}^{N}((d_t - d_i)_j - (d_t \bar{-} d_i))\right)^2$$

The variance of the standard deviation of a set of target position arrays subtracted from a set of user position arrays.
N=The length of the target position (the number of elements in the array).
j=The standard deviation index.
k=The variance index.
dt=Target distance arrays.
di=User distance arrays.

Regularity:

$$f(e) = \text{Minimum}\left[\sum_{t=0}^{t=f}\delta\left(\sum_{i=0}^{i=N}e\right)\right]$$

Finding the minimum of the application of the sum of an error array on a delta distribution.
e=Error array.
N=The length of the target position (the number of elements in the array).
t=Time.
i=Index of error array.

Predictability:

$$f(t+1)=kf(t_{-n},t_0)$$

A factor of k applied to any function listed on this sheet.
k=Arbitrary constant.
t=Input elements to any function f.

Peak Performance:

$$f(p)=\text{Maximum}[\text{scores}[t_0:t_f]]$$

The maximum value of any indexed portion of the scores array.
t0=Beginning index.
tf=Ending index Thereafter as illustrated at 334 the results or a score calculation are displayed at 336.

As mentioned hereinbefore it is part and parcel of the subject invention that an extremely accurate cognitive assessment method needs to be utilized in order for one to be able to detect the efficacy or toxicity of a particular drug or compound. The use of any of the techniques including anticipatory timing, variability, regularity, predictability of peak performance may be used singly or in combination to accurately hone in on any effects of the drug or compound on the individual taking the test. This means that whatever baseline database is established, the variance from this baseline readily provides a first indicator of the ability of the administered drug or component to affect the body. If there is any effect the drug can be selected for further evaluation. If the drug or compound has no effect on cognitive performance, then it can be assumed that there will be no drug efficacy whatsoever. It can also show that there will be no toxicity.

Having ascertained that there is a cognitive performance enhancement or deprivation due to the administration of the compound or the drug, then one can utilize the correlation between anticipatory timing, variability, regularity, predictability, or peak performance and a particular disease or condition to ascertain with particularity the efficacy of the drug, or for instance any toxicity that may accompany the administration of the drug.

In summary, what is described is the utilization of smooth pursuit paradigms to ascertain cognitive performance as a measure of drug efficacy or toxicity for use as a screening tool and also to quantify the effect of the drug on the individual taking the test.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A method for conducting pharmaceutical drug testing to ascertain the efficacy or toxicity of a candidate target drug comprising the steps of:
   administering the target drug to a test subject and,
   measuring the reaction of the test subject to the administration of the target drug utilizing smooth pursuit cognitive testing, wherein the smooth pursuit cognitive testing includes:
      presenting a smoothly moving object on a screen;
      using one or more cameras to detect gaze direction of one or more eyes of the test subject while the test subject visually tracks the smoothly moving object presented on the screen, and
      determining cognitive performance of the test subject in accordance with the test subject's performance in visually tracking the smoothly moving object presented on the screen.

2. The method of claim 1, and further including utilizing smooth pursuit cognitive testing prior to the introduction of the target drug into the test subject and determining a baseline therefrom.

3. The method of claim 2, wherein the smooth pursuit cognitive testing done after the introduction of the drug is compared to the baseline to determine if the drug has affected cognitive function or behavior.

4. The method of claim 3, wherein if cognitive function or behavior has been affected, clinical trial testing continues and wherein if no cognitive function or behavior affect has been determined, further product development of the drug is discontinued.

5. The method of claim 1, wherein presenting a smoothly moving object on a screen comprises presenting the moving object on a curvilinear path.

6. The method of claim 1, wherein the smooth pursuit cognitive testing includes calibration, target acquisition and a saccading test.

7. The method of claim 1, wherein the smooth pursuit cognitive testing includes a data cleansing step.

8. The method of claim 7, wherein the data cleansing step includes a filtration step that includes noise filtration and eliminates outlying data.

9. The method of claim 1, wherein the smooth pursuit cognitive testing includes cognitive metrics and data analysis that includes one of anticipatory timing, variability, regularity, predictability and peak performance.

10. The method of claim 9, wherein the cognitive metrics include a combination of two or more of anticipatory timing, variability, regularity, predictability and peak performance.

11. The method of claim 1, wherein the drug testing includes testing of a compound.

12. The method of claim 11, wherein the compound includes vitamins and non-drug classified substances.

13. A method of clinical drug testing, comprising the steps of:
providing a portable unit for performing an eye tracking function in which an individual is asked to peer into the unit and to visually track an icon moving on a screen within the unit; and,
performing a smooth pursuit cognitive testing procedure to determine the affect of any administered target drug on the behavior of a test taking subject, wherein performing the smooth pursuit cognitive testing procedure includes:
presenting the moving icon on the screen within the unit;
using one or more cameras, located within the unit, to detect gaze direction of one or more eyes of the test taking subject while the test taking subject visually tracks the moving icon presented on the screen within the unit, and
determining cognitive performance of the test subject in accordance with the test taking subject's performance in visually tracking the moving icon presented on the screen.

14. The method of claim 13, wherein if it is determined that the target drug has no effect on cognitive function or behavior on the test taking subject, then clinical drug testing for the target drug is discontinued.

15. The method of claim 14, wherein if it is determined that the target drug affects cognitive function or behavior of the test taking subject, then the effect in terms of test results is measured against a baseline previously established for the test taking subject.

16. The method of claim 15, and further including the step of correlating the test results with a physiological condition of the test taking subject.

17. The method of claim 16, wherein the correlation is utilized to provide a measure of the efficacy of the target drug.

18. The method of claim 16, wherein the correlation is made to deleterious reactions of the test taking subject to the administration of the target drug corresponding to toxicity.

19. A method for clinical drug testing comprising the steps of:
providing a mobile eye-tracking smooth pursuit cognitive testing unit;
administering a target drug to a test taking subject; and
in conjunction with administering the target drug to the test taking subject, monitoring cognitive function of the test taking subject utilizing the mobile unit, wherein monitoring cognitive function of the testing taking subject includes:
presenting a smoothly moving object on a screen in the mobile unit;
using one or more cameras, in the mobile unit, to detect gaze direction of one or more eyes of the test taking subject while the test taking subject visually tracks the smoothly moving object presented on the screen, and
determining cognitive performance of the test taking subject in accordance with the test taking subject's performance in visually tracking the smoothly moving object presented on the screen.

20. The method of claim 19, wherein determining cognitive performance of the test taking subject includes determine one or more cognitive metrics including at least one of anticipatory timing, variability, regularity, predictability and peak performance.

21. The method of claim 20, wherein the unit includes a face mask to which the test taking subject presses his or her face, and wherein the test taking subject maintains positive pressure of his or her face against the face mask during smooth pursuit cognitive testing.

* * * * *